(12) United States Patent
Gordeev et al.

(10) Patent No.: US 9,771,394 B2
(45) Date of Patent: Sep. 26, 2017

(54) ANTIMICROBIAL POLYMYXINS FOR TREATMENT OF BACTERIAL INFECTIONS

(71) Applicant: MICURX PHARMACEUTICALS, INC., Hayward, CA (US)

(72) Inventors: Mikhail Fedorovich Gordeev, Castro Valley, CA (US); Jinqian Liu, Fremont, CA (US); Xinghai Wang, Hayward, CA (US); Zhengyu Yuan, Hayward, CA (US)

(73) Assignee: MICURX PHARMACEUTICALS, INC., George Town, Grand Cayman (KY)

(*) Notice: Subject to any disclaimer, the term of this patent is extended or adjusted under 35 U.S.C. 154(b) by 0 days.

(21) Appl. No.: 14/972,031

(22) Filed: Dec. 16, 2015

(65) Prior Publication Data

US 2016/0185823 A1 Jun. 30, 2016

Related U.S. Application Data

(60) Provisional application No. 62/092,780, filed on Dec. 16, 2014.

(51) Int. Cl.
  *C07K 7/52* (2006.01)
  *C07K 7/62* (2006.01)
  *A61K 38/00* (2006.01)

(52) U.S. Cl.
  CPC ............... *C07K 7/52* (2013.01); *C07K 7/62* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 3,450,687 A | 6/1969 | Hobbs et al. | |
| 4,091,092 A | 5/1978 | Parker et al. | |
| 6,380,356 B1 | 4/2002 | Griffin et al. | |
| 8,415,307 B1 | 4/2013 | Curran et al. | |
| 2006/0004185 A1 | 1/2006 | Leese et al. | |
| 2009/0215677 A1 | 8/2009 | Vaara et al. | |
| 2010/0160215 A1 | 6/2010 | Leese | |
| 2012/0283176 A1 | 11/2012 | Vaara et al. | |
| 2012/0316105 A1 | 12/2012 | Magee et al. | |
| 2014/0162937 A1 | 6/2014 | Vaara et al. | |
| 2015/0031602 A1 | 1/2015 | Saadi et al. | |

FOREIGN PATENT DOCUMENTS

| | | |
|---|---|---|
| CN | 103130876 A | 6/2013 |
| CN | 103923190 A | 7/2014 |
| DE | 1906699 A1 | 2/1970 |
| JP | 5353680 | 5/1978 |
| WO | WO 2006/045156 A1 | 5/2006 |
| WO | WO 2007/066906 A1 | 6/2007 |
| WO | WO 2008/017734 A1 | 2/2008 |
| WO | WO 2010/091294 A2 | 8/2010 |
| WO | WO 2010/130007 A1 | 11/2010 |
| WO | WO 2011/026529 A1 | 3/2011 |
| WO | WO 2012/051663 A1 | 4/2012 |
| WO | WO 2012/168820 A1 | 12/2012 |
| WO | WO 2013/072695 A1 | 5/2013 |
| WO | WO 2013/112548 A1 | 8/2013 |
| WO | WO 2014/028087 A1 | 2/2014 |
| WO | WO 2014/108469 A1 | 7/2014 |
| WO | WO 2014/188178 A1 | 11/2014 |
| WO | WO 2015/135976 A1 | 9/2015 |
| WO | WO 2015/149131 A1 | 10/2015 |

OTHER PUBLICATIONS

PCT/ISA/206 Invitation to Pay Additional Fees and partial International Search Report for PCT/US2015/066210 mailed Apr. 25, 2016.
PCT/ISA/220 and PCT/ISA/210 International Search Report for PCT/US2015/066210 mailed Jul. 20, 2016.
PCT/ISA/237 Written Opinion of the International Searching Authority for PCT/US2015/066210 mailed Jul. 20, 2016.
Bergen, Phillip, et al., "Colistin methanesulfonate is an inactive prodrug of colistin against *Pseudomonas aeruginosa*", Antimicrob. Agents Chemother. 2006, 50(6), 1953-1958.

(Continued)

*Primary Examiner* — Christina Bradley

(74) *Attorney, Agent, or Firm* — Squire Patton Boggs (US) LLP

(57) ABSTRACT

The present invention provides antimicrobial polymyxin compounds of the following formula I:

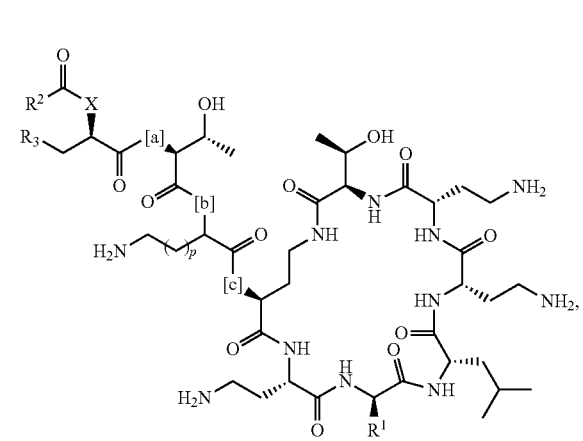

Figure 1:
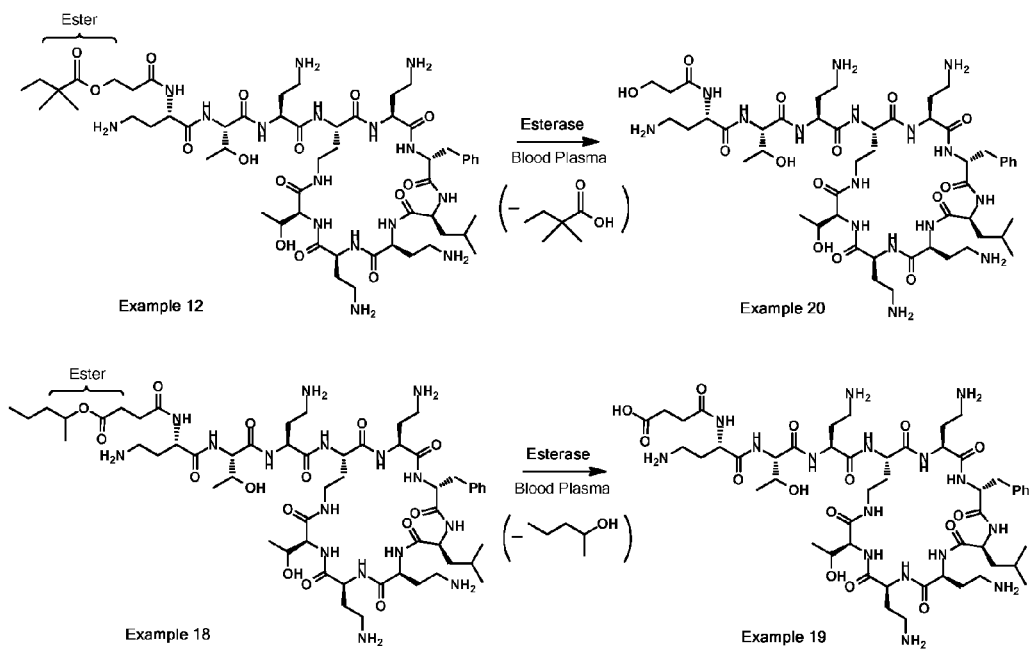

or pharmaceutically acceptable salts, hydrates, or solvates thereof that are antibacterial agents, pharmaceutical compositions containing them, methods for their use, and methods for preparing these compounds.

34 Claims, 2 Drawing Sheets

(56) References Cited

OTHER PUBLICATIONS

Cohen, S., et al., "Inhibition of mycobacterial esterases by polymyxin B.", Antiobiot. Chemother. (Northfield) 1954, 4(1), 18-24, abstract only.

Dalfino, Lidia, et al., "High-dose, extended-interval colistin administration in critically ill patients: is this the right dosing strategy? A Preliminary Study", CID 2012, 54, 1720-1726.

De Visser, P.C., et al., "Solid-phase synthesis of polymyxin B1 and analogues via a safety-catch approach", J. Peptide Res. 2003, 61, 298-306.

Feeley, T.W., "Aerosol polymyxin and pneumonia in seriously ill patients", N. Engl. J. Med. 1975, 293(10), 471-475, abstract only.

Huttunen, Kristiina M., et al., "Prodrugs—from Serendipity to rational design", Pharmacol. Rev. 2011, 63(3), 750-771.

Kassamali, Zahra, et al., "Microbiological assessment of polymyxin B components tested alone and in combination", Antimicrob. Agents and Chemother. 2015, 59(12), 7823-7825.

Keirstead, Natalie D., et al., "Early prediction of polymyxin-induced nephrotoxicity with next-generatoin urinary kidney injury biomarkers", Toxicology Sciences 2014, 137(2), 278-291.

Li, Bryan, et al., "Syntheses of Dap-3 polymyxin analogues via a Tris-Boc-Protected polymyxin B Heptapeptide", Synthesis 2015, 47, 2088-2092.

Magee, Thomas V., et al., "Discovery of Dap-3 polymyxin analogues for the treatment of multidrug-resistant gram-negative nosocomial infections", J. Med. Chem. 2013, 56(12), 5079-5093.

O'Dowd, Hardwin, et al., "Preparation of tetra-Boc-protected polymyxin B nonapeptide", Tetrahedron Letters 2007, 48, 2003-2005.

Okimura, Keiko, et al., "Semi-synthesis of polymyxin B (2-10) and colistin (2-10) analogs employing the trichloroethoxycarbonyl (Troc) group for side chain protection of α, γ-Diaminobutyric acid residues", Chem. Pharm. Bull. 2007, 55(12), 1724-1730.

Roberts, Kade D., et al., "Antimicrobial activity and toxicity of the major lipopeptide components of polymyxin B and colistin: last-line antibiotics against multidrug-resistant gram-negative bacteria", ACS Infect. Dis. 2015, 1(11), 568-575.

Sharma, S.K., et al., "Solid-phase total synthesis of polymyxin B1", J. Peptide Res. 1999, 53, 501-506.

Takhi, Mohamed, et al., "Discovery of azetidine based ene-amides as potent bacterial enoyl ACP reductase (FabI) inhibitors", Eur. J. Med. Chem. 2014, 84, 382-394, abstract only.

Velkov, Tony, et al., "Pharmacology of polymyxins: new insights into an 'old' class of antibiotics", Future Microbiol. Jun. 8, 2013(6), doi: 10.2217/fmb.13.39, 20 pages.

Velkov, Tony, et al., "Structure—activity relationships of polymyxin antibiotics", J. Med. Chem. 2010, 53(5), 1898-1916.

Wood, G.C., "Aerosolized antibiotics for treating hospital-acquired and ventilator-associated pneumonia", Expert Rev. Anti. Infect. Ther. 2011, 9(11), 993-1000, abstract only.

Figure 1. Metabolic break-down of soft drug compounds of Examples 12 and 18 into respective metabolites, compounds of Examples 20 and 19.

Figure 2:
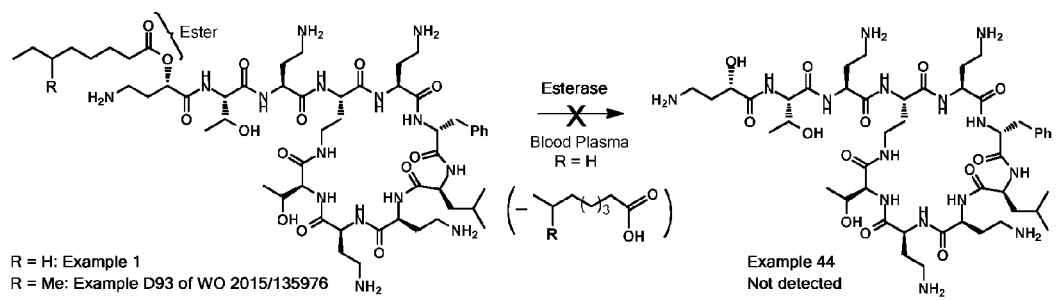

Figure 2. Lack of metabolism for the reference compound of Example 1, with its structure compared to the structure of the ester D93 of the publication WO 2015/135976.

ANTIMICROBIAL POLYMYXINS FOR TREATMENT OF BACTERIAL INFECTIONS

FIELD OF THE INVENTION

Provided herein are novel derivatives of polymyxins, pharmaceutical compositions thereof, methods for their use, and methods for preparing of the same. These compounds have potent activities against pathogenic microbial (bacterial) species.

BACKGROUND OF THE INVENTION

Antimicrobial agents to combat tough-to-treat Gram-negative infections are urgently needed. The current Gram-negative antibiotics have become less effective due to a widespread bacterial resistance. The new antibacterial should possess useful levels of activity against certain human and veterinary pathogens, including Gram-negative pathogens implicated in serious infections, such as *Acinetobacter baumannii*, *Pseudomonas aeruginosa*, and *Klebsiela pneumoniae*.

Among other antibacterials, polymyxins stand out for their high potency against Gram-negative pathogens, including *Pseudomonas aeruginosa*. This class is comprised of several structurally related cyclic peptide analogs, including polymyxin B (PMB) and polymyxin E (colistin), as described, for example, by Velkov et al. in *J. Med. Chem.*, 2010, vol. 53, pp. 1898-1916.

Unfortunately, while being highly potent against bacteria, polymyxins suffer from toxicity inherent in the cationic peptide class. This leads to the high frequency of serious adverse effects, chiefly due to a persistence of polymyxins in vivo after administration to a mammal or human, with predominant accumulation of these agents in kidneys.

The accumulation of colistin in kidney tissues causes severe side effects, up to and including the organ failure. Provided herein are new polymyxin compounds with significantly improved safety and reduced propensity for adverse effects, as compared to other polymyxin pharmaceuticals.

Various polymyxin derivatives and structurally related cyclopeptides have been described, for example, in publications WO 2015/149131, WO 2015/135976, US 2015/0031602, WO 2014/188178, WO 2014/108469, CN 103923190, US 2014/0162937, WO 2014/028087, WO 2013/112548, CN 103130876, WO 2013/072695, WO 2012/168820, WO 2012051663, US 2012/0283176, US 2010/0160215, US 2009/0215677, WO 2008/017734, WO 2006/045156, US 2006/0004185, U.S. Pat. No. 6,380,356, and U.S. Pat. No. 3,450,687. None of these references specifically describe or generally contemplate the compounds of the present invention, nor the new concept for reducing nephrotoxicity of the polymyxin antibiotics provided herein.

SUMMARY OF THE INVENTION

Provided herein are compounds with useful antibacterial activity, in particular, against Gram-negative microorganisms.

It is known that the antimicrobial (antibacterial) activity of polymyxins generally parallels the mammalian toxicity thereof. Thus, more potent antibacterials of this class are generally more toxic (see, for example, Keirstead et al. in *Toxicol. Sci.* 2014, vol. 137, pp. 278-291). The adverse effects of polymyxins result from accumulation thereof in kidneys due to the binding of these molecules to kidney tubule cells (nephrons), followed by mammalian membranes disruption and subsequent nephrotoxicity, especially if a longer therapy is required.

The new polymyxins provided herein exhibit potent antibacterial activity in vitro and in vivo, while being markedly less toxic to a mammalian subject under the treatment. This combination of the antibacterial activity and the improved tolerability is achieved with a unique design of the compounds provided herein.

In contrast to the conventional polymyxins described in prior art, the compositions provided herein are novel polymyxin structures incorporating at least one metabolically (chemically or biochemically) labile functionality (such as an ester, carbamate, or a phosphate group) that is cleaved in vivo after the drug has exerted its desired bactericidal effect. Importantly, the new molecules exhibit sufficient metabolic stability and residence time to exhibit the desired antibacterial effect, but then metabolically degrade in vivo, thus avoiding a harmful accumulation in organ tissues, such as kidneys. Since this metabolic process results in far less toxic (compared to the parent drug) metabolite(s), the adverse effects (such as nephrotoxicity) are minimized or eliminated.

This general approach relates to "a soft drug" medicinal chemistry strategy, as described for anti-inflammatory steroids by Brutsche et al. in *Lancet*. 2000, vol. 356, pp. 556-561.

It is important to distinguish the soft drug design from an opposing concept of "a prodrug", wherein a labile derivative of the drug is provided to impart, for example, an improved solubility or reduced acute toxicity, as reviewed, for example, by Huttinen et al. in *Pharmacol. Rev.* 2011, vol. 63, pp. 750-771. While both classes are subject to in vivo metabolism, the critical difference between soft drugs and prodrugs is that a soft drug is active before it is metabolized, whereas a prodrug produces the highly active drug only after it is metabolized, and is normally inactive in its non-metabolized form. Effectively, the soft drug is the true drug (i.e., the active entity), while the prodrug is merely a delivery form for the active drug. Certain ester prodrugs of polymyxins have been reported, as described, for example, by Hobbs in a patent publication FR 6035 19680708. The prodrug form of colsitin, colistin methanesulfonate, was described, for example, by Bergen et al. in Antimicrob. Agents Chemother. 2006, vol. 50, pp. 1953-1958. Importantly, the latter therapeutic agent still suffers from the typical for colistin nephrotoxicity, since the released from this prodrug colistin still accumulates in kidney.

No prior literature reported any polymyxin soft drug design or application to limit the long-term systemic exposure and the tissue accumulation of polymyxins, the cause of nephrotoxicity of this class. Furthermore, this class is known to inhibit certain enzyme classes similar to those involved in common metabolic processes. Thus, polymyxin B inhibition of esterase enzymes was described by Cohen et al. in *Antibiot. Chemother.* 1954, pp. 18-24. Therefore, one skilled in biochemistry would ordinarily anticipate that no metabolic degradation of a polymyxin ester derivative is feasible for the purpose of creating a soft drug polymyxin.

Surprisingly, the compounds provided herein are metabolized in vivo after exerting the desired antibacterial effect thereof. Thus, no excessive accumulation of said compounds in tissues is possible by virtue of the unique design that promotes a metabolism of the antibacterial compounds provided herein. The metabolic processes involved may include, for example, esterase-mediated cleavage of an ester group, phosphatase-mediated cleavage of a phosphate or phosphonate group, hydrolase-mediated cleavage of a carbamate group, or reductase-mediated cleavage of a hydroxylamine derivative. Importantly, aforementioned designer groups are selectively incorporated into polymyxin structures to comply with the structure-activity relationship (SAR) for this class, without diminishing the antibacterial efficacy, and even serving to maximize the latter.

One skilled in art would appreciate that not every potential substrate for metabolic degradation is suitable for use as a therapeutic soft drug. Before said degradation takes place, the intact soft drug molecule must reside in vivo for a time period sufficient to exert its antibacterial effect in blood and/or tissues. If the degradation process is too rapid, then amount of the intact soft drug capable of antibacterial action will be insufficient for pathogen eradication, resulting in a lack of therapeutic effect. Such compounds cannot serve as soft drugs.

On the other hand, if a potential polymyxin soft drug is too stable in vivo, it would still exert nephrotoxicity, which is manifested after accumulation in kidneys of the intact drug. As a result, such a compound would not be degraded at a sufficient rate (after the antibacterial effect is achieved), leading to its accumulation and nephrotoxicity. As a result, such compounds also cannot serve as soft drugs.

In effect, the soft drug structure must reconcile two opposing properties: long enough residence time in vivo, and sufficiently rapid metabolic degradation. Surprisingly, compounds described herein satisfy the strict requirement for the relative stability of the soft drug needed for antibacterial effect, as well as the controlled metabolic degradation of such compounds that prevents excessive accumulation in tissues and the resulting nephrotoxicity.

In addition to a metabolic degradation, compounds provided herein may be degraded in vivo through a chemical cleavage, such as pH-dependent self-cleavage known for molecules bearing both an ester group and a free amine group. When these two groups are in relative proximity to each other, and the amine groups is essentially free (under neutral or physiological pH conditions), the amine group may be acylated by the ester group, resulting in the acyl group being transfer from the oxygen atom to the nitrogen atom. This alteration of the structure of the parent active drug may result in a less active or inactive degradant product with a reduced propensity for adverse effects.

In one aspect, the aforementioned metabolic or chemical degradation of the compounds provided herein results in significantly less toxic degradation product(s), for example, with a reduced net (total) molecular positive charge, with this charge implicated in the binding of other polymyxins to mammalian membranes and their accumulation in kidney tissues.

In another aspect, the aforementioned metabolic or chemical degradation of the compounds provided herein results in significantly fewer toxic degradation products with a truncated (minimized or cut) lipophilic side chains, with this side chain is implicated in the disruption of mammalian membranes and nephrotoxicity caused by the polymyxin drugs colistin and polymyxin B.

In one aspect, provided herein is a compound of formula I:

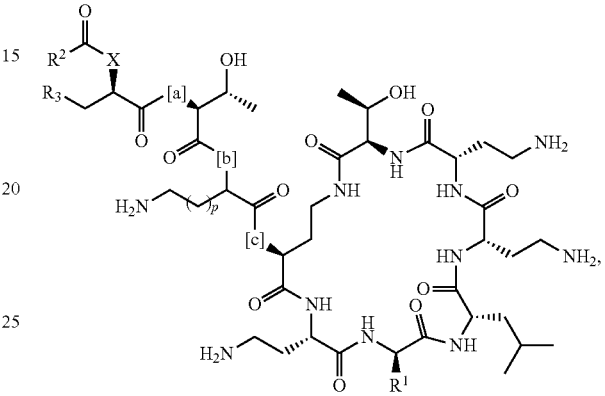

or a pharmaceutically acceptable salt, solvate, or hydrate thereof wherein:

$R^1$ is $CH_2CH(CH_3)_2$ or $CH_2Ph$; and wherein

X is O, NH, $N(C_{1-6}alkyl)$, —NHC(=O)CH($CH_2CH_2NH_2$)O—, —OC(=O)CH($CH_2CH_2NH_2$)NH—, or —NHC(=O)CH($CH_2CH_2NH_2$)NH— connected to —C(=O)$R^2$ at the latter NH group, and $R^3$ is $NH_2$, $CH_2NH_2$ or imidazolyl; or X is N and $R^3$ is NH or $N(C_{1-6}alkyl)$ and $R^3$ and X taken together comprise $NHCH_2CH_2N$ or $N(C_{1-6}alkyl)CH_2CH_2N$; and with additional following provisions:

when X is O, —NHC(=O)CH($CH_2CH_2NH_2$)O—, or —OC(=O)CH($CH_2CH_2NH_2$)NH—, then $R^2$ is $C_{1-14}alkyl$, $C_{3-12}cycloalkyl$, aryl, arylalkyl, biaryl, biarylalkyl, arylheteroaryl, heteroarylaryl, dihydrofuran-2(3H)-one)-3-yl, aryl-dihydrofuran-2(3H)-one)-3-yl, $C_{1-14}alkyl$-dihydrofuran-2 (3H)-one)-3-yl, tetrahydro-2H-pyran-2-one-3-yl, aryl-tetrahydro-2H-pyran-2-one-3-yl, $C_{1-14}alkyl$-tetrahydro-2H-pyran-2-one-3-yl, $NH(C_{1-14}alkyl)$, NH(Ar), NH-(5 to 6-member heteroaromatic group containing at least one of N, S, and O atoms and the remaining atoms are carbon), $OC_{1-14}alkyl$, OAr, $NH(OC_{1-14}alkyl)$, aryl[C(=O)$OR^4$]$_r$, biaryl[C(=O)$OR^4$]$_r$, aryl[OC(=O)$R^4$]$_r$, biaryl[OC(=O)$R^4$]$_r$, aryl-OC(=O)$NR^4R^5$, biaryl-OC(=O)$NR^4R^5$, or heteroarylalkyl; or $R^2$ is $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, or L-P(=O)($OR^{11}$)($OR^{12}$);

when X is NH, $N(C_{1-6}alkyl)$, or NHC(=O)CH($CH_2CH_2NH_2$)NH— connected to C(=O)$R^2$ at the latter NH, then $R^2$ is aryl[C(=O)$OR^4$]$_r$, biaryl[C(=O)$OR^4$]$_r$, aryl[OC(=O)$R^4$]$_r$, biaryl[-OC(=O)$R^4$]$_r$, aryl-OC(=O)$NR^4R^5$, biaryl-OC(=O)$NR^4R^5$, $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, dihydrofuran-2(3H)-one)-3-yl, aryl-dihydrofuran-2(3H)-one)-3-yl, $C_{1-14}alkyl$-dihydrofuran-2 (3H)-one)-3-yl, tetrahydro-2H-pyran-2-one-3-yl, aryl-tetrahydro-2H-pyran-2-one-3-yl, $C_{1-14}alkyl$-tetrahydro-2H-pyran-2-one-3-yl, or L-P(=O)($OR^{11}$)($OR^{12}$);

when $R^3$ and X taken together comprise $NHCH_2CH_2N$ or $N(C_{1-6}alkyl)CH_2CH_2N$, then $R^2$ is defined as above for when X is NH, $-NHC(=O)CH(CH_2CH_2NH_2)NH-$ or $-NHC(=O)CH(CH_2CH_2NH_2)O-$;

wherein r is 1 or 2;

L is selected from O, NH, $N(C_{1-6}alkyl)$, $C_{1-6}alkylene$, $(CR^4R^5)_m(CR^6R^7)_n(CR^9R^{10})_o$, $CR^4=CR^6-(CR^9R^{10})_o$, $(CR^4R^5)_m-CR^6=CR^{10}$, $O(CR^4R^5)_m(CR^6R^7)_n(CR^9R^{10})_o$, $NH(CR^4R^5)_m(CR^6R^7)_n(CR^9R^{10})_o$, $N(C_{1-6}alkyl)(CR^4R^5)_m(CR^6R^7)_n(CR^9R^{10})_o$, $(CR^4R^5)_m(CR^6R^7)_n(CR^9R^{10})_oO$, $(CR^4R^5)_m(CR^6R^7)_n(CR^9R^{10})_oNH$, and $(CR^4R^5)_m(CR^6R^7)_n(CR^9R^{10})_oN(C_{1-6}alkyl)$;

$R^4$ through $R^7$, $R^9$ and $R^{10}$ are independently H, $NH_2$, halo, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; and $R^8$ is H, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; or any two of $R^4$ through $R^{10}$, together with the atom(s) to which they are attached form a 4 to 7-member saturated or unsaturated heterocycle containing at least one O atom, or containing one O atom and an additional heteroatom independently selected from N and S and wherein remaining atoms are carbon; or any two of $R^4$ through $R^{10}$ together with the atom(s) to which they are attached form a 5 to 7-member saturated or unsaturated heterocycle wherein the ring optionally comprises an additional heteroatom selected from N, O, and S and wherein the remaining atoms are carbon; or any of i) $R^4$ and $R^5$, ii) $R^6$ and $R^7$, iii) $R^4$ and $R^6$, iv) $R^9$ and $R^{10}$, v) $R^6$ and $R^{10}$, and vi) $R^4$ and $R^9$, together with the atom to which they are attached form a $C_{3-6}$cycloalkylene; or $R^6$ and $R^8$ together with the atom to which they are attached form a 4 to 6-member saturated heterocycle containing at least one O atom wherein the heterocycle optionally comprises an additional heteroatom selected from N, O, and S and wherein the remaining atoms are carbon; and $R^{11}$ and $R^{12}$ are independently H, $N(C_{1-6}alkyl)$, $C_{1-14}alkyl$, $C_{3-6}cycloalkyl$, aryl, arylalkyl, biaryl, biarylalkyl, or heteroarylalkyl; or $R^{11}$ and $R^{12}$ together with the two oxygen atoms to which they are attached form a 5 to 7-member saturated heterocycle wherein the 2, 3, or 4 additional atoms are carbon; or either or both of i) $R^4$ and $R^{11}$ and ii) $R^6$ and $R^{12}$ together with atoms to which they are attached form a 5 to 7-member saturated heterocycle containing one O atom and one P atom and where the remaining atoms are carbon;

wherein m, n, o, and p are independently selected from 0, 1, and 2 and wherein when L is $(CR^4R^5)_m(CR^6R^7)_n(CR^9R^{10})_o$, then $m+n+o\geq1$; and each of [a], [b], and [c] is independently selected from NH, $N(C_{1-6}alkyl)$ and O;

provided that when each of [a], [b], and [c] is NH, X is O, and $R^3$ is $CH_2NH_2$, then $R^2$ is not 5-methyl-heptyl.

In another aspect is a pharmaceutical composition comprising a therapeutically effective amount of a compound of Formula I and a pharmaceutically acceptable carrier.

In another aspect is a method for the treatment of a microbial or bacterial infection in a mammal comprising administering to the mammal a therapeutically effective amount of a compound of Formula I.

Also provided are closely related to polymyxin B and colistin analogs of the same class, differing from above structures in a side chain, or by up to 2 amino acids in a cyclopeptide core of said molecules, in place of certain amino acids present in polymyxin B and colistin.

These encompass, for example, polymyxin A, polymyxin F, polymyxin S1, polymyxin K, or octapeptin derivatives incorporating metabolically labile groups similar to the group $R^2$ provided herein. It is understood that such molecules may also be present in the antibacterial agent provided herein, along with the compounds of formulas I-V.

In another aspect is provided the group $R^2$ in a compound of formulas I-V incorporates a different from polymyxins antimicrobial class structure(s) acting at an additional biological target(s). This modification may be employed to achieve an optimal antimicrobial spectrum, for example, to target both Gram-negative and Gram-positive pathogens, or polymyxin-resistant bacteria, or Mycobacteria. Said antimicrobial structures $R^2$ may incorporate antibacterial agents or bioactive structural elements thereof selected from protein synthesis inhibitors (for example, oxazolidinones, phenicols, aminoglycosides, oxaboroles, peptide deformylase inhibitors, tetracyclines, mupirocin, or fusidic acid), cell wall biosynthesis inhibitors (for example, beta-lactams, cycloserine, or fosfomycin), gyrase A and/or topoisomerase IV inhibitors (for example, fluoroquinolones or pyridones), dihydrofolate inhibitors (for example, trimethoprim), folate synthesis inhibitors (for example, sulfa drugs), fatty acid biosynthesis (FAB) inhibitors (for example, structures described in the PCT WO 2011026529, or additional inhibitor structures reviewed, for example, in *Europ. J. Med. Chem.* 2014, vol. 84, pp. 382-394), or bacterial efflux pump inhibitors (for example, di-, tri-, or polipeptidic fragments containing basic amino acids, such as arginine and/or lysine).

In another aspect, the group $R^2$ in a compound of formulas I-V incorporates an iron-chelating siderophore group (for example, a catechol or halogenated catechol group, N-hydroxy amide group, or a 6-membered amide or N-hydroxy amide nitrogen-containing heterocyclic ring) introduced to increase the antibacterial activity of a compound of formulas I-V by employing the bacterial iron transport system, for more efficient drug delivery to a bacterial target.

In additional aspect is provided a pharmaceutical composition comprising a compound of formulas I-V, or a pharmaceutically acceptable salt, prodrug, solvate, or hydrate thereof, and a pharmaceutically acceptable carrier, excipient or diluent.

In an another aspect is provided a method for treating microbial (bacterial) infections in humans or other warm-blooded animals by administering to the subject in need a therapeutically effective amount of a compound of formulas I-V or a pharmaceutically acceptable salt, prodrug, solvate, or hydrate thereof. The compound of formulas I-V may be administered, for example, orally, parenterally, transdermally, topically, rectally, or intranasally, including said administration as liquid or solid aerosol form.

In yet another aspect is provided novel intermediates and processes for preparing compounds of formulas I-V.

LISTING OF THE DRAWINGS

FIG. 1. depicts the metabolic break-down of soft drug compounds of Examples 12 and 18 into respective metabolites, compounds of Examples 20 and 19.

FIG. 2. depicts the lack of metabolism for the reference compound of Example 1, with its structure compared to the structure of the ester D93 of the publication WO 2015/135976.

DETAILED DESCRIPTION OF THE INVENTION

Unless otherwise stated, the following terms used in the specification and Claims have the meanings given below.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-14}$ alkyl refers to alkyl of one to fourteen carbon atoms, inclusive.

The term alkyl refers to both straight and branched saturated hydrocarbon groups. Reference to an individual radical such as "propyl" embraces only the straight chain radical, and a branched chain isomer such as "isopropyl" being specifically referred to. Unless specified otherwise "alkyl" contains 1-12 carbon atoms. In addition to any group specifically recited in any of the embodiments or claims, the alkyl group is optionally substituted with one, two, three, or four substituents selected from the group consisting of halo, hydroxy, cyano, $C_{1-12}$ alkyl, $C_{3-7}$cycloalkyl, aryl, biaryl, heterocyclic, and heteroaryl (Het) group. In some embodiments, alkyl includes, but is not limited to, difluoromethyl, 2-fluoroethyl, trifluoroethyl, (adamantane-1-yl)methyl, 3-(cyclohexyl)propyl, 4-propylcyclohexyl, —CH=CH-aryl, —CH=CH-heterocyclic, —CH=CH-heteroaryl, —CH$_2$-phenyl, biphenylmethyl, and the like. In some embodiments, alkyl is unsubstituted.

The term "alkylene" refers to a divalent alkyl group. Unless specified otherwise linear "alkylene" contains 1-12 carbon atoms. The alkylene group is optionally substituted as described for alkyl. In some embodiments, alkylene is unsubstituted.

The term alkenyl refers to both straight and branched hydrocarbon groups containing at least one double bond, and in some embodiments 1, 2, or 3 double bonds. Unless specified otherwise "alkenyl" contains 2-12 carbon atoms. In addition to any group specifically recited in any of the embodiments or claims, the alkenyl is optionally substituted with one, two, or three substituents selected from the group consisting of halo, $C_{1-12}$ alkyl, $C_{3-7}$cycloalkyl, aryl, biaryl, heterocyclic, and heteroaryl. In some embodiments, alkenyl includes, but is not limited to, difluoromethyl, 2-fluoroethyl, trifluoroethyl, (adamantane-1-yl)methyl, 3-(cyclohexyl)propyl, 4-propylcyclohexyl, —CH=CH-aryl, —CH=CH-heterocyclic, —CH=CH-heteroaryl, —CH$_2$-phenyl, biphenylmethyl, and the like. In some embodiments, alkenyl is unsubstituted.

The term alkenylene refers to a divalent alkenyl group. Unless specified otherwise "alkenylene" contains 2-12 carbon atoms. The alkenylene group is optionally substituted as described for alkenyl. In some embodiments, the alkenylene group is unsubstituted.

The term "cycloalkyl" or "carbocycle" means a cyclic saturated, monovalent, monocyclic or bicyclic, saturated or unsaturated hydrocarbon group of three to 18 (in some embodiments, three to six) carbon atoms. In some embodiments, cycloalkyl includes but is not limited to cyclopropyl, cyclohexyl, cyclododecanoyl, and the like. In addition to any group specifically recited in any of the embodiments or claims, the cycloalkyl group is optionally substituted with one, two, or three substituents selected from the group consisting of halo, $C_{1-12}$ alkyl, $C_{3-7}$cycloalkyl, aryl, heterocyclic and heteroaryl. In some embodiments, cycloalkyl is unsubstituted.

The term "cycloalkylene" means a divalent cycloalkyl group or divalent carbocycle group. In addition to any group specifically recited in any of the embodiments or claims, the cycloalkylene group is optionally substituted as described for cycloalkyl. In some embodiments, the cycloalkylene is unsubstituted. In some or any embodiments, the $C_{3-6}$cycloalkylene group formed by any of i) $R^4$ and $R^5$, ii) $R^6$ and $R^7$, iii) $R^4$ and $R^6$, iv) $R^9$ and $R^{10}$, v) $R^6$ and $R^{10}$, and vi) $R^4$ and $R^9$, together with the atom to which they are attached form a $C_{3-6}$cycloalkylene is optionally substituted with one or two groups independently selected from $C_{1-6}$alkyl and aryl.

The term "heteroalkyl" means an alkyl or cycloalkyl group, as defined above, having a substituent containing a heteroatom selected from N, O, and $S(O)_n$, where n is an integer from 0 to 2, where in some embodiments the substituent includes, hydroxy (OH), $C_{1-4}$alkoxy, amino, thio (—SH), and the like. Said heteroatom may be incorporated in any part of the heteroalkyl group [e.g., heteroalkyl can be $C_{1-4}$alkylC(=O)OC$_{3-6}$cycloalkylNH$_2$], or contain a heterocyclic substituent [e.g., heteroalkyl can be 2-(4-morpholino)ethyl]. In some embodiments, substituents include —NR$_a$R$_b$, —OR$_a$, and —S(O)$_n$R$_c$, wherein each R$_a$ is independently hydrogen, $C_{1-4}$alkyl, $C_{3-6}$cycloalkyl, optionally substituted aryl, optionally substituted heterocyclic, or —C(O)R (where R is $C_{1-4}$alkyl); each R$_b$ is independently hydrogen, $C_{1-4}$alkyl, —SO$_2$R (where R is $C_{1-4}$alkyl or $C_{1-4}$hydroxyalkyl), —SO$_2$NRR' (where R and R' are independently of each other hydrogen or $C_{1-4}$alkyl), or —CONR'R" (where R' and R" are independently of each other hydrogen or $C_{1-4}$alkyl); n is an integer from 0 to 2; and each R$_c$ is independently hydrogen, $C_{1-4}$alkyl, $C_{3-6}$cycloalkyl, optionally substituted aryl, or NR$_a$R$_b$ where R$_a$ and R$_b$ are as defined above. In some embodiments, heteroalkyl includes, but is not limited to 2-methoxyethyl (—CH$_2$CH$_2$OCH$_3$), 2-hydroxyethyl (—CH$_2$CH$_2$OH), hydroxymethyl (—CH$_2$OH), 2-aminoethyl (—CH$_2$CH$_2$NH$_2$), 2-dimethylaminoethyl (—CH$_2$CH$_2$NHCH$_3$), benzyloxymethyl, thiophen-2-ylthiomethyl, and the like.

The term "halo" refers to fluoro (F), chloro (Cl), bromo (Br), or iodo (I).

The term "aryl" refers to phenyl, or naphthyl. In addition to any group specifically recited in any of the embodiments or claims, the aryl is optionally substituted with 1 to 3 substituents independently selected from halo, —C$_{1-12}$alkyl (unsubstituted or substituted, in one embodiment with 1, 2, or 3 halo), aryl, —OH, —OC$_{1-12}$alkyl, —S(O)$_n$C$_{1-4}$alkyl (wherein n is 0, 1, or 2), —C$_{1-4}$alkylNH$_2$, —NHC$_{1-4}$alkyl, —C(=O)H, C(=O)OR$^a$, OC(=O)R$^a$, OC(=O)NR$^a$R$^c$, OC(=O)heteroaryl, OC(=O)(heterocyclic ring) and —C=N—OR$_d$ wherein R$_d$ is hydrogen or —C$_{1-4}$alkyl.

The term "arylalkyl" refers to an alkyl group substituted with an aryl group, each as defined herein, including where the aryl and alkyl are optionally substituted as described in their respective definitions.

The term "arylheteroaryl" refers to an aryl group substituted with a heteroaryl group, each as defined herein, including where the aryl and heteroaryl are optionally substituted as described in their respective definitions.

The term "heteroarylaryl" refers to a heteroaryl group substituted with an aryl group, each as defined herein, including where the aryl and heteroaryl are optionally substituted as described in their respective definitions.

The term "biaryl" refers to an aryl group as defined herein substituted with another aryl group as defined herein, including where the aryl groups are independently optionally substituted as described in the definition.

The term "biarylalkyl" refers to an alkyl group substituted with an aryl group which is substituted with another aryl group, each as defined herein, including where each aryl independently and alkyl are optionally substituted as described in their respective definitions The terms heterocyclic, heterocyclic ring and heterocycle refer to a monocyclic or bicyclic aromatic ring or a saturated or unsaturated, monocyclic or bicyclic ring that is not aromatic comprising 3 to 12 carbon atoms and 1 to 4 heteroatoms independently selected from the group consisting of oxygen, nitrogen, P(=O), and S(O)$_m$ within the ring, wherein m is an integer from 0 to 2. In addition to any group specifically recited in any of the embodiments or claims, the heterocyclic ring is optionally substituted with one, two, or three halo, C(=O)OR$^a$, OC(=O)R$^a$, OC(=O)NR$^a$R$^b$, —C$_{1-20}$alkyl, —OH, —NH$_2$, —OC$_{1-20}$alkyl, —S(O)$_m$C$_{1-20}$alkyl (wherein m is 0, 1, or 2), —C$_{1-20}$alkyl-NH$_2$, —NHC$_{1-4}$alkyl, —C(=O)H, or —C=N—OR$_d$ wherein each R$^a$, R$^b$ and R$_d$ is independently hydrogen or C$_{1-20}$alkyl. In some embodiments, the heterocyclic ring is unsubstituted. In some or any embodiments, the 4 to 7 or 5 to 7 membered ring formed by any two of R$^4$ through R$^{10}$ and/or formed by R$^{11}$ and R$^{12}$ and/or formed by R$^4$ and R$^{11}$ and/or formed by R$^6$ and R$^{12}$ is optionally substituted as described herein for heterocycle. In some or any embodiments, the 4 to 7 membered ring formed by R$^{11}$ and R$^{12}$ and/or formed by R$^4$ and R$^{11}$ and/or formed by R$^6$ and R$^{12}$ is optionally substituted with one or two groups independently selected from C$_{1-6}$alkyl and aryl.

The term "unsaturated" in the context of the term cycloalkyl, cycloalkylene, and heterocycle refers to a partially unsaturated, but not aromatic ring.

In some embodiments, heterocyclic rings include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isoxazolidone, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiadiazole tetrazole, thiazolidine, thiophene, benzo[b]thiophene, morpholinyl, thiomorpholinyl (also referred to as thiamorpholinyl), piperidinyl, pyrrolidine, tetrahydrofuranyl, 1,3-benzoxazine, 1,4-oxazine-3-one, 1,3-benzoxazine-4-one, pyrrolidine, pyrrolidine-2-one, oxazolidine-2-one, azepine, perhydroazepine, perhydroazepine-2-one, perhydro-1,4-oxazepine, perhydro-1,4-oxazepine-2-one, perhydro-1,4-oxazepine-3-one, perhydro-1,3-oxazepine-2-one, azabicyclo[3.1.0]hexane and the like, and N-oxides of said nitrogen heterocycles. In addition to any group specifically recited in any of the embodiments or claims, heterocyclic rings include substituted and unsubstituted rings, including those substituted with groups selected from C(=O)OR$^a$, OC(=O)R$^a$, OC(=O)NR$^a$R$^b$ where each R$^a$ and R$^b$ are independently hydrogen or C$_{1-6}$alkyl.

The term heteroaryl refers to a five- (5) or six- (6) membered C- or N-linked heterocyclic ring, optionally fused to a benzene or to another heterocyclic ring (wherein at least one of the heterocyclic rings is aromatic). In some embodiments, heteroaryl includes, but is not limited to, pyridine, thiophene, furan, pyrazole, indole, benzimidazole, quinoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxaz-olyl, 4-isoxazolyl, 5-isox-azolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, and 1,2,4-dithiazolone. In addition to any group specifically recited in any of the embodiments or claims, heteroaryl groups include substituted and unsubstituted rings, including those substituted with groups selected from C(=O)OR$^a$, OC(=O)R$^a$, and OC(=O)NR$^a$R$^b$ where each R$^a$ and R$^b$ are independently hydrogen or C$_{1-6}$alkyl. In some embodiments, heteroaryl is unsubstituted.

The term "heteroarylalkyl" refers to an alkyl group substituted with an heteroaryl group, each as defined herein.

Unless specified otherwise, "carbon atom" means the atom of element carbon optionally substituted with H, halo, NR$^a$R$^b$, C$_{3-7}$ cycloalkyl, aryl, heteroaryl, or with a heterocyclic ring. Carbon atom comprises atoms with sp3, sp2, and sp electronic hybridization.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compound D93 of WO 2015/135976 has the following structure:

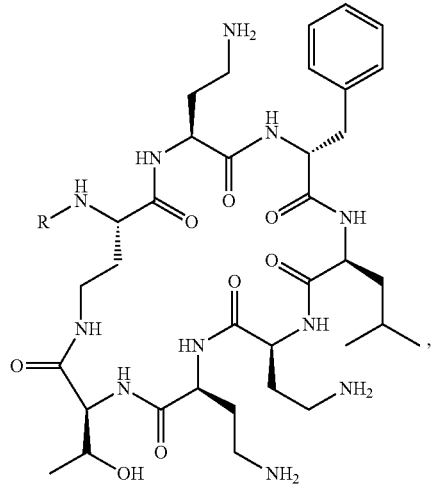

Polymyxin B heptapeptide scaffold (PMBH)

where the R group in the above structure is:

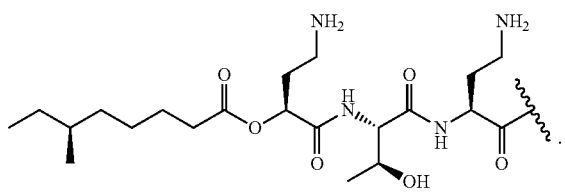 [SMILES: *C(=O)[C@H](CCN)NC(=O)[C@@H](NC(=O)[C@H](CCN)OC(=O)CCCC[C@@H](C)CC)[C@H](C)O]

This compound is specifically excluded from any of the aspects and embodiments described herein.

In some embodiments, the compound of formula I or II is that wherein when X is O, then $R^2$ is not $C_{1-14}$alkyl.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds provided herein may possess one or more asymmetric centers; such compounds can therefore be produced as individual (R)- or (S)-stereoisomers or as mixtures thereof. Unless indicated otherwise, the description or naming of a particular compound in the specification and Claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A hydrogen (H) or carbon (C) substitution for compounds of the formula I include a substitution with any isotope of the respective atom. Thus, a hydrogen (H) substitution includes a $^1H$, $^2H$ (deuterium), or $^3H$ (tritium) isotope substitution, as may be desired, for example, for a specific therapeutic or diagnostic therapy, or metabolic study application, or stability enhancement. Optionally, a compound of this invention may incorporate a known in the art radioactive isotope or radioisotope, such as $^3H$, $^{15}O$, $^{12}C$, or $^{13}N$ isotope, to afford a respective radiolabeled compound of formula I.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and Claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating," "treatment," or "therapy" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry, i.e., an atom or group capable of being displaced by a nucleophile and includes halogen, $C_{1-4}$alkylsulfonyloxy, ester, or amino such as chloro, bromo, iodo, mesyloxy, tosyloxy, trifluorosulfonyloxy, methoxy, N,O-dimethylhydroxyl-amino, and the like.

"Prodrug" means any compound which releases an active parent drug according to a compound provided herein in vivo when such prodrug is administered to a mammalian subject. Prodrugs of a compound of provided herein are prepared by modifying functional groups present in a compound provided herein in such a way that the modifications may be cleaved in vivo to release the parent compound. Prodrugs include compounds provided herein wherein a hydroxy, sulfhydryl, amido or amino group in the compound is bonded to any group that may be cleaved in vivo to regenerate the free hydroxyl, amido, amino, or sulfhydryl group, respectively. Examples of prodrugs include, but are not limited to esters (e.g., acetate, formate, benzoate, phosphate or phosphonate derivatives), carbamates (e.g., N,N-dimethylaminocarbonyl) of hydroxy functional groups in compounds provided herein, and the like.

The term "mammal" refers to all mammals including humans, livestock, and companion animals.

The compounds described herein are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Illustrative Embodiments

Within the broadest definition of the present invention, certain compounds of the compounds of formula I may be preferred. Specific and preferred values listed below for radicals, substituents, and ranges, are for illustration only; they do not exclude other defined values or other values within defined ranges for the radicals and substituents.

In some preferred compounds described herein $C_{1-14}$alkyl can be methyl, ethyl, propyl, isopropyl, butyl, iso-butyl, sec-butyl, octyl, nonyl, decyl, and isomeric forms thereof.

In some preferred compounds described herein $C_{2-12}$alkenyl can be vinyl, propenyl, allyl, butenyl, and isomeric forms thereof (including cis and trans isomers).

In some preferred compounds described herein $C_{3-7}$cycloalkyl can be cyclopropyl, cyclobutyl, cyclopentyl, cyclohexyl, and isomeric forms thereof.

In some preferred compounds described herein $C_{1-14}$heteroalkyl can be hydroxymethyl, hydroxyethyl, 2-(N,N-dimethylamino)ethyl, 2-(4-morpholino)ethyl, and 2-methoxyethyl.

In some preferred compounds described herein halo can be fluoro (F) or chloro (Cl).

It will also be appreciated by those skilled in the art that compounds described herein may have additional chiral centers and be isolated in optically active and racemic forms. The present invention encompasses any racemic, optically active, tautomeric, geometric, or stereoisomeric form, or mixture thereof, of a compound of the invention.

Any embodiment described herein can be combined with any other embodiment described herein.

In one embodiment is provided a compound of the formula Ia:

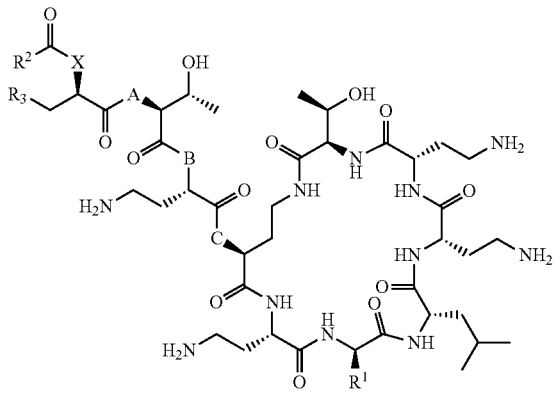

or a pharmaceutically acceptable salt, solvate, or hydrate thereof wherein:
$R^1$ is $CH_2CH(CH_3)_2$ or $CH_2Ph$; and wherein when X is O or —NHC(=O)CH(CH$_2$CH$_2$NH$_2$)O—, then $R^2$ is $C_{1-14}$alkyl, $C_{3-12}$cycloalkyl, aryl, arylalkyl, biaryl, biarylalkyl, arylheteroaryl, heteroarylaryl, aryl-C(=O)OR$^4$, biaryl-C(=O)OR$^4$, aryl-OC(=O)R$^4$, biaryl-OC(=O)R$^4$, aryl-OC(=O)NR$^4$R$^5$, biaryl-OC(=O)NR$^4$R$^5$, or heteroarylalkyl; and wherein when X is NH, then $R^2$ is aryl-C(=O)OR$^4$, biaryl-C(=O)OR$^4$, aryl-OC(=O)R$^4$, aryl-OC(=O)NR$^4$R$^5$, biaryl-OC(=O)NR$^4$R$^5$, $(CR^4R^5)_m(CR^6R^7)_nC(=O)OR^8$, $(CR^4R^5)_m(CR^6R^7)_nOC(=O)R^8$, $(CR^4R^5)_m(CR^6R^7)_nP(=O)(OR^8)_2$, or $(CR^4R^5)_m(CR^6R^7)_nO(P=O)(OR^8)_2$, wherein $R^4$, $R^5$, $R^6$, $R^7$, and $R^8$ are independently selected from H, $C_{1-14}$alkyl, $C_{3-6}$cycloalkyl, aryl, arylalkyl, biaryl, biarylalkyl, or heteroarylalkyl; or either of $R^4$ and $R^5$ or $R^6$ and $R^7$ taken together form a $C_{3-6}$cycloalkyl group; and wherein m and n are independently selected from 0 to 2; and wherein $R^3$ is $CH_2NH_2$ or imidazolyl, and wherein A, B, and C are independently selected from NH or O.

In one embodiment, in a compound of formula Ia $R^1$ is $CH_2CH(CH_3)_2$ or $CH_2Ph$, and $R^3$ is $CH_2NH_2$, and wherein A, B, and C are all NH.

In another embodiment, provided are compounds of formula Ia and with a proviso excluding the compounds provided in the prior art, such as colistin, polymyxin B, and those reported in publications WO 2013/072695, US 2012/0316105, U.S. Pat. No. 8,415,307, WO 2010/091294, WO 2010/130007, US 2010/0160215, WO 2007/066906, US 2006/0004185, U.S. Pat. No. 4,091,092, JP 5,305,3680, JP 4,601,6152, and DE 1,906,699.

In another embodiment is provided a compound of the formula IIa:

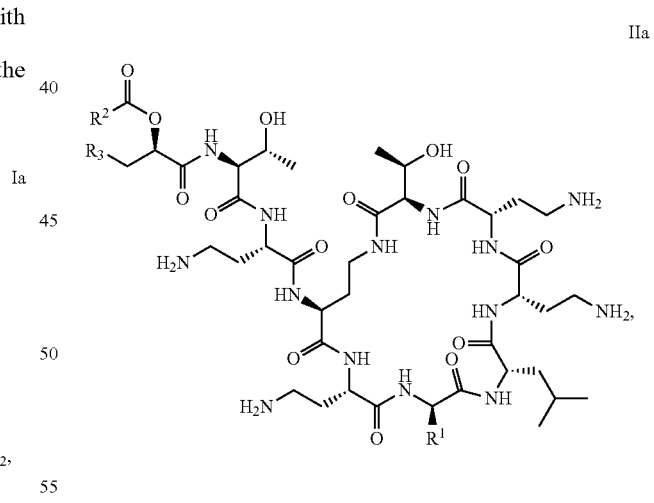

or a pharmaceutically acceptable salt, solvate, or hydrate thereof wherein:
$R^1$ is $CH_2CH(CH_3)_2$ or $CH_2Ph$; and wherein $R^2$ is $C_{1-14}$alkyl, $C_{3-12}$cycloalkyl, aryl, arylalkyl, biaryl, biarylalkyl, aryl-C(=O)OR$^4$, biaryl-C(=O)OR$^4$, aryl-OC(=O)R$^4$, aryl-OC(=O)NR$^4$R$^5$, biaryl-OC(=O)NR$^4$R$^5$, or heteroarylalkyl; and wherein $R^3$ is $CH_2NH_2$ or imidazolyl.

In additional embodiment provided herein is a compound of the following formula IIIa:

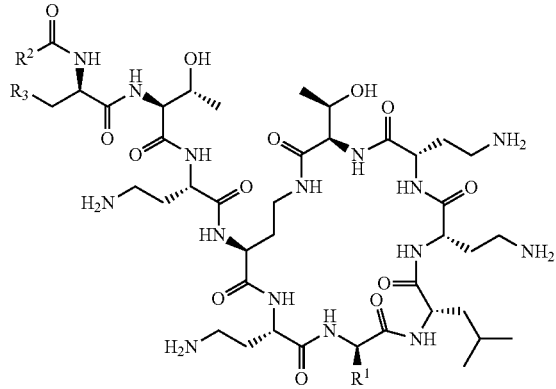

IIIa or a pharmaceutically acceptable salt, solvate, or hydrate thereof wherein:
$R^1$ is $CH_2CH(CH_3)_2$ or $CH_2Ph$; and wherein $R^2$ is aryl-C(=O)$OR^4$, biaryl-C(=O)$OR^4$, aryl-OC(=O)$R^4$, biaryl-OC(=O)$R^4$, aryl-OC(=O)$NR^4R^5$, biaryl-OC(=O)$NR^4R^5$, $(CR^4R^5)_m(CR^6R^7)_nC$(=O)$OR^8$ or $(CR^4R^5)_m(CR^6R^7)_nOC$(=O)$R^8$, wherein $R^4$, $R^5$, $R^6$, $R^7$, and $R^8$ are independently selected from H, $C_{1-14}$alkyl, $C_{3-6}$cycloalkyl, aryl, arylalkyl, biaryl, biarylalkyl, or heteroarylalkyl; or either of $R^4$ and $R^5$ or $R^6$ and $R^7$ taken together form a $C_{3-6}$cycloalkyl group; and wherein m and n are independently selected from 0 to 2; and wherein $R^3$ is $CH_2NH_2$ or imidazolyl.

In another embodiment, the present invention provides a compound of the following formula IVa:

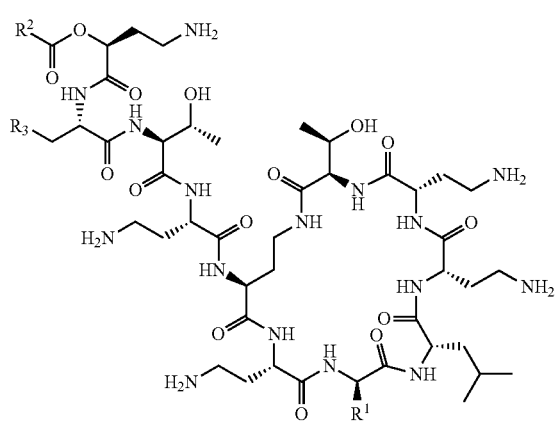

IVa or a pharmaceutically acceptable salt, solvate, or hydrate thereof wherein:
$R^1$ is $CH_2CH(CH_3)_2$ or $CH_2Ph$; and wherein $R^2$ is aryl-C(=O)$OR^4$, biaryl-C(=O)$OR^4$, aryl-OC(=O)$R^4$, biaryl-OC(=O)$R^4$, aryl-OC(=O)$NR^4R^5$, biaryl-OC(=O)$NR^4R^5$, $(CR^4R^5)_m(CR^6R^7)_nC$(=O)$OR^8$ or $(CR^4R^5)_m(CR^6R^7)_nOC$(=O)$R^8$, wherein $R^4$, $R^5$, $R^6$, $R^7$, and $R^8$ are independently selected from H, $C_{1-14}$alkyl, $C_{3-6}$cycloalkyl, aryl, arylalkyl, biaryl, biarylalkyl, or heteroarylalkyl; or either of $R^4$ and $R^5$ or $R^6$ and $R^7$ taken together form a $C_{3-6}$cycloalkyl group; and wherein m and n are independently selected from 0 to 2; and wherein $R^3$ is $CH_2NH_2$ or imidazolyl.

One preferred group of compounds of the formula IIa is illustrated below:

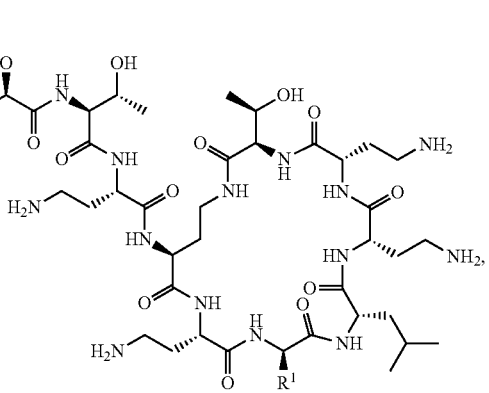

IIa wherein $R^1$ is $CH_2CH(CH_3)_2$ or $CH_2Ph$; and wherein $R^2$ is selected from groups below:

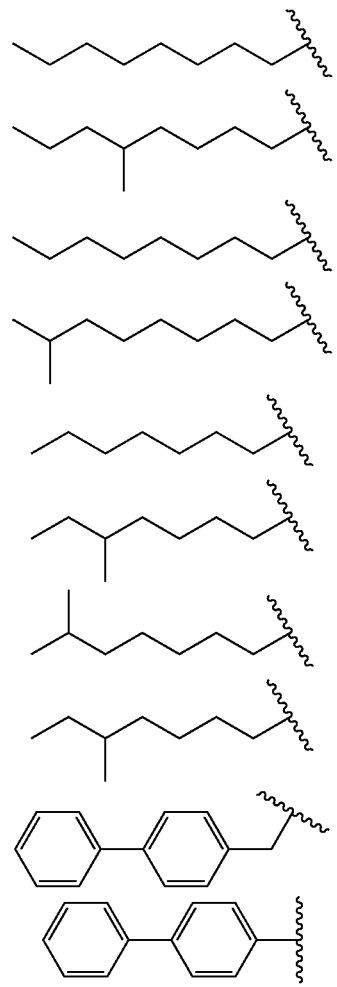

17
-continued
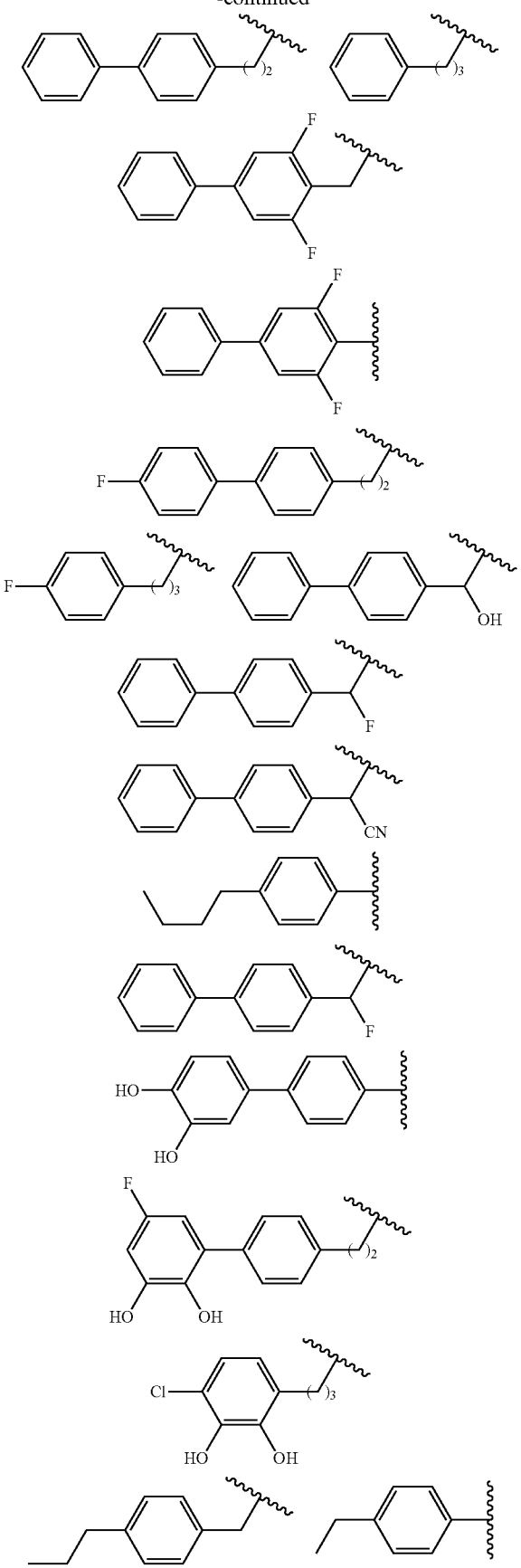
18
-continued
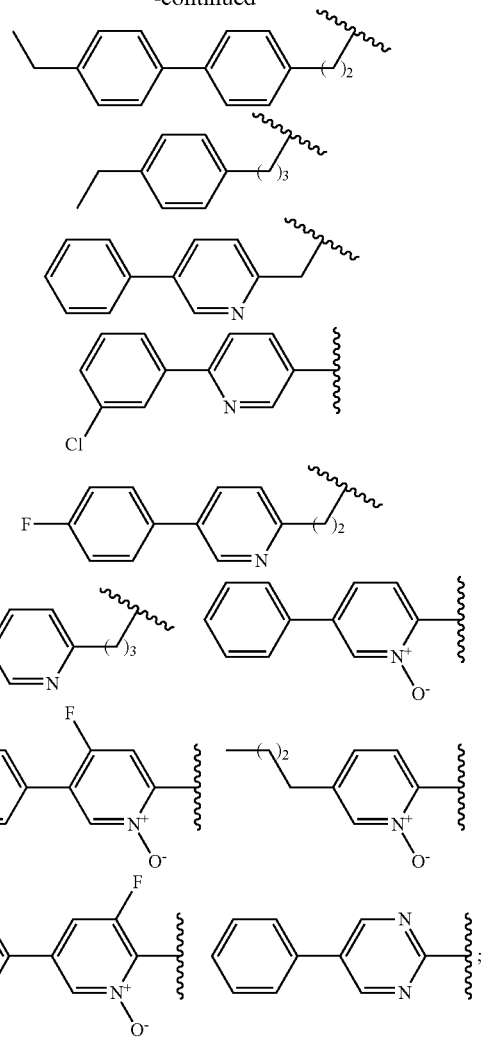
and $R^3$ is $CH_2NH_2$ or imidazolyl.
One preferred group of compounds of the formula IIIa is illustrated below:
IIIa
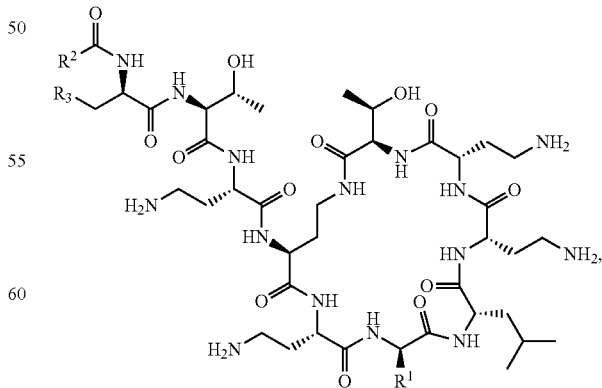
wherein $R^1$ is $CH_2CH(CH_3)_2$ or $CH_2Ph$; and wherein $R^2$ is selected from groups below:

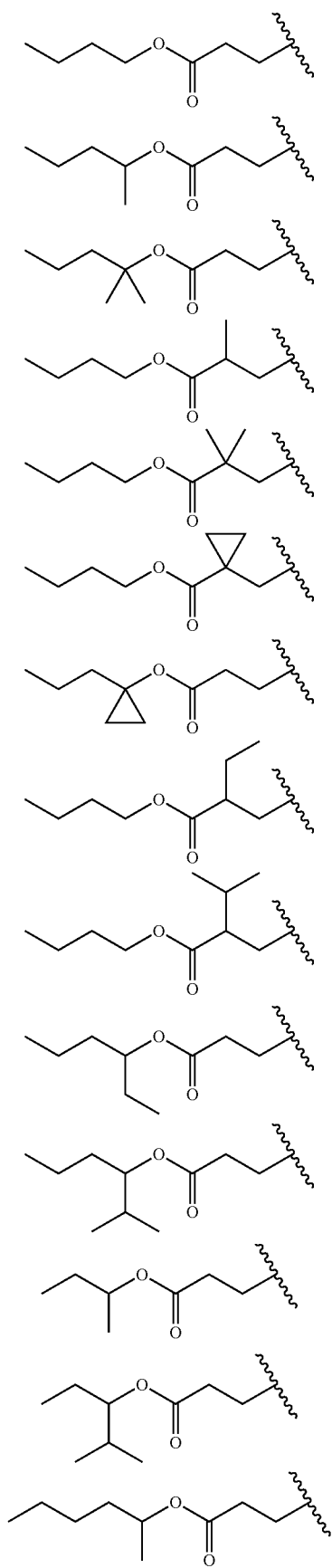
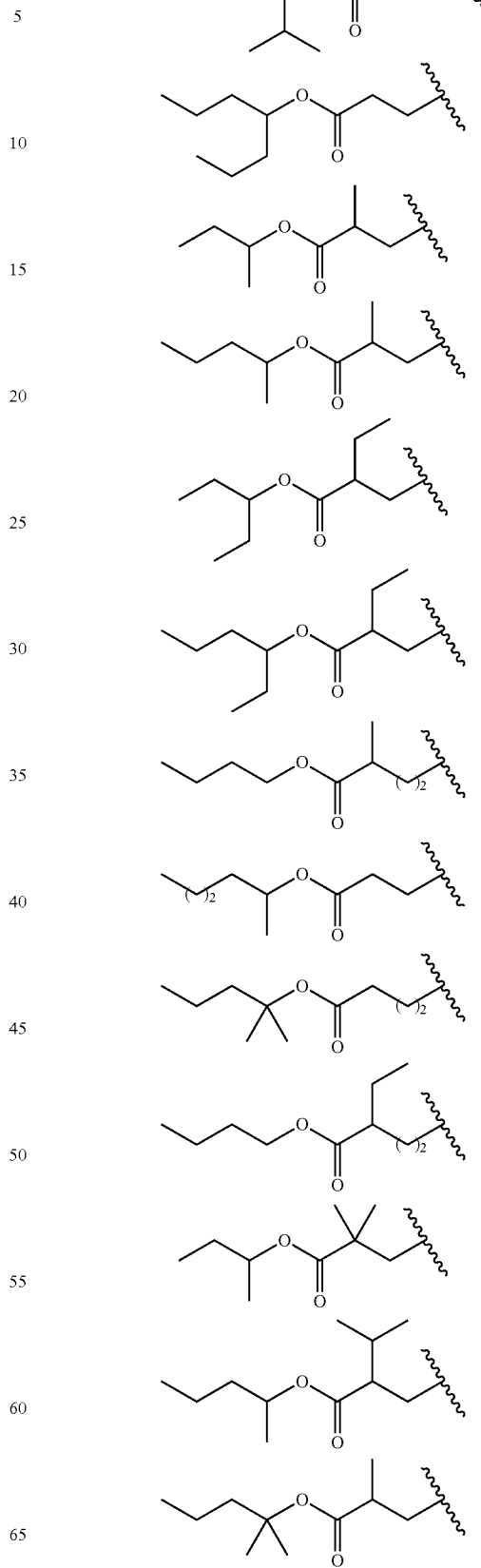

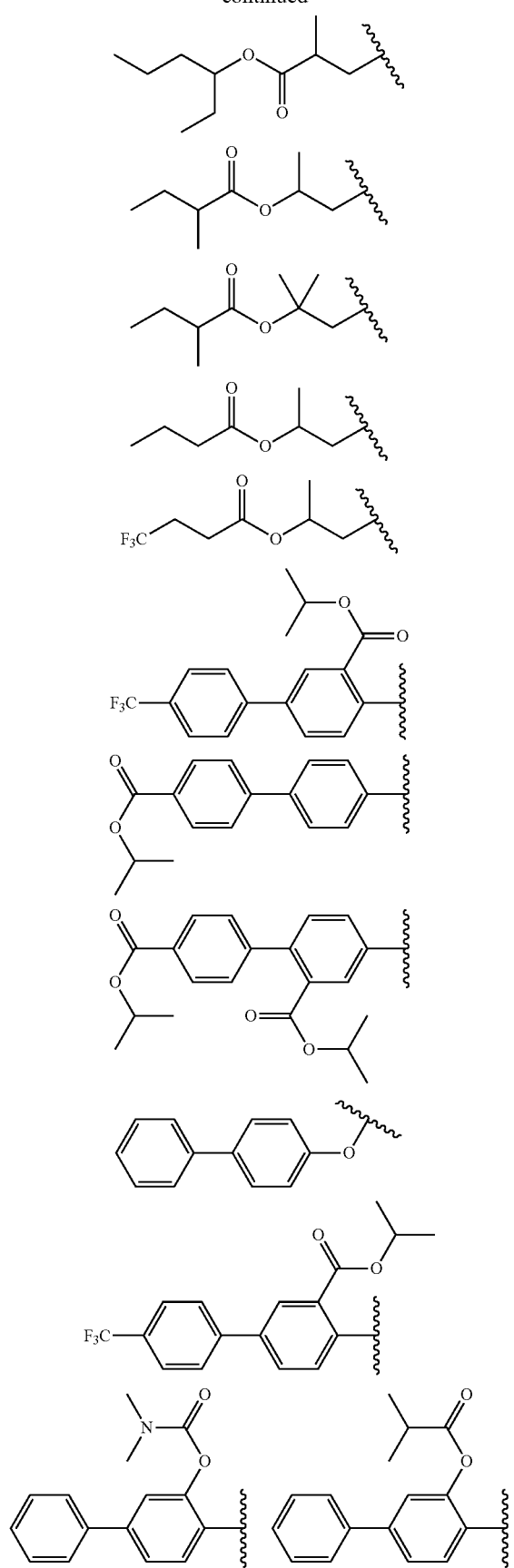
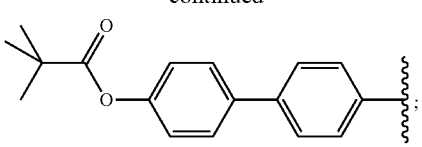
and $R^3$ is $CH_2NH_2$ or imidazolyl.
One preferred group of compounds of the formula IVa is illustrated below:
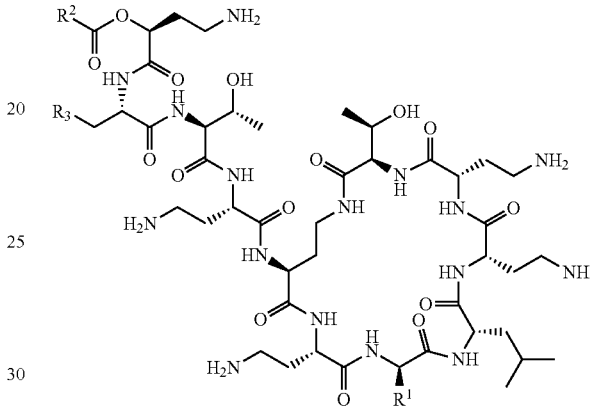
wherein $R^1$ is $CH_2CH(CH_3)_2$ or $CH_2Ph$; and wherein $R^2$ is selected from groups below:
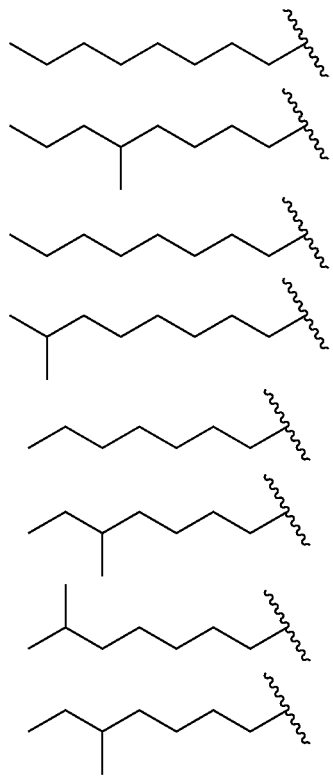

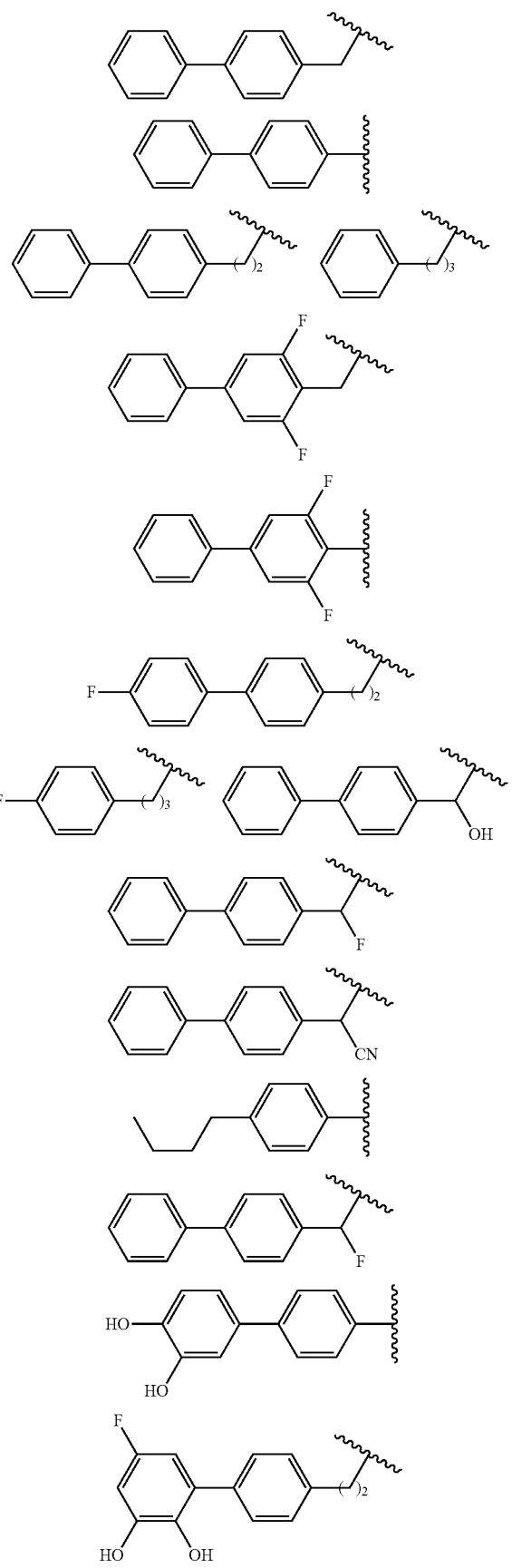
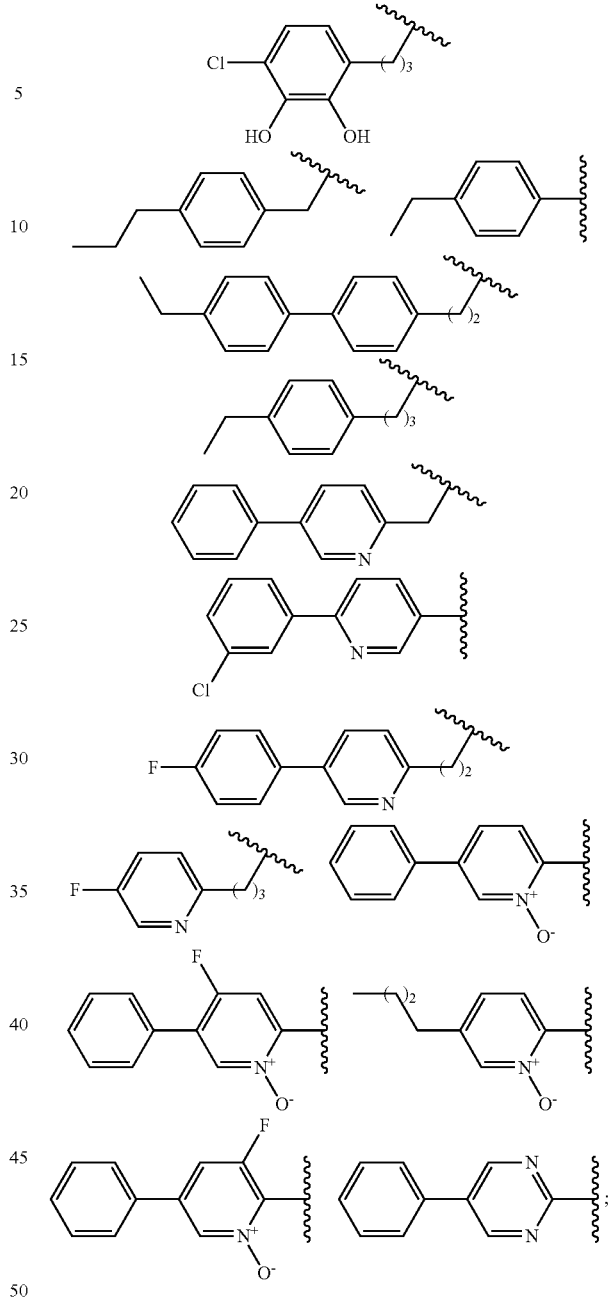

and R³ is CH₂NH₂ or imidazolyl.

In some or any embodiments, the compound of formula I, is that where p is 1;
R¹ is CH₂CH(CH₃)₂ or CH₂Ph;
[a], [b], and [c] are each NH;
X is O; R³ is CH₂NH₂ or NH₂; and R² is $C_{1-14}$alkyl, aryl, arylalkyl, biaryl, biarylalkyl, heteroaryl, dihydrofuran-2(3H)-one-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR¹¹)(OR¹²); or X is —NHC(=O)CH(CH₂CH₂NH₂)O— or —OC(=O)CH(CH₂CH₂NH₂)NH—; R³ is CH₂NH₂ or NH₂; and R² is $C_{1-14}$alkyl, aryl, arylalkyl, biaryl, biarylalkyl, heteroaryl, or L-P(=O)(OR¹¹)(OR¹²); or X is NH; R³ is CH₂NH₂ or NH₂; and R² is (CR⁴R⁵)ₘ(CR⁶R⁷)ₙC(=O)OR⁸, (CR⁴R⁵)ₘ(CR⁶R⁷)ₙOC(=O)R⁸, aryl[C(=O)OR⁴]ᵣ, biaryl[C(=O)OR⁴]ᵣ, aryl[OC(=O)R⁴]ᵣ, biaryl[-OC(=O)OR⁴]ᵣ, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C₁₋₁₄alkyl-dihydrofuran-2(3H)-one)-3-yl, tetrahydro-2H-pyran-2-one-3-yl, aryl-tetrahydro-2H-pyran-2-one-3-yl, C₁₋₁₄alkyl-tetrahydro-2H-pyran-2-one-3-yl, or L-P(=O)(OR¹¹)(OR¹²); or X is N and R³ is NH or N(C₁₋₆alkyl) and R³ and X taken together comprise NHCH₂CH₂N or N(C₁₋₆alkyl)CH₂CH₂N; and R² is (CR⁴R⁵)ₘ(CR⁶R⁷)ₙC(=O)OR⁸; CR⁴R⁵)ₘ(CR⁶R⁷)ₙ OC(=O)R⁸; and wherein r is 1 or 2;

L is NH, N(CH₃), CF₂, CH₂, CH(CH₃), C(CH₃)₂, CH₂CH₂, CH₂CF₂, CF₂CH₂, CH₂CH(CH₃), CH(CH₃)CH₂, CH₂CH₂C(CH₃)₂O, OC(CH₃)₂CH₂CH₂, CH₂CH₂C(CH₃)₂NH, NHC(CH₃)₂CH₂CH₂, CH₂CH(n-hexyl), CH(n-hexyl)CH₂, CH₂CH₂C(i-Pr)₂O, OC(i-Pr)₂CH₂CH₂, OCH(CH₃)CH₂CH₂, CH₂CH₂CH(CH₃)O,

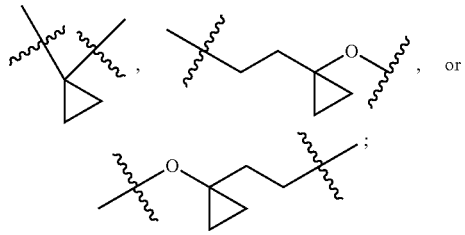

R⁴ through R⁷ are independently H, halo, C₁₋₁₄alkyl; and R⁸ is H or C₁₋₁₄alkyl; or either or both of i) R⁴ and R⁵ and ii) R⁶ and R⁷, together with the atom to which they are attached form a C₃₋₆cycloalkylene;

R⁶ and R⁸ together with the atoms to which they are attached form a 4 to 6-member saturated heterocycle containing at least one O atom wherein the heterocycle optionally comprises an additional heteroatom selected from N, O, and S, and wherein the remaining atoms are carbon;

R¹¹ and R¹² are independently H, or C₁₋₁₄alkyl; or R¹¹ and R¹² together with the two oxygen atoms to which they are attached form a 6-member saturated heterocycle wherein the 3 additional atoms are carbon optionally substituted with C₁₋₆alkyl; and wherein m, n, and o are independently selected from 0, 1, and 2; and provided that when X is O, then R² is not 5-methyl-heptyl.

In some or any embodiments, the compound of formula I, II, III, IV, or V, is that where [a] is NH; and all other groups are as defined in any of the aspects and/or embodiments described herein. In some or any embodiments, the compound of formula I, II, III, IV, or V, is that where [a] is N(C₁₋₆alkyl); and all other groups are as defined in any of the aspects and/or embodiments described herein. In some or any embodiments, the compound of formula I, II, III, IV, or V, is that where [a] is O; and all other groups are as defined in any of the aspects and/or embodiments described herein.

In some or any embodiments, the compound of formula I, II, III, IV, or V, is that where [b] is NH; and all other groups are as defined in any of the aspects and/or embodiments described herein. In some or any embodiments, the compound of formula I, II, III, IV, or V, is that where [b] is N(C₁₋₆alkyl); and all other groups are as defined in any of the aspects and/or embodiments described herein. In some or any embodiments, the compound of formula I, II, III, IV, or V, is that where [b] is O; and all other groups are as defined in any of the aspects and/or embodiments described herein.

In some or any embodiments, the compound of formula I, II, III, IV, or V, is that where [c] is NH; and all other groups are as defined in any of the aspects and/or embodiments described herein. In some or any embodiments, the compound of formula I, II, III, IV, or V, is that where [c] is N(C₁₋₆alkyl); and all other groups are as defined in any of the aspects and/or embodiments described herein. In some or any embodiments, the compound of formula I, II, III, IV, or V, is that where [c] is O; and all other groups are as defined in any of the aspects and/or embodiments described herein.

In some or any embodiments, the compound of formula I, II, III, IV, or V, is that where [a], [b], and [c] are NH; and all other groups are as defined in any of the aspects and/or embodiments described herein. In some or any embodiments, the compound of formula I, II, III, IV, or V, is that where [a], [b], and [c] are N(C₁₋₆alkyl); and all other groups are as defined in any of the aspects and/or embodiments described herein. In some or any embodiments, the compound of formula I, II, III, IV, or V, is that where [a], [b], and [c] are O; and all other groups are as defined in any of the aspects and/or embodiments described herein.

In some or any embodiments, the compound of formula I, II, III, IV, or V, is that where R¹ is CH₂CH(CH₃)₂; and all other groups are as defined in any of the aspects and/or embodiments described herein.

In some or any embodiments, the compound of formula I, II, III, IV, or V, is that where R¹ is CH₂Ph; and all other groups are as defined in any of the aspects and/or embodiments described herein.

In some or any embodiments, the compound of formula I, II, III, IV, or V, is that where p is 0; and all other groups are as defined in any of the aspects and/or embodiments described herein. In some or any embodiments, the compound of formula I, II, III, IV, or V, is that where p is 1; and all other groups are as defined in any of the aspects and/or embodiments described herein. In some or any embodiments, the compound of formula I, II, III, IV, or V, is that where p is 2; and all other groups are as defined in any of the aspects and/or embodiments described herein.

In some or any embodiments, the compound of formula I, is that where X is N and R³ is NH or N(C₁₋₆alkyl) and R³ and X taken together comprise NHCH₂CH₂N or N(C₁₋₆alkyl)CH₂CH₂N; and R² is defined as above for when X is NH, —NHC(=O)CH(CH₂CH₂NH₂)NH—, —NHC(=O)CH(CH₂CH₂NH₂)O—, or —OC(=O)CH(CH₂CH₂NH₂)NH—; and all other groups are as defined in any embodiments described herein. In some or any embodiments, the compound of formula I, is that where R³ and X taken together comprise NHCH₂CH₂N or N(C₁₋₆alkyl)CH₂CH₂N; and R² is C₁₋₁₄alkyl, C₃₋₁₂cycloalkyl, aryl, aryl alkyl, biaryl, biarylalkyl, arylheteroaryl, heteroarylaryl, dihydrofuran-2(3H)-one)-3-yl, aryl-dihydrofuran-2(3H)-one)-3-yl, C₁₋₁₄alkyl-dihydrofuran-2(3H)-one)-3-yl, tetrahydro-2H-pyran-2-one-3-yl, aryl-tetrahydro-2H-pyran-2-one-3-yl, C₁₋₁₄alkyl-tetrahydro-2H-pyran-2-one-3-yl, NH(C₁₋₁₄alkyl), NH(Ar), NH-(5 to 6-member heteroaromatic group containing at least one of N, S, and O atoms and the remaining atoms are carbon), OC₁₋₁₄alkyl, OAr, NH(OC₁₋₁₄alkyl), aryl[C(=O)OR⁴]ᵣ, biaryl[C(=O)OR⁴]ᵣ, aryl[OC(=O)R⁴]ᵣ, biaryl[OC(=O)R⁴]ᵣ, aryl-OC(=O)

$NR^4R^5$, biaryl-OC(=O)$NR^4R^5$, or heteroarylalkyl; or $R^2$ is $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, or L-P(=O)(OR^{11})(OR^{12})$; and all other groups are as defined in any of the embodiments described herein. In some or any embodiments, the compound of formula I, is that where $R^3$ and X taken together comprise $NHCH_2CH_2N$ or $N(C_{1-6}alkyl)CH_2CH_2N$; and $R^2$ is aryl[C(=O)$OR^4$]$_r$, biaryl[C(=O)$OR^4$]$_r$, aryl[OC(=O)$R^4$]$_r$, biaryl[-OC(=O)$OR^4$]$_r$, aryl-OC(=O)$NR^4R^5$, biaryl-OC(=O)$NR^4R^5$, $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR^{11})(OR^{12})$; and all other groups are as defined in any of the embodiments described herein.

In some or any embodiments, the compound of formula I or II, is that where $R^3$ is $NH_2$, $CH_2NH_2$ or imidazolyl; X is O; and $R^2$ is $C_{1-14}$alkyl, $C_{3-12}$cycloalkyl, aryl, arylalkyl, biaryl, biarylalkyl, heteroaryl, arylheteroaryl, heteroarylaryl, $NH(C_{1-14}$ alkyl), NH(Ar), NH-(5 to 6-member heteroaromatic group containing at least one of N, S, and O atoms and the remaining atoms are carbon), $OC_{1-14}$alkyl, OAr, $NH(OC_{1-14}$alkyl), aryl[C(=O)$OR^4$]$_r$, biaryl[C(=O)$OR^4$]$_r$, aryl[OC(=O)$R^4$]$_r$, biaryl[OC(=O)$R^4$]$_r$, aryl-OC(=O)$NR^4R^5$, biaryl-OC(=O)$NR^4R^5$, or heteroarylalkyl; or $R^2$ is $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR^{11})(OR^{12})$; and all other groups are as defined in any of the embodiments described. In some or any embodiments, the compound of formula I or II, is that where $R^3$ is $NH_2$, $CH_2NH_2$ or imidazolyl; X is O; and $R^2$ is $C_{1-14}$alkyl, aryl, arylalkyl, biaryl, biarylalkyl, heteroaryl, or L-P(=O)(OR^{11})(OR^{12})$; and all other groups are as defined in any embodiments described herein. In some or any embodiments, the compound of formula I or II, is that where $R^3$ is $NH_2$, $CH_2NH_2$ or imidazolyl; X is O; and $R^2$ is aryl, arylalkyl, biaryl, biarylalkyl, heteroaryl, or L-P(=O)(OR^{11})(OR^{12})$; and all other groups are as defined in any embodiments described herein. In some or any embodiments, the compound of formula I or II, is that where $R^3$ is $NH_2$, $CH_2NH_2$ or imidazolyl; X is O; and $R^2$ is $C_{1-14}$alkyl, aryl, arylalkyl, biaryl, biarylalkyl, heteroaryl, or L-P(=O)(OR^{11})(OR^{12})$; where each aryl and heteroaryl are independently optionally substituted with 1, 2, or 3 groups independently selected from halo, —$C_{1-12}$alkyl, and hydroxy; where alkyl and $C_{1-14}$alkyl are optionally substituted with 1, 2, 3, or 4 groups independently selected from halo, hydroxy, and cyano; and all other groups are as defined in any embodiments described herein.

In some or any embodiments, the compound of formula I or IV, is that where $R^3$ is $NH_2$, $CH_2NH_2$ or imidazolyl; X is —NHC(=O)CH(CH$_2$CH$_2$NH$_2$)O— connected to —C(=O)$R^2$ at the latter O; $R^2$ is $C_{1-14}$alkyl, $C_{3-12}$cycloalkyl, aryl, arylalkyl, biaryl, biarylalkyl, arylheteroaryl, heteroarylaryl, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, $NH(C_{1-14}$alkyl), NH(Ar), NH-(5 to 6-member heteroaromatic group containing at least one of N, S, and O atoms and the remaining atoms are carbon), $OC_{1-14}$alkyl, OAr, $NH(OC_{1-14}$alkyl), aryl[C(=O)$OR^4$]$_r$, biaryl[C(=O)$OR^4$]$_r$, aryl[OC(=O)$R^4$]$_r$, biaryl[OC(=O)$R^4$]$_r$, aryl-OC(=O)$NR^4R^5$, biaryl-OC(=O)$NR^4R^5$, or heteroarylalkyl; or $R^2$ is $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, or L-P(=O)(OR^{11})(OR^{12})$; and all other groups are as defined in any of the embodiments described. In some or any embodiments, the compound of formula I or IV, is that where $R^3$ is $NH_2$, $CH_2NH_2$ or imidazolyl; X is —NHC(=O)CH(CH$_2$CH$_2$NH$_2$)O— connected to —C(=O)$R^2$ at the latter O; $R^2$ is $C_{1-14}$alkyl, aryl, arylalkyl, biaryl, biarylalkyl, heteroaryl, or L-P(=O)(OR^{11})(OR^{12})$; and all other groups are as defined in any of the embodiments described. In some or any embodiments, the compound of formula I or IV, is that where $R^3$ is $NH_2$, $CH_2NH_2$ or imidazolyl; X is —NHC(=O)CH(CH$_2$CH$_2$NH$_2$)O— connected to —C(=O)$R^2$ at the latter O; $R^2$ is $C_{1-14}$alkyl, aryl, arylalkyl, biaryl, biarylalkyl, heteroaryl, or L-P(=O)(OR^{11})(OR^{12})$; where each aryl and heteroaryl are independently optionally substituted with 1, 2, or 3 groups independently selected from halo, —$C_{1-12}$alkyl, and hydroxy; where alkyl and $C_{1-14}$alkyl are optionally substituted with 1, 2, 3, or 4 groups independently selected from halo, hydroxy, and cyano; and all other groups are as defined in any embodiments described herein.

In some or any embodiments, the compound of formula I, is that where $R^3$ is $NH_2$, $CH_2NH_2$ or imidazolyl; X is O, —NHC(=O)CH(CH$_2$CH$_2$NH$_2$)O—, or —OC(=O)CH(CH$_2$CH$_2$NH$_2$)NH—; and $R^2$ is $C_{1-14}$alkyl, $C_{3-12}$cycloalkyl, aryl, arylalkyl, biaryl, biarylalkyl, arylheteroaryl, heteroarylaryl, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, $NH(C_{1-14}$alkyl), NH(Ar), NH-(5 to 6-member heteroaromatic group containing at least one of N, S, and O atoms and the remaining atoms are carbon), $OC_{1-14}$alkyl, OAr, $NH(OC_{1-14}$alkyl), aryl[C(=O)$OR^4$]$_r$, biaryl[C(=O)$OR^4$]$_r$, aryl[OC(=O)$R^4$]$_r$, biaryl[OC(=O)$R^4$]$_r$, aryl-OC(=O)$NR^4R^5$, biaryl-OC(=O)$NR^4R^5$, or heteroarylalkyl; or $R^2$ is $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, or L-P(=O)(OR^{11})(OR^{12})$; and all other groups are as defined in any embodiments described herein. In some or any embodiments, the compound of formula I, is that where $R^3$ is $NH_2$, $CH_2NH_2$ or imidazolyl; X is O, —NHC(=O)CH(CH$_2$CH$_2$NH$_2$)O— (connected to —C(=O)$R^2$ at the latter O), or —OC(=O)CH(CH$_2$CH$_2$NH$_2$)NH— (connected to —C(=O)$R^2$ at the NH); $R^2$ is $C_{1-14}$alkyl, aryl, arylalkyl, biaryl, biarylalkyl, heteroaryl, or L-P(=O)(OR^{11})(OR^{12})$; and all other groups are as defined in any of the embodiments described. In some or any embodiments, the compound of formula I, is that where $R^3$ is $NH_2$, $CH_2NH_2$ or imidazolyl; X is O, —NHC(=O)CH(CH$_2$CH$_2$NH$_2$)O— (connected to —C(=O)$R^2$ at the latter O), or —OC(=O)CH(CH$_2$CH$_2$NH$_2$)NH— (connected to —C(=O)$R^2$ at the NH); $R^2$ is $C_{1-14}$alkyl, aryl, arylalkyl, biaryl, biarylalkyl, heteroaryl, or L-P(=O)(OR^{11})(OR^{12})$; where each aryl and heteroaryl are independently optionally substituted with 1, 2, or 3 groups independently selected from halo, —$C_{1-12}$alkyl, and hydroxy; where alkyl and $C_{1-14}$alkyl are optionally substituted with 1, 2, 3, or 4 groups independently selected from halo, hydroxy, and cyano; and all other groups are as defined in any embodiments described herein.

In some or any embodiments, the compound of formula I, is that where $R^3$ is $NH_2$, $CH_2NH_2$ or imidazolyl; X is NH, $N(C_{1-6}alkyl)$, or NHC(=O)CH(CH$_2$CH$_2$NH$_2$)NH— connected to C(=O)R² at the latter NH; and R² is aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, (CR⁴R⁵)$_m$(CR⁶R⁷)$_n$C(=O)OR⁸, (CR⁴R⁵)$_m$(CR⁶R⁷)$_n$OC(=O)R⁸, (CR⁴R⁵)$_m$[N(C$_{1-6}$alkyl)O]C(=O)OR⁸, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); and all other groups are as defined in any embodiments described herein. In some or any embodiments, the compound of formula I, is that where R³ is NH₂, CH₂NH₂ or imidazolyl; X is NH, N(C$_{1-6}$alkyl), or NHC(=O)CH(CH₂CH₂NH₂)NH— connected to C(=O)R² at the latter NH; and R² is (CR⁴R⁵)$_m$(CR⁶R⁷)$_n$C(=O)OR⁸, (CR⁴R⁵)$_m$(CR⁶R⁷)$_n$OC(=O)R⁸, aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); and all other groups are as defined in any embodiments described herein. In some or any embodiments, the compound of formula I, is that where R³ is NH₂, CH₂NH₂ or imidazolyl; X is NH, N(C$_{1-6}$alkyl), or NHC(=O)CH(CH₂CH₂NH₂)NH— connected to C(=O)R² at the latter NH; and R² is (CR⁴R⁵)$_m$(CR⁶R⁷)$_n$C(=O)OR⁸, (CR⁴R⁵)$_m$(CR⁶R⁷)$_n$OC(=O)R⁸, aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); where R⁸ in C(=O)OR⁸ and R⁴ in each C(=O)OR⁴ are independently C$_{1-14}$alkyl or C$_{3-6}$cycloalkyl; or R⁶ and R⁸ together with the atoms to which they are attached form a 4 to 6-member saturated heterocycle containing at least one O atom wherein the heterocycle optionally comprises an additional heteroatom selected from N, O, and S, and wherein the remaining atoms are carbon; where R⁴, R⁵, R⁶, and R⁷ in each CR⁴R⁵ and each CR⁶R⁷ are independently hydrogen or C$_{1-14}$alkyl; and where each aryl is additionally optionally substituted with 1, 2, or 3 groups independently selected from C$_{1-12}$alkyl and halo; and all other groups are as defined in any embodiments described herein.

In some or any embodiments, the compound of formula I or III, is that where R³ is NH₂, CH₂NH₂ or imidazolyl; X is NH; and R² is aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, (CR⁴R⁵)$_m$(CR⁶R⁷)$_n$C(=O)OR⁸, (CR⁴R⁵)$_m$(CR⁶R⁷)$_n$OC(=O)R⁸, (CR⁴R⁵)$_m$[N(C$_{1-6}$alkyl)O]C(=O)OR⁸, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); and all other groups are as defined in any embodiments described herein. In some or any embodiments, the compound of formula I or III, is that where R³ is NH₂, CH₂NH₂ or imidazolyl; X is NH; and R² is (CR⁴R⁵)$_m$(CR⁶R⁷)$_n$C(=O)OR⁸, (CR⁴R⁵)$_m$(CR⁶R⁷)$_n$OC(=O)R⁸, aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); and all other groups are as defined in any embodiments described herein. In some or any embodiments, the compound of formula I or III, is that where R³ is NH₂, CH₂NH₂ or imidazolyl; X is NH; and R² is (CR⁴R⁵)$_m$(CR⁶R⁷)$_n$C(=O)OR⁸, (CR⁴R⁵)$_m$(CR⁶R⁷)$_n$OC(=O)R⁸, aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); where R⁸ in C(=O)OR⁸ and R⁴ in each C(=O)OR⁴ are independently C$_{1-14}$alkyl or C$_{3-6}$cycloalkyl; or R⁶ and R⁸ together with the atoms to which they are attached form a 4 to 6-member saturated heterocycle containing at least one O atom wherein the heterocycle optionally comprises an additional heteroatom selected from N, O, and S, and wherein the remaining atoms are carbon; where R⁴, R⁵, R⁶, and R⁷ in each CR⁴R⁵ and each CR⁶R⁷ are independently hydrogen or C$_{1-14}$alkyl; and where each aryl is additionally optionally substituted with 1, 2, or 3 groups independently selected from C$_{1-12}$alkyl and halo; and all other groups are as defined in any embodiments described herein.

In some or any embodiments, the compound of formula I, is that where R³ is NH₂, CH₂NH₂ or imidazolyl; X is N(C$_{1-6}$alkyl); and R² is aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, (CR⁴R⁵)$_m$(CR⁶R⁷)$_n$C(=O)OR⁸, (CR⁴R⁵)$_m$(CR⁶R⁷)$_n$OC(=O)R⁸, (CR⁴R⁵)$_m$[N(C$_{1-6}$alkyl)O]C(=O)OR⁸, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); and all other groups are as defined in any embodiments described herein. In some or any embodiments, the compound of formula I, is that where R³ is NH₂, CH₂NH₂ or imidazolyl; X is N(C$_{1-6}$alkyl); and R² is (CR⁴R⁵)$_m$(CR⁶R⁷)$_n$C(=O)OR⁸, (CR⁴R⁵)$_m$(CR⁶R⁷)$_n$OC(=O)R⁸, aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); and all other groups are as defined in any embodiments described herein. In some or any embodiments, the compound of formula I, is that where R³ is NH₂, CH₂NH₂ or imidazolyl; X is N(C$_{1-6}$alkyl); and R² is (CR⁴R⁵)$_m$(CR⁶R⁷)$_n$C(=O)OR⁸, (CR⁴R⁵)$_m$(CR⁶R⁷)$_n$OC(=O)R⁸, aryl[C(=O)OR⁴]$_r$, biaryl[C(=O)OR⁴]$_r$, aryl[OC(=O)R⁴]$_r$, biaryl[-OC(=O)OR⁴]$_r$, aryl-OC(=O)NR⁴R⁵, biaryl-OC(=O)NR⁴R⁵, dihydrofuran-2(3H)-one)-3-yl, aryl-dihydrofuran-2(3H)-one)-3-yl, C$_{1-14}$alkyl-dihydrofuran-2(3H)-one)-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR¹¹)(OR¹²); where R⁸ in C(=O)OR⁸ and R⁴ in each C(=O)OR⁴ are independently C$_{1-14}$alkyl or C$_{3-6}$cycloalkyl; or R⁶ and R⁸ together with the atoms to which they are attached form a 4 to 6-member saturated heterocycle containing at least one O atom wherein the heterocycle optionally comprises an additional heteroatom selected from N, O, and S, and wherein the remaining atoms are carbon; where $R^4$, $R^5$, $R^6$, and $R^7$ in each $CR^4R^5$ and each $CR^6R^7$ are independently hydrogen or $C_{1-14}$alkyl; and where each aryl is additionally optionally substituted with 1, 2, or 3 groups independently selected from $C_{1-12}$alkyl and halo; and all other groups are as defined in any embodiments described herein.

In some or any embodiments, the compound of formula I, is that where $R^3$ is $NH_2$, $CH_2NH_2$ or imidazolyl; X is $NHC(=O)CH(CH_2CH_2NH_2)NH$ connected to $C(=O)R^2$ at the latter NH; and $R^2$ is aryl[$C(=O)OR^4$]$_r$, biaryl[$C(=O)OR^4$]$_r$, aryl[$OC(=O)R^4$]$_r$, biaryl[$-OC(=O)OR^4$]$_r$, aryl-OC$(=O)NR^4R^5$, biaryl-$OC(=O)NR^4R^5$, $(CR^4R^5)_m(CR^6R^7)_nC(=O)OR^8$, $(CR^4R^5)_m(CR^6R^7)_nOC(=O)R^8$, $(CR^4R^5)_m[N(C_{1-6}alkyl)O]C(=O)OR^8$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR$^{11}$)(OR$^{12}$); and all other groups are as defined in any embodiments described herein. In some or any embodiments, the compound of formula I, is that where $R^3$ is $NH_2$, $CH_2NH_2$ or imidazolyl; X is $NHC(=O)CH(CH_2CH_2NH_2)NH$ connected to $C(=O)R^2$ at the latter NH; and $R^2$ is $(CR^4R^5)_m(CR^6R^7)_nC(=O)OR^8$, $(CR^4R^5)_m(CR^6R^7)_nOC(=O)R^8$, aryl[$C(=O)OR^4$]$_r$, biaryl[$C(=O)OR^4$]$_r$, aryl[$OC(=O)R^4$]$_r$, biaryl[$-OC(=O)OR^4$]$_r$, aryl-OC$(=O)NR^4R^5$, biaryl-OC$(=O)NR^4R^5$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR$^{11}$)(OR$^{12}$); and all other groups are as defined in any embodiments described herein. In some or any embodiments, the compound of formula I, is that where $R^3$ is $NH_2$, $CH_2NH_2$ or imidazolyl; X is $NHC(=O)CH(CH_2CH_2NH_2)NH$ connected to $C(=O)R^2$ at the latter NH; and $R^2$ is $(CR^4R^5)_m(CR^6R^7)_nC(=O)OR^8$, $(CR^4R^5)_m(CR^6R^7)_nOC(=O)R^8$, aryl[$C(=O)OR^4$]$_r$, biaryl[$C(=O)OR^4$]$_r$, aryl[$OC(=O)R^4$]$_r$, biaryl[$-OC(=O)OR^4$]$_r$, aryl-OC$(=O)NR^4R^5$, biaryl-OC$(=O)NR^4R^5$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR$^{11}$)(OR$^{12}$); where $R^8$ in $C(=O)OR^8$ and $R^4$ in each $C(=O)OR^4$ are independently $C_{1-14}$alkyl or $C_{3-6}$cycloalkyl; or $R^6$ and $R^8$ together with the atoms to which they are attached form a 4 to 6-member saturated heterocycle containing at least one O atom wherein the heterocycle optionally comprises an additional heteroatom selected from N, O, and S, and wherein the remaining atoms are carbon; where $R^4$, $R^5$, $R^6$, and $R^7$ in each $CR^4R^5$ and each $CR^6R^7$ are independently hydrogen or $C_{1-14}$alkyl; and where each aryl is additionally optionally substituted with 1, 2, or 3 groups independently selected from $C_{1-12}$alkyl and halo; and all other groups are as defined in any embodiments described herein.

In some or any embodiments, the compound of formula I, is that where a) X is O; $R^3$ is $NH_2$, $CH_2NH_2$ or imidazolyl; and $R^2$ is $C_{1-14}$alkyl, aryl, arylalkyl, biaryl, biarylalkyl, heteroaryl, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR$^{11}$)(OR$^{12}$); or b) X is —NHC(=O)CH(CH$_2$CH$_2$NH$_2$)O— connected to —C(=O)R$^2$ at the latter O; R$^3$ is NH$_2$, CH$_2$NH$_2$ or imidazolyl; and R$^2$ is $C_{1-14}$alkyl, aryl, arylalkyl, biaryl, biarylalkyl, heteroaryl, or L-P(=O)(OR$^{11}$)(OR$^{12}$); or c) X is NH; $R^3$ is $NH_2$, $CH_2NH_2$ or imidazolyl; and $R^2$ is $(CR^4R^5)_m(CR^6R^7)_nC(=O)OR^8$, $(CR^4R^5)_m(CR^6R^7)_nOC(=O)R^8$, aryl[$C(=O)OR^4$]$_r$, biaryl[$C(=O)OR^4$]$_r$, aryl[$OC(=O)R^4$]$_r$, biaryl[$-OC(=O)OR^4$]$_r$, aryl-OC$(=O)NR^4R^5$, biaryl-OC$(=O)NR^4R^5$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR$^{11}$)(OR$^{12}$); or d) X is N and $R^3$ is NH or $N(C_{1-6}$alkyl) and $R^3$ and X taken together comprise $NHCH_2CH_2N$ or $N(C_{1-6}$alkyl)$CH_2CH_2N$; $R^2$ is $(CR^4R^5)_m(CR^6R^7)_nC(=O)OR^8$, or $(CR^4R^5)_m(CR^6R^7)_nOC(=O)R^8$;

and all other groups are as defined in any embodiments described herein.

In some or any embodiments, the compound of formula I, II, III, or IV where $R^2$ is L-P(=O)(OR$^{11}$)(OR$^{12}$); and all other groups are as defined in any embodiments described herein. In some or any embodiments, the compound of formula I, II, III, IV, or V where $R^2$ is L-P(=O)(OR$^{11}$)(OR$^{12}$); L is selected from $CR^4$=$CR^6$—$(CR^9R^{10})_o$, $(CR^4R^5)_m$—$CR^6$=$CR^{10}$, $CF_2$, $(CR^4R^5)_m$, $O(CR^4R^5)_m$, $NH(CR^4R^5)_m$, $N(C_{1-6}$alkyl$)(CR^4R^5)_m$, $(CR^4R^5)_mO$, $(CR^4R^5)_mNH$, $(CR^4R^5)_mN(C_{1-6}$alkyl$)$, $(CR^4R^5)_mCF_2$ and $CF_2(CR^6R^7)$—, and wherein m and n in L are independently 1 or 2; and all other groups are as defined in any embodiments described herein. In some or any embodiments, the compound of formula I, II, III, IV, or V where $R^2$ is L-P(=O)(OR$^{11}$)(OR$^{12}$); L is selected from $CF_2$, $(CR^4R^5)_m$, $O(CR^4R^5)_m(CR^6R^7)_n$, $NH(CR^4R^5)_m$, $N(C_{1-6}$alkyl$)(CR^4R^5)_m$, $(CR^4R^5)_m(CR^6R^7)_nO$, $(CR^4R^5)_mNH$, $(CR^4R^5)_mN(C_{1-6}$ alkyl$)$, $(CR^4R^5)_mCF_2$ and $CF_2(CR^6R^7)_n$, and wherein m and n in L are independently 1 or 2; and all other groups are as defined in any embodiments described herein. In some or any embodiments, the compound of formula I, II, III, IV, or V where $R^2$ is L-P(=O)(OR$^{11}$)(OR$^{12}$); L is selected from $CF_2$, $(CR^4R^5)_m$, $O(CR^4R^5)_m(CR^6R^7)_n$, $NH(CR^4R^5)_m$, $N(C_{1-6}$ alkyl$)(CR^4R^5)_m$, $(CR^4R^5)_m(CR^6R^7)_nO$, $(CR^4R^5)_mNH$, $(CR^4R^5)_mN(C_{1-6}$alkyl$)$, $(CR^4R^5)_mCF_2$ and $CF_2(CR^6R^7)_n$, and wherein m and n in L are independently 1 or 2; $R^4$, $R^5$, $R^6$, and $R^7$ are independently selected from hydrogen, $C_{1-14}$alkyl, and halo or $R^4$ and $R^5$ together with the carbon to which they are attached form a $C_{3-6}$cycloalkylene; or $R^6$ and $R^7$ together with the carbon to which they are attached form a $C_{3-6}$cycloalkylene; and all other groups are as defined in any embodiments described herein. In some or any embodiments, the compound of formula I, II, III, or IV is that where $R^2$ is L-P(=O)(OR$^{11}$)(OR$^{12}$); and $R^{12}$ are independently H, $C_{1-14}$alkyl, $C_{3-6}$cycloalkyl, aryl, or arylalkyl; or $R^{11}$ and $R^{12}$ together with the two oxygen atoms to which they are attached form a 5 to 7-member saturated heterocycle wherein the 2, 3, or 4 additional atoms are carbon optionally substituted with one or two groups independently selected from $C_{1-6}$alkyl and aryl; and all other groups are as defined in any embodiments described herein. In some or any embodiments, the compound of formula I, II, III, or IV is that where $R^{11}$ and $R^{12}$ are independently H or $C_{1-14}$alkyl; or $R^{11}$ and $R^{12}$ together with the two oxygen atoms to which they are attached form a 5 to 7-member saturated heterocycle wherein the 2, 3, or 4 additional atoms are carbon optionally substituted with one or two groups independently selected from $C_{1-6}$alkyl and aryl; and all other groups are as defined in any embodiments described herein.

In some or any embodiments, the compound of formula I, II, III, IV, or V, is that wherein $R^4$ through $R^7$, $R^9$ and $R^{10}$ are independently H, $NH_2$, halo, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; and $R^8$ is H, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; $R^4$ and $R^5$, together with the nitrogen to which they are attached form a 5 to 7-membered saturated or unsaturated heterocycle optionally containing an additional heteroatom independently selected from N and S, and wherein remaining atoms are carbon; any of i) $R^4$ and $R^5$, ii) $R^6$ and $R^7$, iii) $R^4$ and $R^6$, and iv) $R^9$ and $R^{10}$, together with the atom to which they are attached form a $C_{3-6}cycloalkylene$; any of $R^4$ and $R^5$, $R^6$ and $R^7$, $R^4$ and $R^6$, and $R^9$ and $R^{10}$, together with the carbon to which they are attached form a 5 to 7-member saturated or unsaturated heterocycle containing at least one O atom, or containing one O atom and an additional heteroatom independently selected from N and S, and wherein remaining atoms are carbon; or $R^6$ and $R^8$ together with the atoms to which they are attached form a 4 to 6-member saturated heterocycle containing at least one O atom wherein the heterocycle optionally comprises an additional heteroatom selected from N, O, and S and wherein the remaining atoms are carbon; and $R^{11}$ and $R^{12}$ are independently H, $N(C_{1-6}alkyl)$, $C_{1-14}alkyl$, $C_{3-6}cycloalkyl$, aryl, arylalkyl, biaryl, biarylalkyl, or heteroarylalkyl; or $R^{11}$ and $R^{12}$ together with the two oxygen atoms to which they are attached form a 5 to 7-member saturated heterocycle wherein the 2, 3, or 4 additional atoms are carbon optionally substituted with one or two groups independently selected from $C_{1-6}alkyl$ and aryl; or either or both of i) $R^4$ and $R^{11}$ and ii) $R^6$ and $R^{12}$ together with atoms to which they are attached form a 5 to 7-member saturated heterocycle containing one O atom and one P atom and where the remaining atoms are carbon; and all other groups are as defined in any of the aspects and/or embodiments described herein.

In some or any embodiments, the of formula I is according to formula II

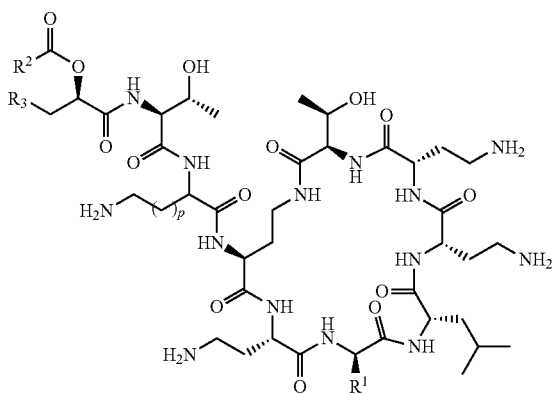

II or a pharmaceutically acceptable salt, solvate, or hydrate thereof.

In some or any embodiments, the compound of formula I is according to formula II wherein
$R^1$ is $CH_2CH(CH_3)_2$ or $CH_2Ph$; and wherein
$R^2$ is $C_{1-14}alkyl$, $C_{1-13}alkylCF_2$—, $C_{3-12}cycloalkyl$, aryl, arylCF$_2$—, arylalkyl, biaryl, arylCF$_2$—, biarylalkyl, heteroaryl, aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, heteroarylalkyl, $(CR^4R^5)_m(CR^6R^7)_n$, $C(=O)OR^8$, $(CR^4R^5)_m(CR^6R^7)_nOC(=O)R^8$, dihydrofuran-2(3H)-one)-3-yl, aryl-dihydrofuran-2(3H)-one)-3-yl, $C_{1-14}alkyl$-dihydrofuran-2(3H)-one)-3-yl, tetrahydro-2H-pyran-2-one-3-yl, aryl-tetrahydro-2H-pyran-2-one-3-yl, $C_{1-14}alkyl$-tetrahydro-2H-pyran-2-one-3-yl, or L-P(=O)(OR$^{11}$)(OR$^{12}$); and wherein L is selected from O, NH, $N(C_{1-6}alkyl)$, $C_{1-6}alkylene$, $(CR^4R^5)_m(CR^6R^7)_n(CR^9R^{10})_o$, $CR^4=CR^6-(CR^9R^{10})_o$, $(CR^4R^5)_m-CR^6=CR^{10}$, $O(CR^4R^5)_m(CR^6R^7)_n(CR^9R^{10})_o$, $NH(CR^4R^5)_m(CR^6R^7)_n(CR^9R^{10})_o$, $N(C_{1-6}alkyl)(CR^4R^5)_m(CR^6R^7)_n(CR^9R^{10})_o$, $(CR^4R^5)_m(CR^6R^7)_n(CR^9R^{10})_oO$, $(CR^4R^5)_m(CR^6R^7)_n(CR^9R^{10})_oNH$, and $(CR^4R^5)_m(CR^6R^7)_n(CR^9R^{10})_oN(C_{1-6}alkyl)$; and wherein $R^4$ through $R^7$, $R^9$ and $R^{10}$ are independently H, $NH_2$, halo, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; and $R^8$ is H, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; or any two of $R^4$ through $R^{10}$, together with the atom(s) to which they are attached form a 4 to 7-member saturated or unsaturated heterocycle containing at least one O atom, or containing one O atom and an additional heteroatom independently selected from N and S and where the remaining atoms are carbon; or any of i) $R^4$ and $R^5$, ii) $R^6$ and $R^7$, iii) $R^4$ and $R^6$, iv) $R^9$ and $R^{10}$, v) $R^6$ and $R^{10}$, and vi) $R^4$ and $R^9$, together with the atom to which they are attached form a $C_{3-6}cycloalkylene$; or any two of $R^4$ through $R^{10}$ together with the atom(s) to which they are attached form a 5 to 7-member saturated or unsaturated heterocycle wherein the ring optionally comprises an additional heteroatom selected from N, O, and S and wherein the remaining atoms are carbon; or $R^6$ and $R^8$ together with the atoms to which they are attached form a 4 to 6-member saturated heterocycle containing at least one O atom wherein the heterocycle optionally comprises an additional heteroatom selected from N, O, and S and wherein the remaining atoms are carbon; and wherein $R^{11}$ and $R^{12}$ are independently H, $N(C_{1-6}alkyl)$, $C_{1-14}alkyl$, $C_{3-6}cycloalkyl$, aryl, arylalkyl, biaryl, biarylalkyl, or heteroarylalkyl; or $R^{11}$ and $R^{12}$ together with the two oxygen atoms to which they are attached form a 5 to 7-member saturated heterocycle wherein the 2, 3, or 4 additional atoms are carbon optionally substituted with $C_{1-6}alkyl$; or either or both of i) $R^4$ and $R^{11}$ and ii) $R^6$ and $R^{12}$ together with atoms to which they are attached form a 5 to 7-member saturated heterocycle containing one O atom and one P atom and where the remaining atoms are carbon optionally substituted with one or two groups independently selected from $C_{1-6}alkyl$ and aryl; and wherein r is 1 or 2; and wherein m, n, o, and p are independently selected from 0, 1, and 2 and wherein when L is $(CR^4R^5)_m(CR^6R^7)_n(CR^9R^{10})_o$, then m+n+o≥1; and wherein $R^3$ is $NH_2$, $CH_2NH_2$ or imidazolyl; and with a proviso that wherein $R^3$ is $CH_2NH_2$, then $R^2$ is not 5-methylheptyl.

In some or any embodiments, the compound of formula I is that wherein $R^3$ is $CH_2NH_2$, and [a], [b], and [c] are all NH; and all other groups are as defined in any of the aspects and/or embodiments described herein.

In some or any embodiments, the compound of formula I or II is that wherein X is O and $R^2$ is selected from alkyl substituted with 1, 2, or 3 halo; biaryl optionally substituted with 1, 2, 3, or 4 groups independently selected from hydroxy and halo; arylheteroaryl optionally substituted with 1, 2, 3, or 4 groups independently selected from hydroxy and halo; heteroarylaryl optionally substituted with 1, 2, 3, or 4 groups independently selected from hydroxy and halo; biarylalkyl where each aryl is independently optionally substituted with 1, 2, 3, or 4 groups independently selected from hydroxy and halo and where the alkyl is optionally substituted with 1 or 2 halo; $(CR^4R^5)_m(CR^6R^7)_nC(=O)OR^8$ or $(CR^4R^5)_m(CR^6R^7)_nOC(=O)R^8$ where m and 2 are each 1, where $R^4$, $R^5$, $R^6$, and $R^7$ are independently hydrogen, methyl, or halo and $R^8$ is or $C_{3-6}$cycloalkyl; dihydrofuran-2(3H)-one)-3-yl; aryl-dihydrofuran-2(3H)-one)-3-yl; $C_{1-14}$alkyl-dihydrofuran-2(3H)-one)-3-yl; tetrahydro-2H-pyran-2-one-3-yl; aryl-tetrahydro-2H-pyran-2-one-3-yl; and $C_{1-14}$alkyl-tetrahydro-2H-pyran-2-one-3-yl; and all other groups are as defined in any embodiments described herein.

In some or any embodiments, the compound of formula I or II is that wherein X is O and $R^2$ is selected from structures below:

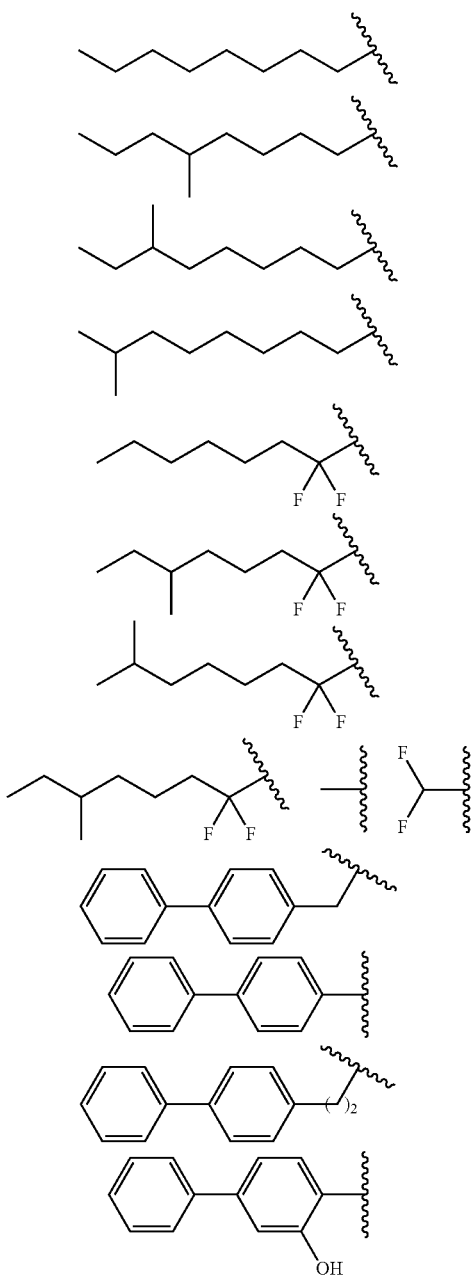

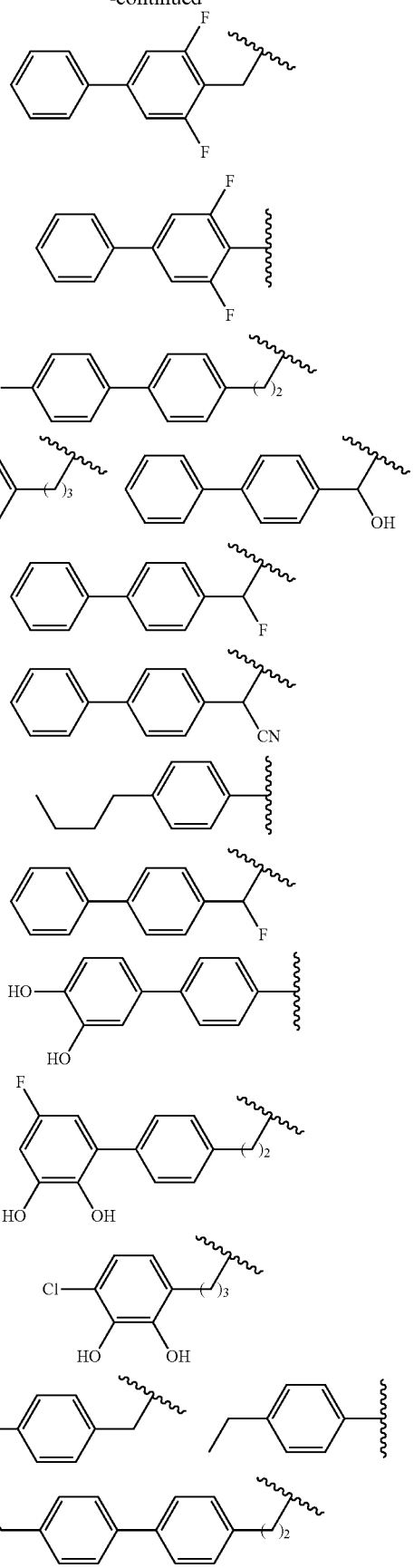

-continued

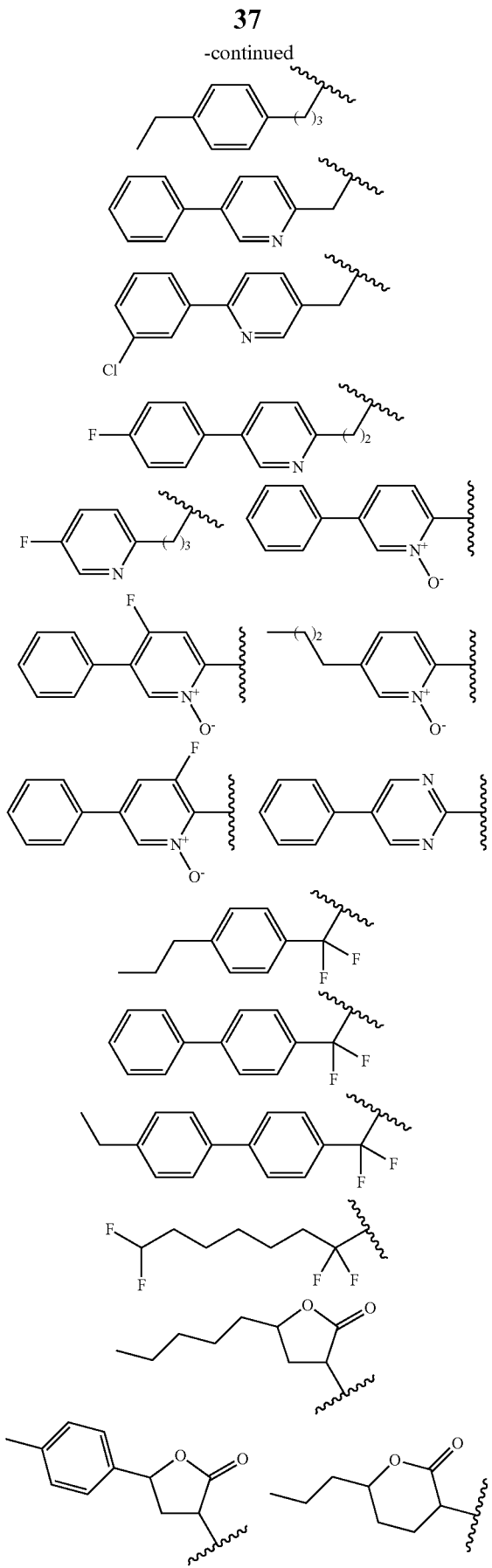

-continued

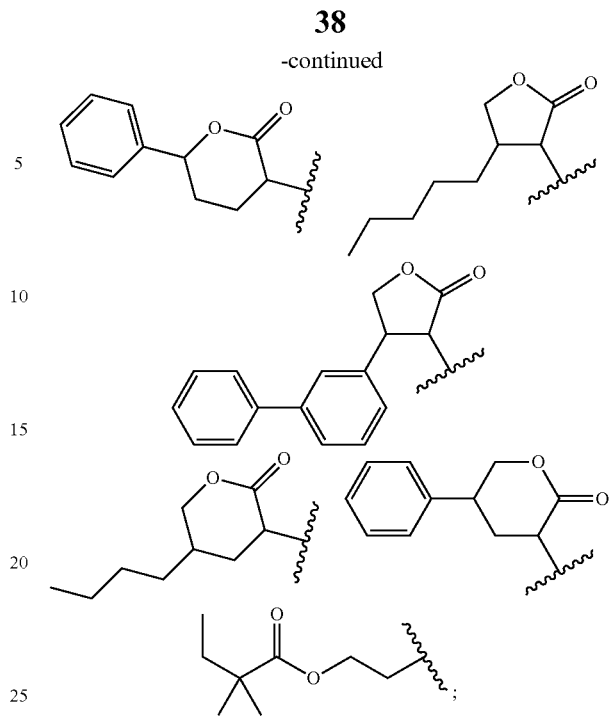

and all other groups are as defined in any embodiments describe herein.

In some or any embodiments, the compound of formula I is according to formula III

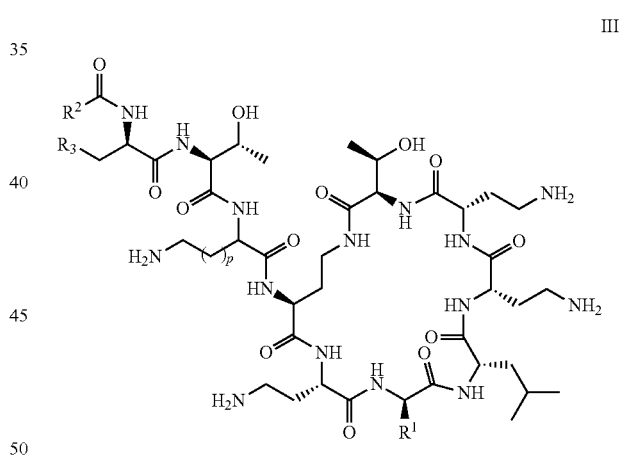

III or a pharmaceutically acceptable salt, solvate, or hydrate thereof.

In some or any embodiments, the compound of formula III is that where $R^1$ is $CH_2CH(CH_3)_2$ or $CH_2Ph$;

$R^2$ is aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, (CR$^4$R$^5$)$_m$(CR$^6$R$^7$)$_n$C(=O)OR$^8$, (CR$^4$R$^5$)$_m$(CR$^6$R$^7$)$_n$OC(=O)R$^8$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, or $C_{1-14}$alkyl-tetrahydro-2H-pyran-2-one-3-yl; wherein $R^4$ through $R^7$ are independently H, NH$_2$, halo, NH(C$_{1-6}$alkyl), NH(OC$_{1-6}$alkyl), C$_{1-14}$alkyl, C$_{3-6}$cycloalkyl, aryl, arylalkyl, biaryl, biarylalkyl, or heteroarylalkyl; and $R^8$ is H, NH(C$_{1-6}$alkyl), NH(OC$_{1-6}$alkyl), C$_{1-14}$alkyl, C$_{3-6}$cycloalkyl, aryl, arylalkyl, biaryl, biarylalkyl, or heteroarylalkyl; or any two of R$^4$ through R$^8$, together with the atom(s) to which they are attached form a 4 to 7-member saturated or unsaturated heterocycle containing at least one O atom, or containing one O atom and an additional heteroatom independently selected from N and S and where the remaining atoms are carbon; or any of i) R$^4$ and R$^5$, ii) R$^6$ and R$^7$, and iii) R$^4$ and R$^6$, together with the atom to which they are attached form a C$_{3-6}$cycloalkylene; or any two of R$^4$ through R$^8$ together with the atom(s) to which they are attached form a 5 to 7-member saturated or unsaturated heterocycle wherein the ring optionally comprises an additional heteroatom selected from N, O, and S and wherein the remaining atoms are carbon; or R$^6$ and R$^8$ together with the atoms to which they are attached form a 4 to 6-member saturated heterocycle containing at least one O atom wherein the heterocycle optionally comprises an additional heteroatom selected from N, O, and S and wherein the remaining atoms are carbon; and wherein r is 1 or 2; and wherein m, n, and p are independently selected from 0 to 2; and R$^3$ is NH$_2$, CH$_2$NH$_2$ or imidazolyl.

In some or any embodiments, the compound of formula I or III is that wherein X is NH and R$^2$ is selected from aryl[C(=O)OR$^4$]$_r$; biaryl[C(=O)OR$^4$]$_r$; aryl[OC(=O)R$^4$]$_r$; biaryl[OC(=O)R$^4$]$_r$; (CR$^4$R$^5$)$_m$(CR$^6$R$^7$)$_n$C(=O)OR$^8$ or (CR$^4$R$^5$)$_m$(CR$^6$R$^7$)$_n$OC(=O)R$^8$ where m and 2 are each 1, R$^4$, R$^5$, R$^6$, and R$^7$ are independently hydrogen, methyl, or halo and R$^8$ is C$_{1-14}$alkyl or C$_{3-6}$cycloalkyl; dihydrofuran-2(3H)-one)-3-yl; aryl-dihydrofuran-2(3H)-one)-3-yl; C$_{1-14}$alkyl-dihydrofuran-2(3H)-one)-3-yl; tetrahydro-2H-pyran-2-one-3-yl; aryl-tetrahydro-2H-pyran-2-one-3-yl; and C$_{1-14}$alkyl-tetrahydro-2H-pyran-2-one-3-yl; and where r is 1 or 2 and where each aryl is independently additionally optionally substituted with 1 or 2 groups independently selected from halo and hydroxy; and all other groups are as defined in any embodiments described herein.

In some or any embodiments, the compound of formula I or III is that wherein X is NH and R$^2$ is selected from structures below:

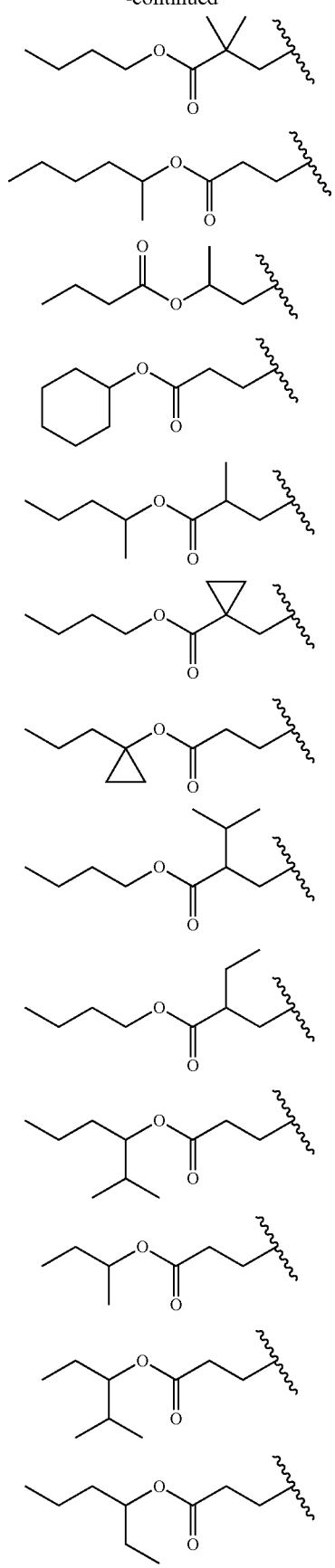

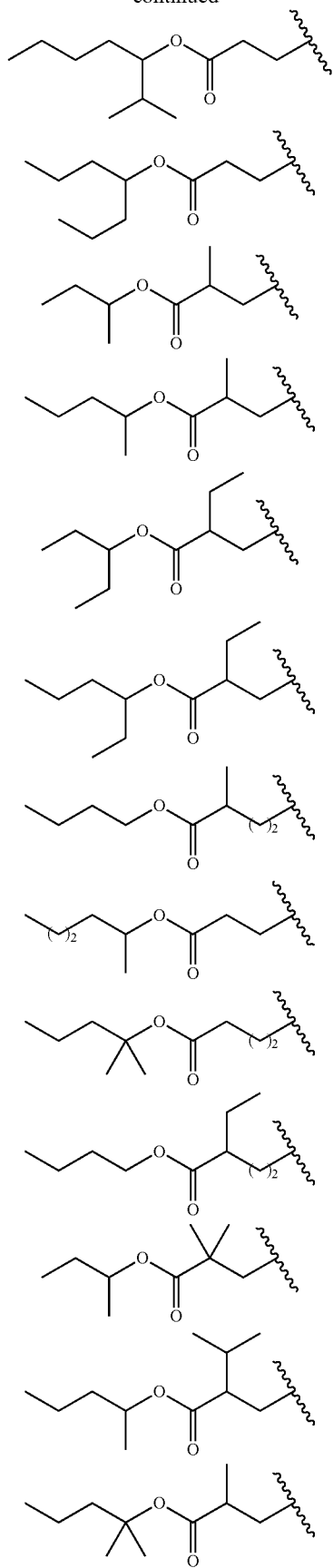
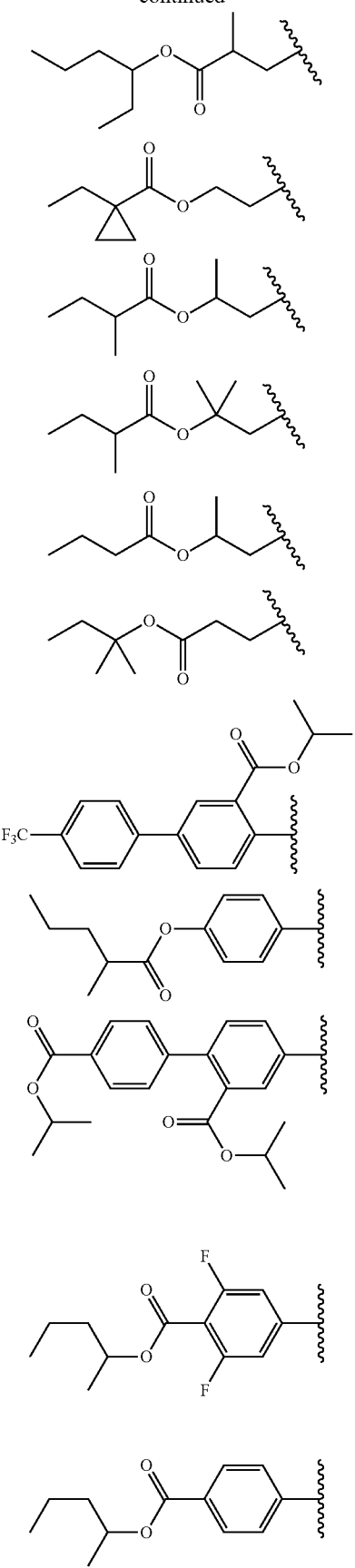

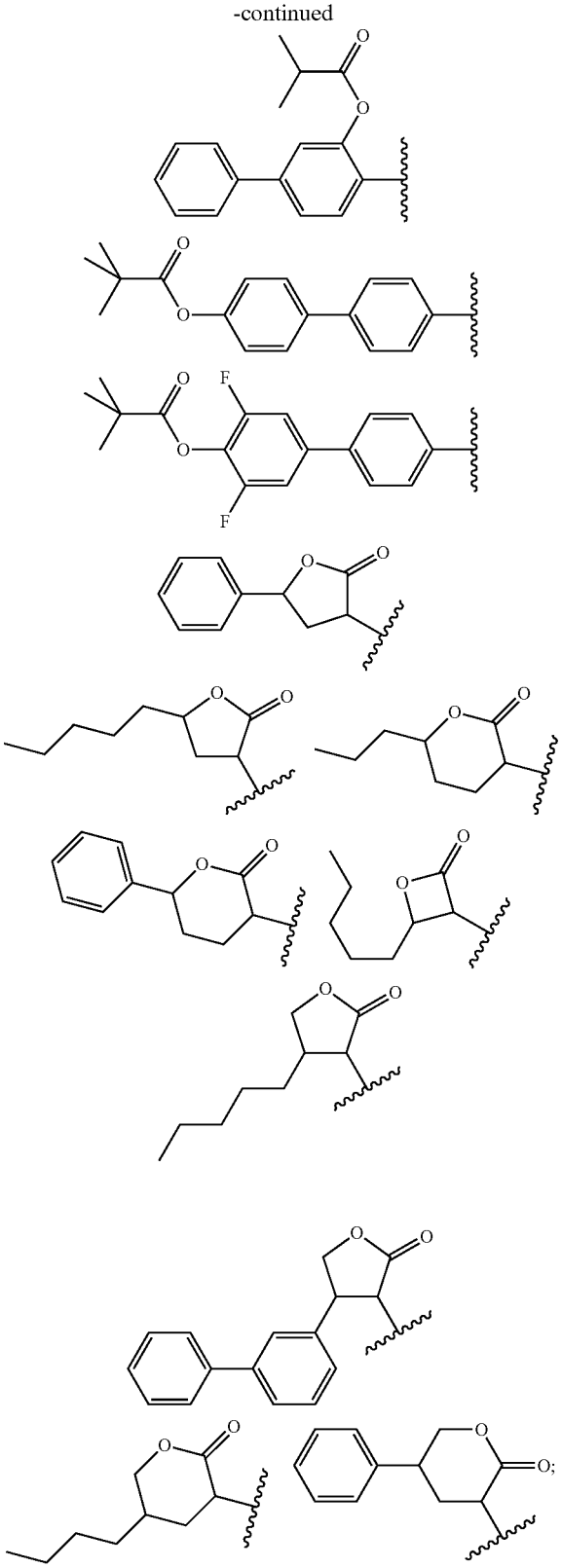

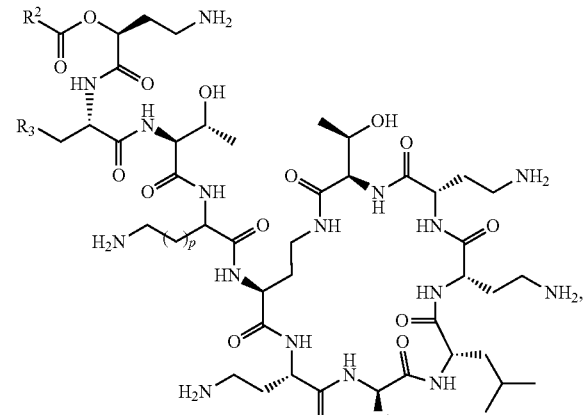

or a pharmaceutically acceptable salt, solvate, or hydrate thereof.

In some or any embodiments, the compound of formula IV is that wherein $R^1$ is $CH_2CH(CH_3)_2$ or $CH_2Ph$;

$R^2$ is aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, $(CR^4R^5)_m(CR^6R^7)_nC(=O)OR^8$, or $(CR^4R^5)_m(CR^6R^7)_nOC(=O)R^8$, dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl; wherein $R^4$ through $R^7$ are independently H, halo, $NH_2$, NH($C_{1-6}$alkyl), NH(OC$_{1-6}$alkyl), $C_{3-6}$cycloalkyl, aryl, arylalkyl, biaryl, biarylalkyl, or heteroarylalkyl; and $R^8$ is H, NH($C_{1-6}$alkyl), NH(OC$_{1-6}$alkyl), $C_{1-14}$alkyl, $C_{3-6}$cycloalkyl, aryl, arylalkyl, biaryl, biarylalkyl, or heteroarylalkyl; or any two of $R^4$ through $R^8$, together with the atom(s) to which they are attached form a 4 to 7-member saturated or unsaturated heterocycle containing at least one O atom, or containing one O atom and an additional heteroatom independently selected from N and S and where the remaining atoms are carbon; or any of i) $R^4$ and $R^5$, ii) $R^6$ and $R^7$, and iii) $R^4$ and $R^6$, together with the atom to which they are attached form a $C_{3-6}$cycloalkylene; or any two of $R^4$ through $R^8$ together with the atom(s) to which they are attached form a 4 to 7-member saturated or unsaturated heterocycle wherein the ring optionally comprises an additional heteroatom selected from N, O, and S and wherein the remaining atoms are carbon; or $R^6$ and $R^8$ together with the atoms to which they are attached form a 4 to 6-member saturated heterocycle containing at least one O atom wherein the heterocycle optionally comprises an additional heteroatom selected from N, O, and S and wherein the remaining atoms are carbon; and wherein r is 1 or 2; and wherein m, n, and p are independently selected from 0 to 2; and $R^3$ is $NH_2$, $CH_2NH_2$ or imidazolyl.

In some or any embodiments, the compound of formula I or IV is that wherein X is —NHC(=O)CH(CH$_2$CH$_2$NH$_2$)O— and $R^2$ selected from structures below:

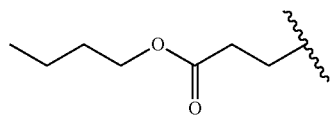

and all other groups are as defined in any of the aspects and/or embodiments described herein.

In some or any embodiments, the compound of formula I is according to formula IV

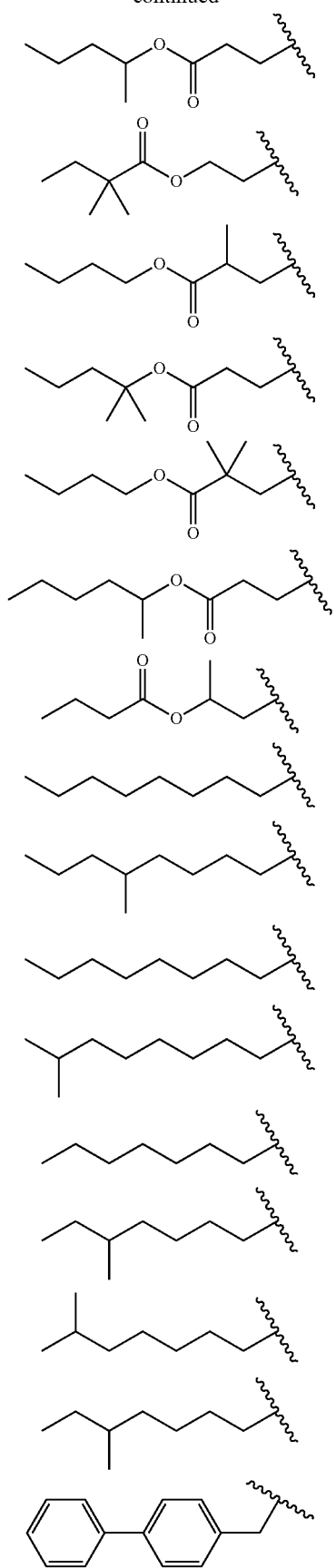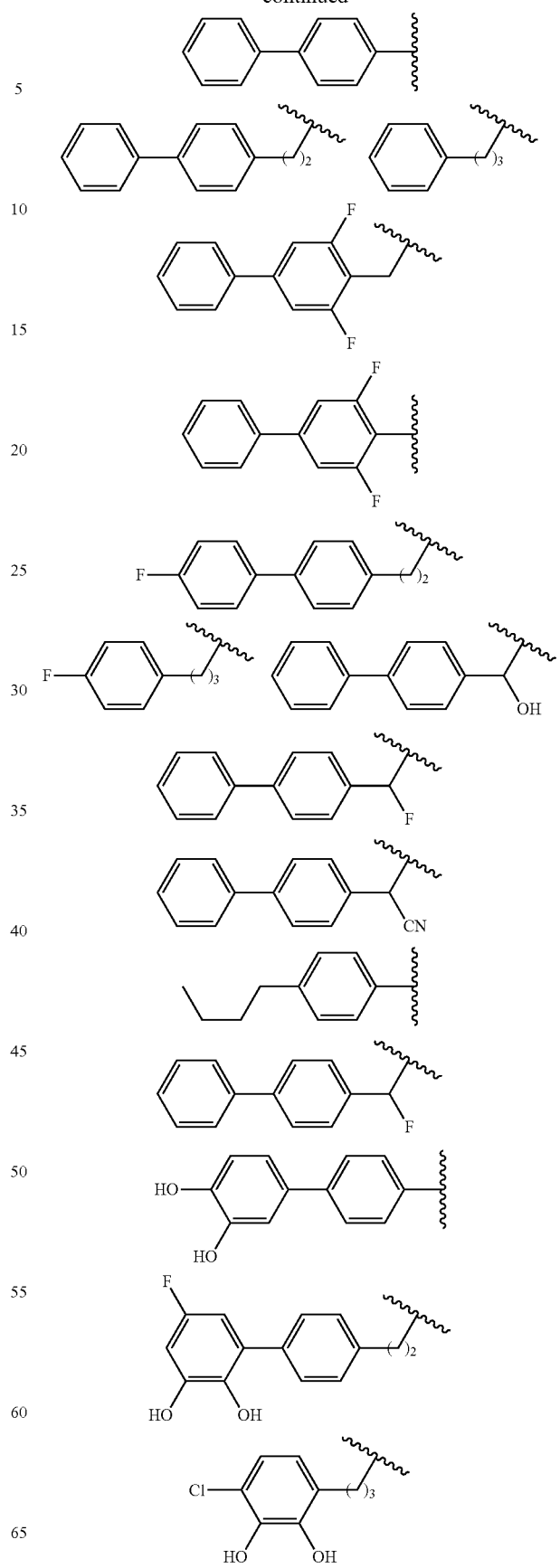

-continued

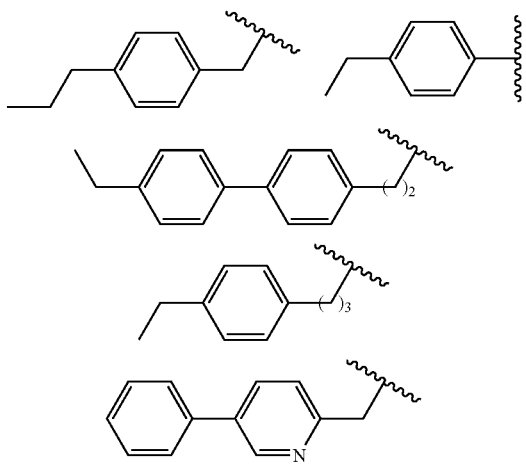

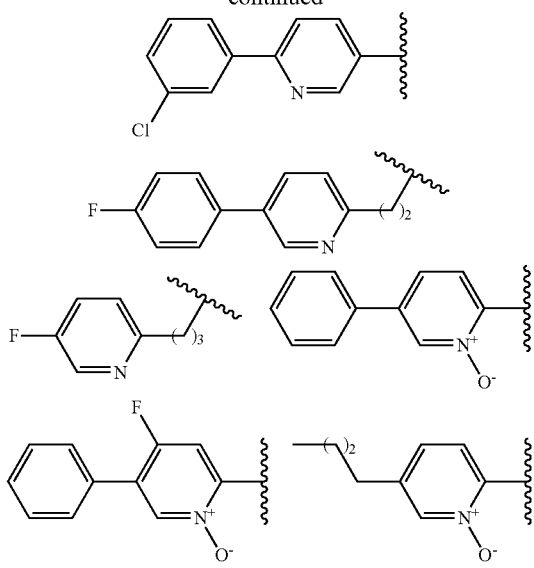

-continued

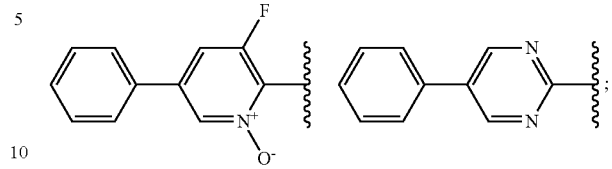

and all other groups are as defined in any of the aspects and/or embodiments described herein.

In some or any embodiments, the compound of formula I is according to formula V

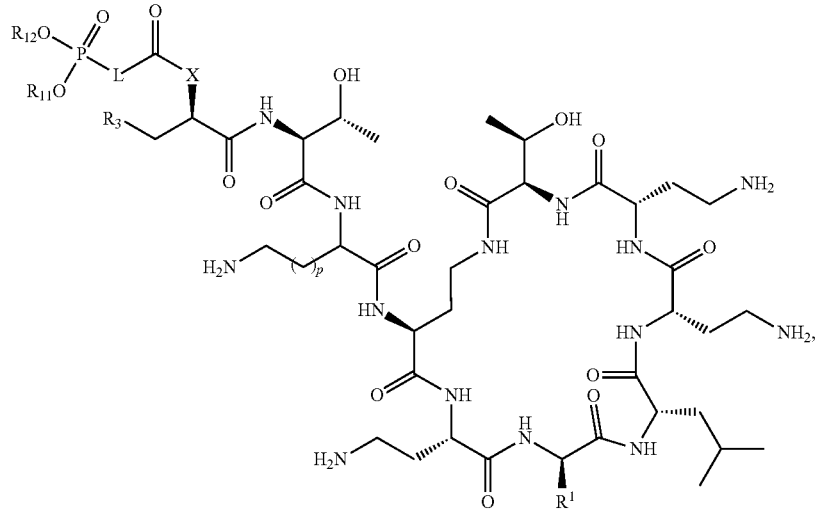

V or a pharmaceutically acceptable salt, solvate, or hydrate thereof.

In some or any embodiments, the compound of formula I or IV is that wherein $R^1$ is $CH_2CH(CH_3)_2$ or $CH_2Ph$; and wherein X is NH, $N(C_{1-6}alkyl)$, or O; and $R^3$ is $NH_2$, $CH_2NH_2$ or imidazolyl; or X is N or $N(C_{1-6}alkyl)$ and $R^3$ is NH and $R^3$ and X taken together comprise group $NHCH_2CH_2N$ or $N(C_{1-6}alkyl)CH_2CH_2N$; and wherein L is selected from O, NH, $N(C_{1-6}alkyl)$, $C_{1-6}alkylene$, $(CR^4R^5)_m(CR^6R^7)_n(CR^9R^{10})_o$, $CR^4=CR^6-(CR^9R^{10})_o$, $(CR^4R^5)_m-CR^6=CR^{10}$, $O(CR^4R^5)_m(CR^6R^7)_n(CR^9R^{10})_o$, $NH(CR^4R^5)_m(CR^6R^7)_n(CR^9R^{10})_o$, $N(C_{1-6}alkyl)(CR^4R^5)_m(CR^6R^7)_n(CR^9R^{10})_o$, $(CR^4R^5)_m(CR^6R^7)_n(CR^9R^{10})_oO$, $(CR^4R^5)_m(CR^6R^7)_n(CR^9R^{10})_oNH$, and $(CR^4R^5)_m(CR^6R^7)_n(CR^9R^{10})_oN(C_{1-6}alkyl)$;

$R^4$ through $R^7$, $R^9$ and $R^{10}$ are independently H, $NH_2$, halo, $NH(C_{1-6}alkyl)$, NH(OC 6alkyl), $C_{1-14}alkyl$, $C_{3-6}cycloalkyl$, aryl, arylalkyl, biaryl, biarylalkyl, or heteroarylalkyl; or any two of $R^4$ through $R^7$, $R^9$ and $R^{10}$, together with the atom(s) to which they are attached form a 4 to 7-member saturated or unsaturated heterocycle containing at least one O atom, or containing one O atom and additional heteroatom independently selected from N and S, and wherein remaining atoms are carbon; or any of i) $R^4$ and $R^5$, ii) $R^6$ and $R^7$, iii) $R^4$ and $R^6$, iv) $R^9$ and $R^{10}$, v) $R^6$ and $R^{10}$, and vi) $R^4$ and $R^9$, together with the atom to which they are attached form a $C_{3-6}$cycloalkylene; or any two of $R^4$ through $R^7$, $R^9$ and $R^{10}$ together with the atom(s) to which they are attached form a 5 to 7-member saturated or unsaturated heterocycle wherein the ring optionally comprises an additional heteroatom selected from N, O, and S and wherein the remaining atoms are carbon; or $R^6$ and $R^{10}$ together with the atoms to which they are attached form a 4 to 6-member saturated heterocycle containing at least one O atom wherein the heterocycle optionally comprises an additional heteroatom selected from N, O, and S and wherein the remaining atoms are carbon; and $R^{11}$ and $R^{12}$ are independently H, $N(C_{1-6}alkyl)$, $C_{1-14}$alkyl, $C_{3-6}$cycloalkyl, aryl, arylalkyl, biaryl, biarylalkyl, or heteroarylalkyl; or $R^{11}$ and $R^{12}$ together with the two oxygen atoms to which they are attached form a 5 to 7-member saturated heterocycle wherein the 2, 3, or 4 additional atoms are carbon optionally substituted with $C_{1-6}$alkyl; or either or both of i) $R^4$ and and ii) $R^6$ and $R^{12}$ together with atoms to which they are attached form a 5 to 7-member saturated heterocycle containing one O atom and one P atom and where the remaining atoms are carbon; and wherein m, n, o, and p are independently selected from 0, 1, and 2 and wherein when L is $(CR^4R^5)_m(CR^6R^7)_n(CR^9R^{10})_o$, then m+n+o≥1; and wherein $R^3$ is $NH_2$, $CH_2NH_2$ or imidazolyl.

In some or any embodiments, the compound of formula V is that wherein L is selected from $CR^4=CR^6—(CR^9R^{10})_o$, $(CR^4R^5)_m—CR^6=CR^{10}$, $CF_2$, $(CR^4R^5)_m$, $O(CR^4R^5)_m$, $NH(CR^4R^5)_m$, $N(C_{1-6}alkyl)(CR^4R^5)_m$, $(CR^4R^5)_mO$, $(CR^4R^5)_mNH$, $(CR^4R^5)_mN(C_{1-6}alkyl)$, $(CR^4R^5)_mCF_2$ and $CF_2(CR^6R^7)_n$, and wherein m and n in L are independently 1 or 2.

In some or any embodiments, the compound of formula I or V is that wherein $(R^{12}O)(R^{11}O)P(=O)$-L-C(=O)— is selected from structures below:

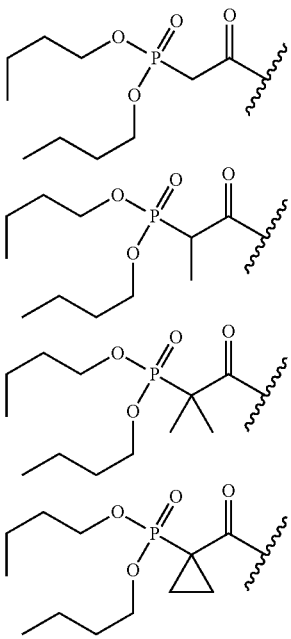
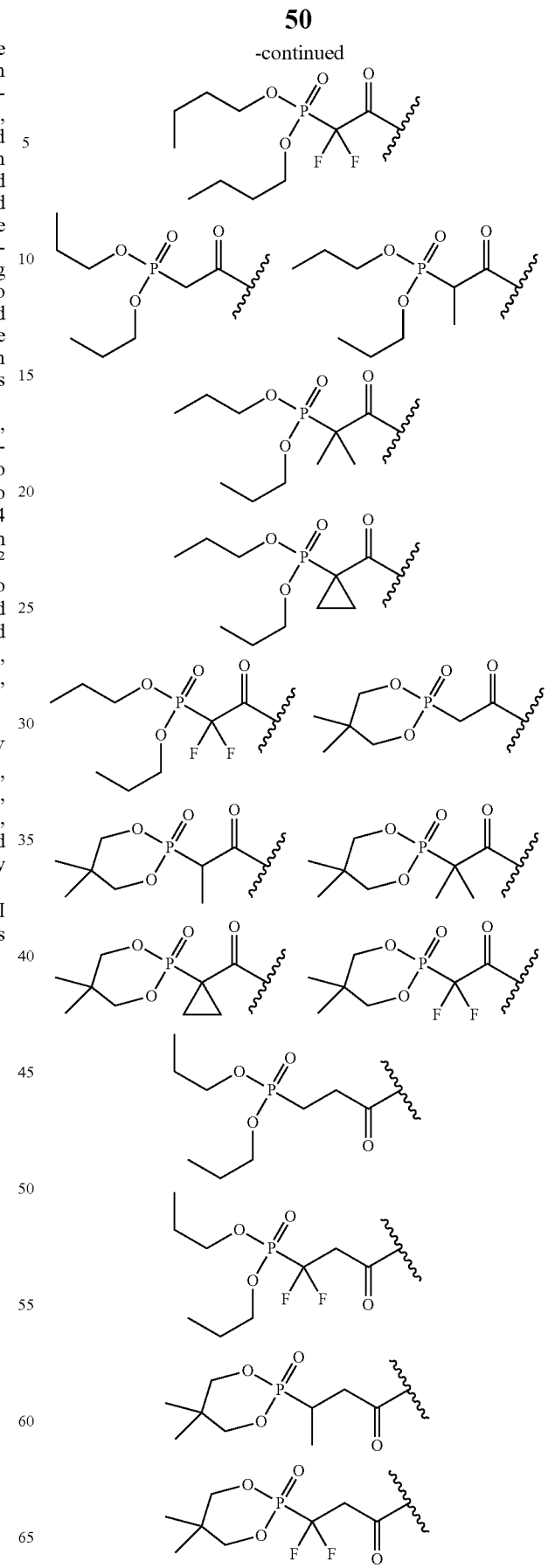

-continued

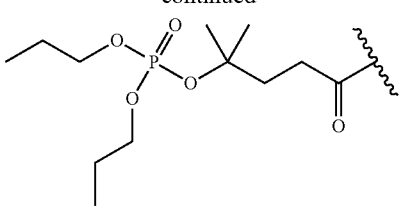
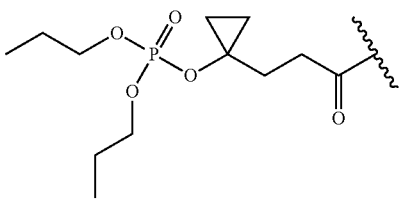
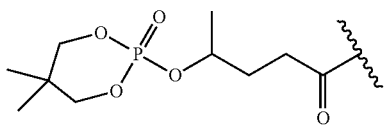
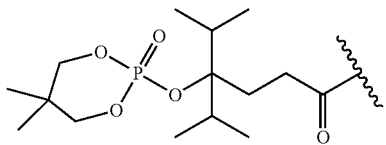
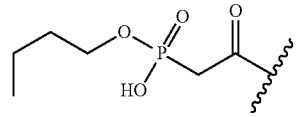
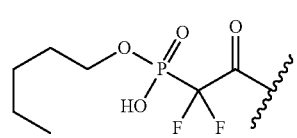
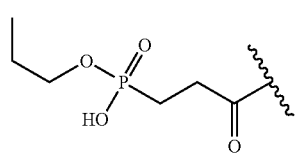
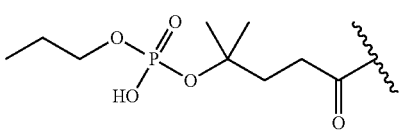
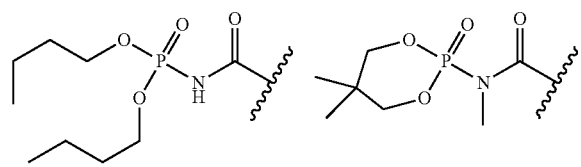
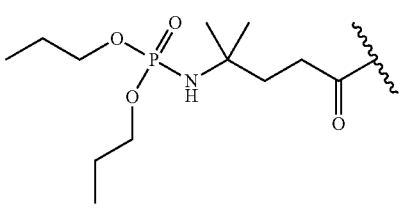

-continued

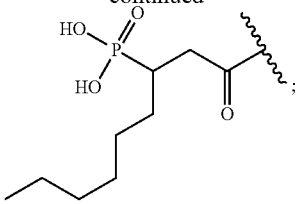

and all other groups are as defined in any of the aspects and/or embodiments described herein.

In some or any embodiments, the compound of formula I, II, III, IV, or V is that where $R^2$ is $(CR^4R^5)_m(CR^6R^7)_nC(=O)OR^8$ or $(CR^4R^5)_m(CR^6R^7)_nOC(=O)R^8$ m is 0, n is 1, and $R^6$ and $R^8$ together with the atoms to which they are attached form a 4 to 6-member saturated heterocycle containing at least one O atom wherein the heterocycle optionally comprises an additional heteroatom selected from N, O, and S, and wherein the remaining atoms are carbon; and all other groups are as defined in any of the aspects and/or embodiments described herein. In some or any embodiments, the compound of formula I, II, III, or IV is that where $R^2$ is dihydrofuran-2(3H)-one)-3-yl, aryl-dihydrofuran-2(3H)-one)-3-yl, $C_{1-14}$alkyl-dihydrofuran-2(3H)-one)-3-yl, tetrahydro-2H-pyran-2-one-3-yl, aryl-tetrahydro-2H-pyran-2-one-3-yl, or $C_{1-14}$alkyl-tetrahydro-2H-pyran-2-one-3-yl; and all other groups are as defined in any of the aspects and/or embodiments described herein.

In some or any embodiments the compound of formula I, II, III, IV, or V is that wherein any of i) $R^4$ and $R^5$, ii) $R^6$ and $R^7$, iii) $R^4$ and $R^6$, and iv) $R^9$ and $R^{10}$, together with the atom to which they are attached form a $C_{3-6}$cycloalkylene; and all other groups are as defined in any of the aspects and/or embodiments described herein.

In some or any embodiments the compound of formula I is that wherein each of [a], [b], and [c] is NH; and all other groups are as defined in any of the aspects and/or embodiments described herein.

In some or any embodiments the compound of formula I, II, III, IV, or V, or as defined in any of the embodiments described herein, is that wherein $R^3$ is $CH_2NH_2$, and wherein p is 1; and all other groups are as defined in any of the aspects and/or embodiments described herein.

In some or any embodiments, the compound is according to any of Examples 1-39 and 41-55 where the compound is a TFA or HCl salt or where the compound is not a TFA or HCl salt; or a pharmaceutically acceptable salt, solvate, or hydrate thereof. In some or any embodiments, the compound of formula I is according to any of Examples 1-18, 21-27, 30-39, 41-43, 45, and 48-55 where the compound is a TFA or HCl salt or where the compound is not a TFA or HCl salt; or a pharmaceutically acceptable salt, solvate, or hydrate thereof.

In some or any embodiments the compound of formula I, II, III, IV, or V, or as defined in any of the embodiments described herein, is that with a half-life in mammalian blood from about 1 h and less than about 36 h.

In some or any embodiments the compound of formula I, II, III, IV, or V, or as defined in any of the embodiments described herein, is that with a half-life in mammalian blood of at least about 1 h but less or equal than about 12 h.

In some or any embodiments the compound of formula I, II, III, IV, or V, or as defined in any of the embodiments described herein, is that possessing at least 3-fold higher efficacy than polymyxin B in eradicating or preventing the growth of the pathogen *Pseudomonas aeruginosa* at identical drugs dosing, as determined by the bacterial colony-forming units count, or by the number of surviving mammals.

In some or any embodiments the compound of formula I, II, III, IV, or V, or as defined in any of the embodiments described herein, is that possessing at least 7-fold higher efficacy than polymyxin B.

In some or any embodiments the compound of formula I, II, III, IV, or V, or as defined in any of the embodiments described herein, is that, wherein the *Pseudomonas aeruginosa* infection is a lung infection or pneumonia.

In some or any embodiments, provided is a method for the treatment of a microbial or bacterial infection in a mammal comprising administering to the mammal a therapeutically effective amount of a compound of formula I, II, III, IV, or V, or as defined in any of the embodiments described herein. In some or any embodiments, provided is a method for the treatment of a microbial or bacterial infection in a mammal comprising administering to the mammal a therapeutically effective amount of a compound of formula I, II, III, IV, or V, or as defined in any of the embodiments described herein wherein the compound is administered to the mammal orally, parenterally, transdermally, topically, rectally, or intranasally in a pharmaceutical composition, including an aerosol form. In some or any embodiments, the method is that wherein the microbial infection is a Gram-negative, Gram-positive, or mycobacterial infection. In some or any embodiments, the method is that wherein the microbial infection is caused by microorganisms selected from *Pseudomonas aeruginosa*, *Acinetobacter baumannii*, *Escherichia coli*, or *Klebsiela pneumoniae*, including polymyxin B or colistin-resistant infection. In some or any embodiments, the method is that wherein the infection is a skin, soft tissue, respiratory, bone, or an eye infection. In some or any embodiments, the method is that wherein the treatment of a microbial or bacterial infection has duration of 14 days or longer, and without manifesting of apparent nephrotoxicity in the mammal under the therapy.

In some or any embodiments is provided a pharmaceutical composition comprising a therapeutically effective amount of a compound of a compound of formula I, II, III, IV, or V, or as defined in any of the embodiments described herein, and a pharmaceutically acceptable carrier.

In some or any embodiments is an intermediate of the following formula

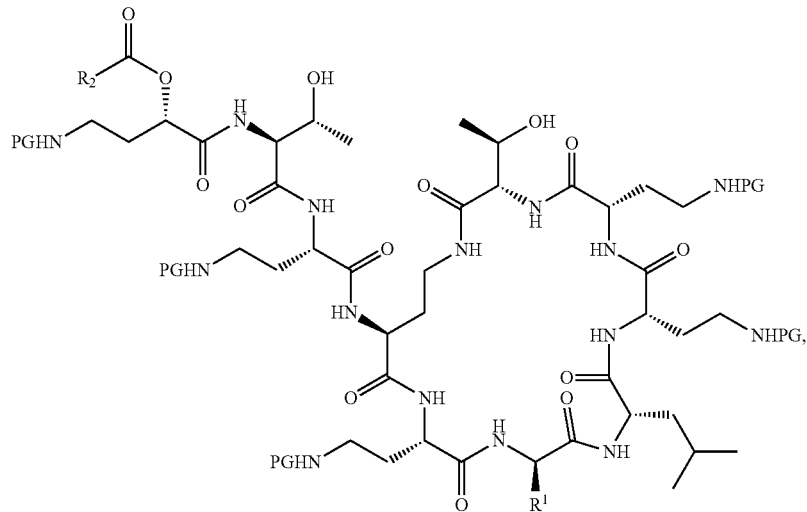

Intermediate 2 wherein PG is a nitrogen protecting group, such as Boc; and $R^1$ and $R^2$ are as defined in the Summary of the Invention or any of the embodiments described herein.

In some or any embodiments is an intermediate of the following formula

Intermediate 4

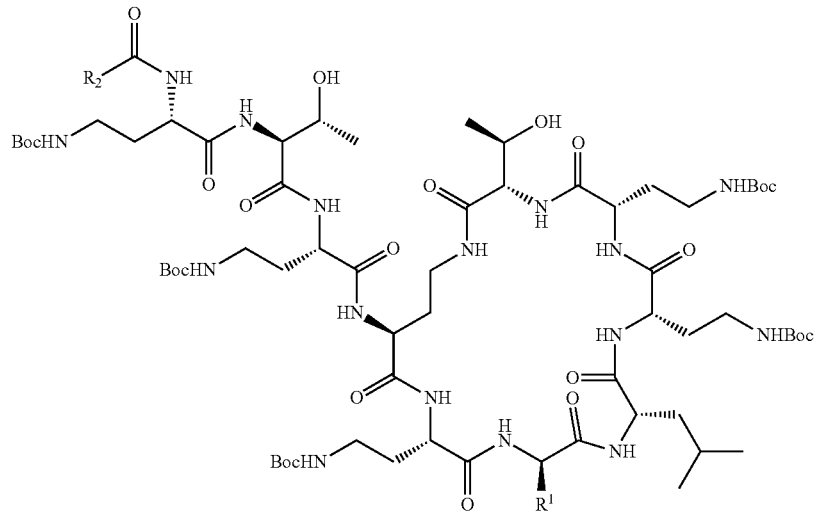

wherein PG is a nitrogen protecting group, such as Boc; and $R^1$ and $R^2$ are as defined in the Summary of the Invention or any of the embodiments described herein.

In some or any embodiments is an intermediate of the following formula

Intermediate 5

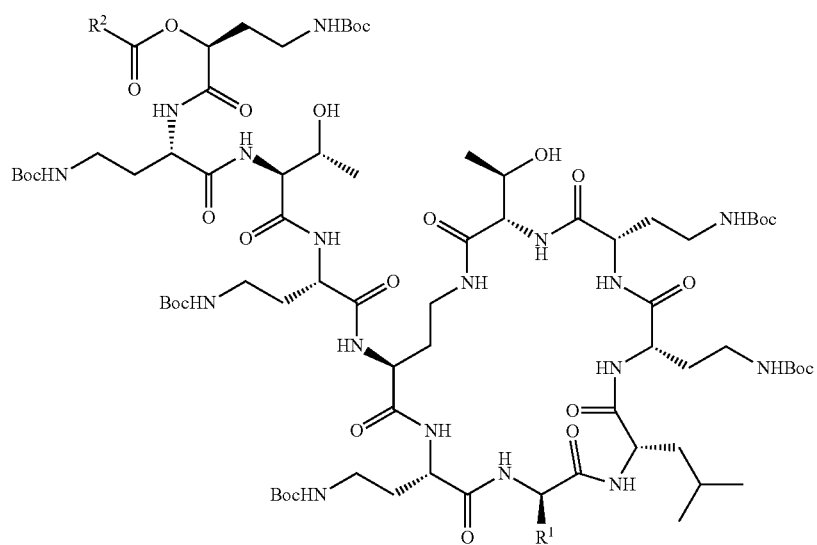

wherein PG is a nitrogen protecting group, such as Boc; and $R^1$ and $R^2$ are as defined in the Summary of the Invention or any of the embodiments described herein.

General Synthetic Schemes

The compounds of this invention can be prepared in accordance with one or more of the Schemes discussed below. General syntheses of certain polymyxin and colistin starting materials have been described in the literature. For example, the preparation of Boc-protected polymyxin nonapeptide was described by O'Dowd et al. in *Tetrahedron Lett.* 2007, vol. 48, pp. 2003-2005. Additional protected polymyxin B nonapeptide and colistin nonapeptide derivatives can be prepared as described by Okimura et al. in *Chem. Pharm. Bull.* 2007, vol. 55, pp. 1724-1730. Likewise, the general peptide acylation chemistry described in the ref. *Tetrahedron Lett.* 2007, vol. 48, pp. 2003-2005 could be used to introduce side chain $R^2$ groups of this invention to arrive at novel compounds invented herein.

The Schemes are presented as illustration only, as multiple specific variations thereof can be employed to access specific compounds, (such as noted above in preferred embodiments) using common building blocks and conventional protection-deprotection methods (such as Boc-, Cbz, and silicon-protection chemistry). Syntheses of the key intermediates have been described elsewhere.

Thus, an exemplary general synthesis of the compounds of formula II is illustrated in the Scheme 1. The intermediate 1 (for $R^1$ is $CH_2Ph$) is made just as described in the ref. *Tetrahedron Lett.* 2007, vol. 48, pp. 2003-2005 (compound 4 therein, PMBN-Boc$_4$). The intermediate 1 (for $R^1$ is $CHMe_2$) can be prepared, for example, as described in the PCT WO 2015/0031602.

Scheme 1. General synthesis of compounds of the formula II where p is 1.
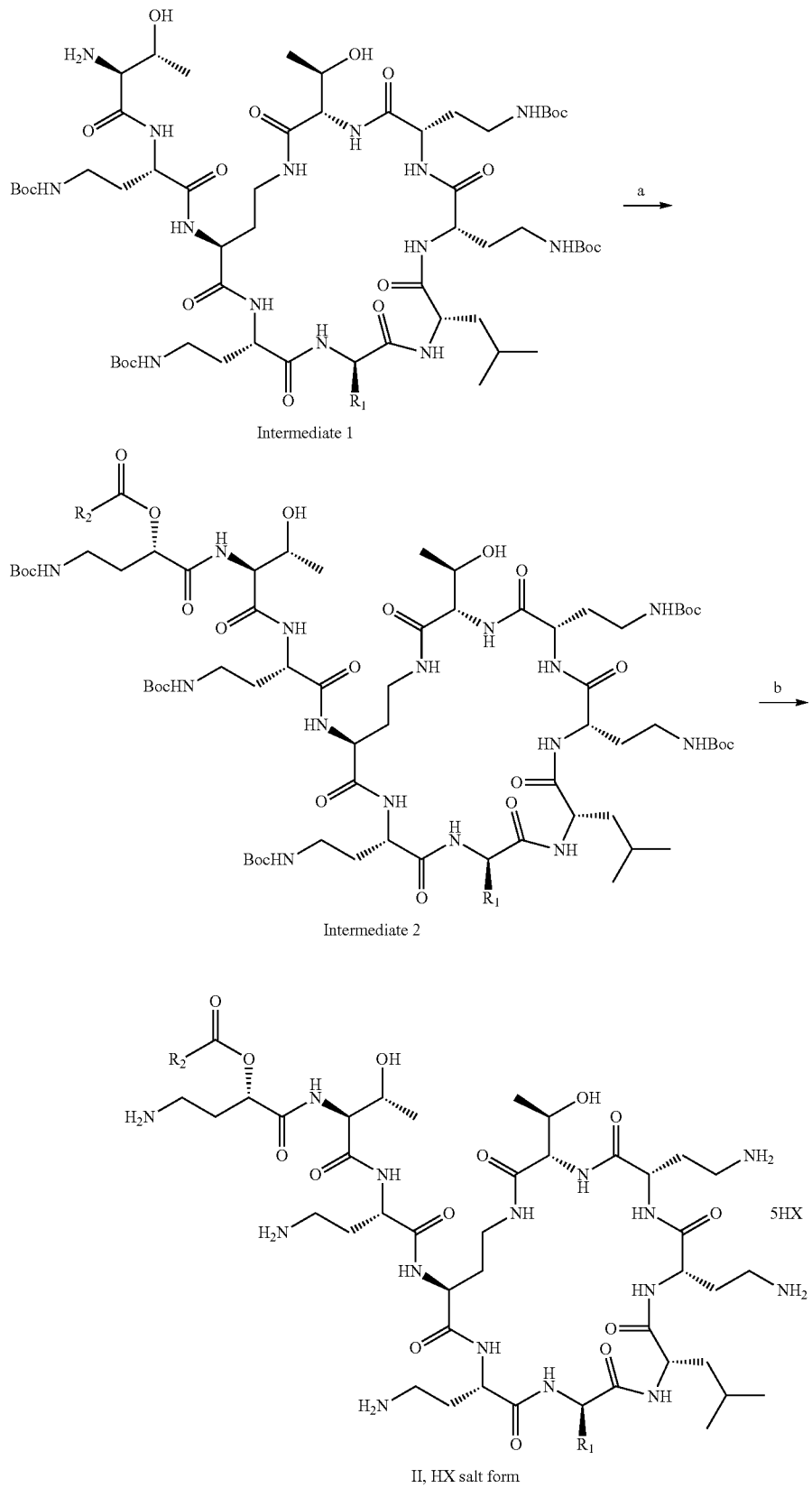

a) (S)-2-acyloxy-4-((tert-butoxycarbonyl)amino)butanoic acid [wherein acyl is R²C(=O)], a coupling agent (HATU, HBTU, DIC, EDC, CDI or the like), base (DIEA, TEA, and the like), one or more aprotic polar solvent(s) (DMF, NMP, MeCN, and the like); b) HX (X=OC(=O)CF$_3$, OC(=O)H, Cl, or the like), optional scavenging reagent (TES, water, anisole, ethanedithiol, and the like), one or more solvent(s) (DCM, DCE, dioxane, MeTHF, or the like).

Other amino acid building blocks, such as (S)-2-acyloxy-4-((tert-butoxycarbonyl)amino)butanoic acid, are readily prepared, for example, by the acylation of commercial (S)-2-hydroxy-4-((tert-butoxycarbonyl)amino)butanoic acid with respective acyl chlorides of a structure R²C(=O)Cl. Optionally, other than tert-butoxycarbonyl (Boc) protective groups are employed, for example, benzyloxycarbonyl (Cbz) group, with subsequent addition of Cbz-deprotective step (for example, using H$_2$/Pd/C, or HBr—AcOH reagents). Variety of other protective groups could be employed, as reviewed, for example by in a monograph *Greene's Protective Groups in Organic Synthesis*, 2007, Wiley.

An exemplary general synthesis of the compounds of formula III is illustrated in the Scheme 2. The Intermediate 1 (for R¹ is CH$_2$Ph) as well as the two steps of this sequence to arrive at the Intermediate 3 is described in the ref. *Tetrahedron Lett.* 2007, vol. 48, pp. 2003-2005.

Scheme 2. General synthesis of the compounds of formula III where p is 1.

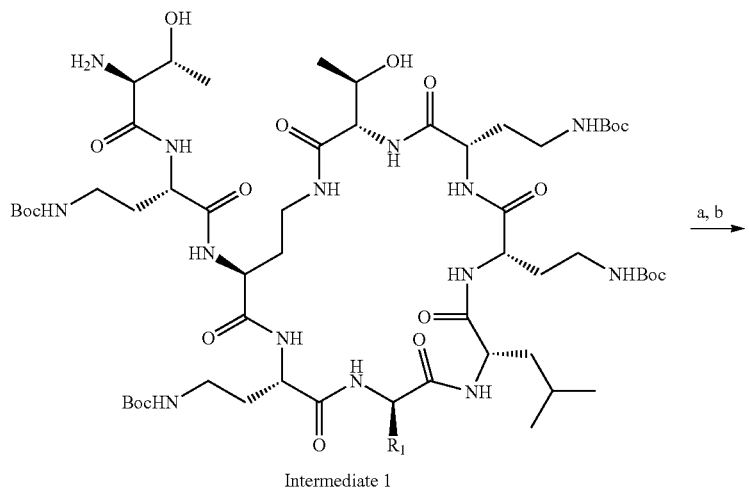

Intermediate 1

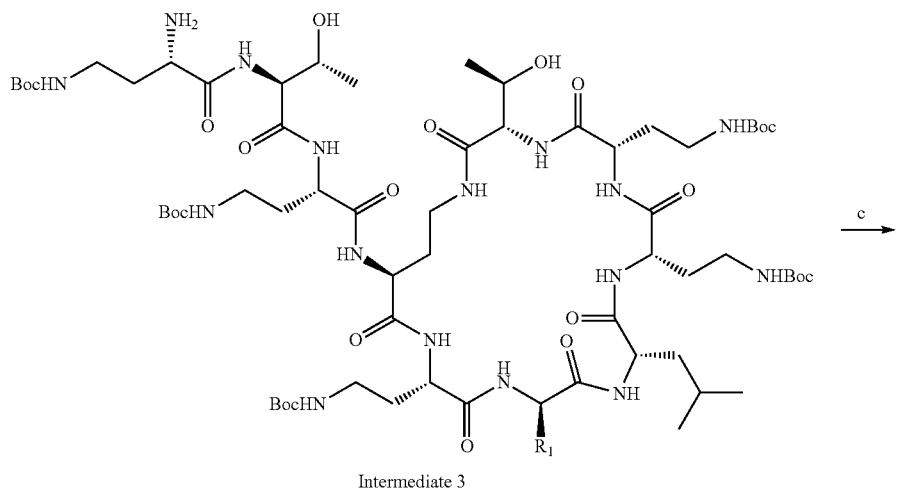

Intermediate 3

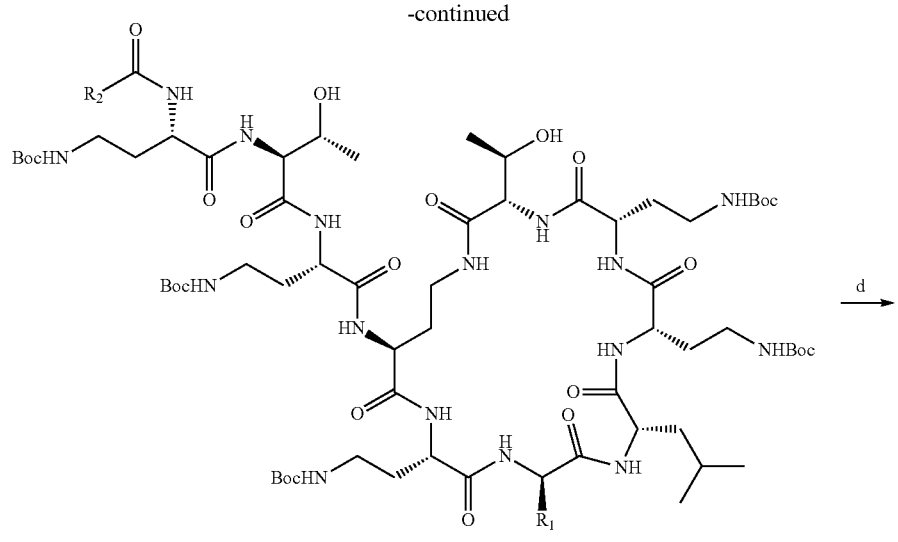

Intermediate 4

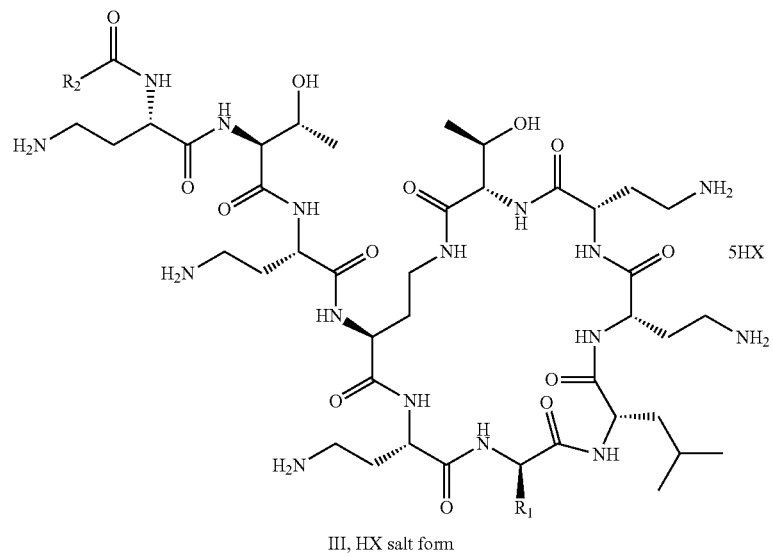

III, HX salt form a) Fmoc-Dab(Boc)-OPfp, DMF; or Fmoc-Dab(Boc)-OH, a coupling agent (HATU, HBTU, DIC, EDC, CDI and the like), base (DIEA, TEA, and the like), one or more aprotic polar solvent(s) NMP, MeCN, and the like); b) piperidine; c) $R^2C(O)OH$, a coupling agent (HATU, HBTU, DIC, EDC, CDI and the like), base (DIEA, TEA, or the like), one or more aprotic polar solvent(s) (DMF, NMP, MeCN, and the like); d) HX (X=$OCOCF_3$, Cl, and the like), optional scavenging reagent (TES, water, anisole, ethanedithiol, and the like), one or more solvent(s) (DCM, DCE, dioxane, MeTHF, and the like).

An exemplary general synthesis of the compounds of formula IV is illustrated in the Scheme 3. Again, the Intermediate 1 (for $R^1$ is $CH_2Ph$) and the first two steps of this sequence to arrive at the Intermediate 3 is described in the ref. *Tetrahedron Lett.* 2007, vol. 48, pp. 2003-2005.

Scheme 3. General synthesis of the compounds of formula IV where p is 1.
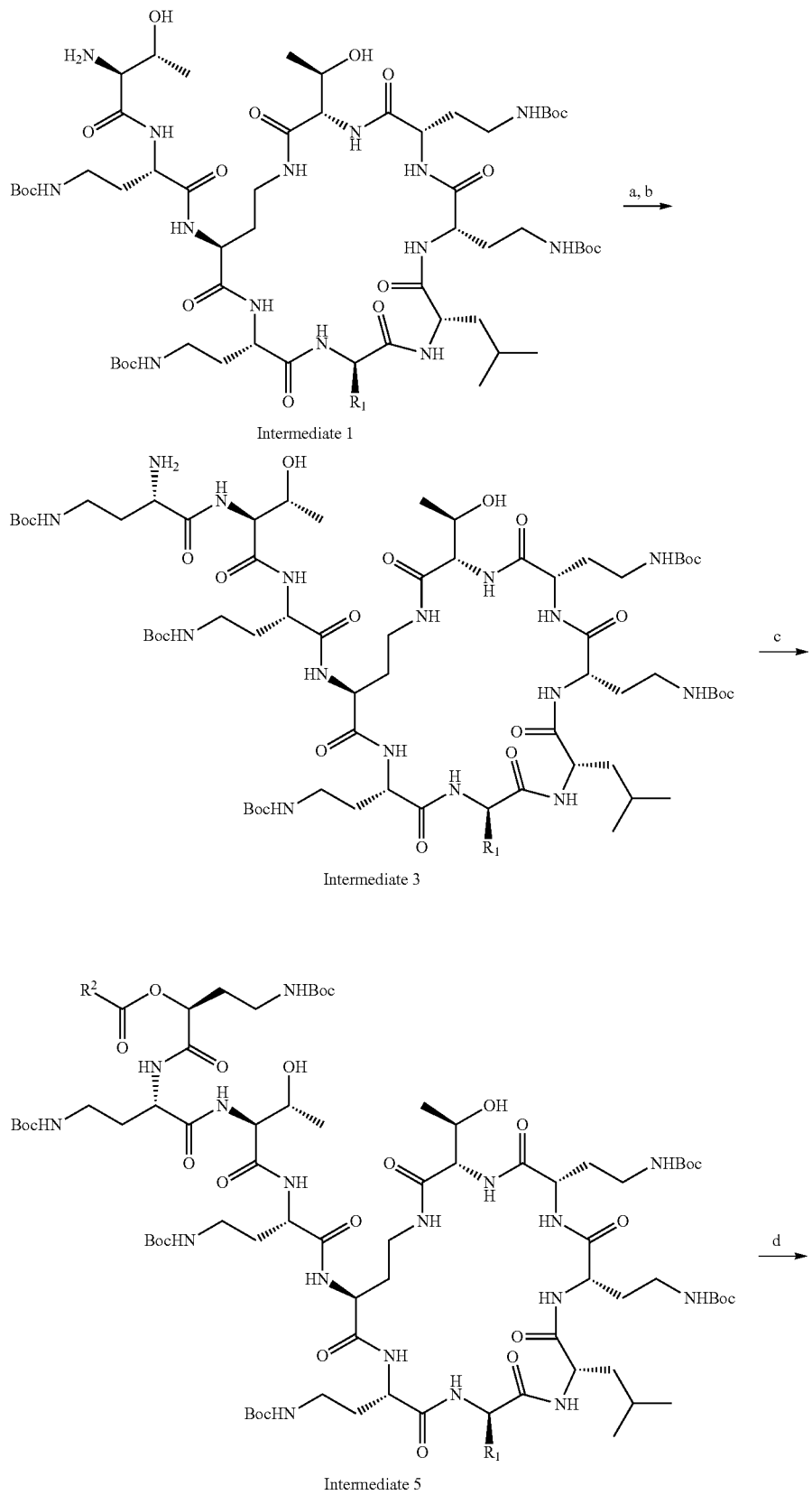
Intermediate 1
Intermediate 3
Intermediate 5

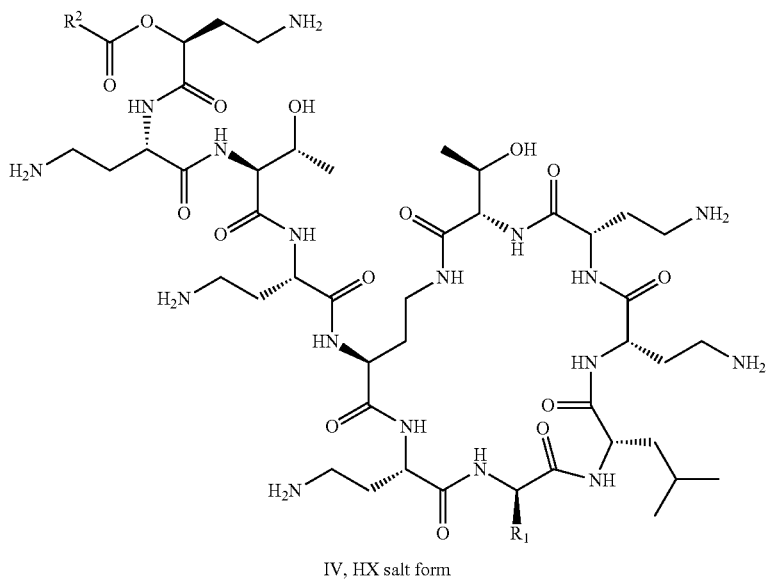

IV, HX salt form a) Fmoc-Dab(Boc)-OPfp, DMF; or Fmoc-Dab(Boc)-OH, a coupling agent (HATU, HBTU, DIC, EDC, CDI and the like), base (DIEA, TEA, and the like), one or more aprotic polar solvent(s) NMP, MeCN, and the like); b) piperidine; c) (S)-2-acyloxy-4-((tert-butoxycarbonyl)amino)butanoic acid [wherein acyl is $R^2C(=O)$], a coupling agent (HATU, HBTU, DIC, EDC, CDI and the like), base (DIEA, TEA, and the like), one or more aprotic polar solvent(s) NMP, MeCN, and the like); d) HX (X=OCOCF$_3$, Cl, and the like), optional scavenging reagent (TES, water, anisole, ethanedithiol, and the like), one or more solvent (DCM, DCE, dioxane, MeTHF, and the like).

Scheme 4. General synthesis of the compounds of formula V where p is 1.

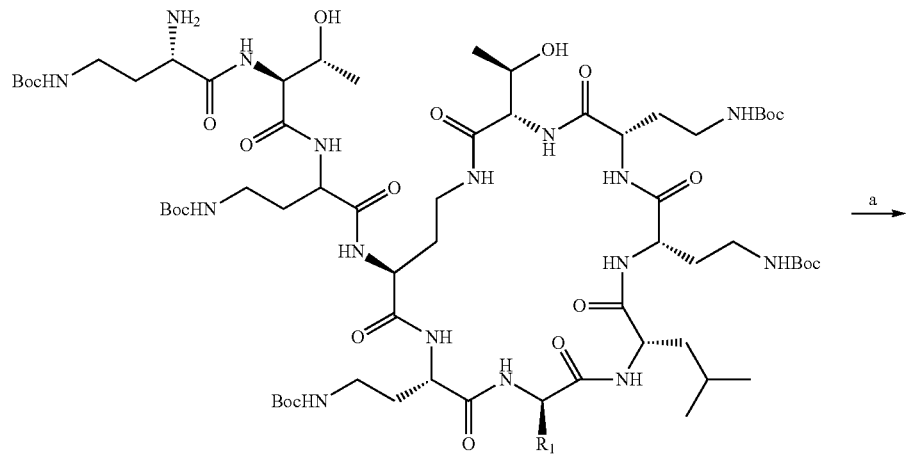

Intermediate 3

-continued
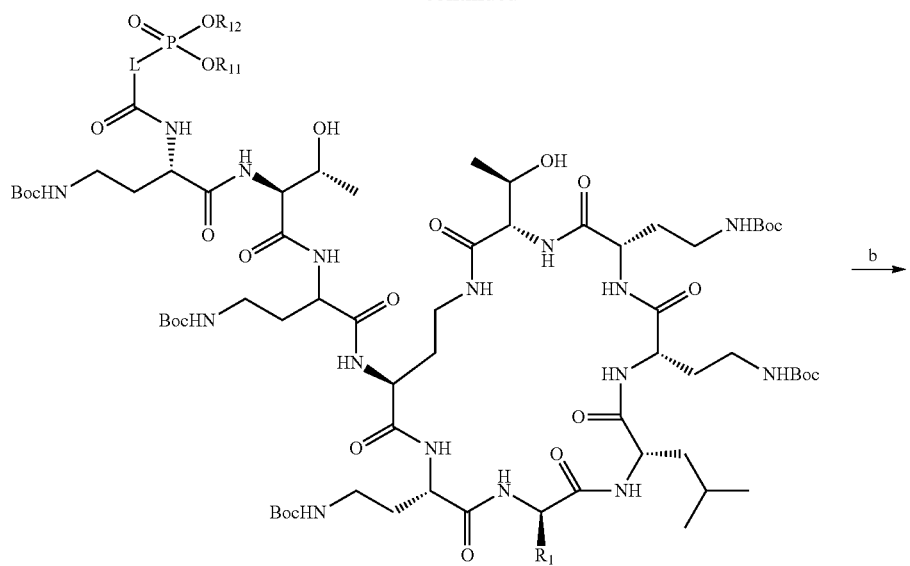
b →
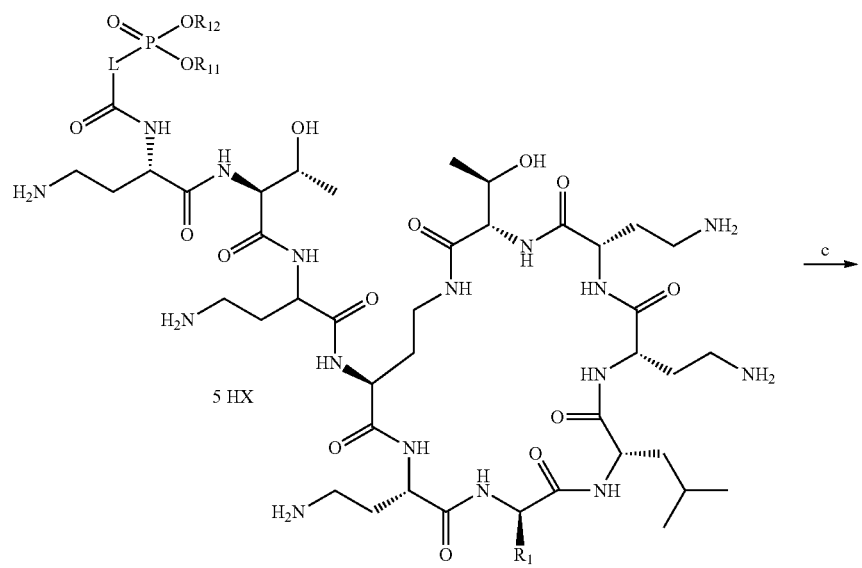
V, HX salt form
c →

-continued

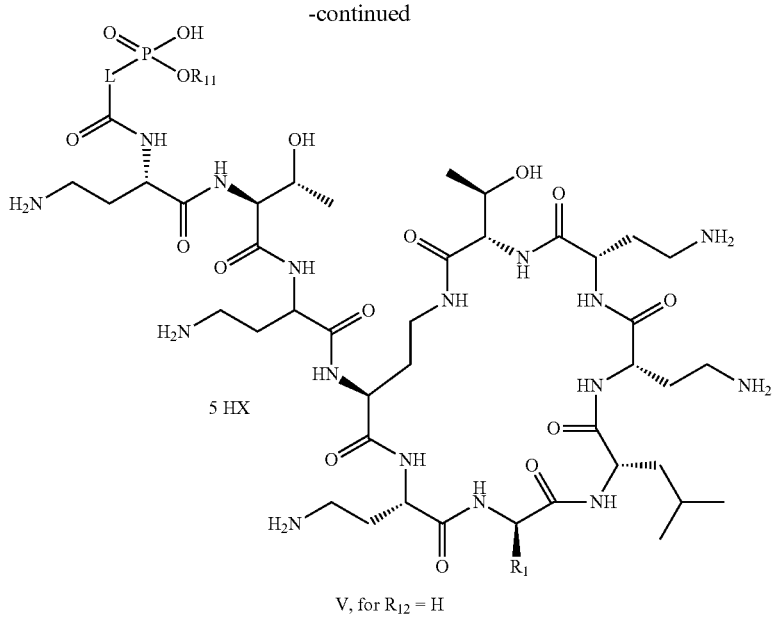

V, for $R_{12}$ = H a) $(R^{12}O)(R^{11}O)P(=O)$-L-COOH, a coupling agent (HATU, HBTU, TBTU DIC, EDC, CDI and the like), base (DIEA, TEA, and the like), one or more aprotic polar solvent (DMF, NMP, MeCN, or the like); b) HX (X=$OCOCF_3$, Cl, and the like), optional scavenging reagent (TES, water, anisole, ethanedithiol, and the like), one or more solvent (DCM, DCE, dioxane, MeTHF, and the like); c) NaI, LiI, $MgI_2$, $MgBr_2$, $Bu_4N^+I^-$ and the like), one or more solvent (acetone, dioxane, THF MeTHF, and the like).

To prepare additional compounds of formulas I-V incorporating the imidazolyl group $R^3$, diaminobutyric acid Fmoc-Dab(Boc)-OH reagent in above exemplary Schemes 1-4 is simply replaced by a protected imidazolyl amino acid derivative, such as Fmoc-His(Boc)-OH, and the syntheses are performed just as illustrated above.

Additional compounds within scope of this invention may incorporate various other amino acids in place of those of formulas I-V but closely related to same, such as for structures of formula VI below (Scheme 5). These are readily prepared via synthetic assembly of the core cyclopeptide, accomplished by standard methods for a solid phase synthesis of polymyxins and related cyclic peptides, as reported, for example, by Sharma et al. in *J. Peptide Res.* 1999, vol. 53, pp. 501-506; by de Visser et al. in *J. Peptide Res.* 2003, vol. 61, pp. 298-306; or by Magee et al. in *J. Med. Chem.* 2013, vol. 56, p 5079.

Scheme 5. General synthesis of compounds of formula VI analogous to those of formulas I-V incorporating various amino acids optionally replacing those in formulas I-V.

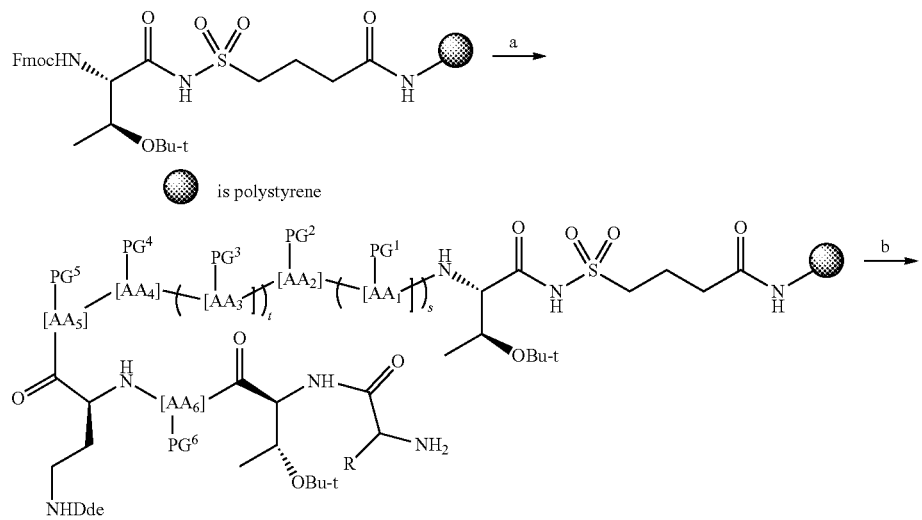

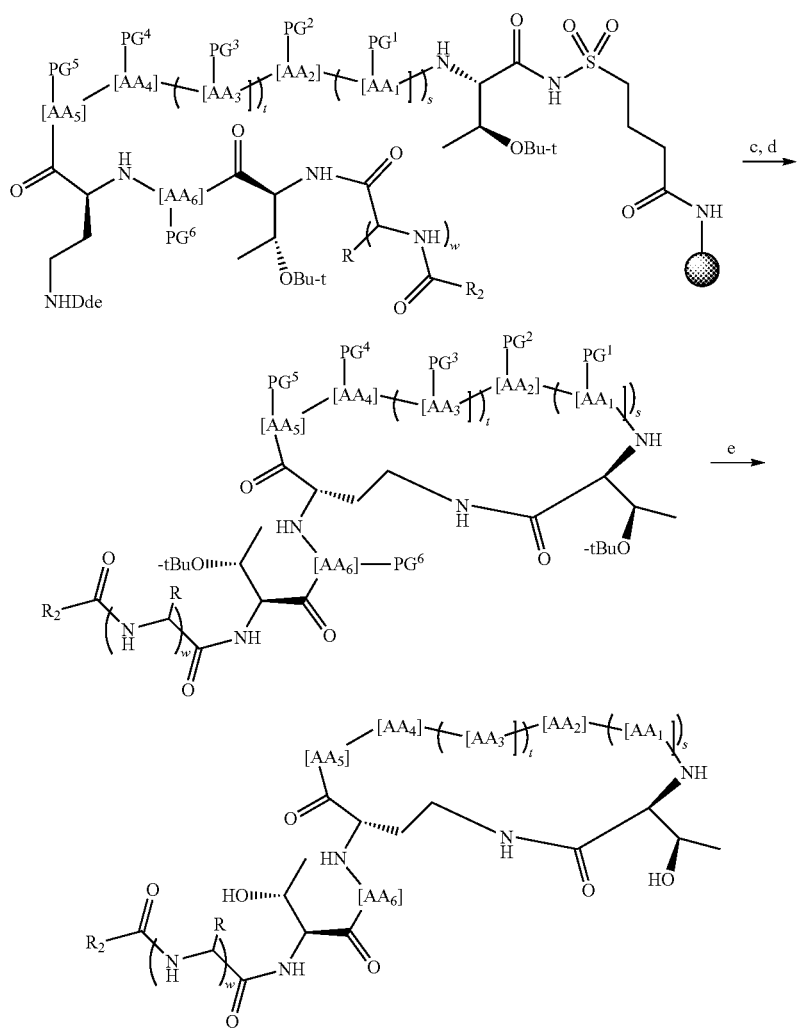
VI for R² designation, see formulas I-V
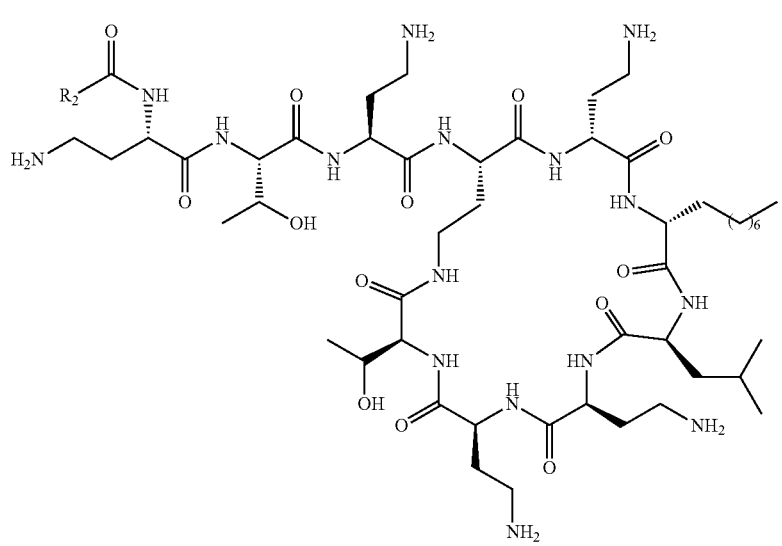
An illustrative structure of formula VI incorporating various amino acids optionally replacing those in formulas I-V.

a) sequential standard amino acid coupling and deprotection steps, repeated as required: i) 20% piperidine in DMF; ii) Fmoc-protected amino acid reagent, a coupling agent (HATU, HBTU, TBTU DIC, EDC, CDI and the like), base (DIEA, TEA, and the like), one or more aprotic polar solvent(s) NMP, MeCN, and the like); iii) 20% piperidine in DMF; b) $R^2COOH$, a coupling agent (HATU, HBTU, DIC, EDC, CDI and the like), base (DIEA, TEA, and the like), one or more aprotic polar solvent(s) NMP, MeCN, and the like); c) sequential steps: i) 2% hydrazine hydrate in DMF; ii) monomethoxytrityl chloride, DIEA; iii) TFA/TIS/DCM 3:5:92 (v/v/v); d) $ICH_2CN$, DIEA, NMP; e) HX (X=$OCOCF_3$, Cl, and the like), optional scavenging reagent (TES, water, anisole, ethanedithiol, and the like), one or more solvent(s) (DCM, DCE, dioxane, MeTHF, and the like); e) HX (X=$OCOCF_3$, Cl, and the like), optional scavenging reagent (TES, water, anisole, ethanedithiol, and the like), one or more solvent(s) (DCM, DCE, dioxane, MeTHF, and the like).

Following routine variations of these published procedures allows one skilled in art to incorporate any amino acid in place of a respective amino acid represented in compounds of formulas I-V, as illustrated in Scheme 5 for compounds of the formula VI (wherein optional AA1 through AA6 represent any (S) or (R)-amino acid, including those protected at optional $NH_2$, amidine, or guanidine group with an acid-cleavable protective group(s) (PG), such as Boc or Trt group; and wherein number of amino acids AA1 through AA6 may vary, for example, depending on the numbers s, t, and w independently selected from is 0, 1 or 2; and wherein R is any substituent that may be incorporated into amino acid, such as H, $H_2NC_{1-12}$alkyl, $H_2NC(=NH)C_{1-12}$alkyl, HN=CH—$NHC_{1-12}$alkyl, HN=$C(C_{1-12}$alkyl)-$NHC_{1-12}$alkyl, $H_2NC(=NH)NHC_{1-12}$alkyl, $C_{3-7}$cycloalkyl, aryl, heteroaryl, and the like; and wherein Dde is N-(1-(4, 4-dimethyl-2,6-dioxocyclohexylidene)ethyl protective group, or the like amine protective group).

Thus, the first intermediate of the Scheme 5 is prepared just as described by de Visser et al. in *J. Peptide Res.* 2003, vol. 61, pp. 298-306, and the rest of the synthesis is performed likewise, with only minor variations of this method, readily performed by one skilled in the peptide synthesis. Optionally, amino acids threonine and diaminobutyric acid may be independently replaced by other commonly known amino acids, such as serine, aminobutyric acid, diaminopropionic acid, histidine and the like. Likewise, natural L-amino acids may be replaced by D-amino acids, or synthetically available amino acids, including replacing alpha-amino acid with beta-amino acids, gamma-amino acids, and the like. One illustrative structure for a compound of formula VI is likewise is exemplified in Scheme 5. Resulted compounds of formula VI incorporating groups $R^2$, with the latter group defined just as for $R^2$ of compounds of formulas I-V, are within the scope of the present invention. Such compounds may likewise offer the benefits of enhanced over polymyxin B and colistin, such as greatly enhanced antibacterial activity and efficacy, including activity against polymyxin B or colistin-resistant bacteria, and/or possessing greatly reduced toxicity, such as nephrotoxicity, while being comparable to or superior than certain compounds of formulas I-V.

Additional syntheses of specific compounds described herein are illustrated by various synthetic Schemes for Examples below.

EXAMPLES

Embodiments described herein are described in the following examples, which are meant to illustrate and not limit the scope of this invention. Common abbreviations well-known to those with ordinary skills in the synthetic art used throughout. NMR means $^1H$ NMR spectra (δ, ppm), analyzed in $D_2O$ solution unless specified otherwise. LCMS means liquid chromatography mass-spectroscopy analysis. Mass-spectroscopy data (m/z) for a positive ionization method are provided. Chromatography means silica gel chromatography unless specified otherwise. TLC means thin-layer chromatography, and PTLC means preparative thin-layer chromatography. HPLC means reverse-phase high-performance liquid chromatography using C18 phase column eluting with gradient of 0.1% TFA in water-MeCN solutions (for TFA salts) or water-MeCN gradients (for HCl salts). DCM means dichloromethane, TEA means triethylamine, TES means $Et_3SiH$, TFA means $CF_3COOH$, Pfp means pentafluorophenyl, HATU is 1-[Bis(dimethylamino)methylene]-1H-1,2,3-triazolo[4,5-b]pyridinium 3-oxide hexafluorophosphate, HBTU is 2-(1H-benzotriazol-1-yl)-1,1,3,3-tetramethyluronium hexafluorophosphate, DIC is diisopropylcarbodiimide, CDI is carbonyldiimidazole, DIEA is diisopropylethylamine, DMF is dimethylformamide, NMP is N-methylpyridine, DCE is dichloroethane, THF is tetrahydrofuran, Fmoc is fluorenylmethyloxycarbonyl chloride, EDC is 1-ethyl-3-(3-dimethylaminopropyl)carbodiimide, Dab is diaminobutyric acid, Boc is tert-butoxycarbonyl, Trt is trityl. Other reagent abbreviations are employed as found in common synthetic literature, including the American Chemical Society list of abbreviations, such as found, for example, in the Journal of Organic Chemistry. Unless specified otherwise, all reagents were either from commercial sources, or made by conventional methods described in available literature. Standard procedures such as amide coupling and deprotection methods are interchangeable and applicable throughout experimental protocols.

Reference Example 1
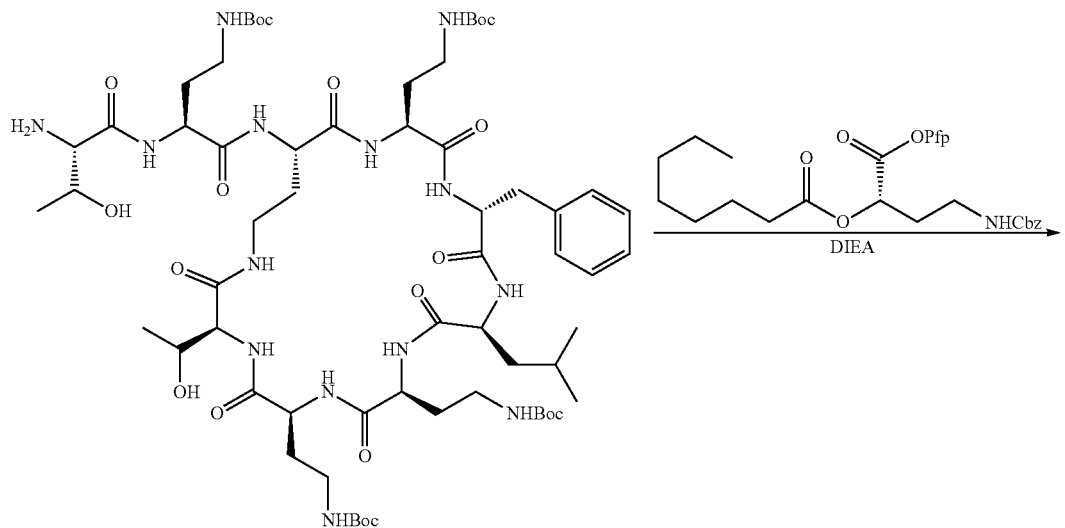
Intermediate 1 (R¹ = CH₂Ph)
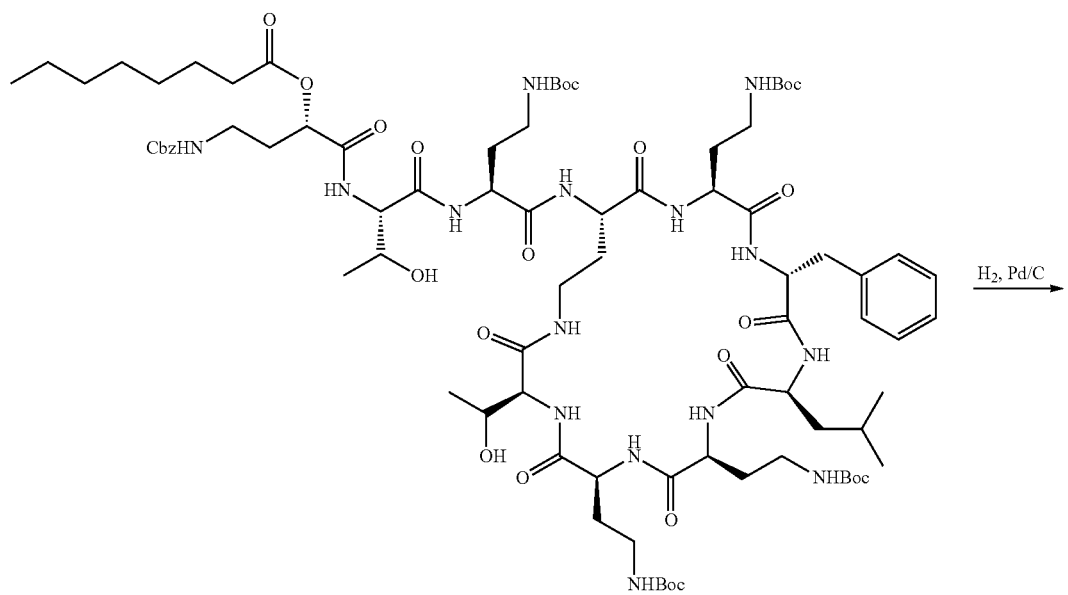
Intermediate 1A

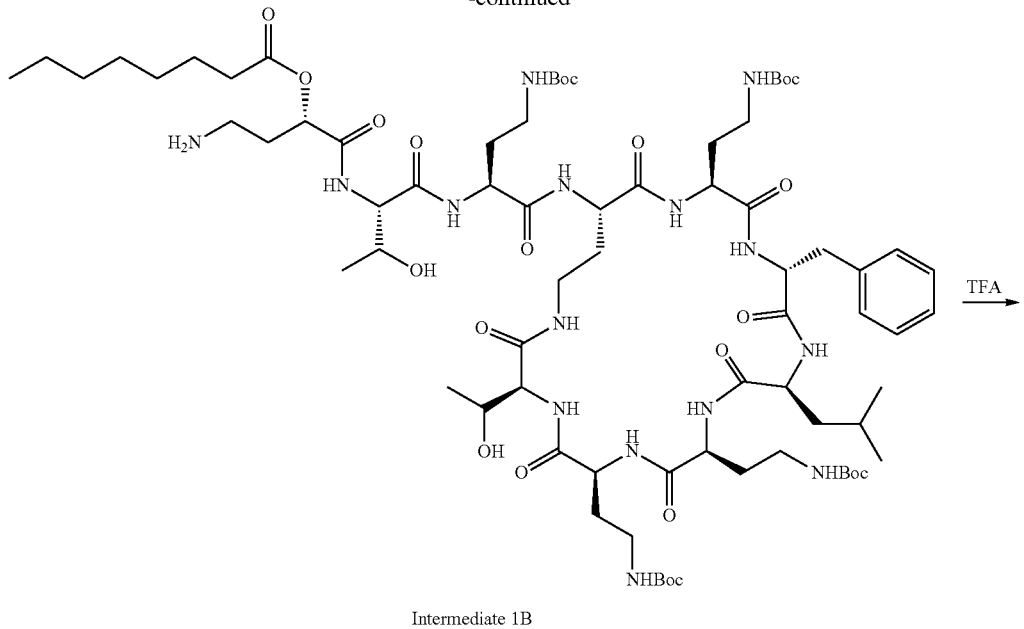

Intermediate 1B

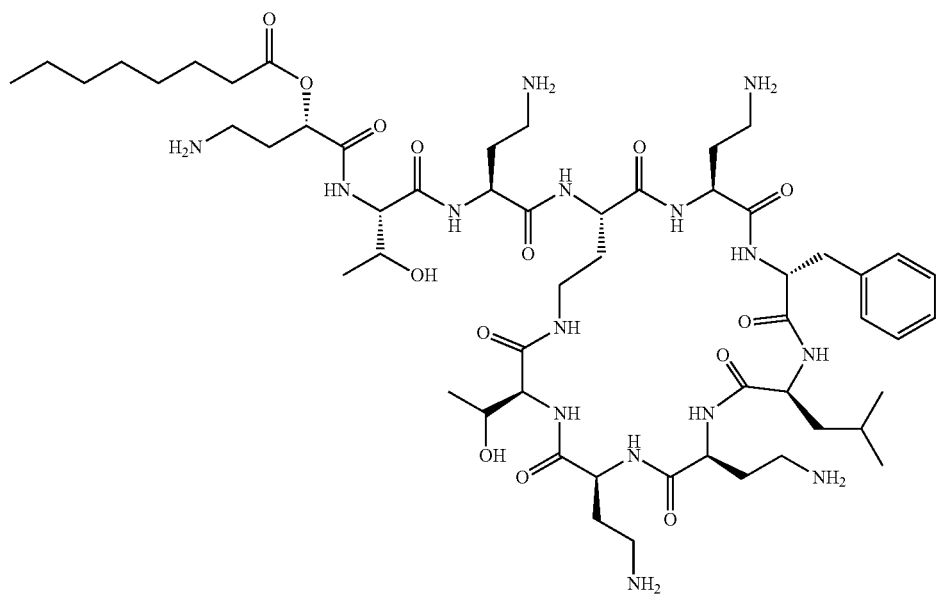

Intermediate 1 TFA salt

Intermediate 1A.

TEA (0.6 ml) was added to a mixture of Intermediate 1 (0.34 g; $R_1$=CH$_2$Ph, prepared as described in the ref. *Tetrahedron Lett.* 2007, vol. 48, pp. 2003-2005) in DMF at ca. −5° C., then ((S)-4-((tert-butoxycarbonyl)amino)-1-oxo-1-(pentafluorophenoxy)butan-2-yl octanoate (0.136 g) was added, and the resulted mixture was allowed to warm up to r.t. and stirred o.n. The mixture was treated with EtOAc/brine, extracted with EtOAc (3×), and the solution was evaporated under vacuum. The residue was purified by PTLC eluting with 10% MeOH/DCM to afford the Intermediate 1A.

Intermediate 1B.

The mixture of Intermediate 1A (58 mg) and 10% Pd/C (19 mg) in MeOH (3 mL) was hydrogenated (1 Torr) for 6 h. The mixture was filtered and solvent evaporated under vacuum to afford the crude product used directly at the next step. MS (m/z): 796 (M+2H).

Reference Compound of Example 1.

Intermediate 1B (0.34 g) was added to TFA/water (v/v 9:1, 6.8 mL) with TES (0.68 mL), and the mixture was stirred at r.t. for 20 min. Volatiles were removed under vacuum, and the resulted crude product was diluted with water and lyophilized o.n. The residue was purified by preparative HPLC to afford the product (TFA salt). MS (m/z): 596.0 (M+2H).

Example 2
Synthesis of the Compound of Example 2:
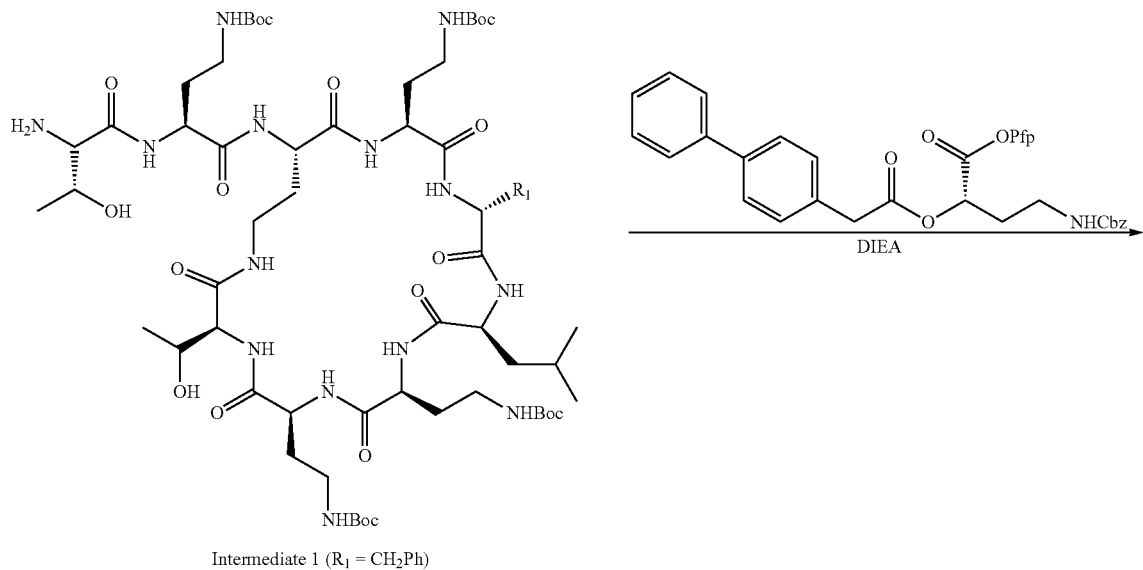
Intermediate 1 (R₁ = CH₂Ph)
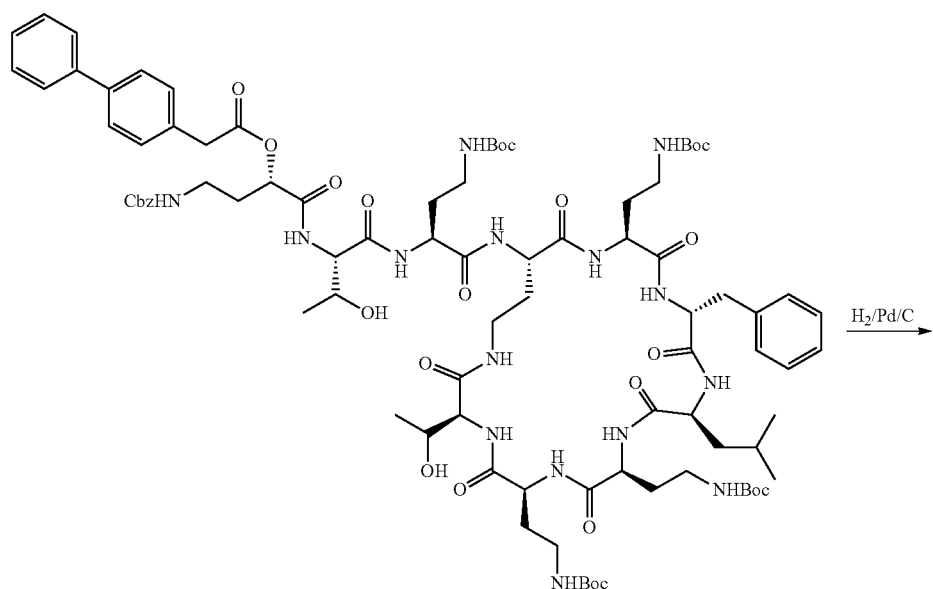
Intermediate 2A

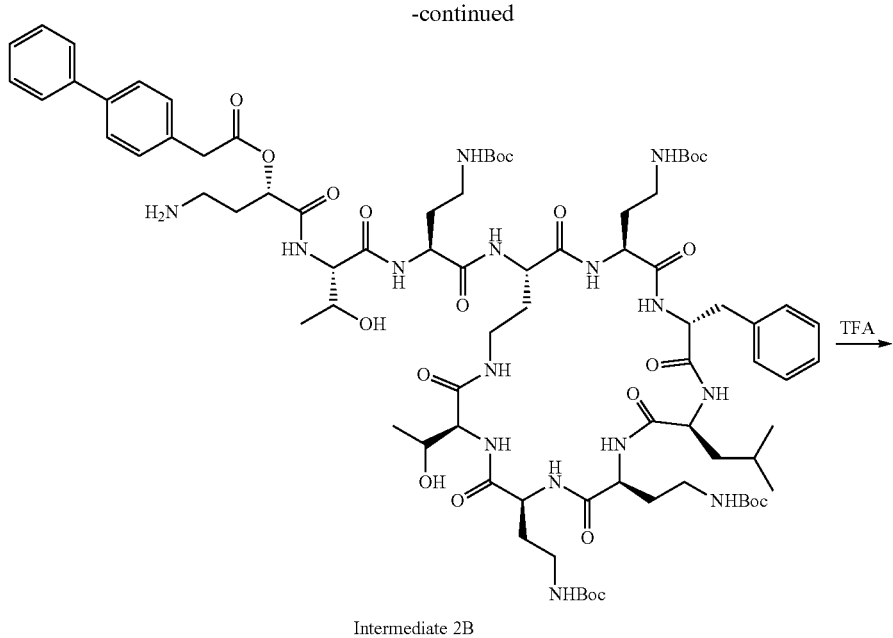

Intermediate 2B

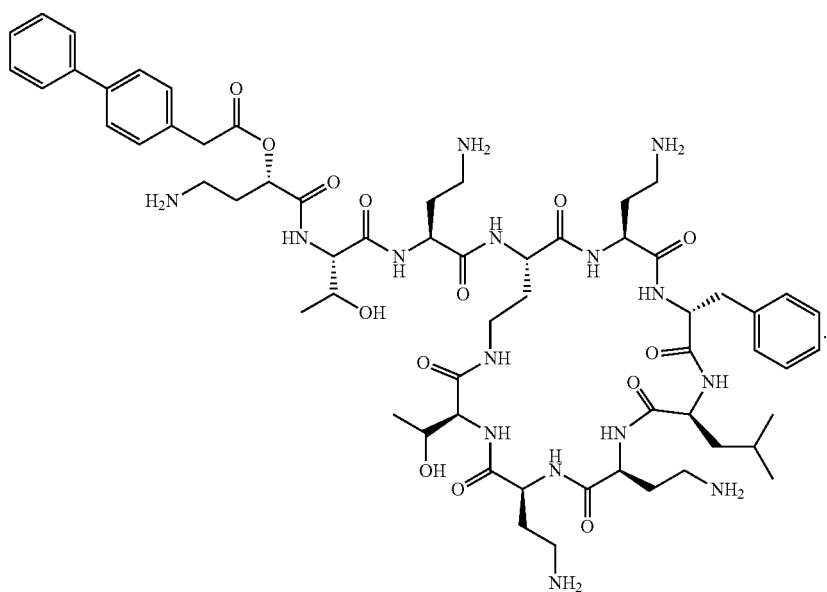

Example 2 TFA salt

The Compound of Example 2.

The Compound of Example 2 (TFA salt) was prepared according to the procedure for synthesis of the compound of Example 1 from Intermediate 1 ($R_1$=$CH_2Ph$) except using (S)-pentafluorophenyl 2-(2-([1,1'-biphenyl]-4-yl)acetoxy)-4-(((benzyloxy)carbonyl)amino)butanoate in place of ((S)-4-((tert-butoxycarbonyl)amino)-1-oxo-1-(pentafluorophenoxy)butan-2-yl octanoate. MS (m/z): 1258.6 (M+H).

Example 3
Synthesis of the Compound of Example 3:
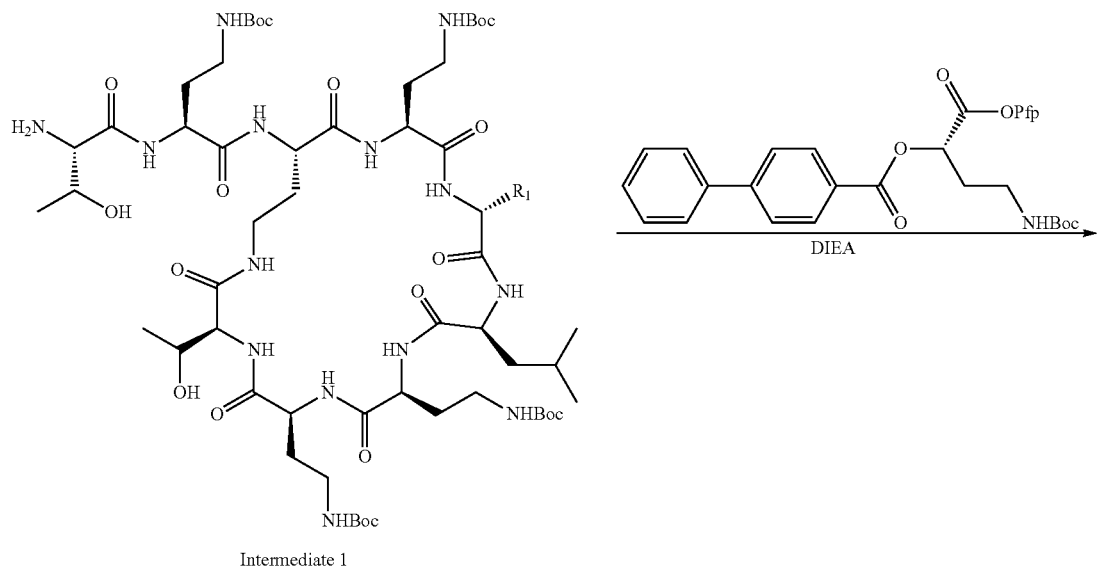
Intermediate 1
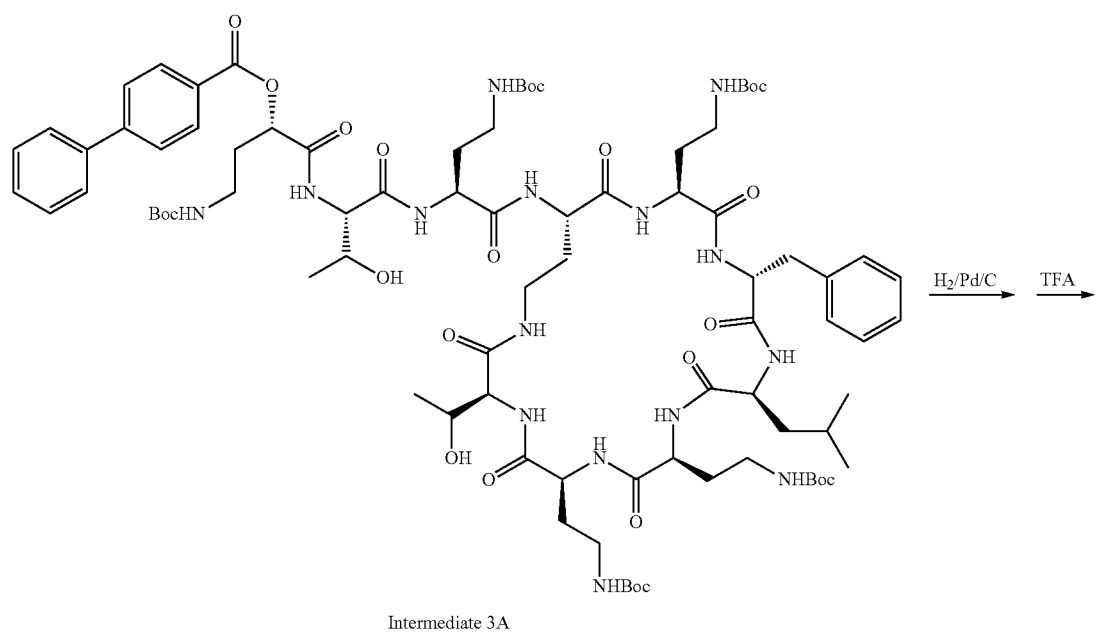
Intermediate 3A

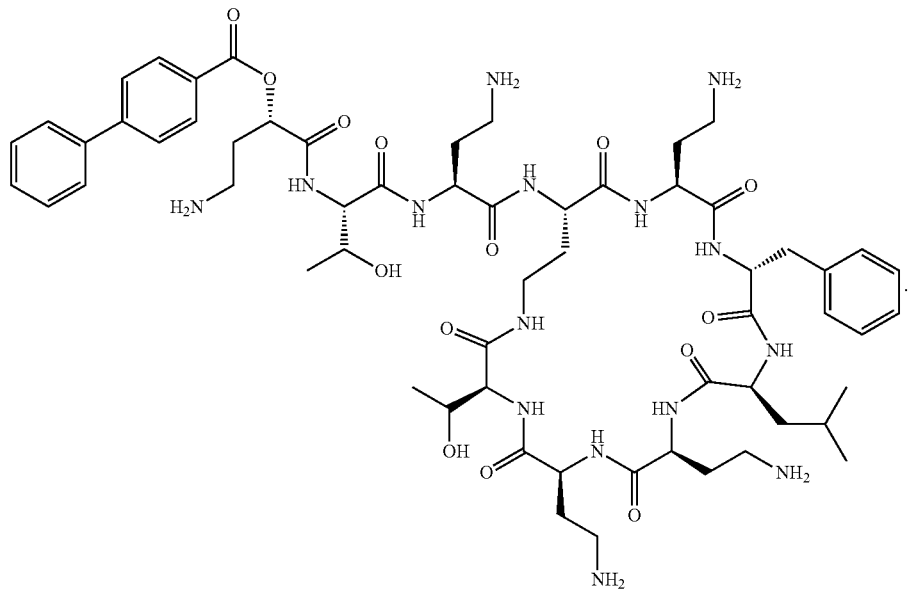

Example 3 TFA salt

The Compound of Example 3.

The Compound of Example 3 (TFA salt) was prepared according to the procedure for synthesis of the compound of Example 1 from Intermediate 1 ($R_1$=$CH_2Ph$) except using (S)-4-((tert-butoxycarbonyl)amino)-1-oxo-1-(perfluorophenoxy)butan-2-yl [1,1'-biphenyl]-4-carboxylate in place of ((S)-4-((tert-butoxycarbonyl)amino)-1-oxo-1-(pentafluorophenoxy)butan-2-yl octanoate. MS (m/z): 1244.5 (M+H).

Example 4

Synthesis of the Compound of Example 4:

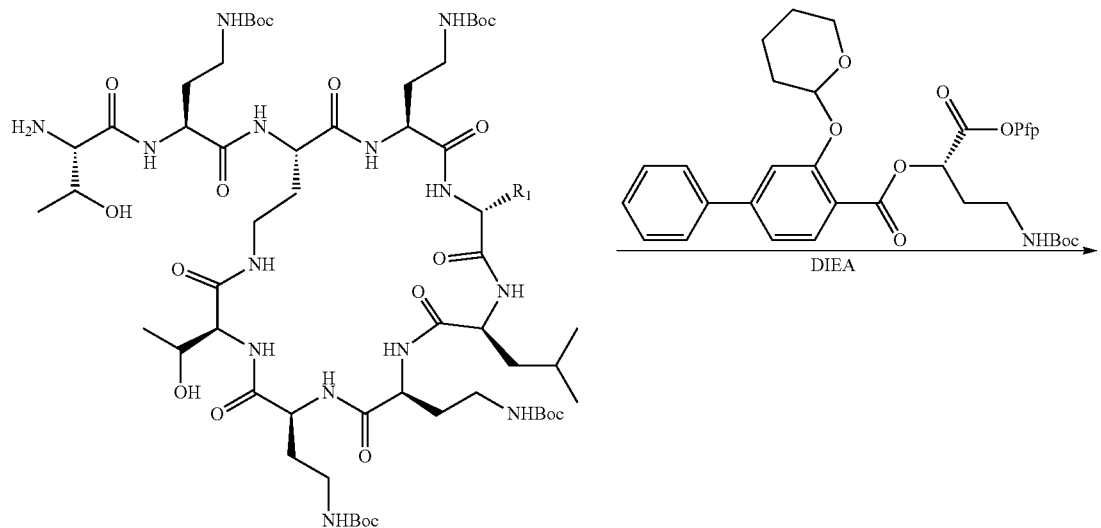

Intermediate 1 ($R^1$ = $CH_2Ph$)

-continued

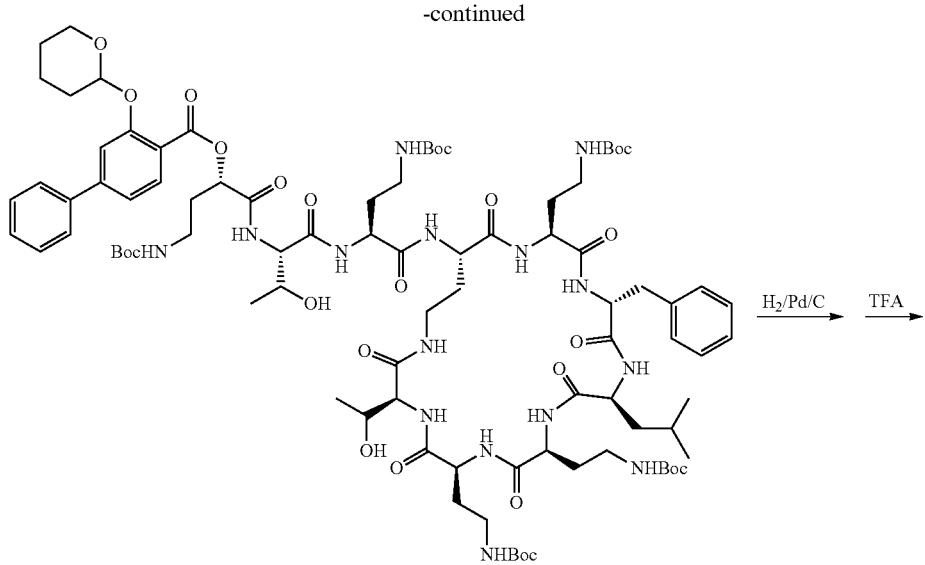

Intermediate 4A

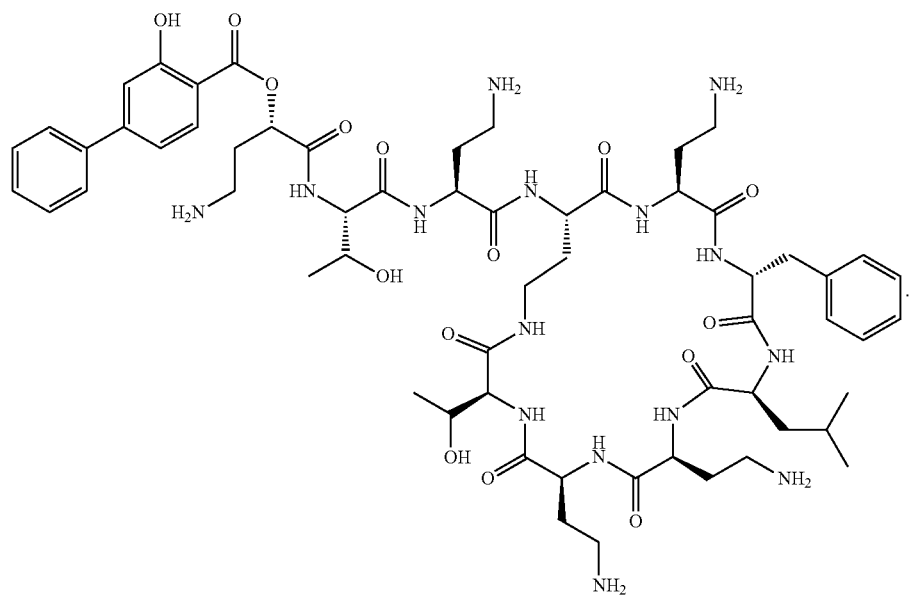

Example 4 TFA salt

The Compound of Example 4.

The Compound of Example 4 (TFA salt) is prepared analogously to the procedure for Example 1 from Intermediate 1 ($R_1$=CH$_2$Ph) using (S)-4-((tert-butoxycarbonyl) amino)-1-oxo-1-(pentafluorophenoxy)butan-2-yl 3-((tetrahydro-2H-pyran-2-yl)oxy)-[1,1'-biphenyl]-4-carboxylate in place of ((S)-4-((tert-butoxycarbonyl)amino)-1-oxo-1-(pentafluorophenoxy)butan-2-yl octanoate.

Example 5
Synthesis of the Compound of Example 5:
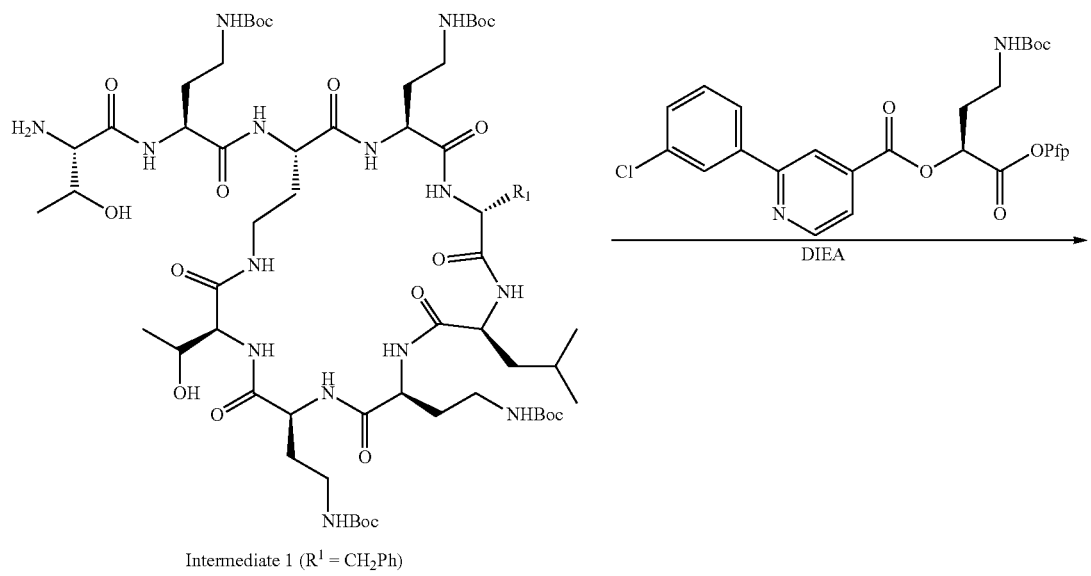
Intermediate 1 (R¹ = CH₂Ph)
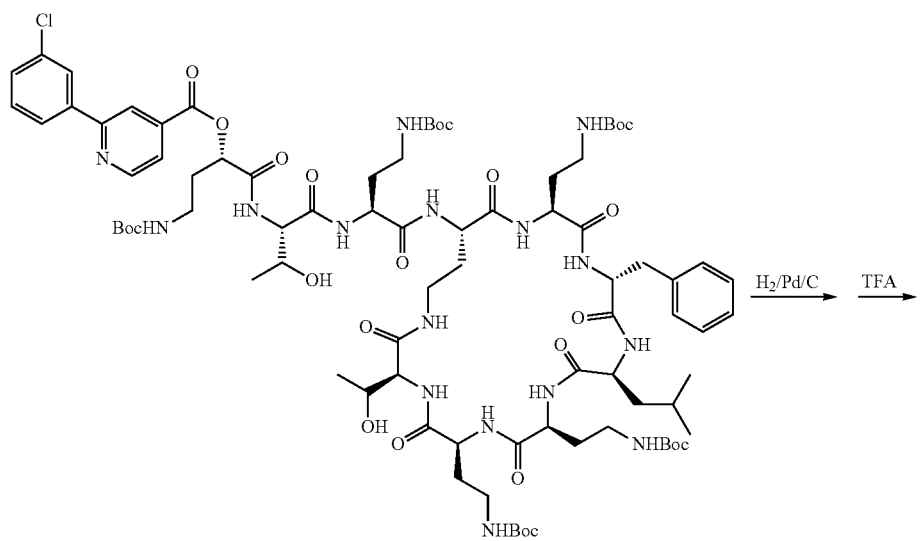
Intermediate 5A

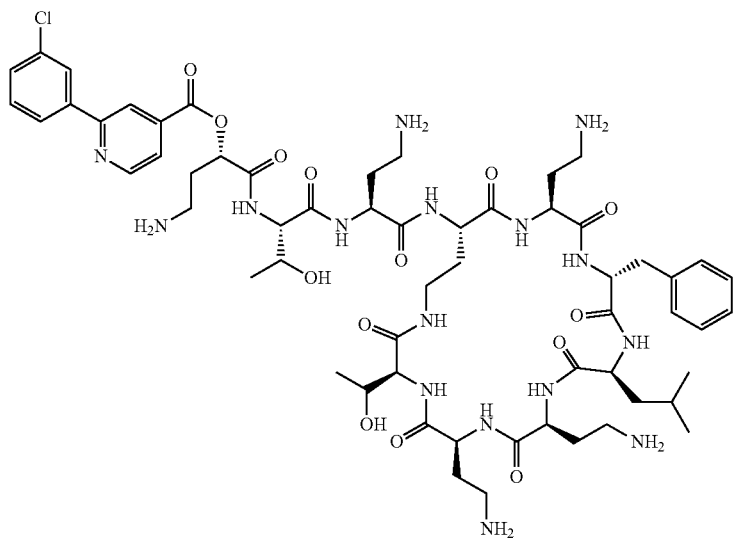

Example 5 TFA salt

The Compound of Example 5.

The Compound of Example 5 (TFA salt) is prepared analogously to the procedure for example 3 from Intermediate 1 (R$_1$=CH$_2$Ph) using (S)-4-((tert-butoxycarbonyl)amino)-1-oxo-1-(pentafluorophenoxy)butan-2-yl 2-(3-chlorophenyl)isonicotinate in place of (S)-4-((tert-butoxycarbonyl)amino)-1-oxo-1-(pentafluorophenoxy)butan-2-yl [1,1'-biphenyl]-4-carboxylate.

Example 6

Synthesis of the Compound of Example 6:

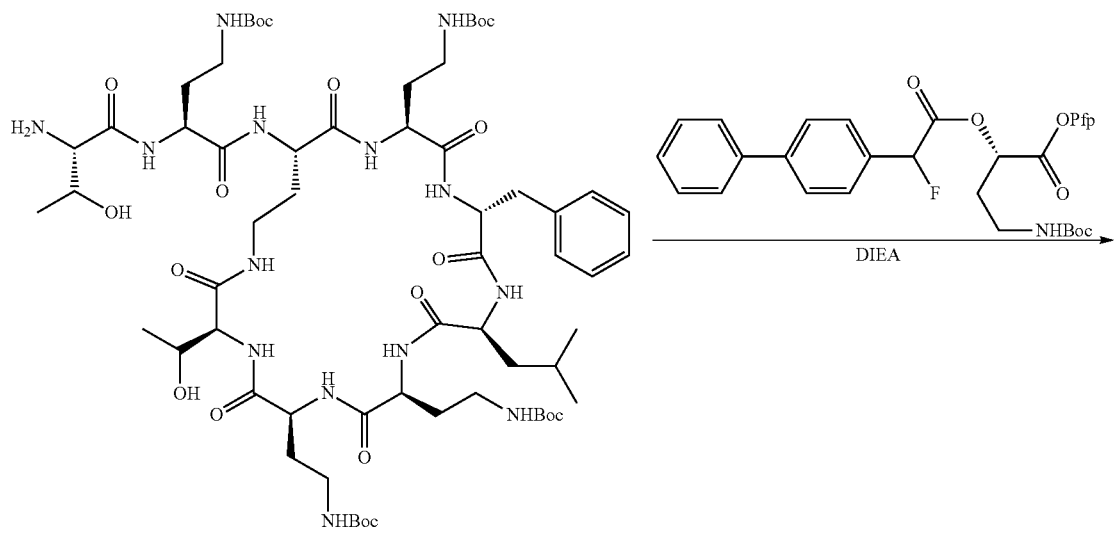

Intermediate 1 (R$_1$ = CH$_2$Ph)

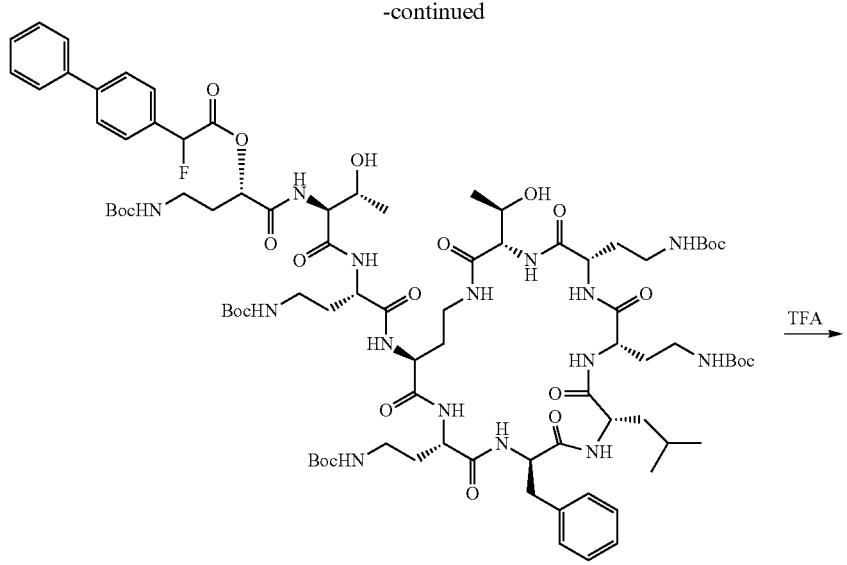
Intermediate 6A
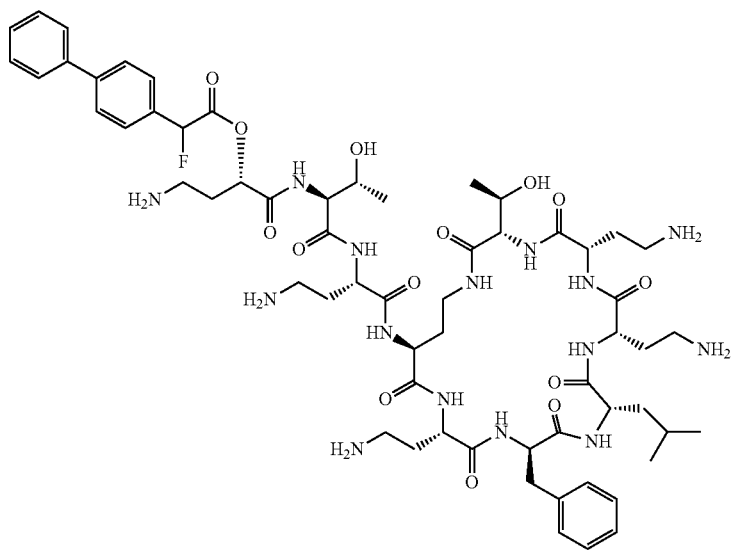
Example 6 TFA salt
The Compound of Example 6.
The Compound of Example 6 (TFA salt) is prepared from Intermediate 1 ($R_1$=$CH_2Ph$), just as described for Example 1 using (2S)-pentafluorophenyl 2-(2-([1,1'-biphenyl]-4-yl)-2-fluoroacetoxy)-4-((tert-butoxycarbonyl)amino)butanoate in place of ((S)-4-((tert-butoxycarbonyl)amino)-1-oxo-1-(pentafluorophenoxy)butan-2-yl octanoate.

Example 7
Synthesis of the Compound of Example 7:
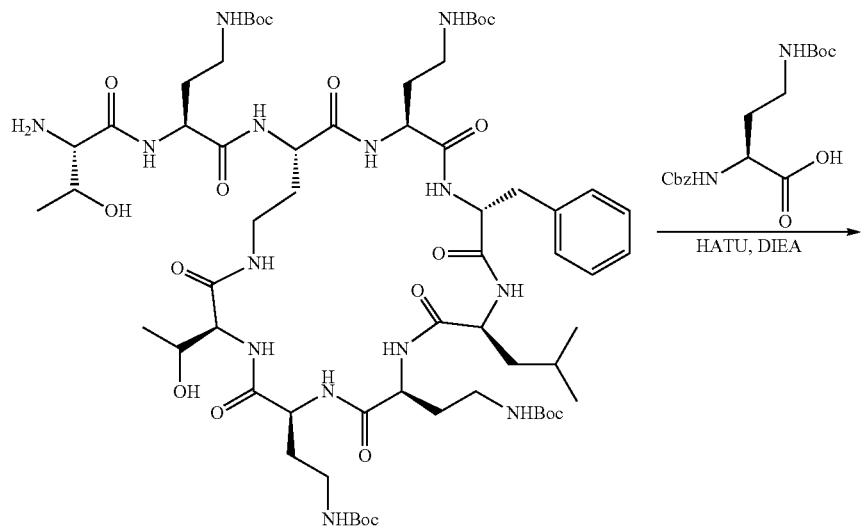
Intermediate 1 ($R_1$ = $CH_2Ph$)
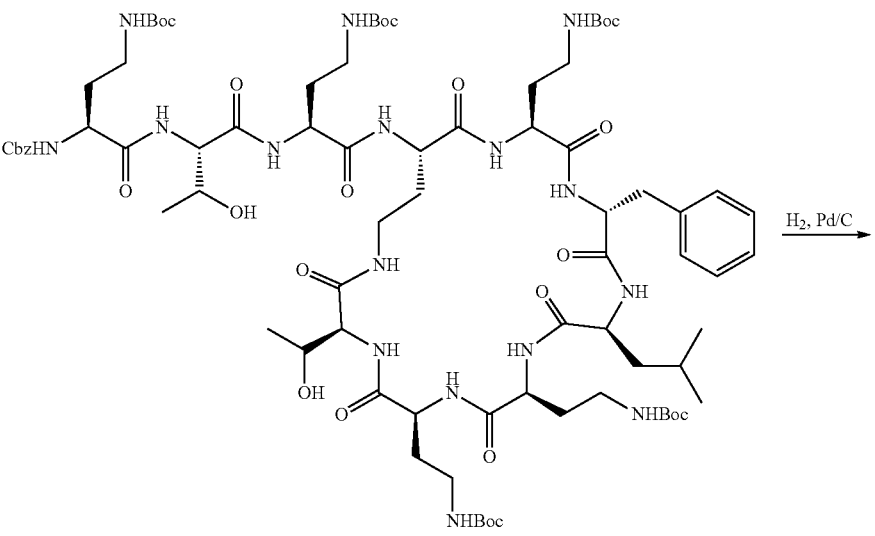
Intermediate 7A 97
98
-continued
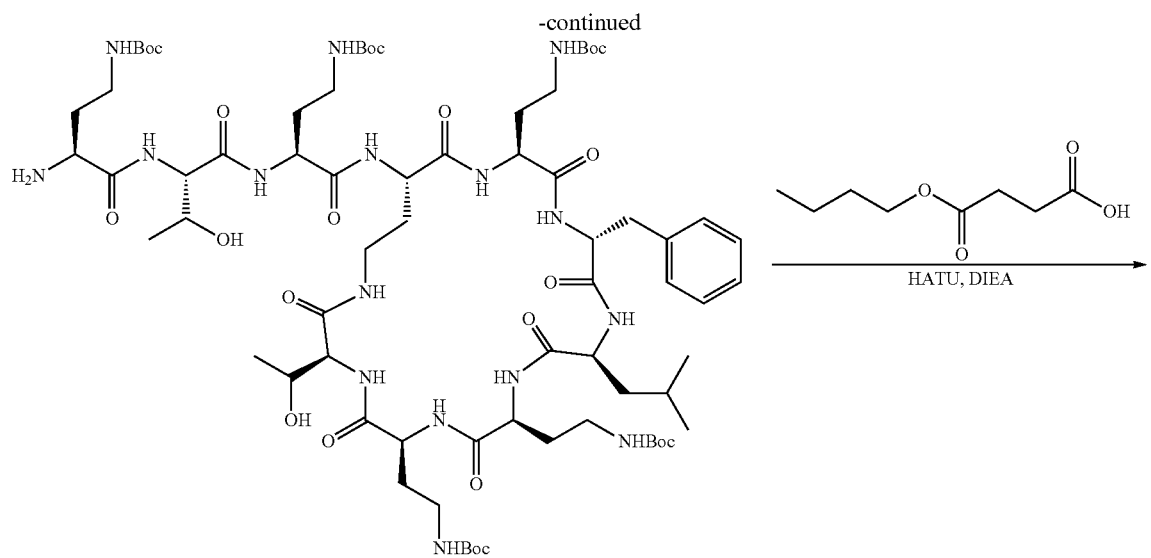
Intermediate 7
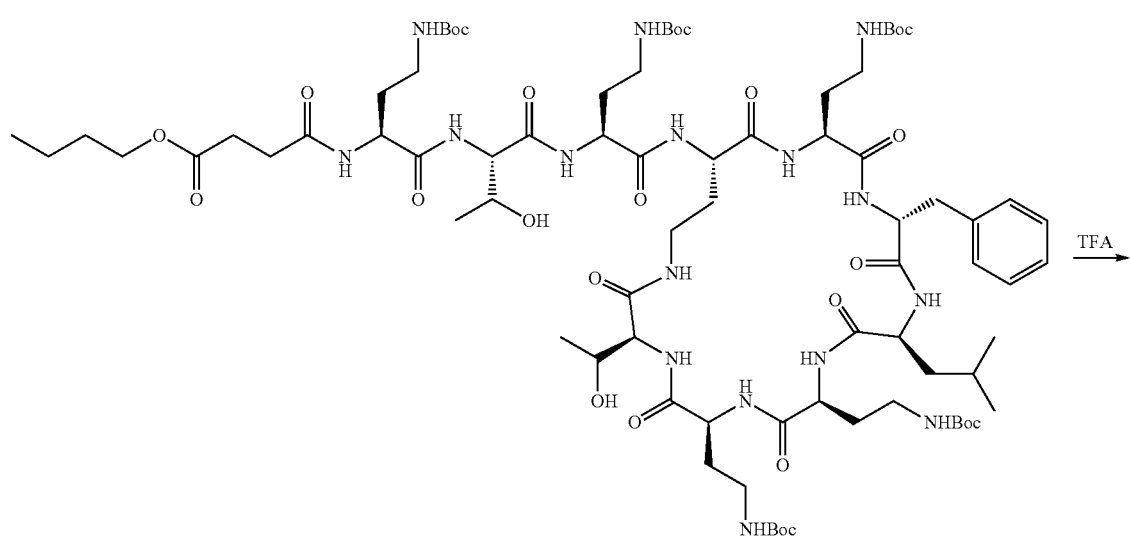
Intermediate 7B
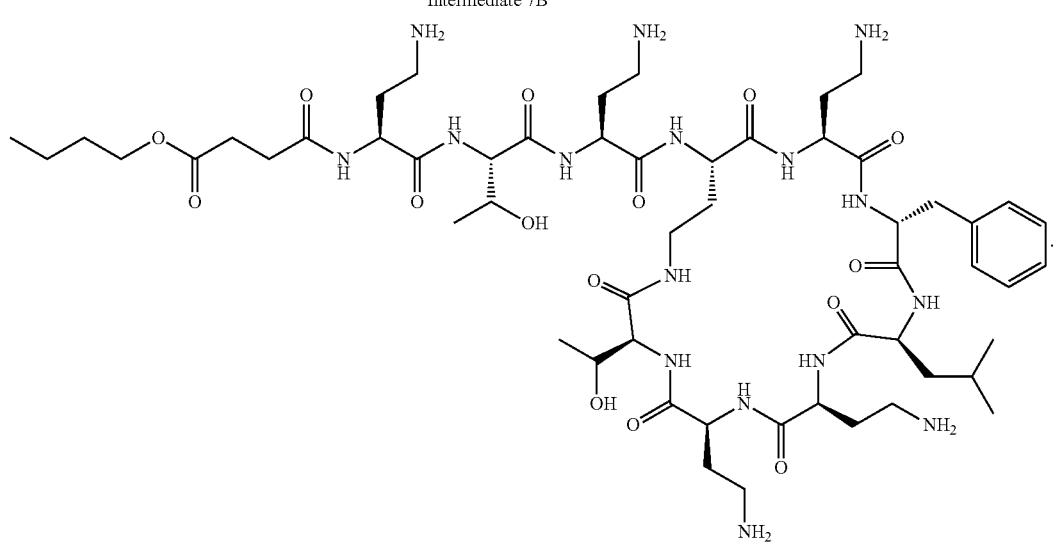
Example 7, TFA salt Intermediate 7A.

A 50 ml flask was charged with Intermediate 1 (681.8 mg, $R_1$=$CH_2Ph$), (R)-2-(((benzyl oxy)carbonyl)amino)-4-((tert-butoxycarbonyl)amino)butanoic acid (176.2 mg), HATU (209.1 mg), DIEA (71.1 mg), anhydrous DCM (5 mL) and dry MeCN (5 mL) under Ar. The mixture was stirred at r.t. for 2 h. Volatiles were removed under vacuum, the residue was dissolved in DCM, washed with water, 5% NaCl, dried over anhydrous $Na_2SO_4$, filtered and concentrated under vacuum to provide crude Intermediate 7A as a white solid.

Intermediate 7 (Same as Intermediate 3).

A 100 mL flask was charged with Intermediate 7A (626.8 mg), 10% Pd/C (300 mg), 0.1 M HCl aq. solution (1.1 ml) and MeOH (50 ml) under $H_2$. The mixture was hydrogenated (1 Torr) at r.t. for 4 h, and then filtered through Celite aiding with MeOH and evaporated under vacuum to provide crude product, purified by HPLC to afford Intermediate 7 as a white solid.

Intermediate 7B.

A 10 ml flask was charged with Intermediate 7 (40.1 mg), 4-butoxy-4-oxobutanoic acid (5.35 mg), HATU (11.7 mg), DIEA (3.98 mg), anhydrous DCM (1 ml) and dry MeCN (1 ml) under Ar. The mixture was stirred at r.t. for 3 h. Volatiles were removed under vacuum, the residue was dissolved in EA, washed with brine, dried over anhydrous $Na_2SO_4$, filtered and concentrated under reduced pressure to afford the Intermediate 7B as a white solid.

The Compound of Example 7.

The Compound of Example 7 (TFA salt) was prepared analogously from the Intermediate 7B just as described for the last step in the preparation of the Compound of Example 1. Off-white solid. NMR: 7.26 (dd, J 13.6, 6.0 Hz, 3H), 7.16 (d, J 8.4 Hz, 2H), 4.48 (dd, J 10.4, 3.6 Hz, 1H), 4.36-4.41 (m, 3H), 4.09-4.24 (m, 8H), 3.99-4.03 (m, 2H), 3.21 (dd, J 14.0, 7.6 Hz, 1H), 2.98 (t, J 9.6 Hz, 11H), 2.72 (d, J 30.0 Hz, 2H), 2.65 (dd, J 16.0, 4.0 Hz, 4H), 2.12 (dd, J 18.0, 10.8 Hz, 6H), 1.94 (d, J 24.8 Hz, 3H), 1.80 (d, J 27.2 Hz, 3H), 1.50 (t, J 8.4 Hz, 1H), 1.21-1.39 (m, 4H), 1.09 (t, J 6.0 Hz, 6H), 0.76-0.81 (m, 4H), 0.66 (d, J 6.0 Hz, 3H), 0.59 (d, J 6.0 Hz, 3H). MS (m/z): 1219.5 (M+H).

Example 8

Synthesis of the Compound of Example 8:

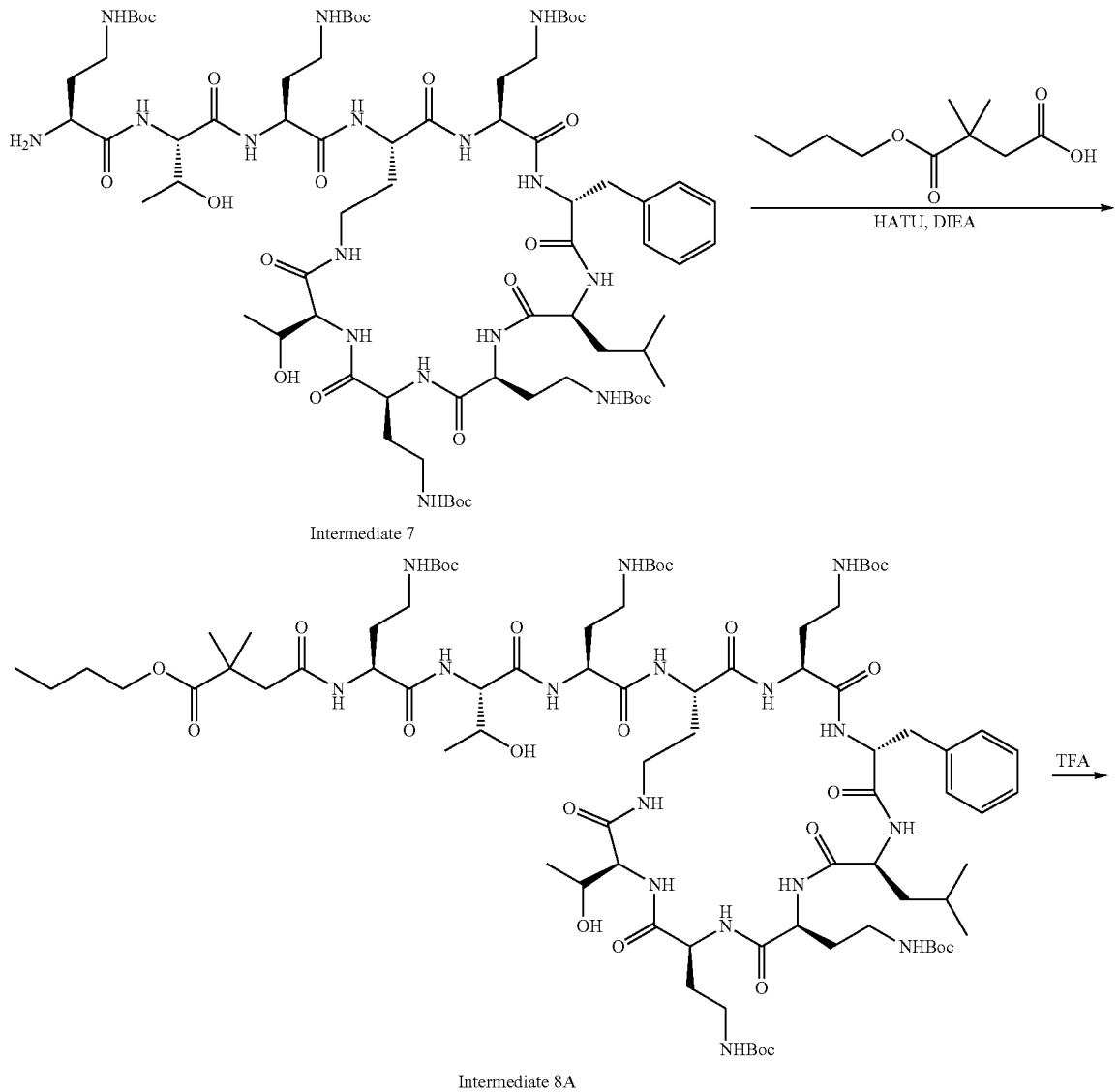

Intermediate 8A

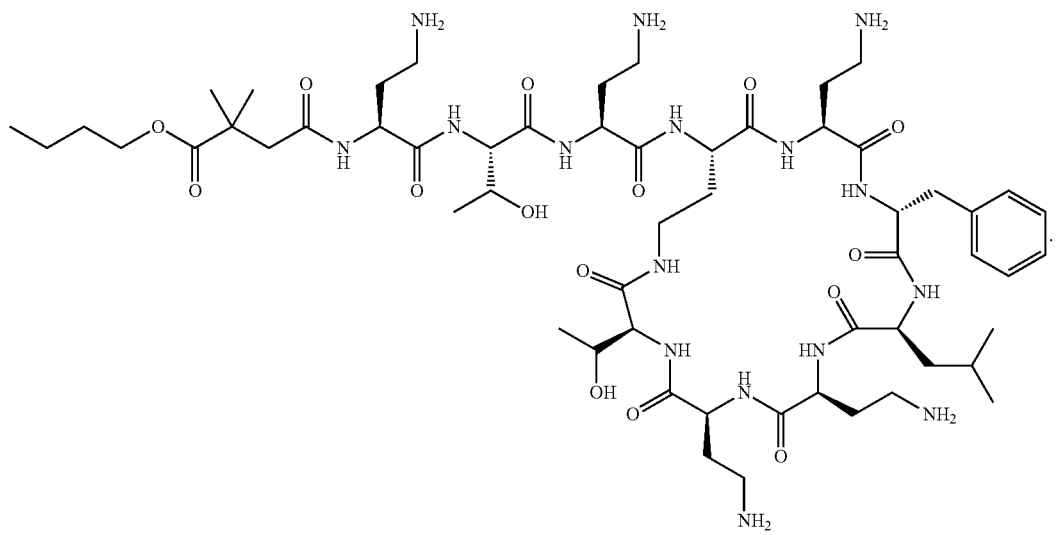

Example 8 TFA salt

Intermediate 8A.

The Intermediate 8A was prepared just as described above for the preparation of the Intermediate 7B, except using 4-butoxy-3,3-dimethyl-4-oxobutanoic acid instead of 4-butoxy-4-oxobutanoic acid.

The Compound of Example 8.

The Compound of Example 8 (TFA salt) was prepared from the Intermediate 8A just as described for the last step in the preparation of the Compound of Example 7, except using Intermediate 8A in place of Intermediate 7B. NMR: 7.21-7.12 (m, 3H); 7.06 (d, J 8 Hz, 2H); 4.38 (t, J 8 Hz, 1H); 4.25-4.33 (m, 3H); 4.13-4.00 (m, 7H); 3.91 (t, J 6 Hz, 2H); 3.52-3.44 (m, 1H); 3.15-3.12 (m, 2H); 3.00-2.80 (m, 10H); 2.67-2.41 (m, 6H); 2.04-1.73 (m, 13H); 1.44-1.39 (m, 2H); 1.30-1.08 (m, 6H); 1.03-0.99 (m, 9H); 0.70 (t, J 8 Hz, 3H); 0.58 (d, J 8 Hz, 3H); 0.514 (d, J 8 Hz, 3H). MS (m/z): 1247.6 (M+H).

Example 9

Synthesis of the Compound of Example 9:

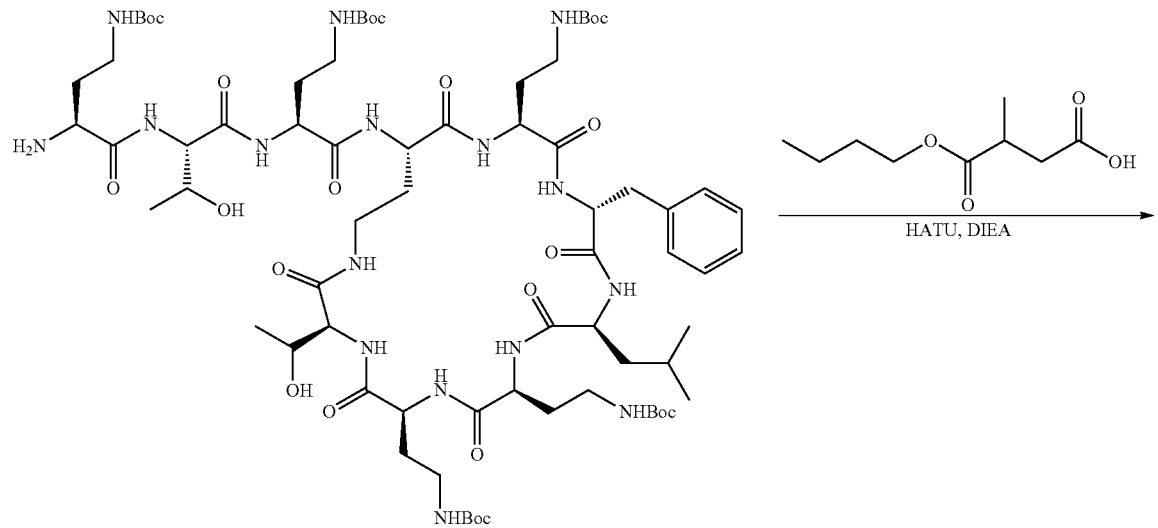

Intermediate 7

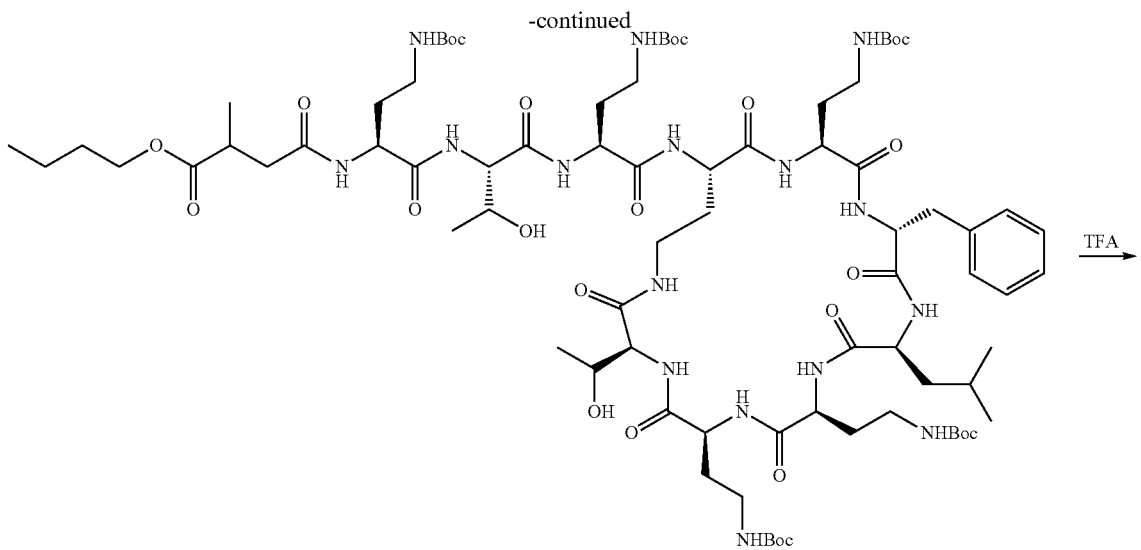

Intermediate 9A

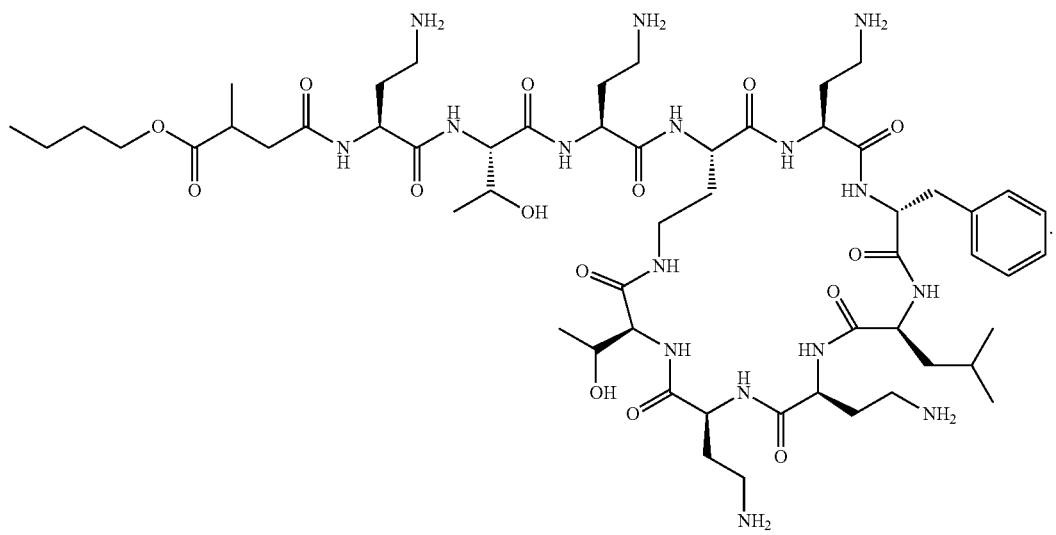

Example 9 TFA salt

Intermediate 9A.

The Intermediate 9A was prepared just as described above for the preparation of the Intermediate 7B, except using 4-butoxy-3-methyl-4-oxobutanoic acid instead of 4-butoxy-4-oxobutanoic acid.

The Compound of Example 9.

The Compound of Example 9 (TFA salt) was prepared from the Intermediate 9A just as described for the last step in the preparation of the Compound of Example 7 using Intermediate 9A in place of Intermediate 7B. NMR: 7.21-7.14 (m, 3H); 7.06 (d, J 8.0 Hz, 2H); 4.38 (t, J 8.0 Hz, 1H); 4.33-4.26 (m, 3H); 4.15-4.00 (m, 7H); 3.95-3.89 (m, 2H); 3.25-3.10 (m, 2H); 2.94-2.84 (m, 10H); 2.75-2.31 (m, 7H); 2.06-1.65 (m, 13H); 1.44-1.39 (m, 2H); 1.12-1.42 (m, 5H); 1.02-0.99 (m, 7H); 0.72-0.68 (m, 3H); 0.56 (d, J 8.0 Hz, 3H); 0.49 (d, J 8.0 Hz, 3H). MS (m/z): 1233.6 (M+H).

Example 10
Synthesis of the Compound of Example 10:
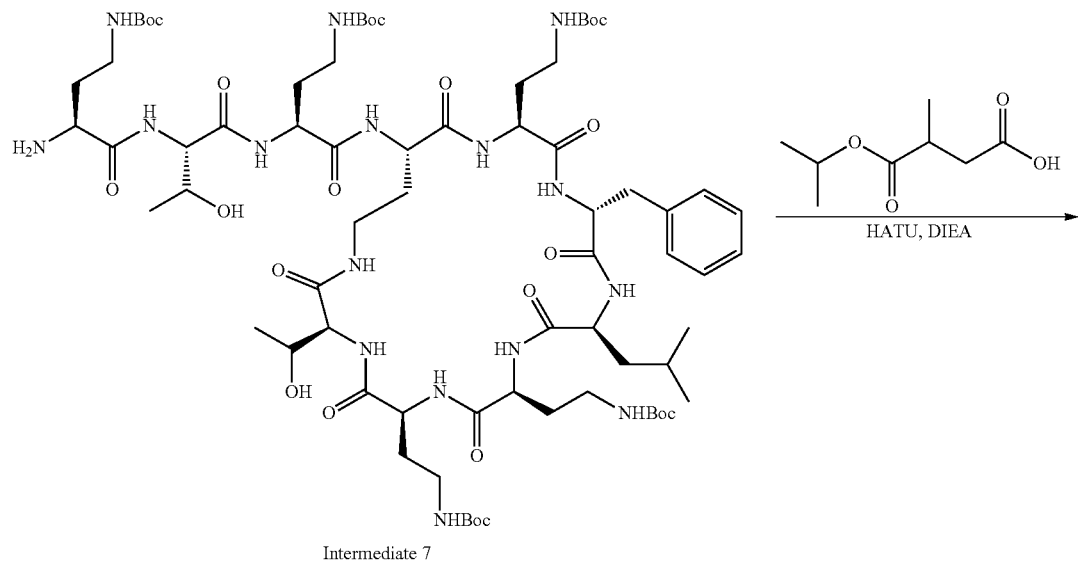
Intermediate 7
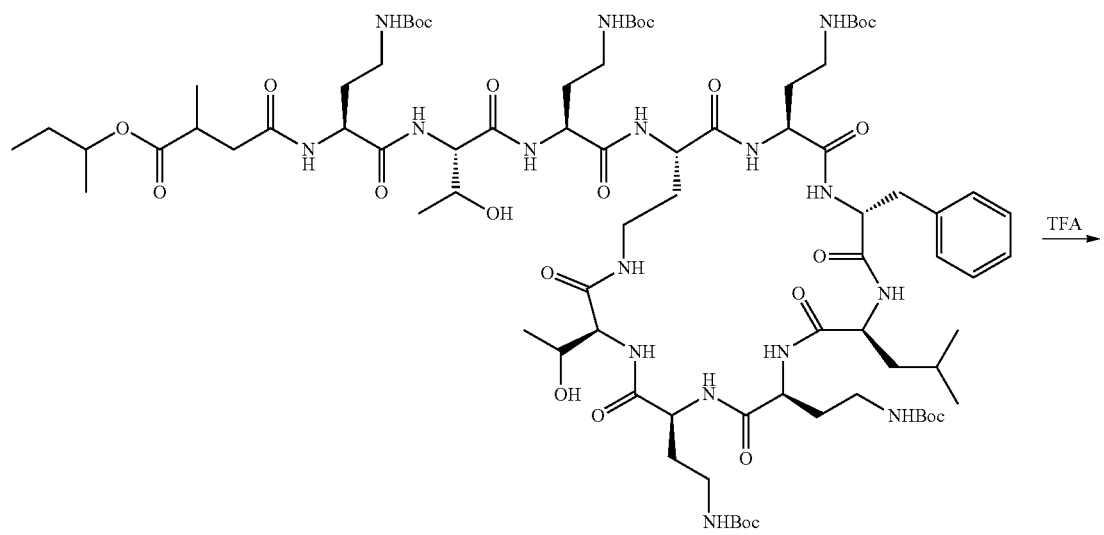
Intermediate 10A

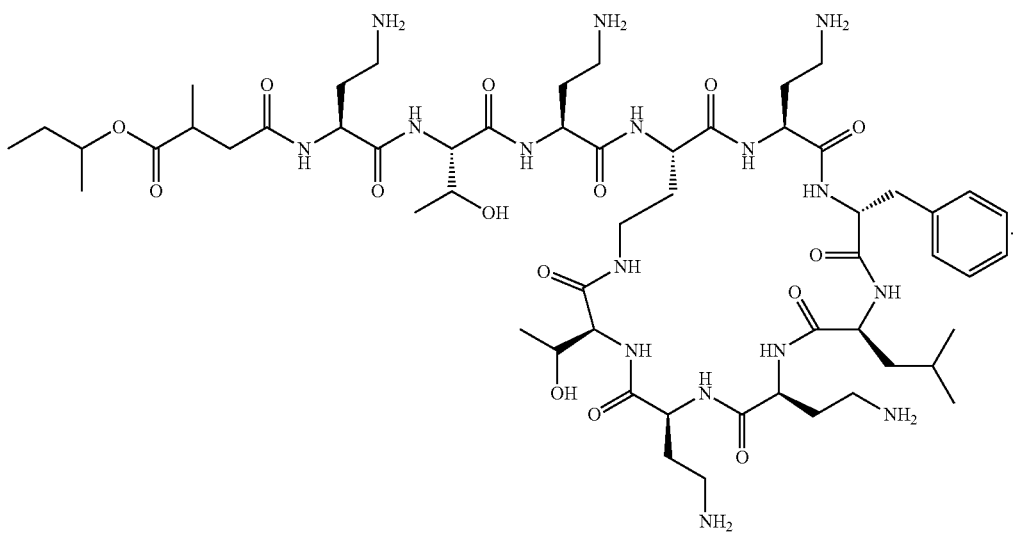
Example 10 TFA salt
The Compound of Example 10.
The Compound of Example 10 (TFA salt) is prepared analogously from the Intermediate 7 just as described for the Compound of Example 7 except using 4-(sec-butoxy)-3-methyl-4-oxobutanoic acid in place of 4-butoxy-4-oxobutanoic acid.
Example 11
Synthesis of the Compound of Example 11:
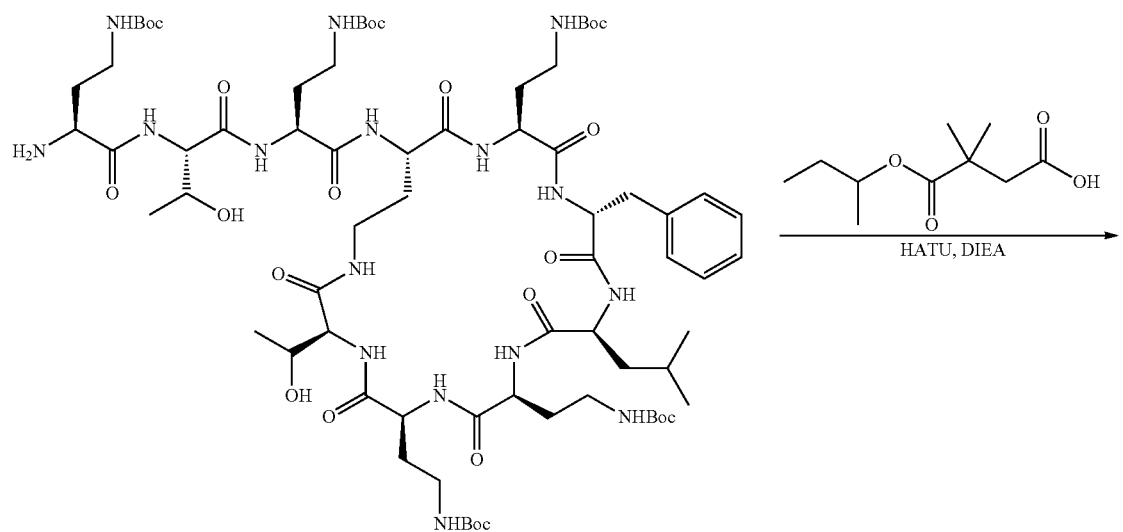
Intermediate 7

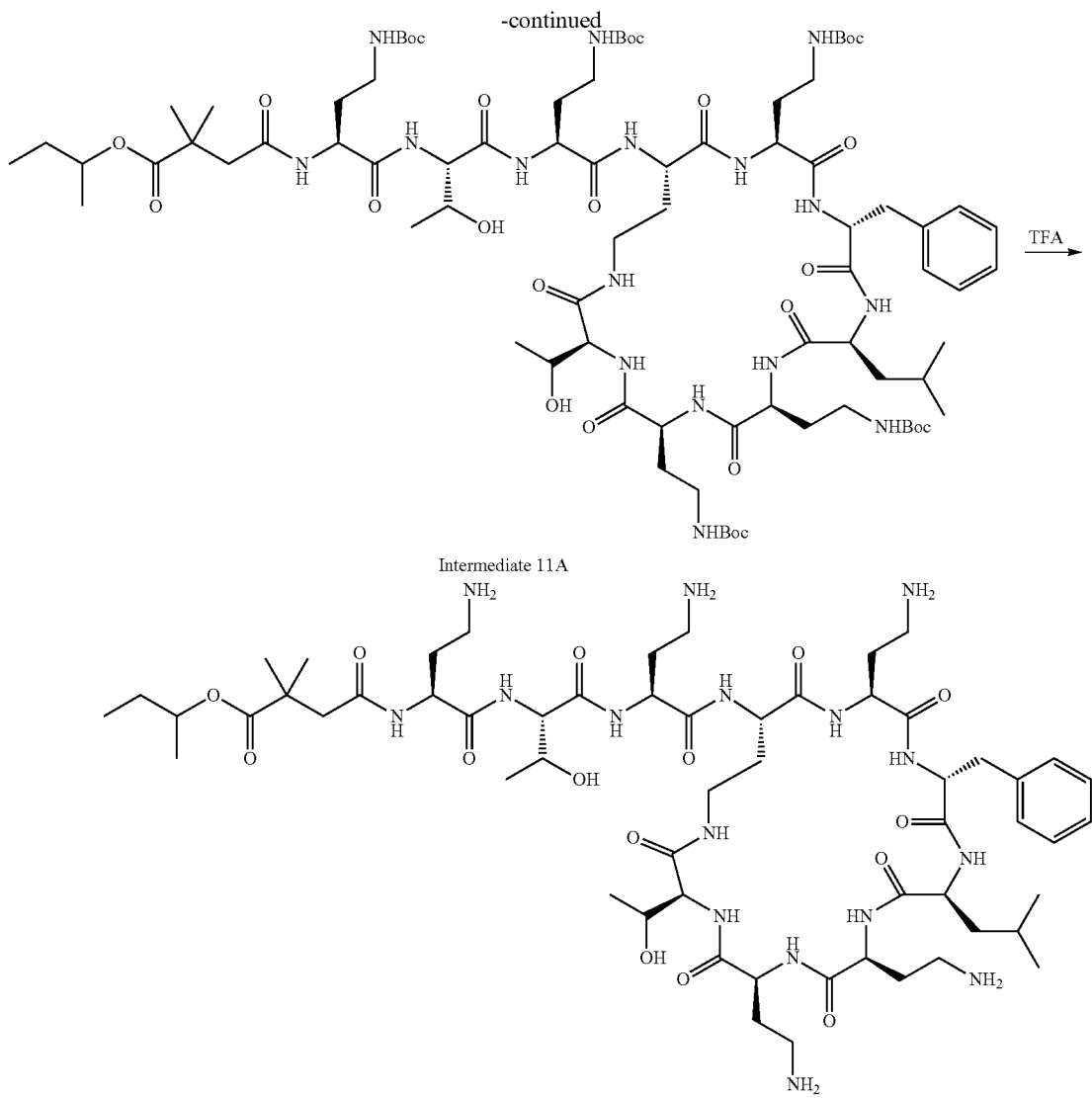
Intermediate 11A
Example 11 TFA salt
The Compound of Example 11.
The Compound of Example 11 (TFA salt) is prepared analogously from the Intermediate 7 just as described for the Compound of Example 7 except using 4-(sec-butoxy)-3,3-dimethyl-4-oxobutanoic acid in place of 4-butoxy-4-oxobutanoic acid.
Example 12
Synthesis of the Compound of Example 12:
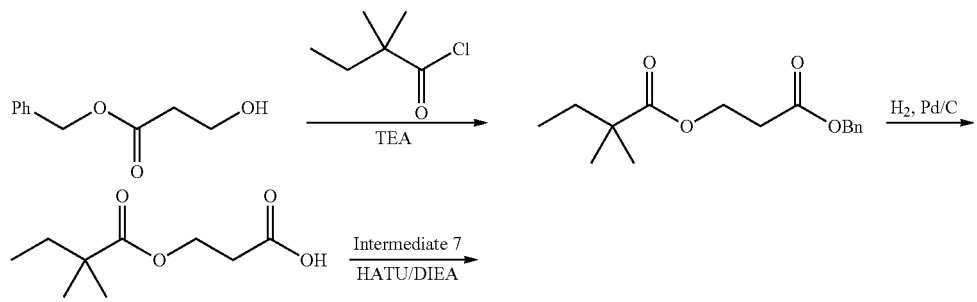

-continued

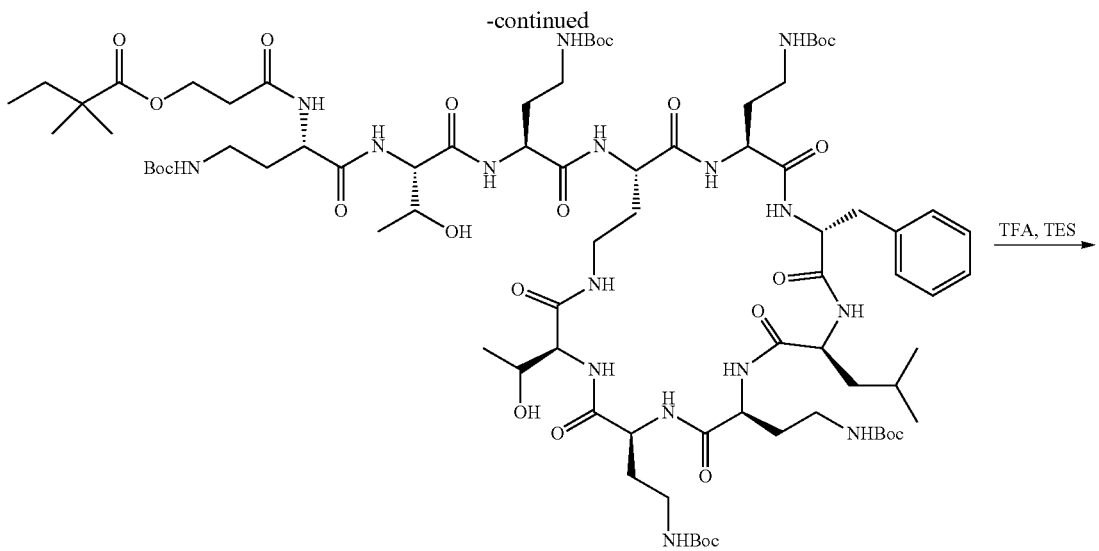

Intermediate 12A

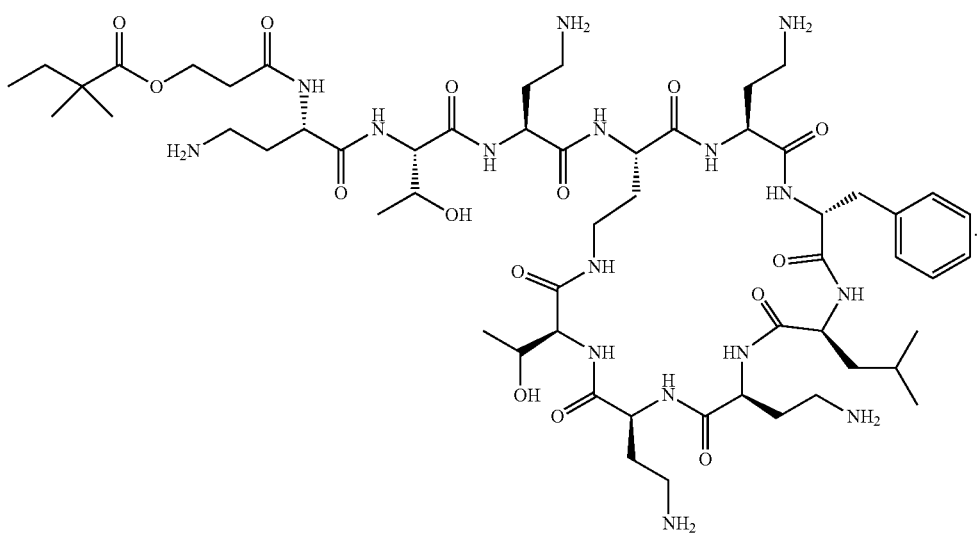

Example 12 TFA salt (3-(Benzyloxy)-3-oxo)propyl 2,2-dimethylbutanoate 2,2-Dimethylbutanoyl chloride (592 mg) was added dropwise with stirring to the mixture of benzyl 3-hydroxypropanoate (720 mg) and TEA (1.1 mL) in DCM (10 mL) at 0° C. The mixture was stirred at r.t. o.n., filtered and the filtrate was evaporated under vacuum. The residue was purified by silica gel column (eluting with 0-30% hexanes-EtOAc gradient to afford the product.

3-(2,2-Dimethylbutanoyloxy)propanoic acid

The mixture of (3-(benzyloxy)-3-oxo)propyl 2,2-dimethylbutanoate (1.1 g) and Pd/C (0.6 g, 56% H₂O) in MeOH (10 mL) was hydrogenated (1 Torr) at rt for 3 h. The mixture was filtered, and solvent evaporated to afford the crude 3-(2,2-dimethylbutanoyloxy)propanoic acid used directly in the next step.

Intermediate 12A.

DIEA (0.148 mL) and HATU (0.342 mg) was added to the mixture of 3-(2,2-dimethylbutanoyloxy)propanoic acid (169 mg) in DCM (25 mL). The mixture was stirred at r.t. for 30 min. Then Intermediate 7 (0.62 g) was added, and the mixture was stirred o.n. and then evaporated under vacuum. The residue was purified by HPLC to give the Intermediate 12A.

The Compound of Example 12.

The mixture of Intermediate 12A (160 mg) and TES (0.2 mL) in TFA/H₂O (3.0 mL/0.4 mL) was stirred at r.t. for 3 h. The mixture was evaporated, and the residue purified by HPLC to afford the Compound of Example 12 (TFA salt). NMR: 7.22-7.14 (m, 3H); 7.06 (d, J 8.0 Hz, 2H); 4.40-4.29 (m, 4H); 4.15 (t, J 4.0 Hz, 3H); 4.11-4.00 (m, 6H); 3.15-3.10 (m, 1H); 2.94-2.88 (m, 10H); 2.68-2.54 (m, 3H); 2.50 (t, J 6.0 Hz, 2H); 2.04-1.68 (m, 14H); 1.35-1.22 (m, 5H); 1.01 (t, J 6.0 Hz, 5H); 0.92 (s, 6H); 0.58 (t, J 6.0 Hz, 6H); 0.49 (d, J 8.0 Hz, 3H). MS (m/z): 1233.6 (M+H).

Example 13
Synthesis of the Compound of Example 13:
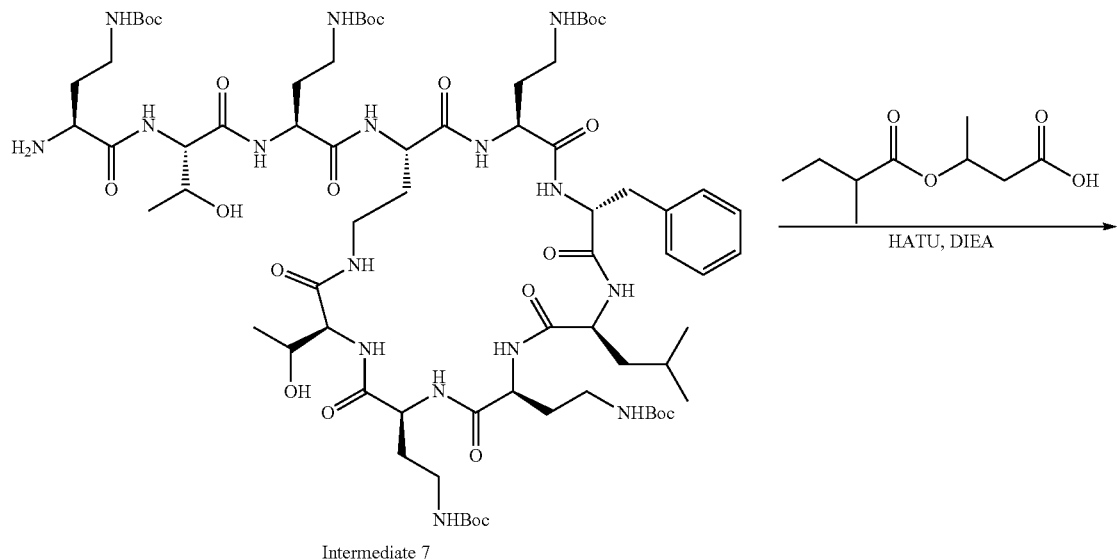
Intermediate 7
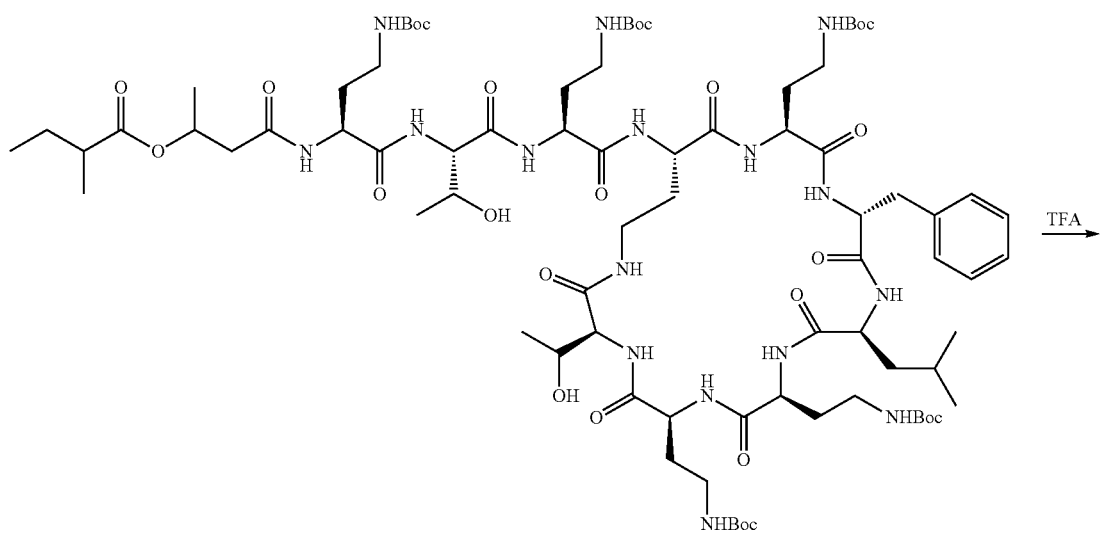
Intermediate 13A

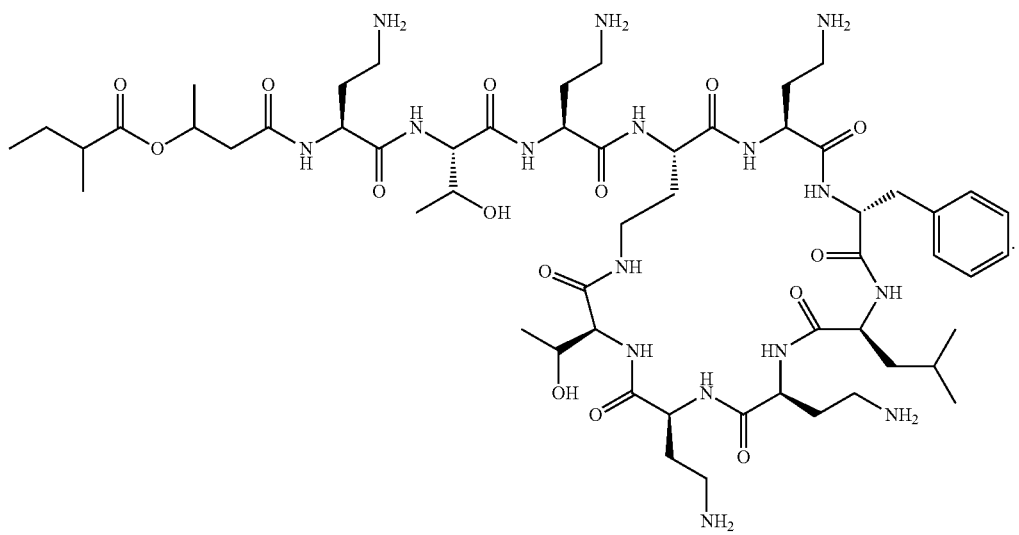
Example 13 TFA salt
The Compound of Example 13.
The Compound of Example 13 (TFA salt) is prepared from the Intermediate 7 just as described for the Compound of Example 7, except using 3-((2-methylbutanoyl)oxy)butanoic acid in place of 4-butoxy-4-oxobutanoic acid.
Example 14
Synthesis of the Compound of Example 14:
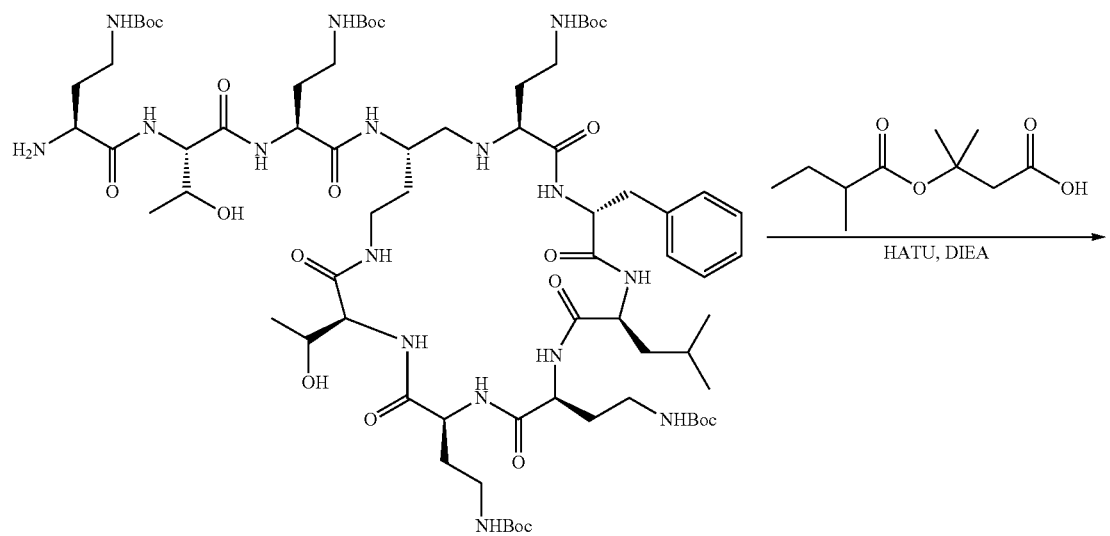
Intermediate 7

-continued
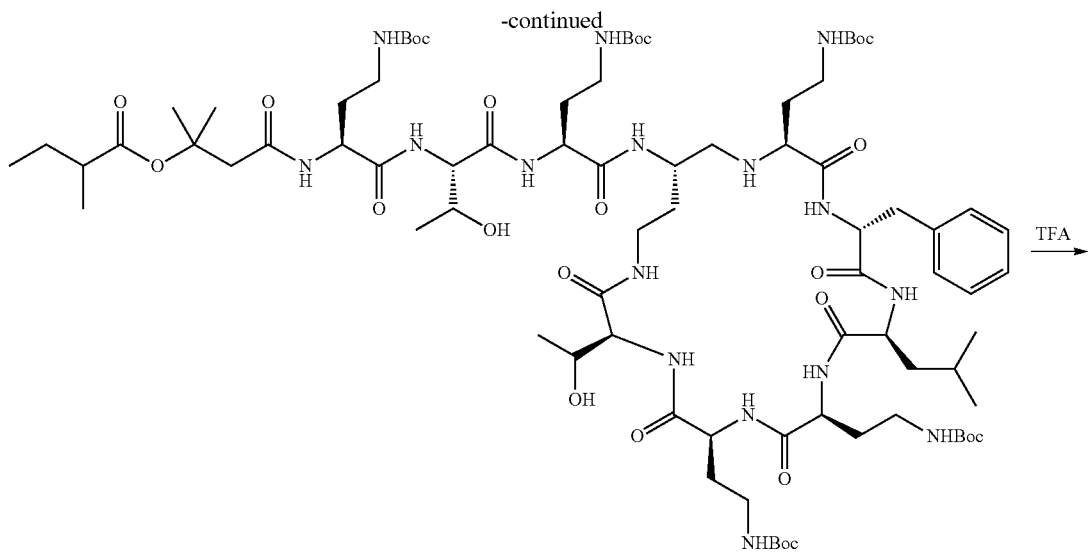
Intermediate 14A
TFA →
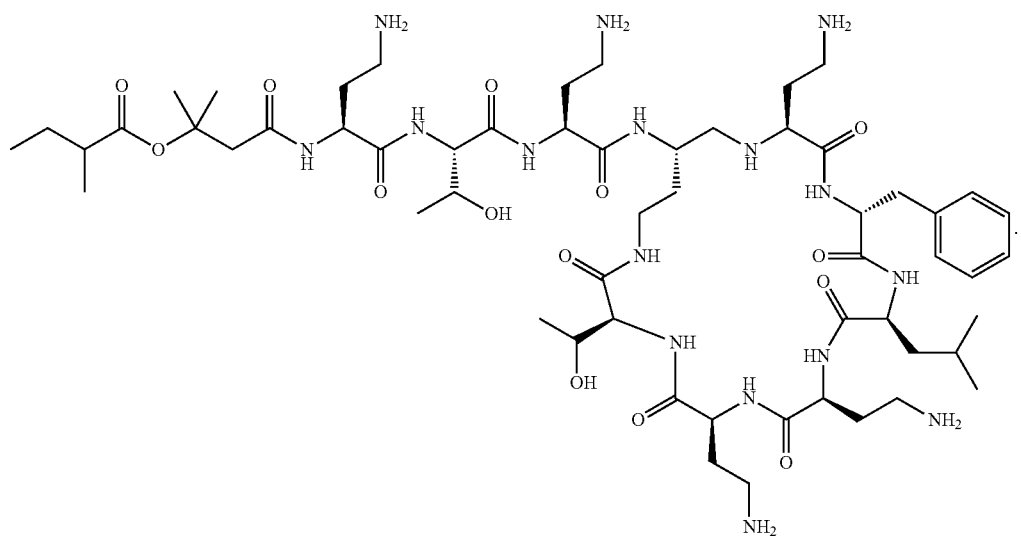
Example 14 TFA salt
The Compound of Example 14.
The Compound of Example 14 (TFA salt) is prepared from the Intermediate 7 just as described for the Compound of Example 7, except using 3-methyl-3-((2-methylbutanoyl)oxy)butanoic acid in place of 4-butoxy-4-oxobutanoic acid.

Example 15
Synthesis of the Compound of Example 15:
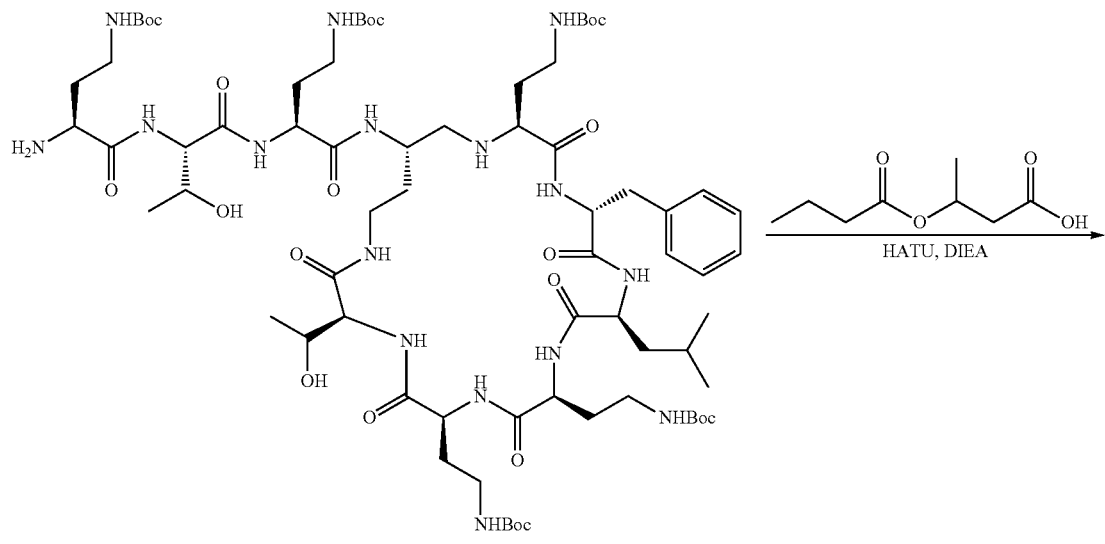
Intermediate 7
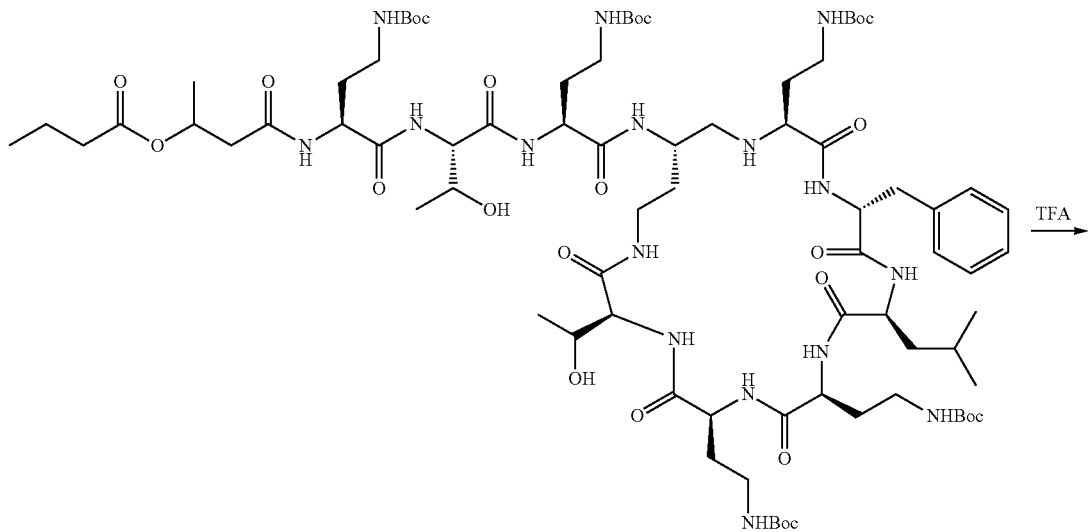
Intermediate 15A

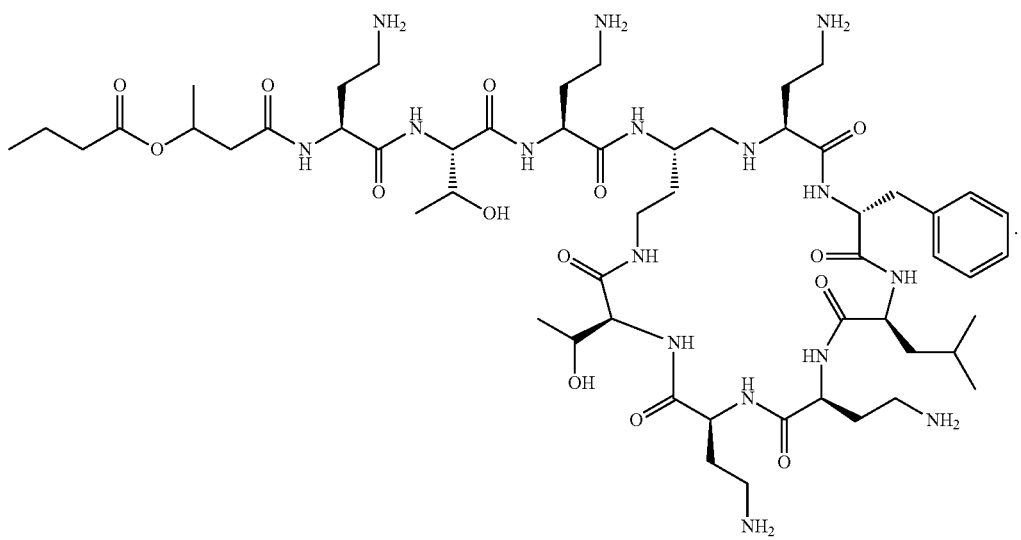
Example 15 TFA salt
The Compound of Example 15.
The Compound of Example 15 (TFA salt) is prepared from the Intermediate 7 just as described for the Compound of Example 7, except using 3-(butyryloxy)butanoic acid in place of 4-butoxy-4-oxobutanoic acid.
Example 16
Synthesis of the Compound of Example 16:
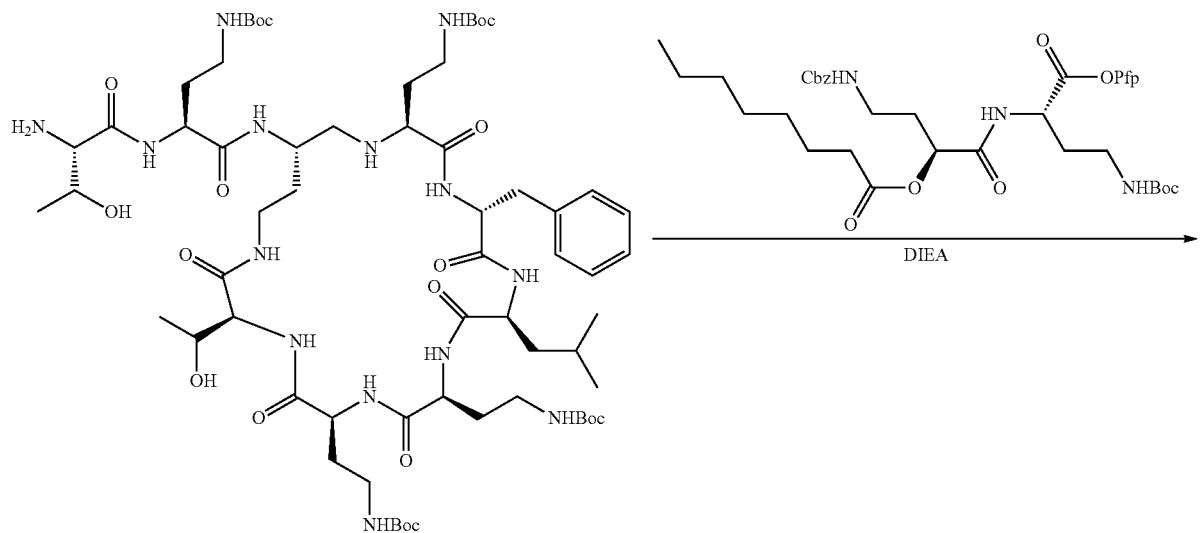
Intermediate 1 ($R^1$ = CH$_2$Ph)

-continued
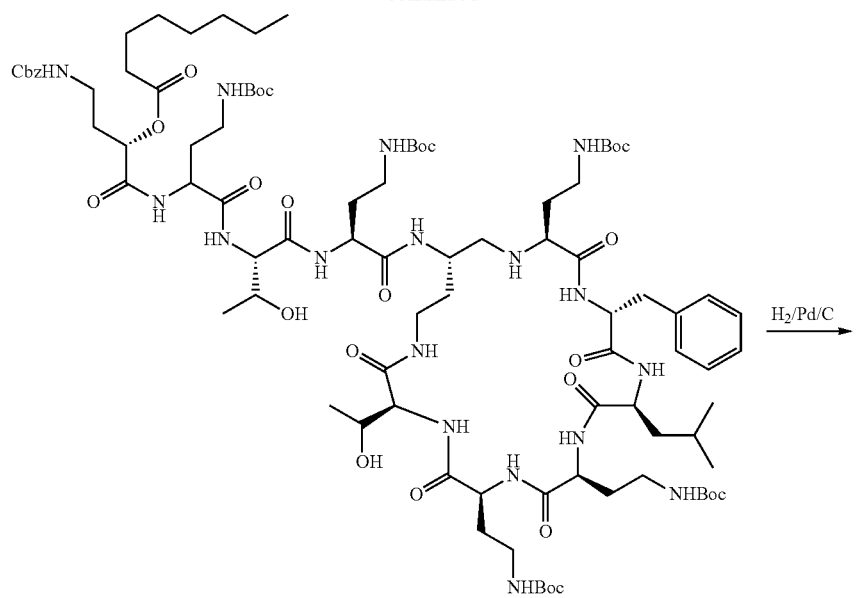
Intermediate 16A
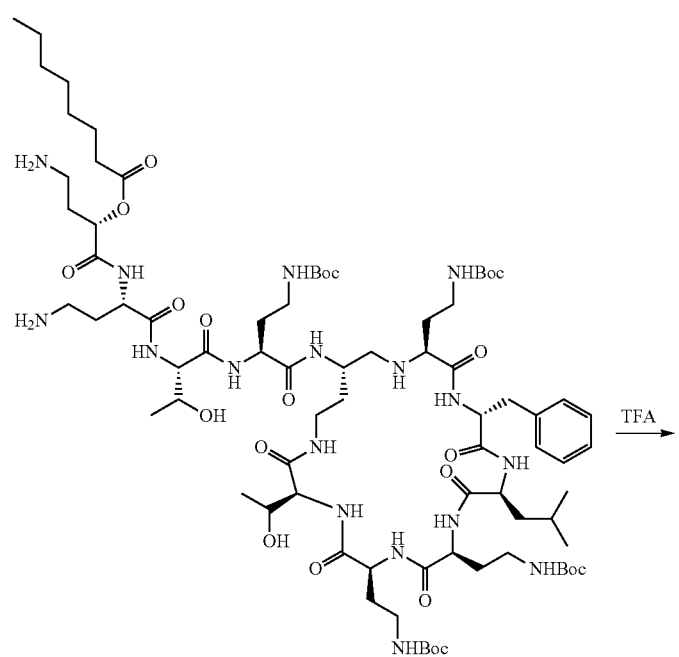
Intermediate 16B

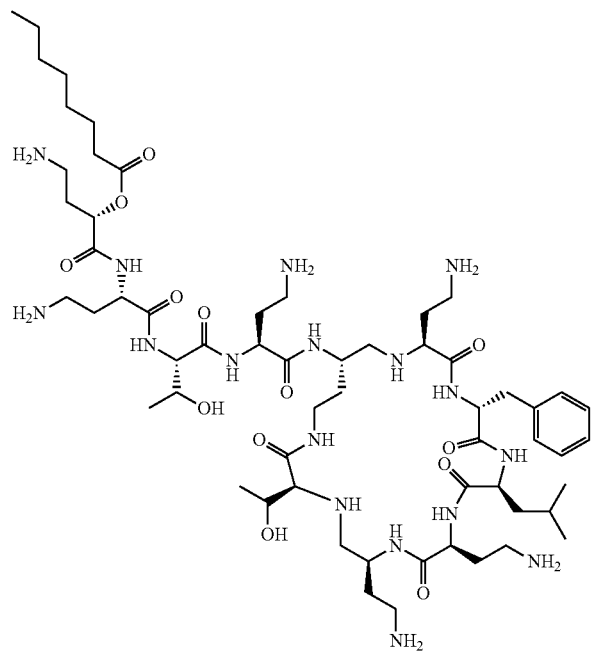

Example 16 TFA salt

The Compound of Example 16.

The Compound of Example 16 (TFA salt) was prepared analogously according to a similar procedure for Example 1 from Intermediate 1 (R$_1$=CH$_2$Ph) using (7R,10S)-16,16-dimethyl-3,8,14-trioxo-10-((pentafluorophenoxy)carbonyl)-1-phenyl-2,15-dioxa-4,9,13-triazaheptadecan-7-yl octanoate in place of ((S)-4-((tert-butoxycarbonyl)amino)-1-oxo-1-(pentafluorophenoxy)butan-2-yl octanoate. MS (m/z): 646 (M+2H).

Example 17

Synthesis of the Compound of Example 17:

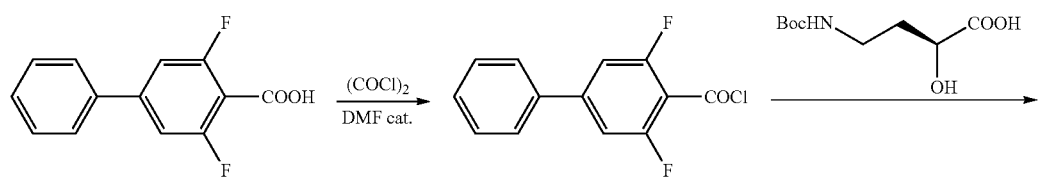

-continued

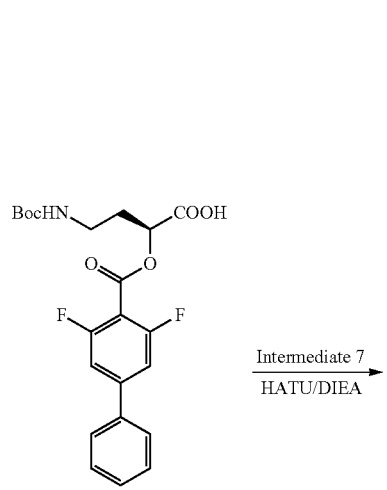

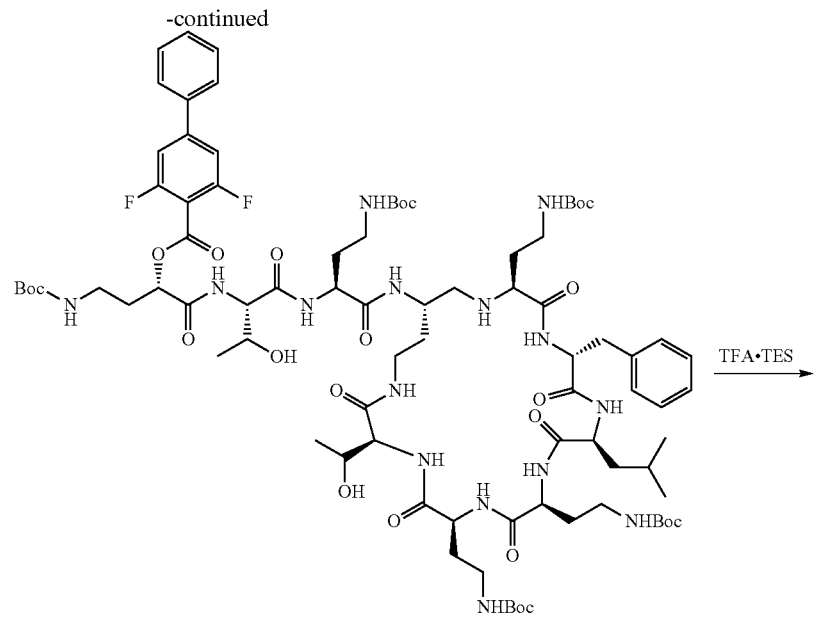

Intermediate 17A

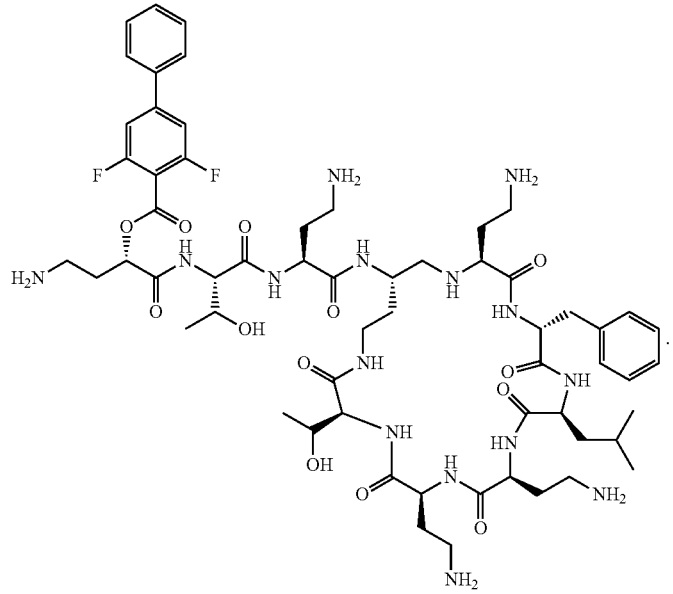

Example 17, TFA salt

4-Phenyl-2,6-difluorobenzoyl chloride

To the stirred mixture of 4-phenyl-2,6-difluorobenzoic acid (840 mg) and (COCl)$_2$ (2 mL) in DCM (2 mL) at r.t. was added DMF (1 drop). The mixture was stirred at r.t. for 2 h and evaporated under vacuum to afford the crude 4-phenyl-2,6-difluorobenzoyl chloride.

(S)-4-((tert-Butoxycarbonyl)amino)-2-((3,5-difluoro-[1,1'-biphenyl]-4-carbonyl)oxy)butanoic acid. The mixture of abive 4-phenyl-2,6-difluorobenzoyl chloride (1.0 g), (S)-4-(tert-butoxycarbonylamino)-2-hydroxybutanoic acid (548 mg) and TEA (1 mL) in DCM/ACN (5 mL/5 mL) was stirred at r.t. o.n. Volatiles were removed under vacuum and the product purified by HPLC to afford (S)-4-((tert-butoxycarbonyl)amino)-2-((3,5-difluoro-[1,1'-biphenyl]-4-carbonyl)oxy)butanoic acid.

Intermediate 17A.

The Intermediate 17A was prepared just as described above for the preparation of the Intermediate 7B, except using (S)-4-((tert-butoxycarbonyl)amino)-2-((3,5-difluoro-[1,1'-biphenyl]-4-carbonyl)oxy)butanoic acid instead of 4-butoxy-4-oxobutanoic acid.

The Compound of Example 17.

The Compound of Example 17 (TFA salt) was prepared just as described for the last step in the preparation of the Compound of Example 7, except using Intermediate 17A instead of 7B. NMR: 7.64 (d, J 5.6 MHz, 2H); 7.41-7.56 (m, 3H); 7.36 (d, J 5.6 MHz, 2H); 7.22-7.27 (m, 3H); 7.10-7.12 (d, J 6.8 Mz, 2H); 5.40-5.41 (dd, J 5.2, 1.2 Mz, 1H); 4.40-4.45 (m, 1H); 4.31-4.36 (m, 2H); 4.15-4.19 (m, 2H); 3.96-4.11 (m, 7H); 3.10-3.15 (m, 1H); 2.83-2.99 (m, 11H); 2.54-2.67 (m, 2H); 1.99-2.03 (m, 6H); 1.68-1.97 (m, 6H); 1.21-1.29 (m, 2H); 1.02 (dd, J 13.2, 6.0 Mz, 6H); 0.61-0.64 (m, 1H); 0.56-0.59 (m, 3H); 0.49-0.52 (m, 3H). MS (m/z): 1280.5 (M+H).

Example 18
Synthesis of the Compound of Example 18:
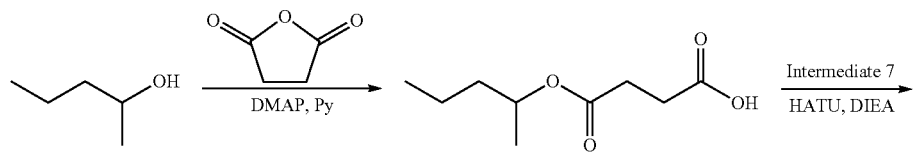
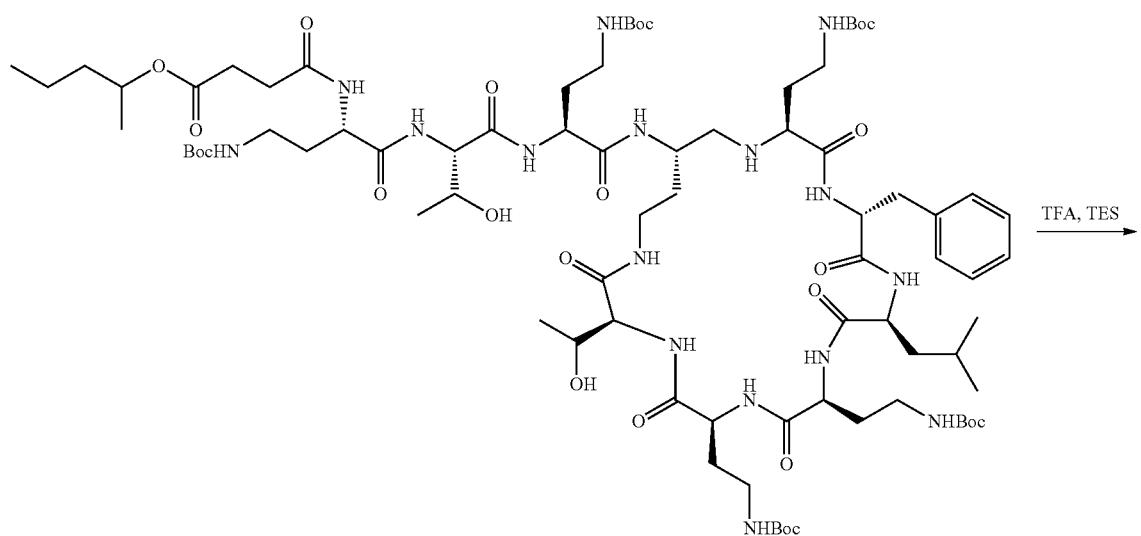
Intermediate 18a
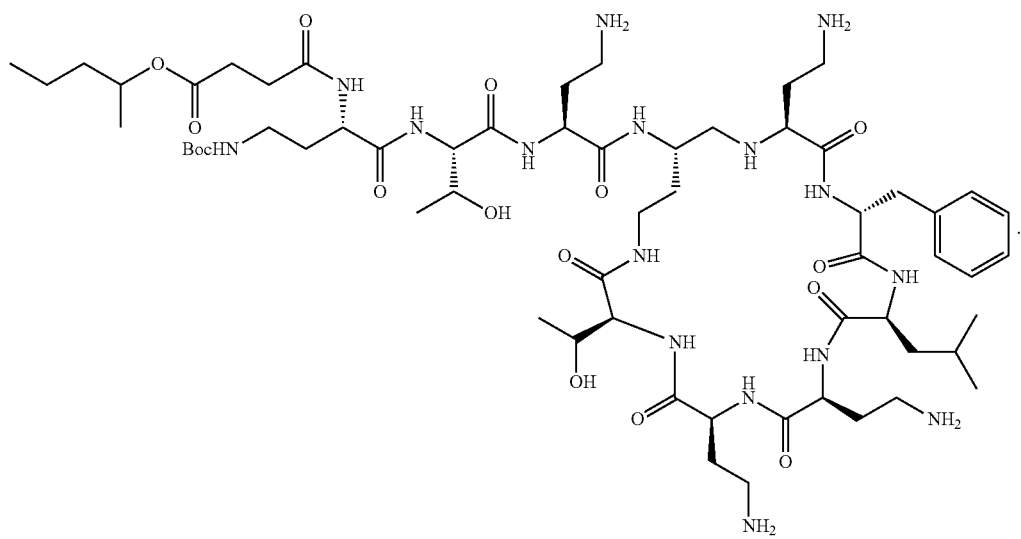
Example 18 TFA salt

4-Oxo-4-(pentan-2-yloxy)butanoic acid

Pentan-2-ol (1.0 g), dihydrofuran-2,5-dione (1.0 g) and DMAP (0.244 g) in Py (10 mL) were stirred at ca. 80° C. for 18 h. Volatiles were removed under vacuum and the residue was dissolved with water/EtOAc (10 mL/20 mL), the EtOAc layer was separated. The water layer was extracted with EtOAc (2×20 mL). The combined organic phase was washed with 1N HCl (4×8 mL) and dried (Na sulfate). Solvent was removed under vacuum to afford the crude product used directly in the next step.

Intermediate 18A.

DIEA (0.247 mL) and HATU (0.57 g) were added to a solution of 4-oxo-4-(pentan-2-yloxy)butanoic acid (0.282 g) in DCM (25 mL). The mixture was stirred at r.t. for 30 min, then Intermediate 7 (1.1 g) was added, and the mixture was stirred o.n., volatiles were evaporated under vacuum, and the residue was purified by HPLC to afford the Intermediate 18A as a white solid. MS (m/z): 1733.4 (M+H).

The Compound of Example 18.

A mixture of Intermediate 18A (255 mg) and TES (0.12 mL) in TFA/H$_2$O (2.5 mL/0.25 mL) was stirred at r.t. for 4 h, evaporated under vacuum, and the residue was purified by HPLC to afford the compound of Example 18 (TFA salt) as an off-white solid. NMR: 7.26-7.19 (m, 3H), 7.10 (d, J 8.0 Hz, 2H), 4.76-4.74 (m, 1H), 4.37-4.32 (m, 4H), 4.19-4.04 (m, 8H); 3.58-3.49 (m, 1H), 3.18-3.16 (m, 1H), 3.00-2.92 (m, 10H), 2.71-2.48 (m, 7H), 2.10-1.70 (m, 13H), 1.41-1.26 (m, 5H), 1.18-1.11 (m, 2H), 1.06-1.10 (m, 7H), 0.71 (t, J 8.0 Hz, 3H), 0.61 (d, J 4.0 Hz, 3H), 0.54 (d, J 4 Hz, 3H). MS (m/z): 1233.5 (M+H).

Example 19

Synthesis of the Compound of Example 19:

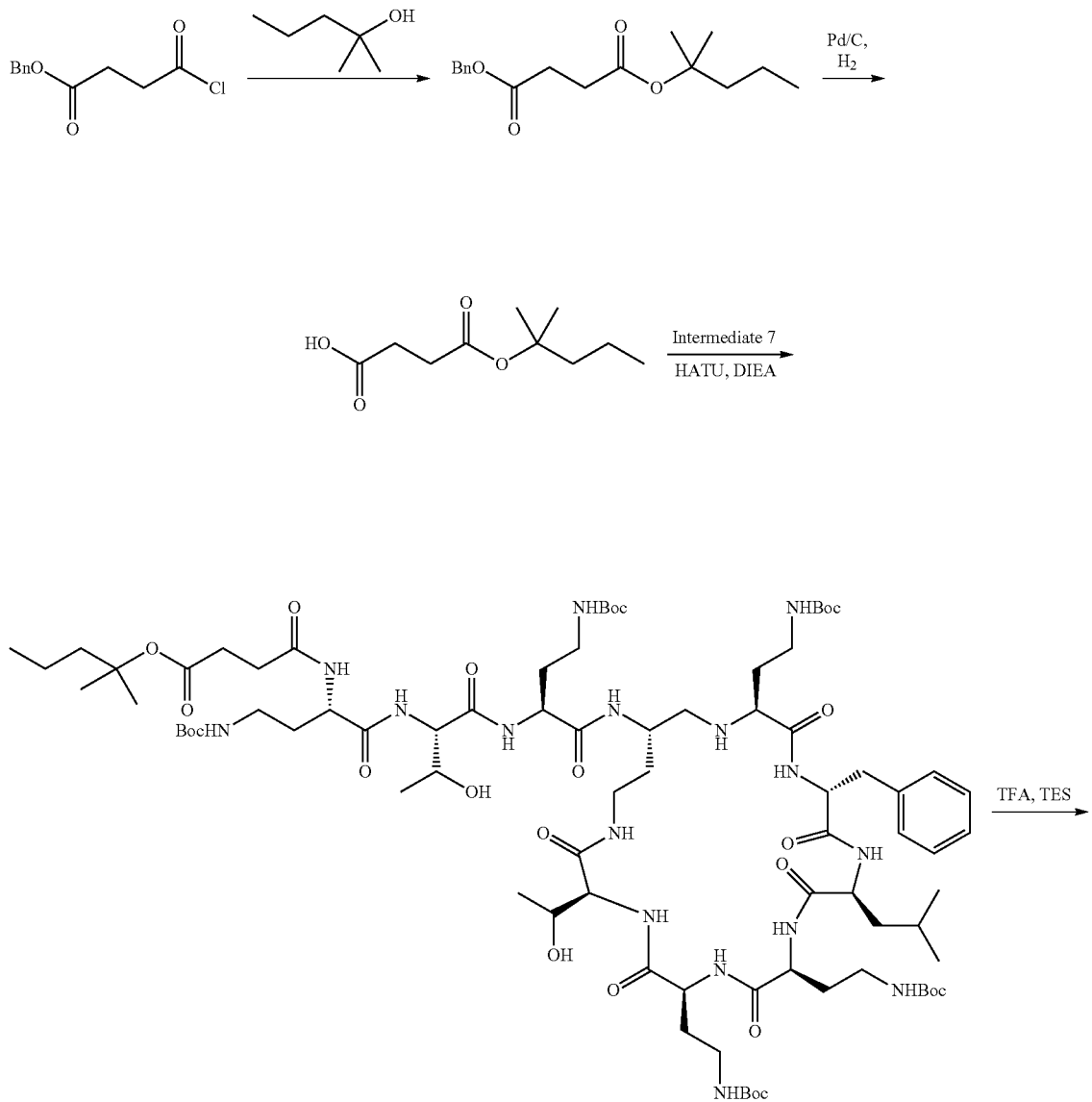

Intermediate 19A

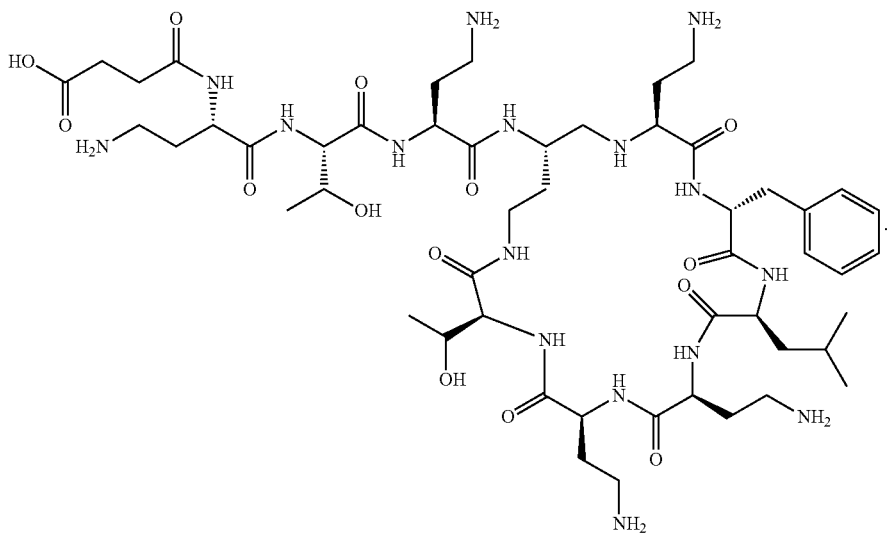

Example 19 TFA salt

Benzyl (2-methylpentan-2-yl)succinate

A solution of benzyl 4-chloro-4-oxobutanoate (3.5 g) in CHCl$_3$ (20 mL) was added to the mixture of 2-methylpentan-2-ol (1.57 g) and Na$_5$P$_3$O$_{10}$ (1.98 g) in CHCl$_3$ (40 mL) at 0° C. The mixture was stirred under reflux for 12 h. The mixture was washed with brine (40 mL), extracted with DCM (2×15 mL), and dried (Na sulfate). Solvent was removed under vacuum, and the residue purified by PTLC to afford 2 g of benzyl (2-methylpentan-2-yl)succinate.

4-((2-Methylpentan-2-yl)oxy)-4-oxobutanoic acid

A mixture of benzyl (2-methylpentan-2-yl)succinate (2.0 g) and wet Pd/C (0.8 g; 56% H$_2$O) in MeOH (20 mL) was hydrogenated (1 Torr) for 6 h. The mixture was filtered and the filtrate was evaporated to afford the crude product used directly at the next step.

Intermediate 19A.

The Intermediate 19A was prepared just as described above for the preparation of the Intermediate 18A, except using 4-(2-methylpentan-2-yloxy)-4-oxobutanoic acid instead of 4-oxo-4-(pentan-2-yloxy)butanoic acid.

The Compound of Example 19.

The Compound of Example 19 (TFA salt) was prepared from the Intermediate 19A just as described for the last step in the preparation of the Compound of Example 18. Off-white solid. NMR: 7.21-7.14 (m, 3H), 7.06 (d, J 8.0 Hz, 2H), 5.35 (br. s, 1H), 4.41-3.95 (m, 11H), 3.26 (m, 1H), 2.90-2.84 (m, 10H), 2.68-2.42 (m, 7H), 2.11-1.61 (m, 13H), 1.28-1.22 (m, 5H), 1.01-0.95 (m, 2H), 0.68 (br. s, 1H), 0.57 (d, J 8.0 Hz, 3H), 0.49 (d, J 4.0 Hz, 3H). MS (m/z): 1163.6 (M+H).

Example 20

Synthesis of the Compound of Example 20:

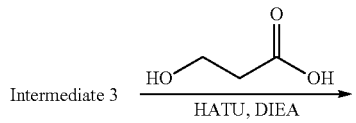

Intermediate 3    HATU, DIEA

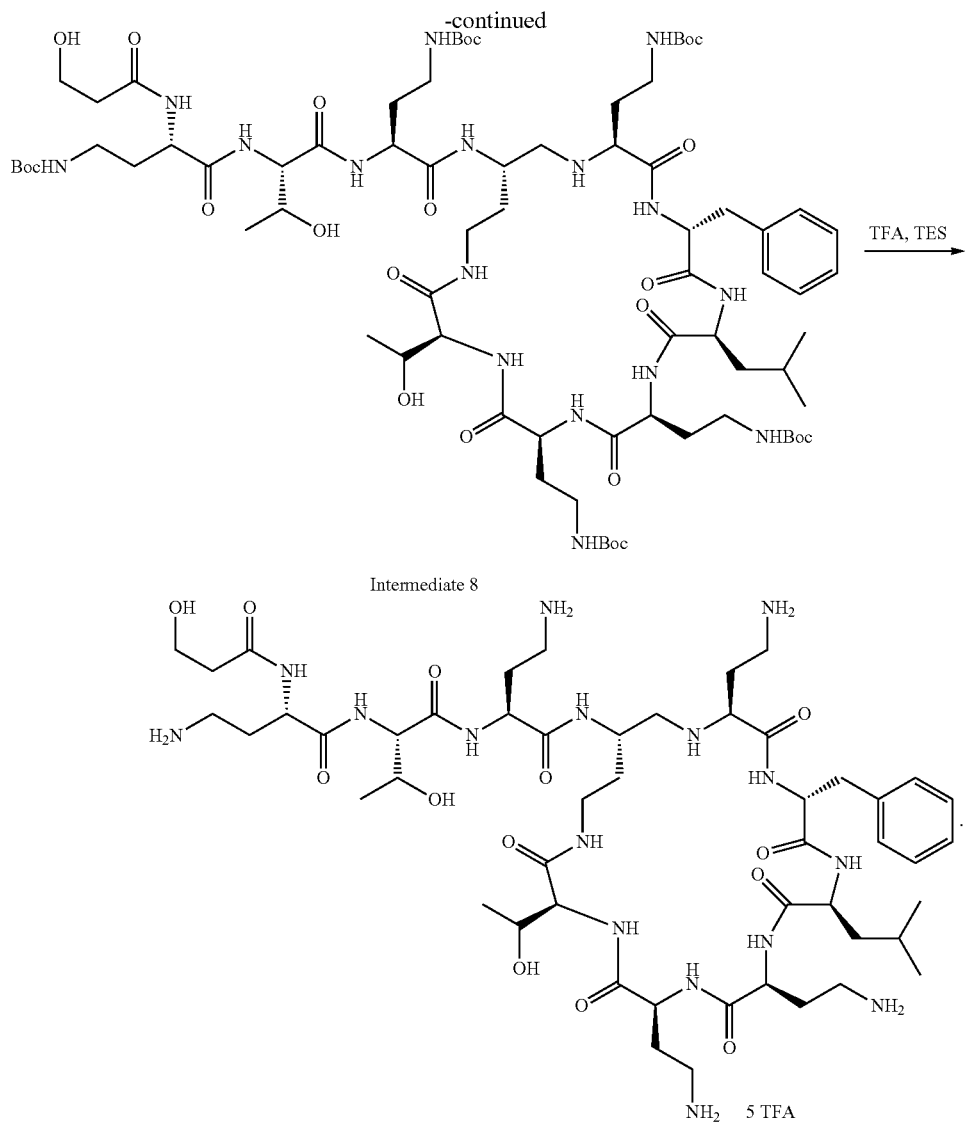

Intermediate 8

Example 20 TFA salt

Intermediate 20A.

The Intermediate 20A was prepared just as described above for the preparation of the Intermediate 18A, except using 3-hydroxypropanoic acid instead of 4-oxo-4-(pentan-2-yloxy)butanoic acid.

The Compound of Example 20.

The Compound of Example 20 (TFA salt) was prepared from the Intermediate 20A just as described for the last step in the preparation of the Compound of Example 18. Off-white solid. NMR: 7.21-7.12 (m, 3H), 7.06 (d, J 4.0 Hz, 2H), 5.37-5.32 (m, 1H), 4.40-4.27 (m, 4H), 4.17-4.01 (m, 8H), 3.66 (t, J 6.0 Hz, 1H), 3.29-3.09 (m, 1H), 2.91-2.88 (m, 10H), 2.66-2.58 (m, 3H), 2.36 (t, J 6.0 Hz, 1H), 2.04-1.61 (m, 14H), 1.30-1.22 (m, 3H), 1.00 (t, J 4.0 Hz, 4H), 0.57 (t, J 8 Hz, 3.0H), 0.50 (d, J 8.0 Hz, 3H). MS (m/z): 1117.6 (M−H$_2$O+H).

Example 21

Synthesis of the Compound of Example 21:

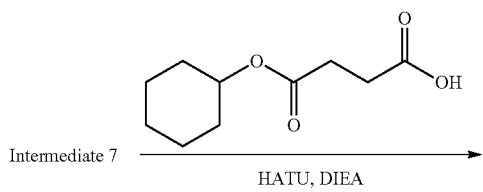

Intermediate 7 $\xrightarrow{\text{HATU, DIEA}}$

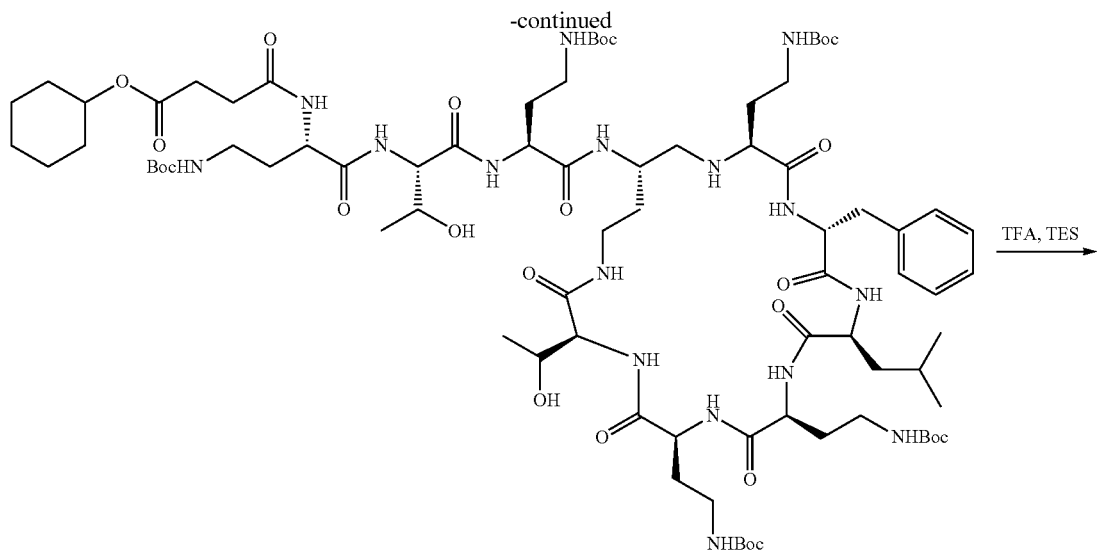

Intermediate 21A

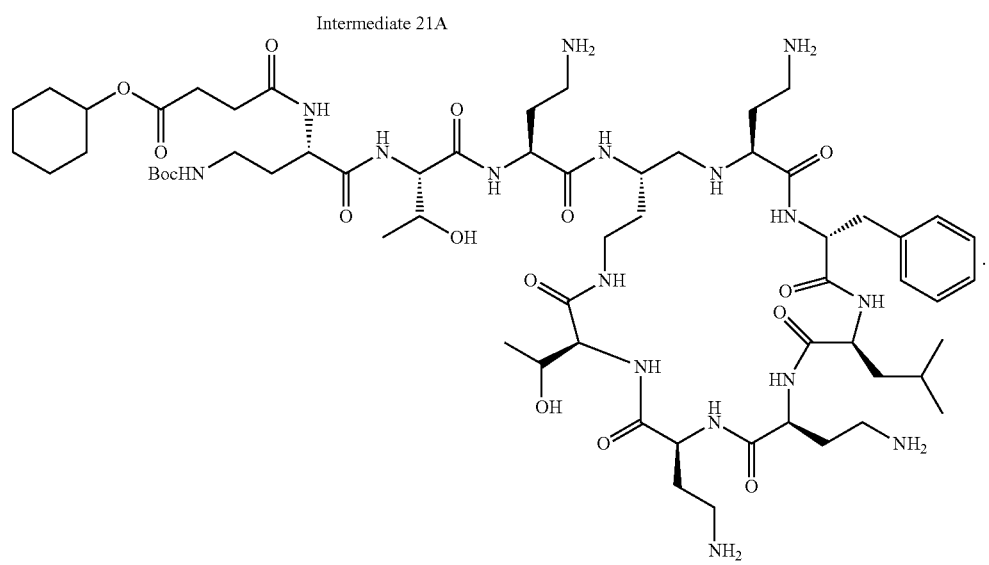

Example 21 TFA salt

Intermediate 21A.

The Intermediate 21A was prepared just as described above for the preparation of the Intermediate 18A, except using 4-(cyclohexyloxy)-4-oxobutanoic acid instead of 4-oxo-4-(pentan-2-yloxy)butanoic acid.

The Compound of Example 21.

The Compound of Example 21 (TFA salt) was prepared from the Intermediate 21A just as described for the last step in the preparation of the Compound of Example 18. Off-white solid. NMR: 7.37-7.18 (m, 3H), 7.09 (d, J 8 Hz, 2H), 4.59-4.57 (m, 2H), 4.44-4.33 (m, 5H), 4.17-4.05 (m, 8H), 3.19-3.15 (m, 2H), 2.95-2.91 (m, 11H), 2.71-2.48 (m, 8H), 2.06-1.51 (m, 20H), 1.34-1.09 (m, 10H), 1.04 (t, J 6 Hz, 5H), 0.67 (d, J 4 Hz, 2H), 0.61 (d, J 4 Hz, 3H), 0.53 (d, J 4 Hz, 3H). MS (m/z): 1245.6 (M+H).

Example 22

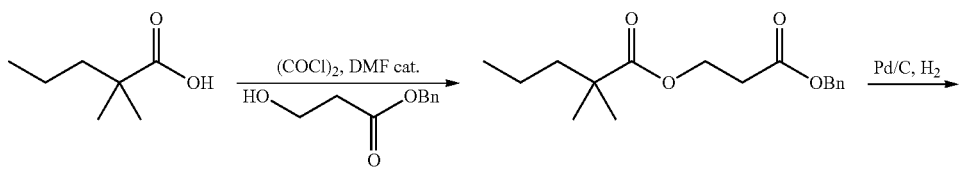

-continued
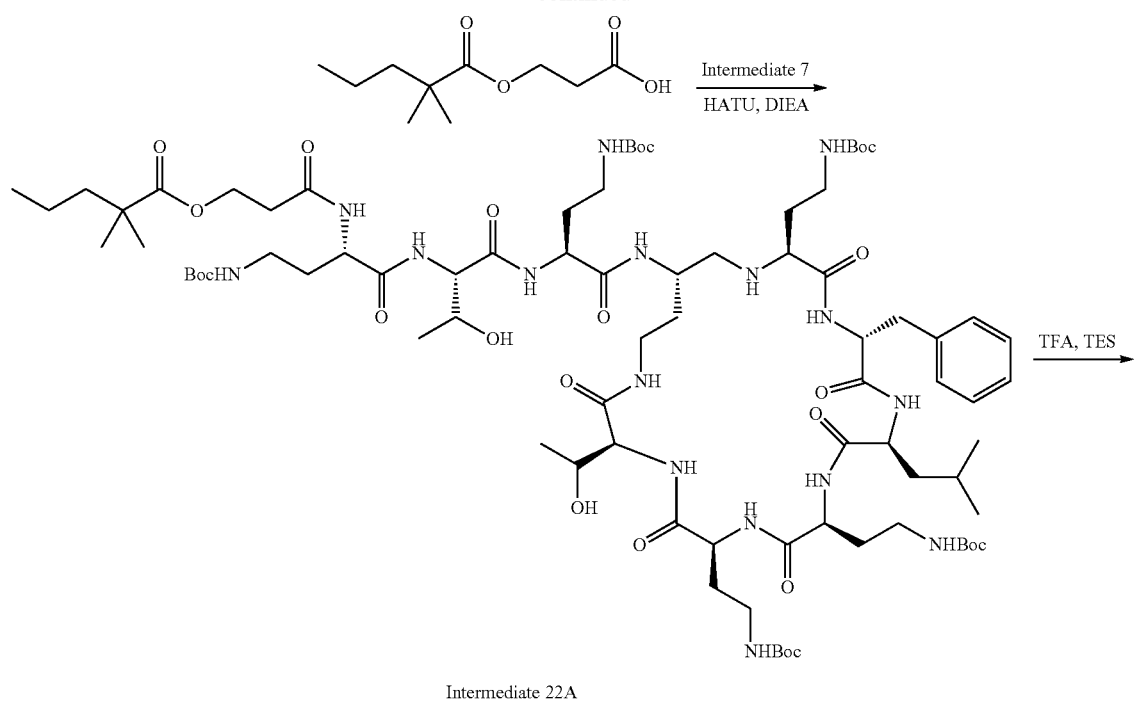
Intermediate 22A
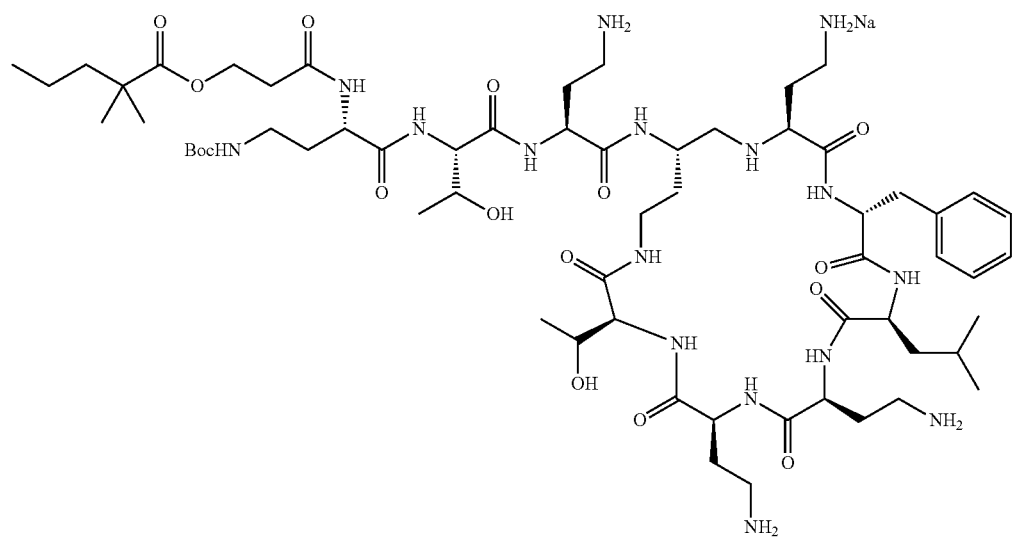
Example 22 TFA salt (3-(Benzyloxy)-3-oxo)propyl 2,2-dimethylpentanoate Oxalyl chloride (2.8 mL) was added dropwise at 0° C. to 2,2-dimethylpentanoic acid (2.6 mL) in DCM (5 mL), followed by cat. DMF (2 drops). The mixture was stirred at r.t. for 1.5 h and concentrated under vacuum. This was dissolved in DCM (5 mL), and the solution was added dropwise with stirring at 0° C. to benzyl 3-hydroxypropanoate (2.6 g) and Et₃N (5.1 mL) in DCM (5 mL). The mixture was stirred at r.t. for 4 h, then washed with brine (10 mL) and extracted with DCM (2×15 mL). The organic phase was dried (Na sulfate) and concentrated under vacuum. The residue was purified by silica gel column chromatography (gradient elution 0-30 percent EtOAc/petroleum ether) to afford the product.

3-((2,2-Dimethylpentanoyl)oxy)propanoic acid

The mixture of (3-(Benzyloxy)-3-oxo)propyl 2,2-dimethylpentanoate (4.1 g) and wet Pd/C (1.2 g; 56% H₂O) in MeOH (40 mL) was hydrogenated (1 Torr) 15 h. The mixture was filtered and evaporated under vacuum to afford the product.

Intermediate 22A.

The Intermediate 22A was prepared just as described above for the preparation of the Intermediate 18A, except using 3-(2,2-dimethylpentanoyloxy)propanoic acid instead of 4-oxo-4-(pentan-2-yloxy)butanoic acid.

The Compound of Example 22.

The Compound of Example 22 (TFA salt) was prepared from the Intermediate 22A just as described for the last step in the preparation of the Compound of Example 18. Off-white solid. NMR: 7.25-7.18 (m, 3H); 7.09 (d, J 8.0 Hz, 2H); 4.44-4.19 (m, 5H); 4.17-4.05 (m, 10H); 3.17-3.15 (m, 2H); 3.08-2.91 (m, 11H); 2.71-2.52 (m, 5H); 2.06-1.76 (m, 16H); 1.33-1.25 (m, 7H); 1.06-1.02 (m, 7H); 0.96 (s, 6H); 0.70-0.66 (t, J 8.0 Hz, 4H); 0.60 (d, J 4.0 Hz, 3H); 0.53 (d, J 4.0 Hz, 3H). MS (m/z): 1247.6 (M+Na).

Example 23

Synthesis of the Compound of Example 23:

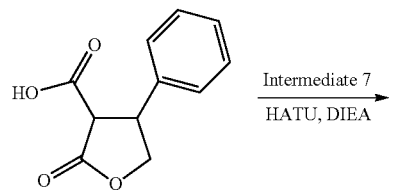

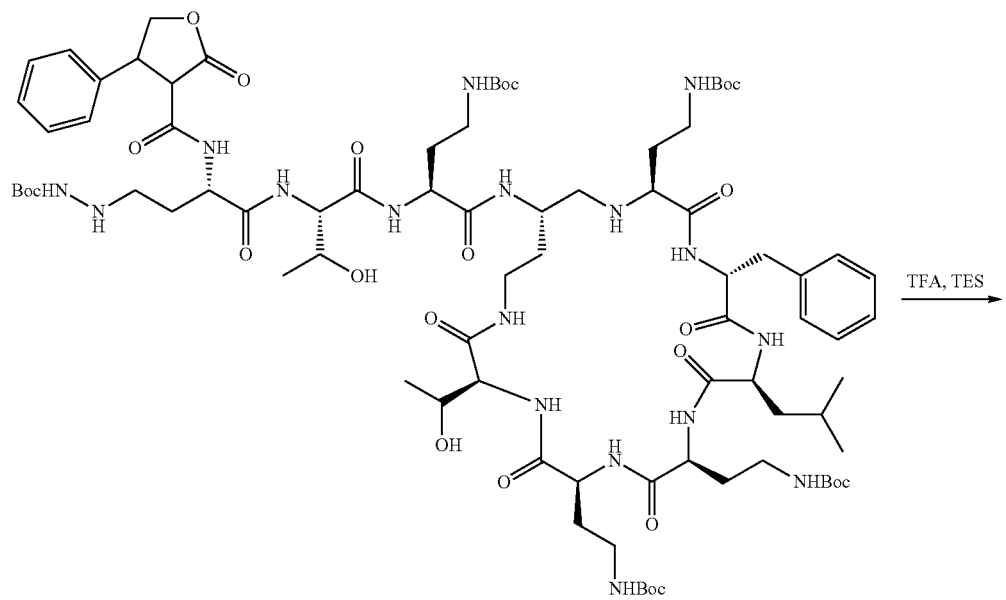

Intermediate 23A

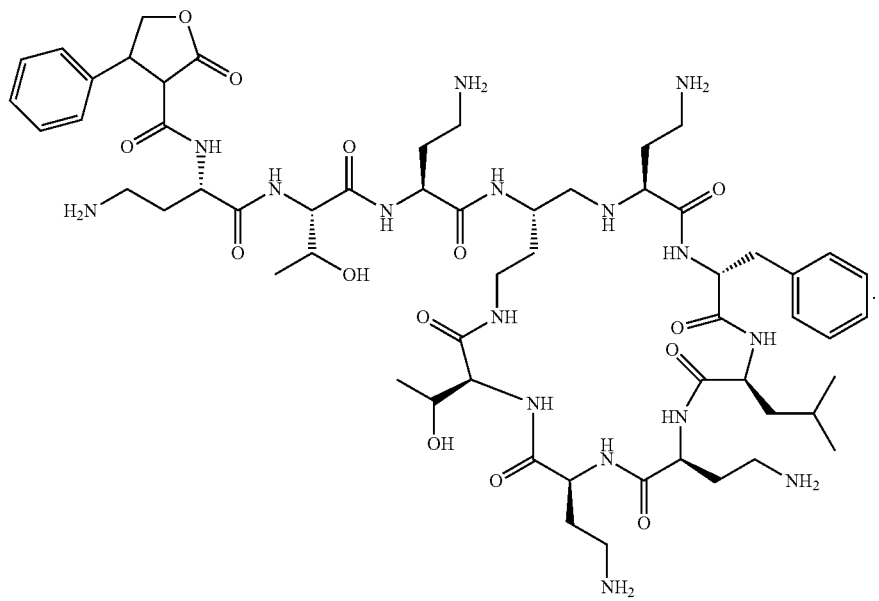

Example 23 TFA salt

The Compound of Example 23.

The Compound of Example 23 (TFA salt) was prepared analogously from the Intermediate 7 just as described for the Compound of Example 18 except using 2-oxo-4-phenyltetrahydrofuran-3-carboxylic acid in place of 4-butoxy-4-oxobutanoic acid. Off-white solid. NMR: 7.37-7.18 (m, 8H), 7.07 (d, J 8.0 Hz, 2H), 4.43-4.37 (m, 2H), 4.36-3.93 (m, 12H), 3.23-3.12 (m, 1H), 3.19-2.81 (m, 10H), 2.78-2.58 (m, 2H), 2.06-1.51 (m, 12H), 1.36-1.09 (m, 3H), 1.04 (t, J 6.0 Hz, 4H), 0.96-0.92 (d, J 4.0 Hz, 1H), 0.61 (d, J 4.0 Hz, 4H), 0.54 (d, J 4.0 Hz, 3H). MS (m/z): 1251.5 (M+H).

Example 24

Synthesis of the Compound of Example 24:

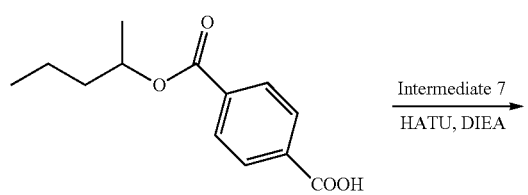

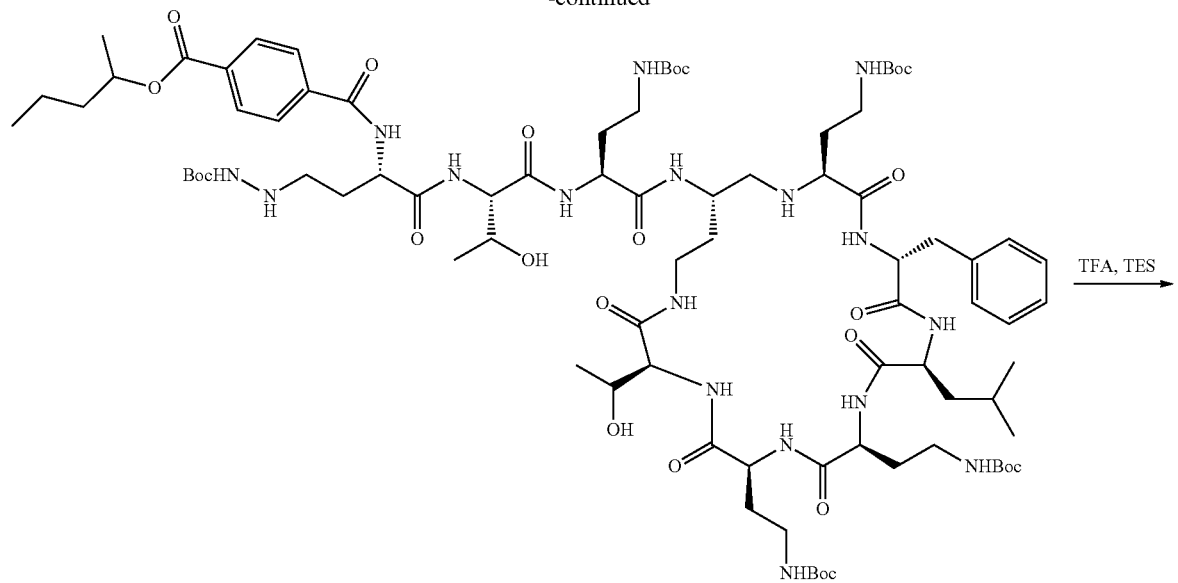
Intermediate 24A
→ TFA, TES
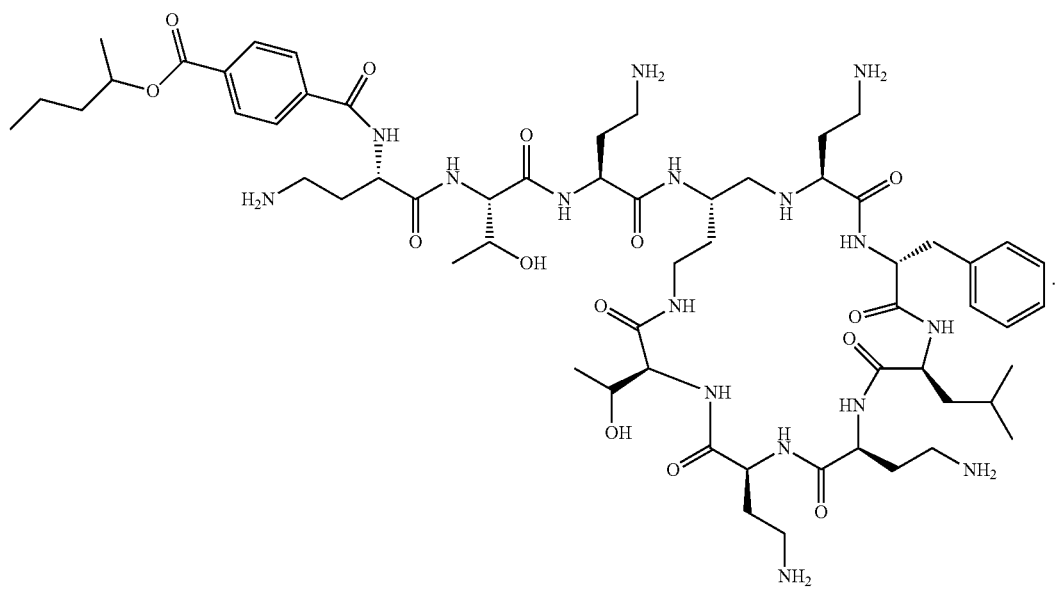
Example 24 TFA salt
The Compound of Example 24.
The Compound of Example 24 (TFA salt) was prepared analogously from Intermediate 7 just as described for the Compound of Example 18 except using 4-((pentan-2-yloxy) carbonyl)benzoic acid in place of 4-butoxy-4-oxobutanoic acid. NMR: 7.79-7.26 (d, J 8.0 Hz, 2H), 7.23-7.21 (d, J 8.0 Hz, 2H), 7.20-7.10 (m, 4H), 7.09-7.08 (m, 2H), 5.07-4.99 (m, 1H), 4.60-4.55 (m, 1H), 4.44-4.39 (m, 1H), 4.37-4.30 (m, 2H), 4.28-4.22 (m, 1H), 4.06-4.01 (m, 7H), 3.21-3.09 (m, 1H), 3.03-2.85 (m, 12H), 2.75-2.56 (m, 2H), 2.10-1.95 (m, 9H), 1.89-1.41 (m, 6H), 1.40-0.84 (m, 12H), 0.84-0.45 (m, 11H). MS (m/z): 1281.6 (M+H).

Example 25

Synthesis of the Compound of Example 25:

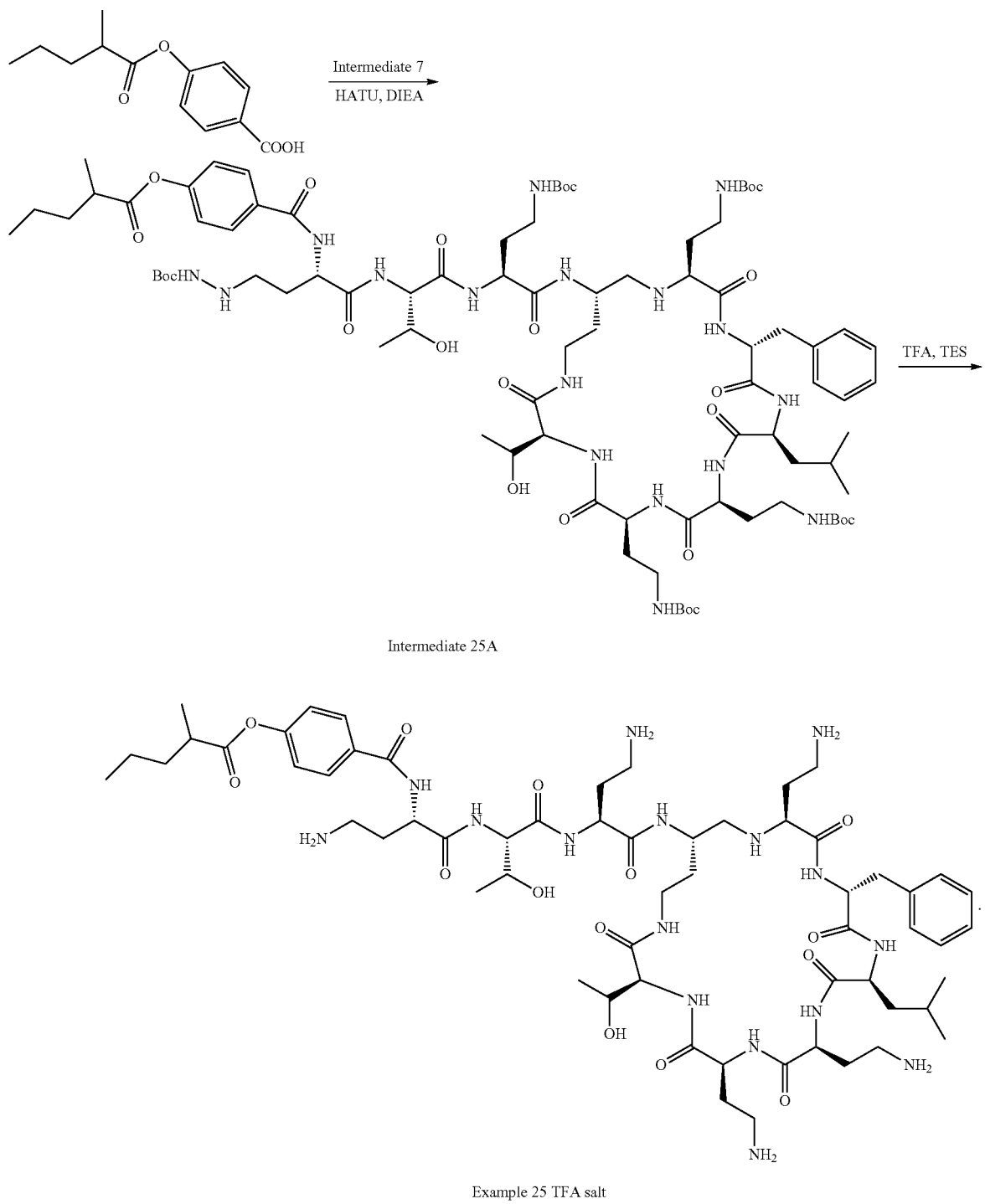

Intermediate 25A

Example 25 TFA salt

The Compound of Example 25.

The Compound of Example 25 (TFA salt) was prepared analogously from the Intermediate 7 just as described for the Compound of Example 18 except using 4-((2-methylpentanoyl)oxy)benzoic acid in place of 4-butoxy-4-oxobutanoic acid. NMR: 7.89-7.85 (m, 2H), 7.23-7.18 (m, 3H), 7.18-7.08 (m, 4H), 4.59-4.52 (m, 1H), 4.43-4.38 (m, 1H), 4.38-4.4.32 (m, 2H), 4.18-4.301 (m, 7H), 3.32-3.12 (m, 1H), 3.08-2.86 (m, 11H), 2.78-2.58 (m, 3H), 2.21-1.62 (m, 13H), 1.62-1.57 (m, 1H), 1.48-1.40 (m, 1H), 1.39-1.20 (m, 4H), 1.18-1.10 (d, J 8.0 Hz, 3H), 1.10-0.98 (m, 5H), 0.81-0.77 (m, 3H), 0.77-0.58 (m, 4H), 0.58-0.51 (m, 3H). MS (m/z): 1281.6 (M+H).

Example 26
Synthesis of the Compound of Example 26:
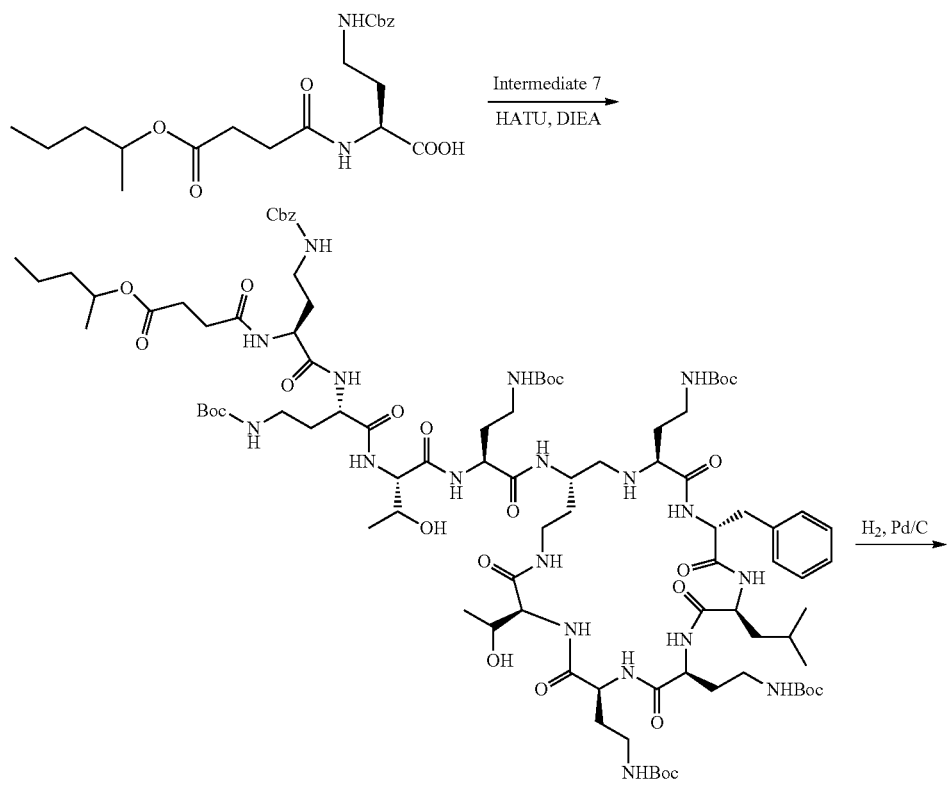
Intermediate 26A
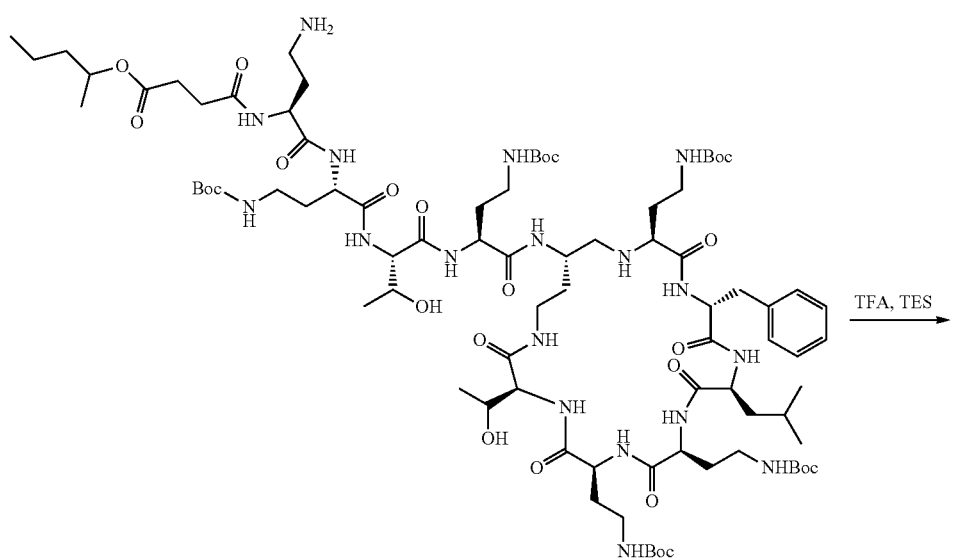
Intermediate 26B

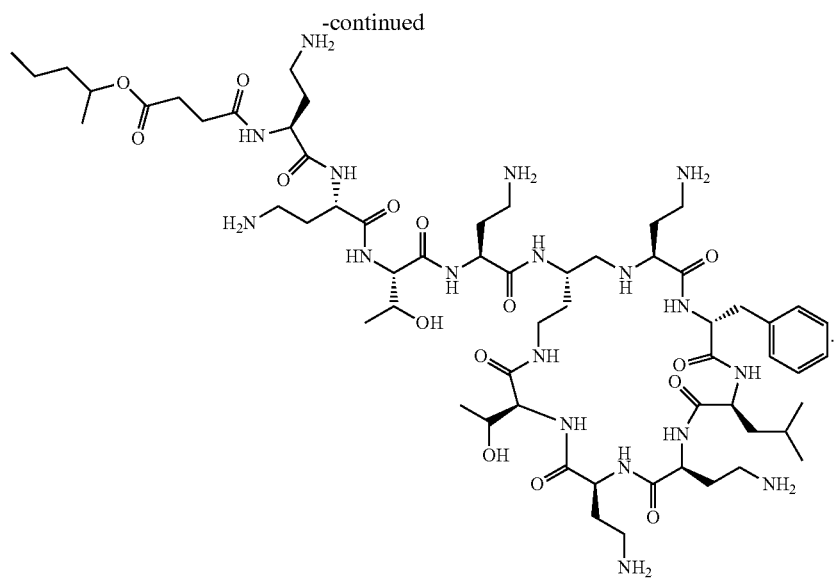

Example 26 TFA salt

Intermediate 26A.

DIEA (0.21 mL) and HATU (456 mg) were added to a solution of (2S)-4-(((benzyloxy)carbonyl)amino)-2-(4-oxo-4-(pentan-2-yloxy)butanamido)butanoic acid (460 mg) in DCM (20 mL). The mixture was stirred at r.t. for 30 min. Then Intermediate 7 (0.83 g) was added, and the mixture was stirred o.n. Volatiles were removed under vacuum, and the residue was purified by HPLC to give Intermediate 26A.

Intermediate 26B.

A solution of Intermediate 26A in MeOH (15 mL) was hydrogenated (1 Torr) in presence of wet Pd/C (130 mg, 56%) for 2 h. The mixture was filtered and volatiles were removed under vacuum to afford the Intermediate (TFA salt) 26B.

The Compound of Example 26.

The Compound of Example 26 (TFA salt) was prepared from the Intermediate 26B just as described for the last step in the preparation of the Compound of Example 18. Off-white solid. NMR: 7.28-7.08 (m, 3H), 7.13-7.08 (m, 2H), 4.48-4.17 (m, 6H), 4.17-4.01 (m, 7H), 3.20-3.09 (m, 1H), 3.09-2.81 (m, 13H), 2.74-2.58 (m, 2H), 2.58-2.40 (m, 5H), 2.17-1.60 (m, 14H), 1.48-1.00 (m, 16H), 0.74-0.68 (t, J 8.0 Hz, 3H), 0.68-0.51 (m, 6H). MS (m/z): 1334.7 (M+H).

Example 27

Synthesis of the Compound of Example 27:

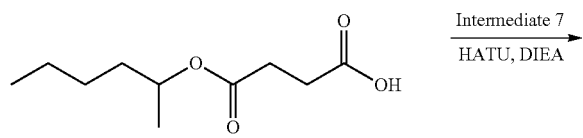

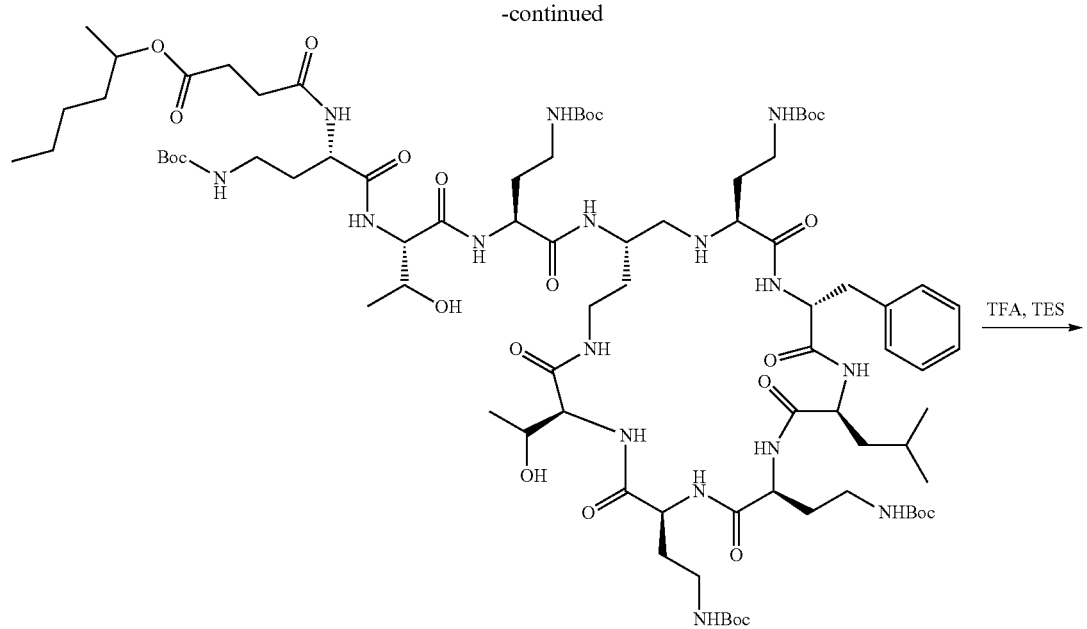

Intermediate 27A

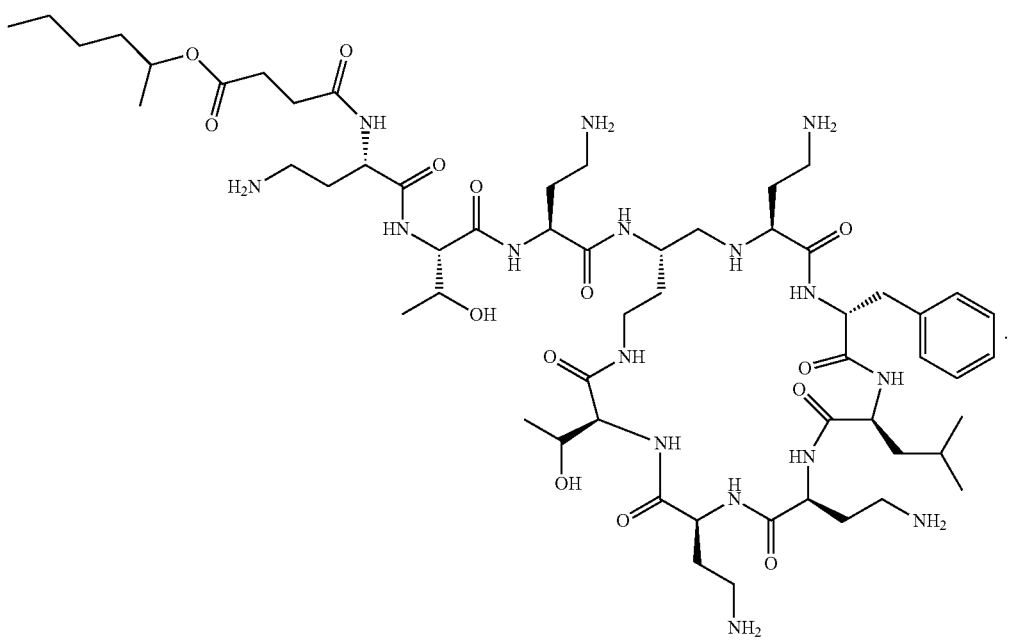

Example 27 TFA salt

The Compound of Example 27.

The Compound of Example 27 (TFA salt) was prepared analogously from the Intermediate 7 just as described for the Compound of Example 18 except using 4-(hexan-2-yloxy)-4-oxobutanoic acid in place of 4-butoxy-4-oxobutanoic acid, except using 4-(hexan-2-yloxy)-4-oxobutanoic acid in place of 4-oxo-4-(pentan-2-yloxy)butanoic acid to prepare respective Intermediate 27A. NMR: 7.28-7.13 (m, 3H), 7.13-7.08 (d, J 8.0 Hz, 2H), 4.78-4.70 (m, 1H), 4.43-4.39 (m, 1H), 4.39-4.32 (m, 3H), 4.20-4.01 (m, 7H), 3.22-3.12 (m, 1H), 3.02-2.88 (m, 11H), 2.74-2.43 (m, 6H), 2.16-1.68 (m, 13H), 1.43-1.18 (m, 4H), 1.18-1.01 (m, 13H), 0.73-0.53 (m, 10H). MS (m/z): 1247.6 (M+H).

Example 28

Synthesis of the Compound of Example 28:

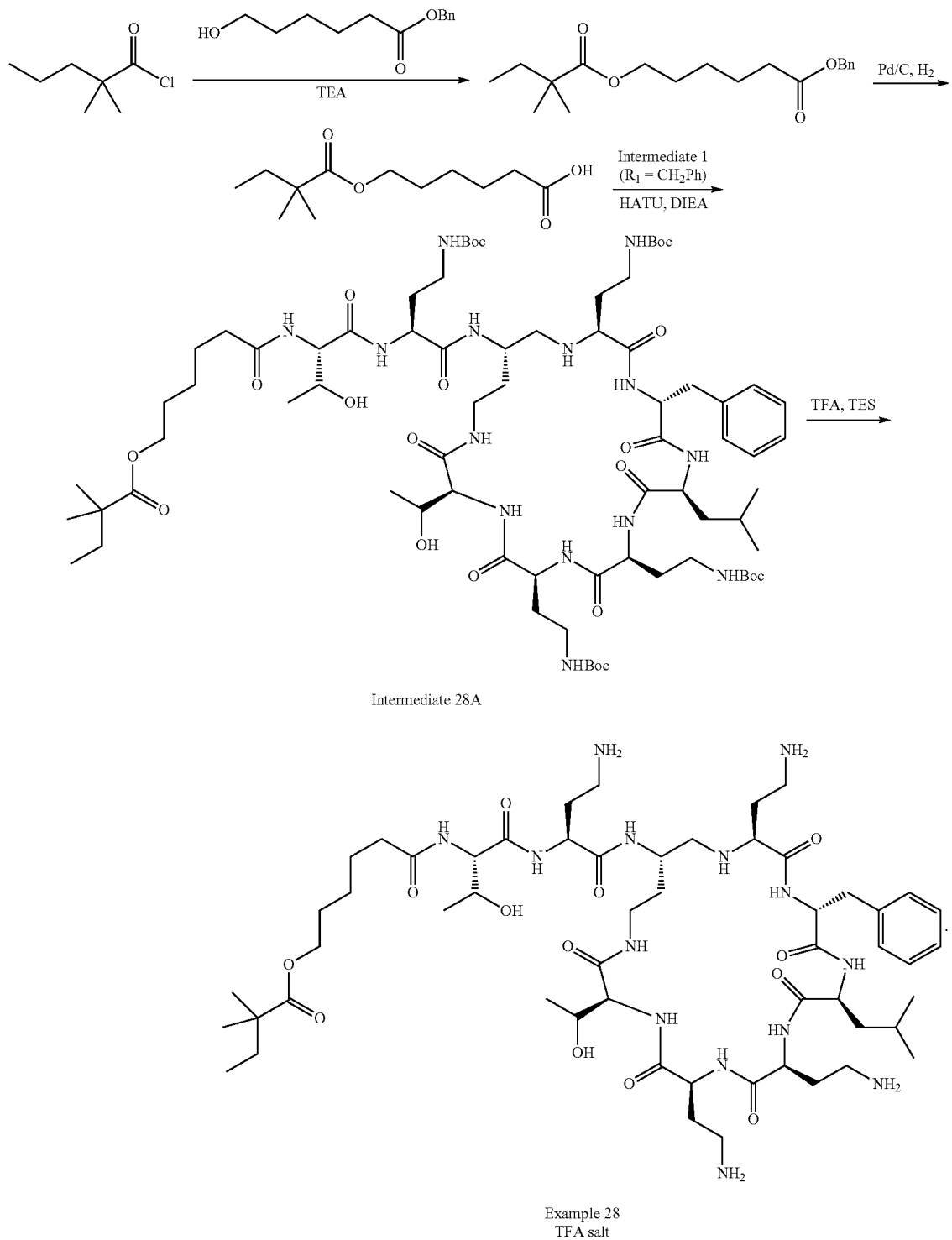

Intermediate 28A

Example 28
TFA salt

Benzyl 6-((2,2-dimethylbutanoyl)oxy)hexanoate 2,2-Dimethylbutanoyl chloride (1.5 mL) was added dropwise with stirring to a solution of benzyl 6-hydroxyhexanoate (2.3 g) and TEA (4.2 mL) in DCM (20 mL), and the mixture was stirred at r.t. for 6 h, then washed with brine (3×10 mL) and dried (Na sulfate). Volatiles were removed under vacuum, and the product was purified by silica gel column chromatography (gradient 0-30% hexanes-EtOAc).

6-((2,2-Dimethylbutanoyl)oxy)hexanoic acid

Benzyl 6-((2,2-dimethylbutanoyl)oxy)hexanoate (1.8 g) and wet Pd/C (0.6 g; 56% H₂O) in MeOH (15 mL) was hydrogenated (1 Torr) for 5 h. The mixture was filtered and evaporated under vacuum to afford the product.

Intermediate 28A.

DIEA (0.21 mL) and HATU (446 mg) were added to a solution of 3-((2,2-dimethylpentanoyl)oxy)propanoic acid (242 mg) in DCM (15 mL). The mixture was stirred at r.t. for 30 min. Then Intermediate 1 (0.8 g) was added, and the mixture was stirred o.n. Volatiles were removed under vacuum evaporated, and the residue taken into EtOAc (80 mL), washed with 0.2% HCl (3×30 mL), sat. NaHCO₃ (2×20 mL) and brine (20 mL), and dried (Na sulfate). Solvent was evaporated under vacuum to afford the crude product used directly at the next step.

The Compound of Example 28.

The mixture of Intermediate 28A (1.15 g) and TES (0.2 mL) in TFA/H₂O (4.0 mL/0.5 mL) was stirred at r.t. for 1.5 h. The mixture was evaporated under vacuum, and residue purified by HPLC to afford the Compound of Example 28 (TFA salt). NMR: 7.25-7.16 (m, 3H); 7.09 (d, J 7.6 Hz, 2H); 4.42 (t, J 8.0 Hz, 1H); 4.34-4.31 (m, 2H); 4.17-4.03 (m, 8H); 3.96 (t, J 2.4 Hz, 2H); 3.23-3.16 (m, 1H); 3.06-2.87 (m, 9H); 2.75-2.58 (m, 2H); 2.29-2.19 (m, 2H); 2.17-1.66 (m, 10H); 1.56-1.45 (m, 4H); 1.40 (dd, J 15.2, 7.2 Hz, 2H); 1.34-1.12 (m, 3H); 1.07 (dd, J 12.8, 2.0 Hz, 6H); 0.98 (s, 6); 0.69-0.67 (m, 1H); 0.62 (dd, J 13.6, 6.4 Hz, 6H); 0.56 (d, J 6.0 Hz, 3H). MS (m/z): 1175.6 (M+H).

Example 29

Synthesis of the Compound of Example 29:

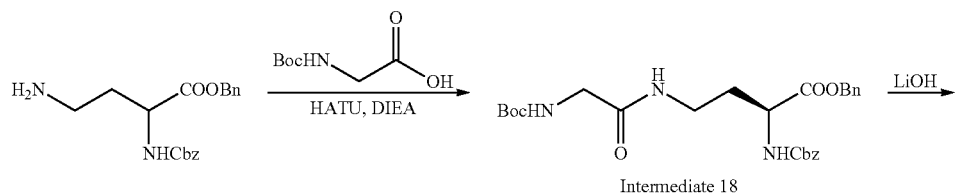

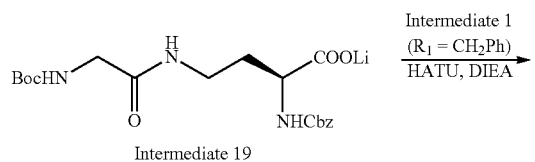

Intermediate 19

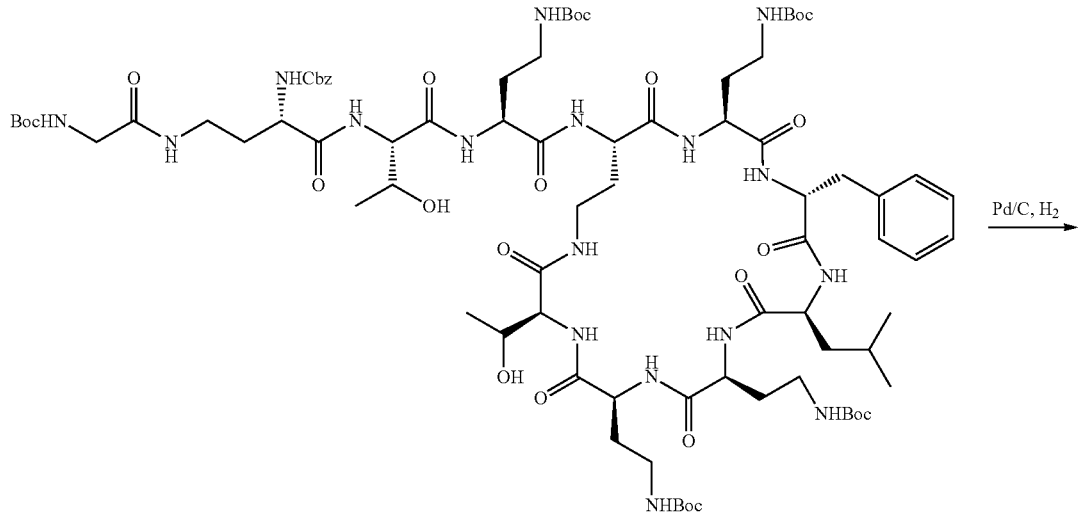

Intermediate 29A

-continued
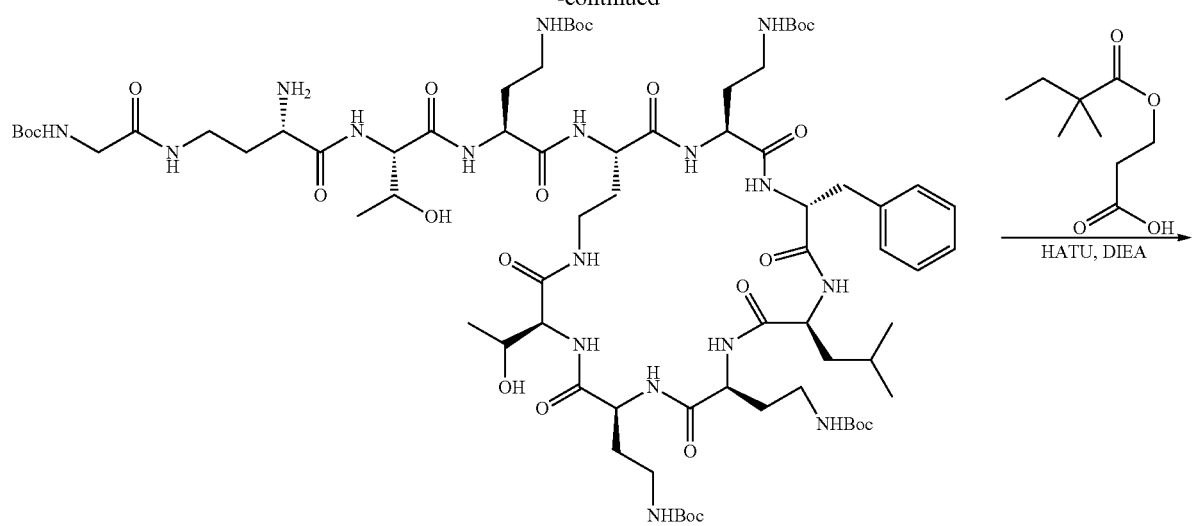
Intermediate 29B
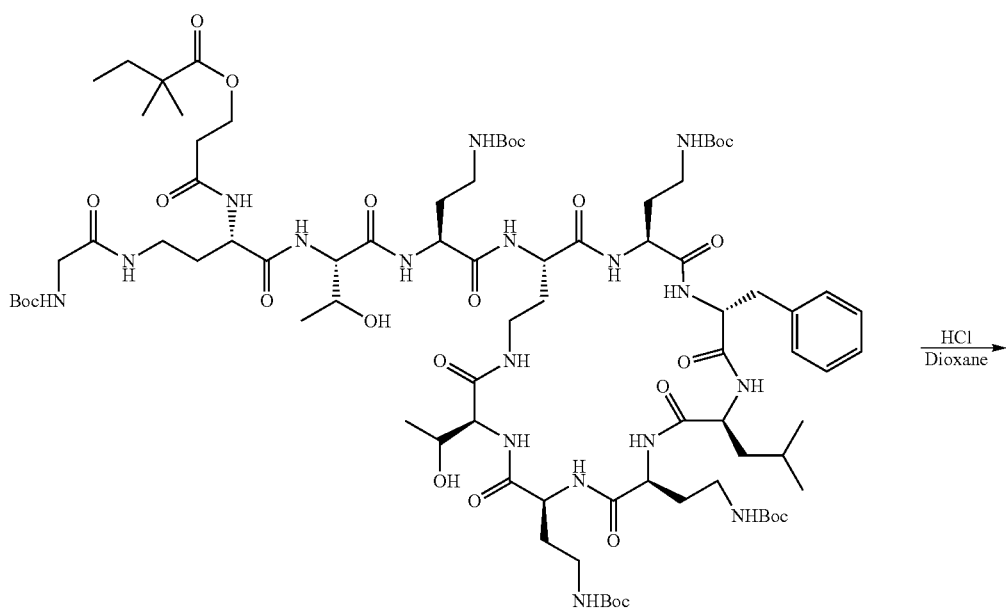
Intermediate 29C

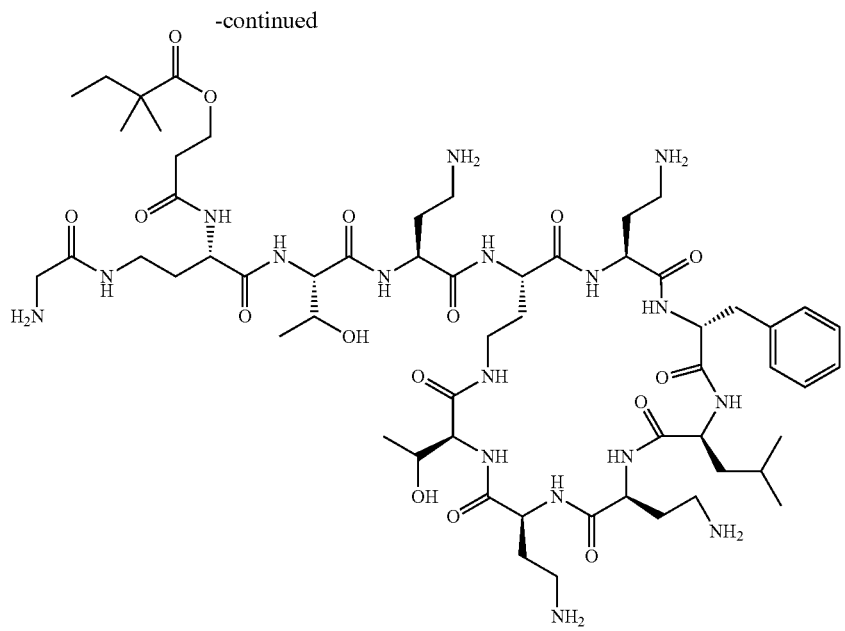

Example 29 HCl salt

Intermediate 18.

DIEA (1.49 mL) and HATU (0.91 g) was added to the mixture of 2-((tert-butoxycarbonyl)amino)acetic acid (0.42 g) in DCM (15 mL), and the mixture was stirred at r.t. for 30 min. Then (S)-benzyl 4-amino-2-(((benzyloxy)carbonyl)amino)butanoate (1.25 g) was added, and the mixture was stirred o.n. Volatiles were removed under vacuum, the residue taken into EtOAc (80 mL), washed with 0.2% HCl (3×20 mL), sat. NaHCO$_3$ (2×20 mL), and brine (20 mL). The organic phase was dried (Na sulfate), and solvent removed under vacuum to afford the product used directly in the next step.

Intermediate 19.

LiOH.H$_2$O (0.093 g) in H$_2$O (6 mL) was added to the crude Intermediate 18 (0.85 g) in THF (8 mL), and the mixture was stirred for 5 h. The mixture was then filtered, and volatiles removed under vacuum to afford the product used directly in the next step.

Intermediate 29A.

DIEA (0.21 mL) and HATU (0.46 g) was added to a solution of the crude Intermediate 19 (0.49 g) in DCM (25 mL), and the mixture was stirred for 30 min. Intermediate 1 (1.5 g) was then added, and the mixture was stirred o.n. Volatiles were removed under vacuum, and the residue taken into EtOAc (80 mL), washed with 0.2% HCl (3×30 mL), sat. NaHCO$_3$ (2×20 mL), brine (20 mL), and dried (Na sulfate). Solvent was evaporated under vacuum to afford the crude product used directly at the next step.

Intermediate 29B.

The mixture of the crude Intermediate 29A (3.5 g) and wet Pd/C (0.8 g; 56% H$_2$O) in MeOH (25 mL) was hydrogenated (1 Torr) for 16 h. The mixture was filtered, solvent was evaporated under vacuum, and the crude product purified by silica gel chromatography (gradient 0-20% MeOH in DCM).

Intermediate 29C.

DIEA (0.09 mL) and HATU (0.19 g) was added to 3-((2,2-dimethylbutanoyl)oxy)propanoic acid (0.094 g) in DCM (10 mL), and the mixture was stirred for 30 min. Intermediate 29B (0.404 g) was then added, and the mixture was stirred o.n. Volatiles were removed under vacuum, and the residue taken into EtOAc (30 mL), washed with 0.2% HCl (3×10 mL), sat. NaHCO$_3$ (2×10 mL), brine (10 mL), and dried (Na sulfate). Solvent was evaporated under vacuum to afford the crude product used directly at the next step.

The Compound of Example 29.

4N HCl in dioxane (3 mL) was added to the Intermediate 29C (0.55 g) in 1,4-dioxane (2 mL) and the mixture was stirred at r.t. for 1.5 h. Ether (10 mL) was added, and the precipitated crude product was filtered, dried, and purified by HPLC to afford the Compound of Example 29 (HCl salt). NMR: 7.28-7.19 (m, 3H); 7.15 (d, J 7.6 Hz, 2H); 4.45 (t, J 8.0 Hz, 1H); 4.38-4.32 (m, 2H); 4.28-4.30 (m, 1H); 4.22-4.06 (m, 10H); 3.66 (s, 2H); 3.22-3.18 (m, 3H); 3.04-2.97 (m, 9H); 2.76-2.66 (m, 2H); 2.58-2.55 (m, 2H); 2.14-1.76 (m, 13H); 1.42-1.28 (m, 4H); 1.07 (t, J 6.0 Hz, 6H); 0.98 (s, 6H); 0.64 (t, J 6.4 Hz, 6H); 0.57 (d, J 4.4 Hz, 3H). MS (m/z): 1290.6 (M+H).

Example 30

Synthesis of the Compound of Example 30:

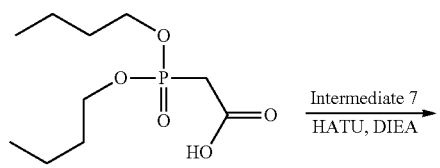

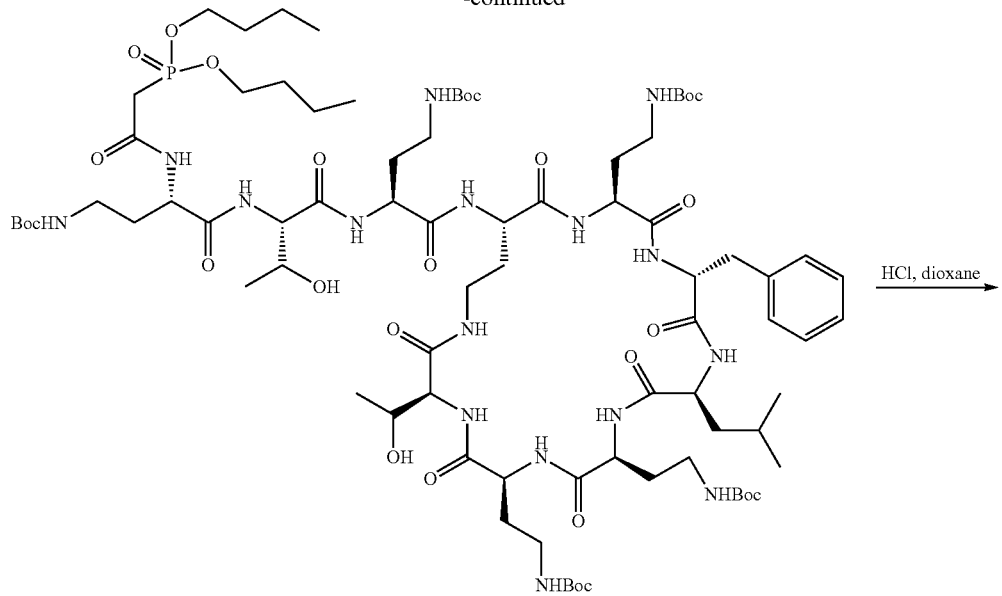

Intermediate 30A

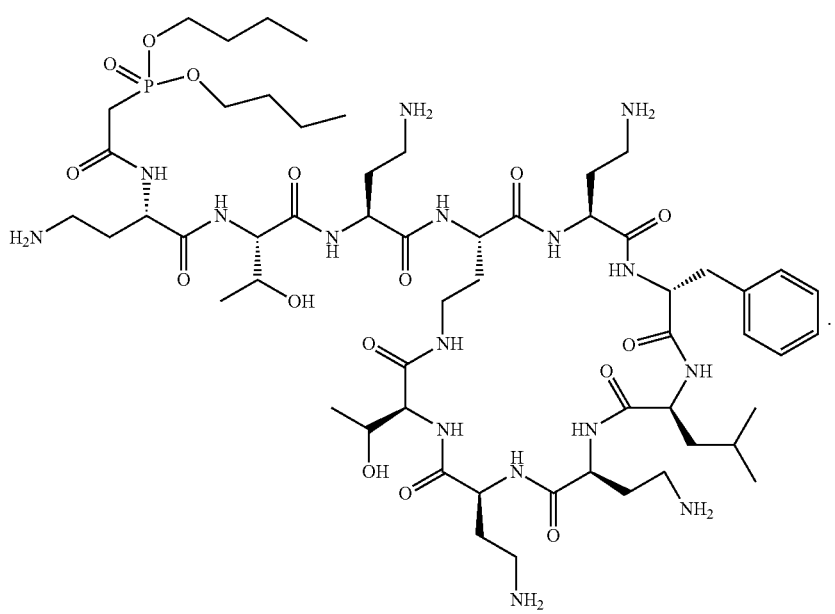

Example 30 HCl salt

Intermediate 30A.

DIEA (0.18 mL) and HATU (0.39 g) were added to 2-(dibutoxyphosphoryl)acetic acid (0.26 g; prepared analogously to Kabachnik et al., *Zh. Obsch. Khimii*, 1971, vol. 41, p. 1426) in DCM (15 mL), and the mixture was stirred for 30 min. Intermediate 7 (0.77 g) was then added, and the mixture was stirred o.n. Volatiles were removed under vacuum evaporated, and the residue taken into EtOAc (60 mL), washed with 0.2% HCl (3×20 mL), sat. NaHCO$_3$ (2×15 mL), brine (15 mL), and dried (Na sulfate). Solvent was evaporated under vacuum to afford the crude product used directly at the next step.

The Compound of Example 30.

4N HCl in 1,4-dioxane (4 mL) was added to the Intermediate 30A (0.98 g) in dioxane (3 mL) and the mixture was stirred at r.t. for 1.5 h. Ether (10 mL) was added, and the precipitated crude product was filtered, dried, and purified by HPLC to afford the Compound of Example 30 (HCl salt). NMR: 7.28-7.19 (m, 3H); 7.15 (d, J 6.8 Hz, 2H); 4.64-4.36 (m, 4H); 4.23 (d, J 4.4 Hz, 1H); 4.18-4.06 (m, 7H); 4.04-3.98 (m, 4H); 3.25-3.18 (m, 1H); 3.05-2.90 (m, 13H); 2.77-2.67 (m, 2H); 2.12-1.57 (m, 13H); 1.56-1.50 (m, 4H); 1.37-1.34 (m, 1H); 1.30-1.21 (m, 5H); 1.08 (t, J 7.6 Hz, 6H); 0.78 (t, J 7.2 Hz, 6H); 0.63 (s, 3H); 0.56 (d, J 4.0 Hz, 3H). MS (m/z): 1297.6 (M+H).

Example 31
Synthesis of the Compound of Example 31:
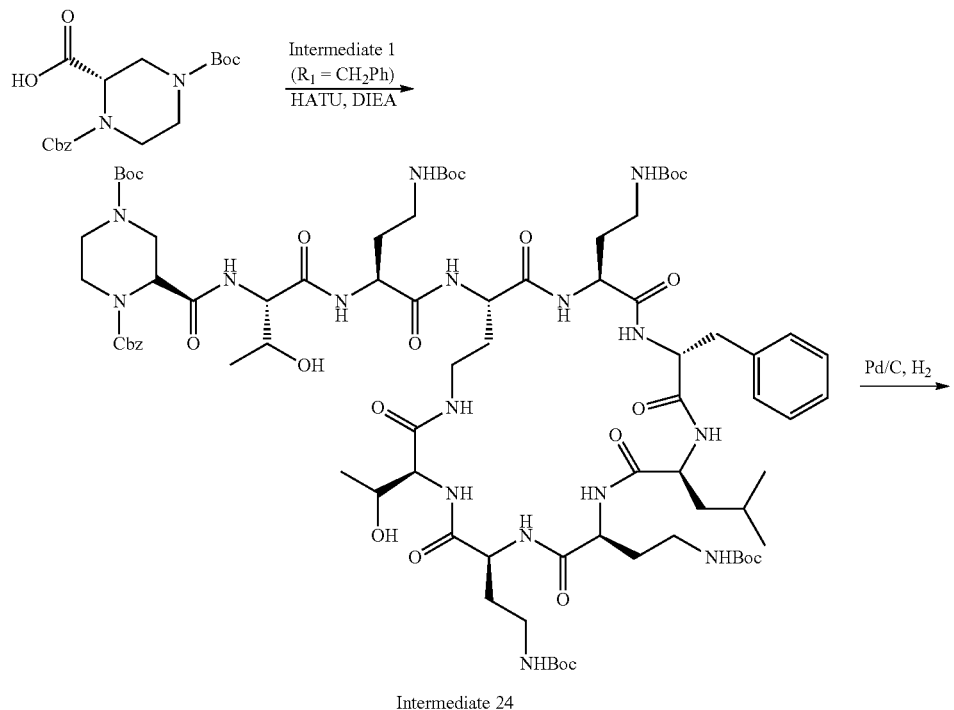
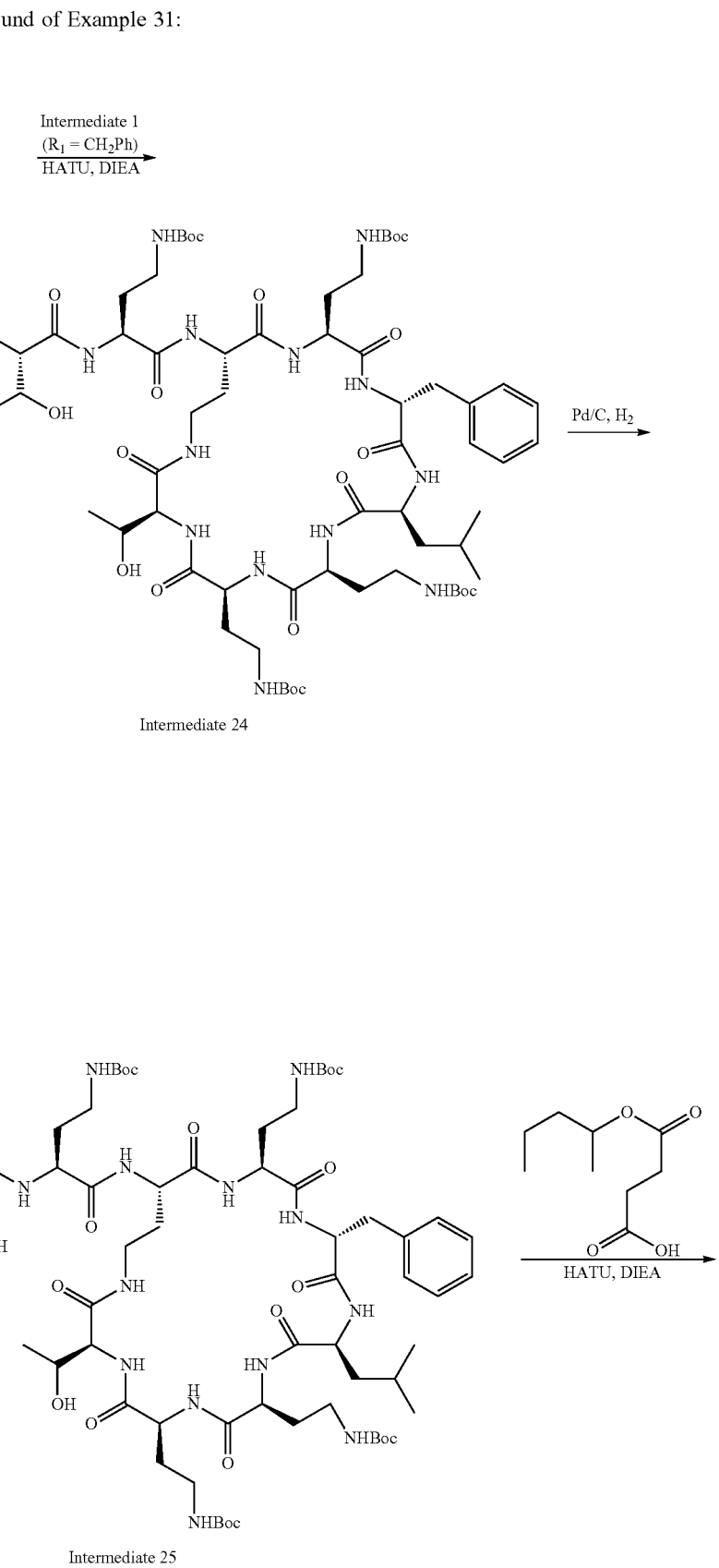

-continued

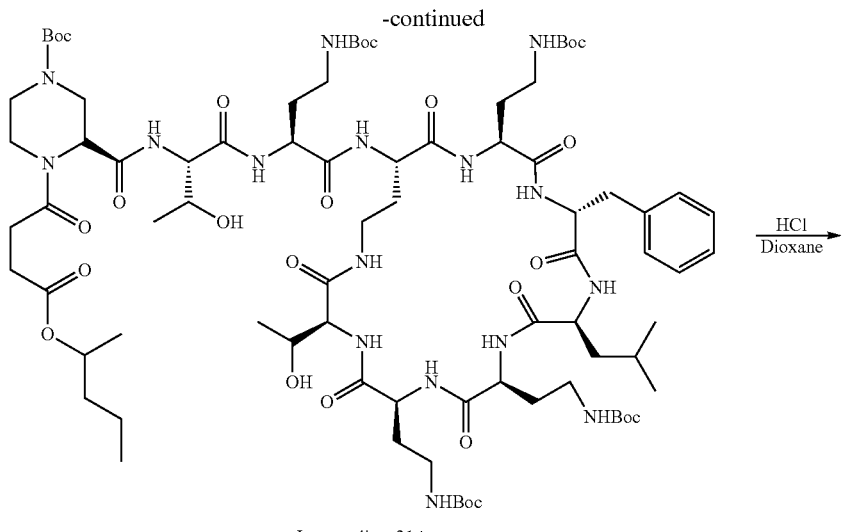

Intermediate 31A

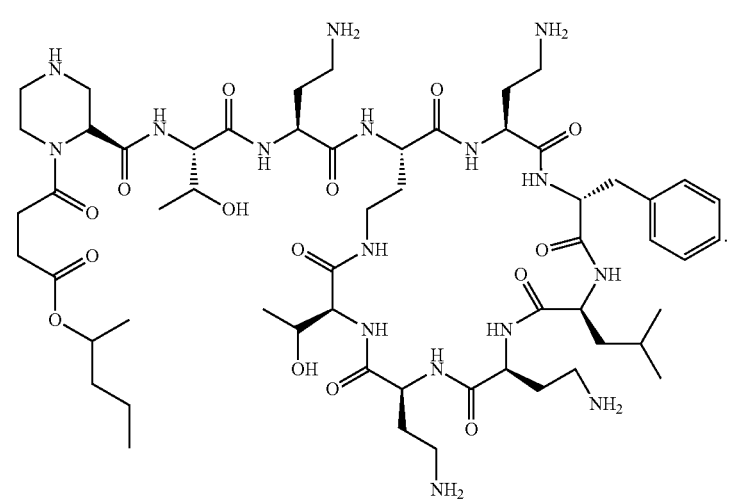

Example 31 HCl salt

Intermediate 24.

DIEA (0.3 mL) and HATU (0.63 g) were added to (S)-1-((benzyloxy)carbonyl)-4-(tert-butoxycarbonyl)piperazine-2-carboxylic acid (0.6 g) in DCM (20 mL), and the mixture was stirred for 30 min. Intermediate 1 (1.5 g) was then added, and the mixture was stirred o.n. Volatiles were removed under vacuum evaporated, and the residue taken into EtOAc (60 mL), washed with 0.2% HCl (3×20 mL), sat. NaHCO₃ (2×15 mL), brine (15 mL), and dried (Na sulfate). Solvent was evaporated under vacuum and the crude product purified by silica gel chromatography (gradient 0-12% MeOH in DCM).

Intermediate 25.

The mixture of Intermediate 24 (1.5 g) and wet Pd/C (1.0 g; 56% H₂O) in MeOH (20 mL) was hydrogenated (1 Torr) for 4 h. The mixture was filtered and solvent evaporated under vacuum to afford the crude product used directly in the next step.

Intermediate 31A.

DIEA (0.11 mL) and HATU (0.23 g) were added to 4-oxo-4-(pentan-2-yloxy)butanoic acid (0.11 g) in DCM (6 mL), and the mixture was stirred for 30 min. Intermediate 25 (0.32 g) was then added, and the mixture was stirred o.n. Volatiles were removed under vacuum, DMF (3 mL) was added, followed by extra DIEA (0.11 mL), and the mixture was stirred for 5 h. Then EtOAc (60 mL) was added, and the organic phase was washed with 0.2% HCl (3×20 mL), sat. NaHCO₃ (20 mL), brine (10 mL), and dried (Na sulfate). Solvent was evaporated under vacuum and to afford the crude Intermediate 31A used directly in the next step.

The Compound of Example 31.

4N HCl in 1,4-dioxane (4 mL) was added to the Intermediate 31A (0.42 g) in dioxane (1 mL) and the mixture was stirred at r.t. for 1 h. Ether (12 mL) was added, and the precipitated crude product was filtered, dried, and purified by HPLC to afford the Compound of Example 31 (HCl salt). NMR: 7.29-7.17 (m, 3H); 7.12 (d, J 7.6 Hz, 2H); 5.29 (br, 1H); 4.79-4.74 (m, 1H); 4.43 (t, J 8.0 Hz, 1H); 4.37-4.32 (m, 2H); 4.24 (d, J 4.4 Hz, 1H); 4.15-4.04 (m, 8H); 3.71 (d, J 13.2 Hz, 1H); 3.44 (t, J 13.2 Hz, 1H); 3.30-3.06 (m, 4H); 3.01-2.87 (m, 10H); 2.74-2.60 (m, 4H); 2.56-2.54 (m, 2H); 2.15-1.66 (m, 10H); 1.47-1.09 (m, 6H); 1.05 (t, J 6.4 Hz, 9H); 0.72 (t, J 8.0 Hz, 3H); 0.64 (br s., 3H); 0.54 (d, J 6.4 Hz, 3H). MS (m/z): 1245.6 (M+H).

Example 32

Synthesis of the Compound of Example 32:

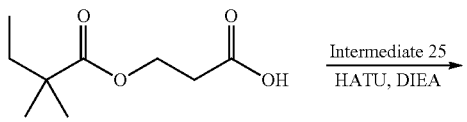

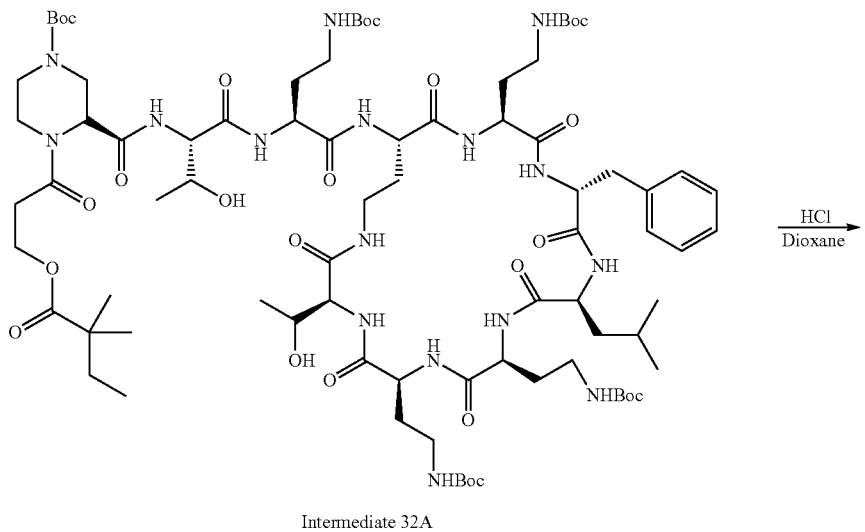

Intermediate 32A

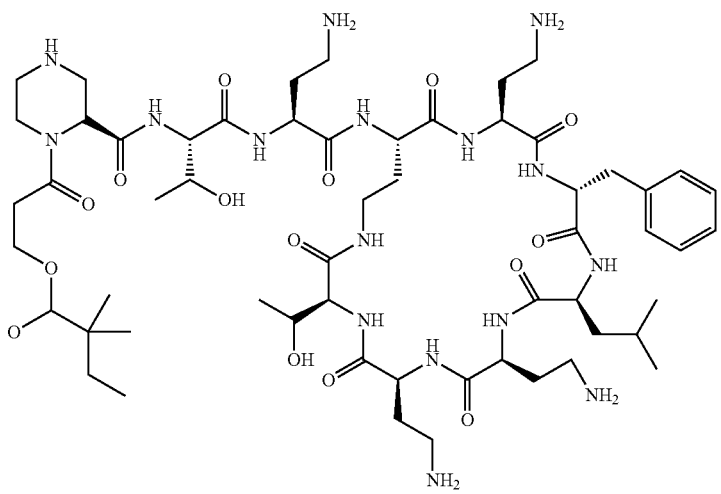

Example 32 HCl salt

Intermediate 32A.

The Intermediate 32A is prepared just as described above for the preparation of the Intermediate 31A, except using 3-(2,2-dimethylbutanoyloxy)propanoic acid instead of 4-oxo-4-(pentan-2-yloxy)butanoic acid.

The Compound of Example 32.

The Compound of Example 32 (HCl salt) was prepared from the Intermediate 32A just as described for the last step in the preparation of the Compound of Example 31. Off-white solid. NMR: 7.25-7.16 (m, 3H); 7.11 (d, J 7.2 Hz, 2H); 5.31 (br, 1H); 4.42 (t, J 8.0 Hz, 1H); 4.36-4.33 (m, 2H); 4.27-4.20 (m, 3H); 4.14-4.03 (m, 8H); 3.72 (d, J 13.4 Hz, 1H); 3.47 (t, J 12.8 Hz, 1H); 3.33 (d, J 12.4 Hz, 1H); 3.25-3.04 (m, 3H); 3.01-2.63 (m, 14H); 2.09-1.69 (m, 10H); 1.40-1.20 (m, 4H); 1.10-1.06 (m, 1H); 1.03 (dd, J 6.0, 4.0 Hz, 5H); 0.96 (s, 6H); 0.62 (t, J 8.8 Hz, 6H); 0.53 (d, J 5.2 Hz, 3H). MS (m/z): 1245.6 (M+H).

Example 33

Synthesis of the Compound of Example 33:

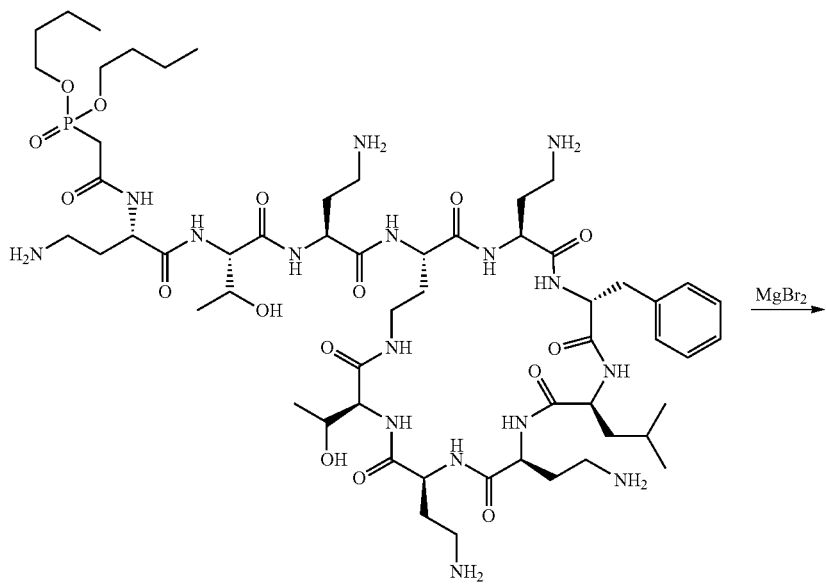

Example 30

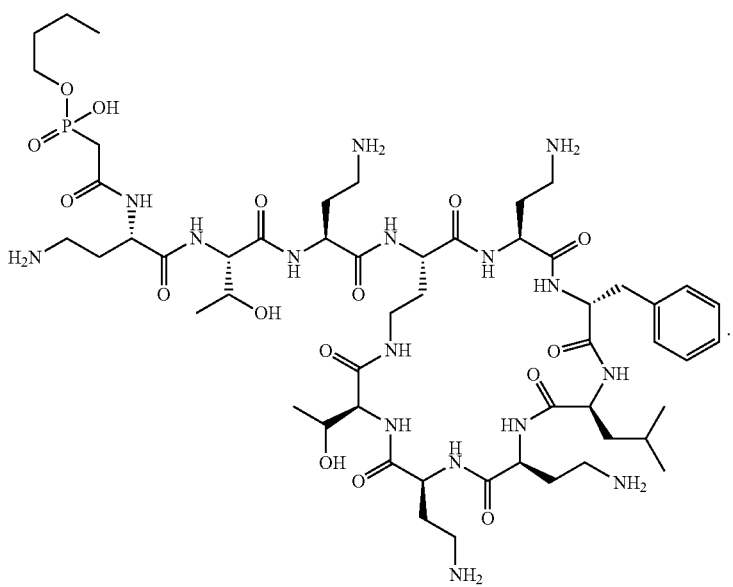

Example 33 HCl salt

The Compound of Example 33.

The compound of Example 30 (75 mg) and MgBr$_2$ (75 mg) in MeCN/NMP (3 mL/1.5 mL) was stirred at 75° C. for 3 h. The mixture was cooled down to rt, concentrated, and purified by HPLC to afford crude product. This was dissolved in 1.2N HCl (2 mL), kept at r.t. for 15 min, and then purified by HPLC to afford the Compound of Example 33 (HCl salt). NMR: 7.45-7.36 (m, 3H); 7.31 (d, J 7.2 Hz, 2H); 4.62 (t, J 8.4 Hz, 1H); 4.55-4.45 (m, 3H); 4.37-4.22 (m, 8H); 3.95 (dd, J 13.6, 6.8 Hz, 2H); 3.42-3.37 (m, 1H); 3.20-3.06 (m, 12H); 2.95-2.81 (m, 4H); 2.34-1.91 (m, 12H); 1.67-1.60 (m, 2H); 1.49-1.38 (m, 4H); 1.22 (dd, J 15.0, 6.4 Hz, 6H); 0.90 (t, J 7.2 Hz, 3H); 0.77 (d, J 5.6 Hz, 3H); 0.68 (d, J 6.0 Hz, 3H). MS (m/z): 1241.5 (M+H).

Example 34
Synthesis of the Compound of Example 34:
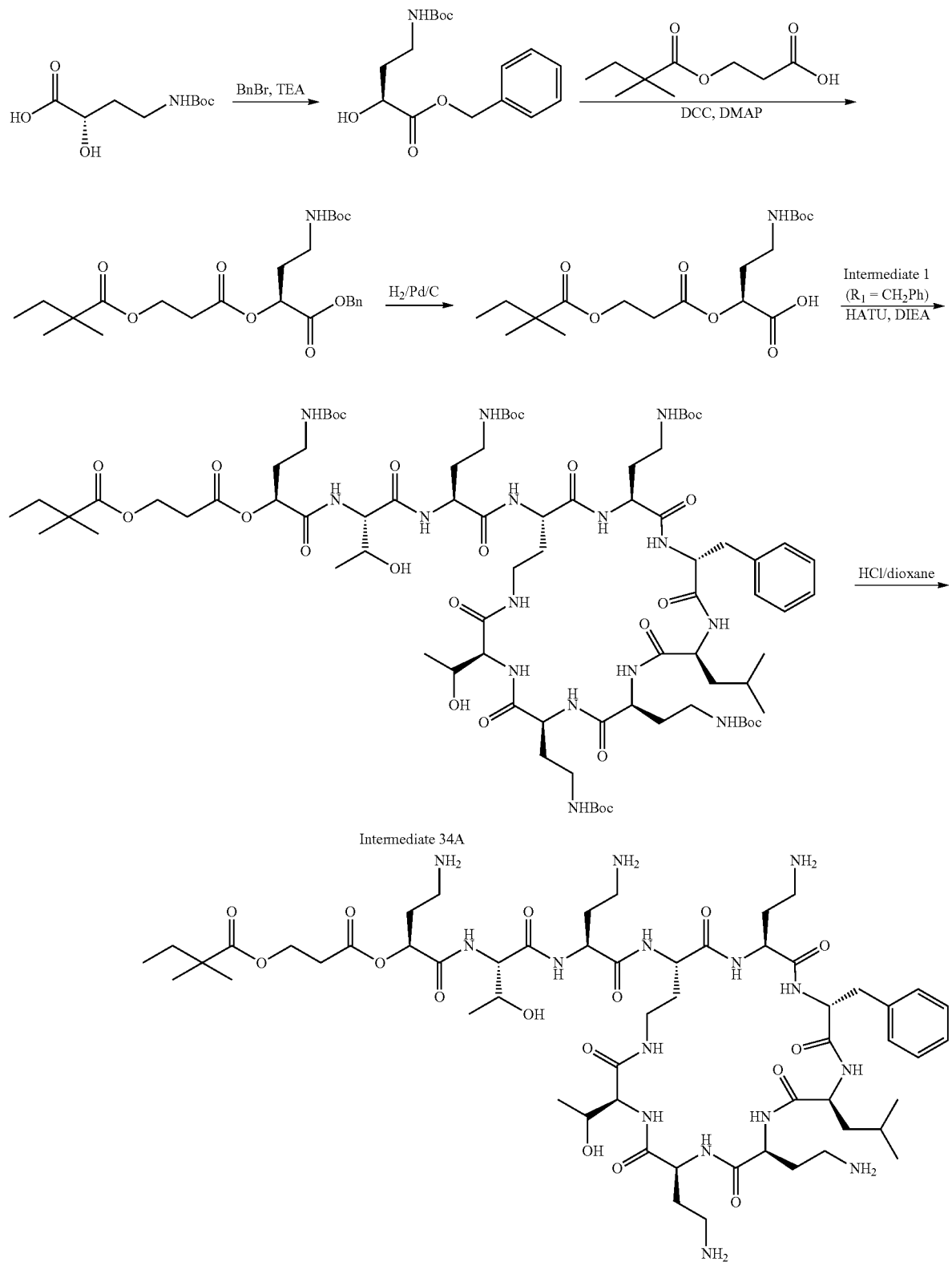
Example 34 HCl salt

(S)-4-((tert-Butoxycarbonyl)amino)-2-hydroxybutanoic acid

Benzyl bromide (3.03 g) was added with stirring to a solution of (S)-4-((tert-butoxycarbonyl)amino)-2-hydroxybutanoic acid (2.72 g) in THF (50 mL) and TEA (4.6 mL) at 0° C. The mixture was allowed to warmed up to r.t. and stirred for 8 h, then treated sat. aq. NH$_4$Cl (50 mL) and extracted with DCM (3×170 mL). Combined organic solution was dried (Na sulfate) and evaporated under vacuum. Crude material was purified by column chromatography (eluent: hexanes to 10% DCM in hexanes, DCM, and 1% MeOH in DCM) to afford the product.

(S)-Benzyl 4-((tert-butoxycarbonyl)amino)-2-((3-((2,2-dimethylbutanoyl)oxy) propanoyl)oxy)butanoate Above ester (310 mg), 3-((2,2-dimethylbutanoyl)oxy) propanoic acid (225.8 mg), DCC (247.4 mg), DMAP (24.4 mg) were mixed together, and then dry DCM (4 mL) was added under Ar. The reaction was stirred at r.t. for 12 h, filtered, and evaporated under vacuum. The residue was purified by column chromatography (gradient 0-30% EtOAc in hexanes) to afford the title compound as a colorless oil.

(S)-4-((tert-Butoxycarbonyl)amino)-2-((3-((2,2-dimethylbutanoyl)oxy) propanoyl)oxy)butanoic acid Above crude benzyl ester (438.3 mg), 10% Pd/C (120 mg) in MeOH (15 mL) was hydrogenated (1 Torr) at rt o.n., filtered and the solvent was evaporated under vacuum to afford the crude product as a colorless oil used directly at the next step.

Intermediate 34A.

HATU (152.1 mg), DIEA (71 uL) were added to the solution of (S)-4-((tert-butoxycarbonyl)amino)-2-((3-((2,2-dimethylbutanoyl)oxy) propanoyl)oxy)butanoic acid (155.8 mg) in DCM (2 mL) under Ar at rt. The mixture was stirred at r.t. for 30 min, Intermediate 1 (272.7 mg) in DCM (2 mL) was then added. The reaction was stirred at rt for 12 h. Volatiles were removed, the residue was dissolved in DMF (2 mL), DIEA (71 uL) was added, and the reaction was stirred at r.t. for 4 h. EtOAc (24 mL) was added. The organic phase was separated, washed with 0.2N HCl aq., sat. NaHCO$_3$ aq. and brine, dried (Na sulfate). Solvent was removed under vacuum and residue was purified by column chromatography (gradient 0-12% MeOH in DCM) to afford the Intermediate 34A as a white solid.

The Compound of Example 34.

The Compound of Example 34 (HCl salt) was prepared from the Intermediate 34A just as described for the last step in the preparation of the Compound of Example 31. Off-white solid. NMR: 7.39-7.32 (m, 3H), 7.24 (d, J 7.2 Hz, 2H), 5.18 (dd, J 7.2, 2.4 Hz, 1H), 4.56 (t, J 8.0 Hz, 1H), 4.49 (dd, J 8.8, 3.6 Hz, 2H), 4.39-4.20 (m, 10H), 3.35-3.27 (m, 1H), 3.16-3.04 (m, 10H), 2.88 (t, J 5.6 Hz, 2H), 2.80-2.73 (m, 1H), 2.25-2.15 (m, 6H), 2.10-1.83 (m, 6H), 1.54-1.34 (m, 4H), 1.19 (dd, J 11.2, 4.8 Hz, 6H), 1.09 (s, 6H), 0.75 (dd, J 12.0, 4.4 Hz, 6H), 0.66 (d, J 5.6 Hz, 3H). MS (m/z): 1234.6 (M+H).

Example 35

Synthesis of the Compound of Example 35:

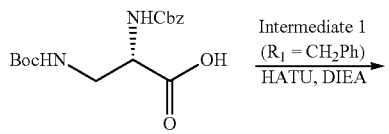

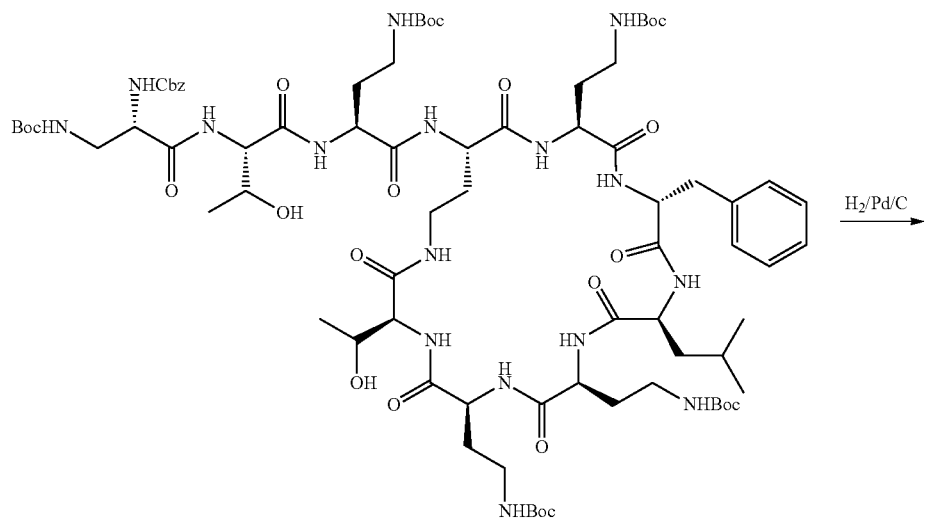

Intermediate 29

177 178
-continued
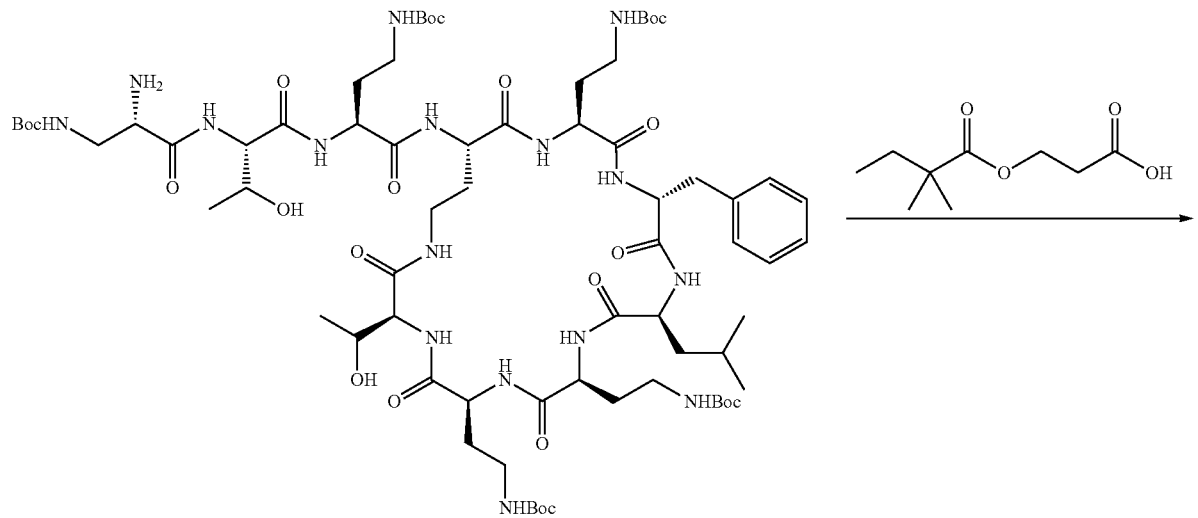
Intermediate 30
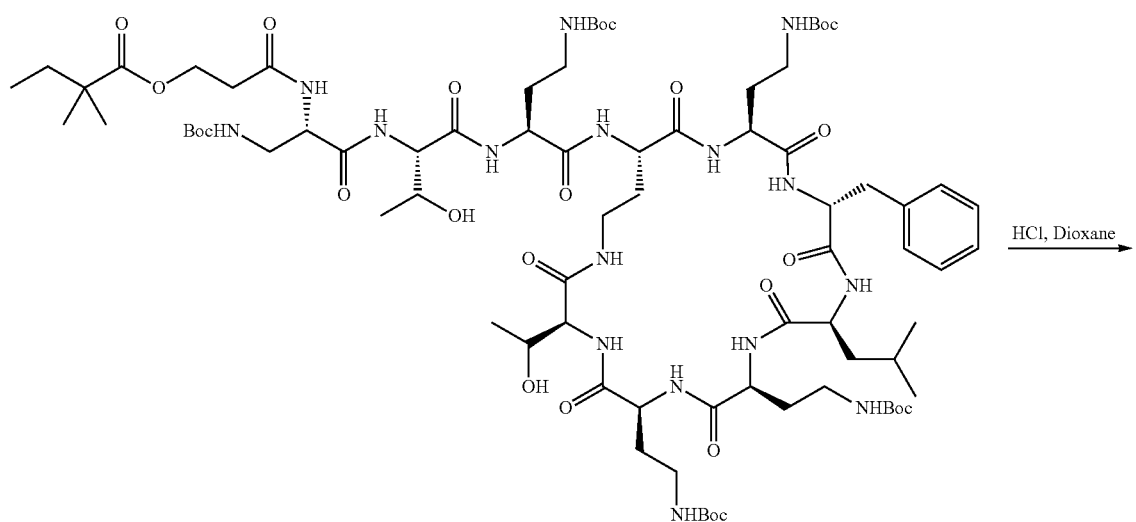
Intermediate 35A
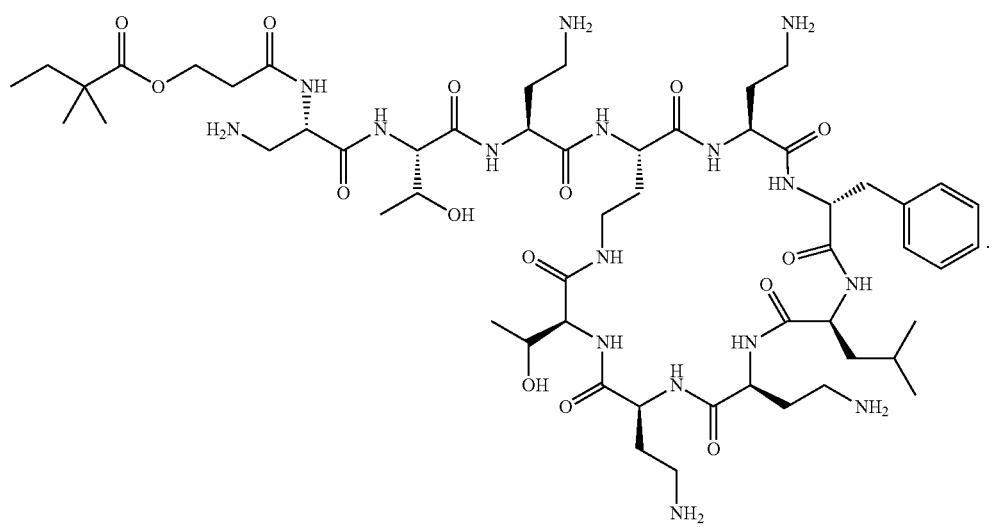
Example 35 HCl salt Intermediate 29.

A mixture of (S)-2-(((benzyloxy)carbonyl)amino)-3-((tert-butoxycarbonyl)amino)propanoic acid (136.5 mg), HATU (153.3 mg), DIEA (71 uL) in DCM (10 mL) was stirred at r.t. for 30 min. A solution of Intermediate 1 (500 mg, $R_1=CH_2Ph$) in DCM (2 mL) was added, and the reaction was stirred at r.t. for 2 h. Volatiles were removed under vacuum, and the crude Intermediate 29 was dried under high vacuum and then used directly in the next step.

Intermediate 30.

A mixture of the Intermediate 29, and 10% Pd/C (234.8 mg) in MeOH (8 mL) was hydrogenated (1 Torr) at r.t. for 4 h, then filtered through Celite. Solvent was removed under vacuum, and the residue purified by column chromatography eluting with DCM, and then 1-12% MeOH in DCM to afford the Intermediate 30 as a light-yellow solid.

Intermediate 35A.

Synthesis of Intermediate 35A was performed as described for the synthesis of Intermediate 30A in the synthesis of Compound of Example 30, except using 3-((2,2-dimethylbutanoyl)oxy)propanoic acid in place of 2-(dibutoxyphosphoryl)acetic acid and using Intermediate 30 in place of the Intermediate 7.

The Compound of Example 35.

Synthesis of the Compound of Example 35 (HCl salt) was performed as described for the synthesis of the Compound of Example 30, except using Intermediate 35A in place of Intermediate 30A to afford the Compound of Example 35 as a white solid. NMR: 7.32-7.24 (m, 3H); 7.16 (d, J 6.8 Hz, 2H); 4.52-4.44 (m, 3H); 4.32-4.11 (m, 10H); 3.46 (dd, J 13.6, 5.6 Hz, 1H), 3.28-2.62 (m, 16H); 2.25-1.80 (m, 11H); 1.48-1.26 (m, 4H); 1.14 (t, J 6.4 Hz, 6H); 1.04 (s, 6H); 0.72-0.60 (m, 10H). MS (m/z): 1219.5 (M+H).

Example 36

Synthesis of the Compound of Example 36:

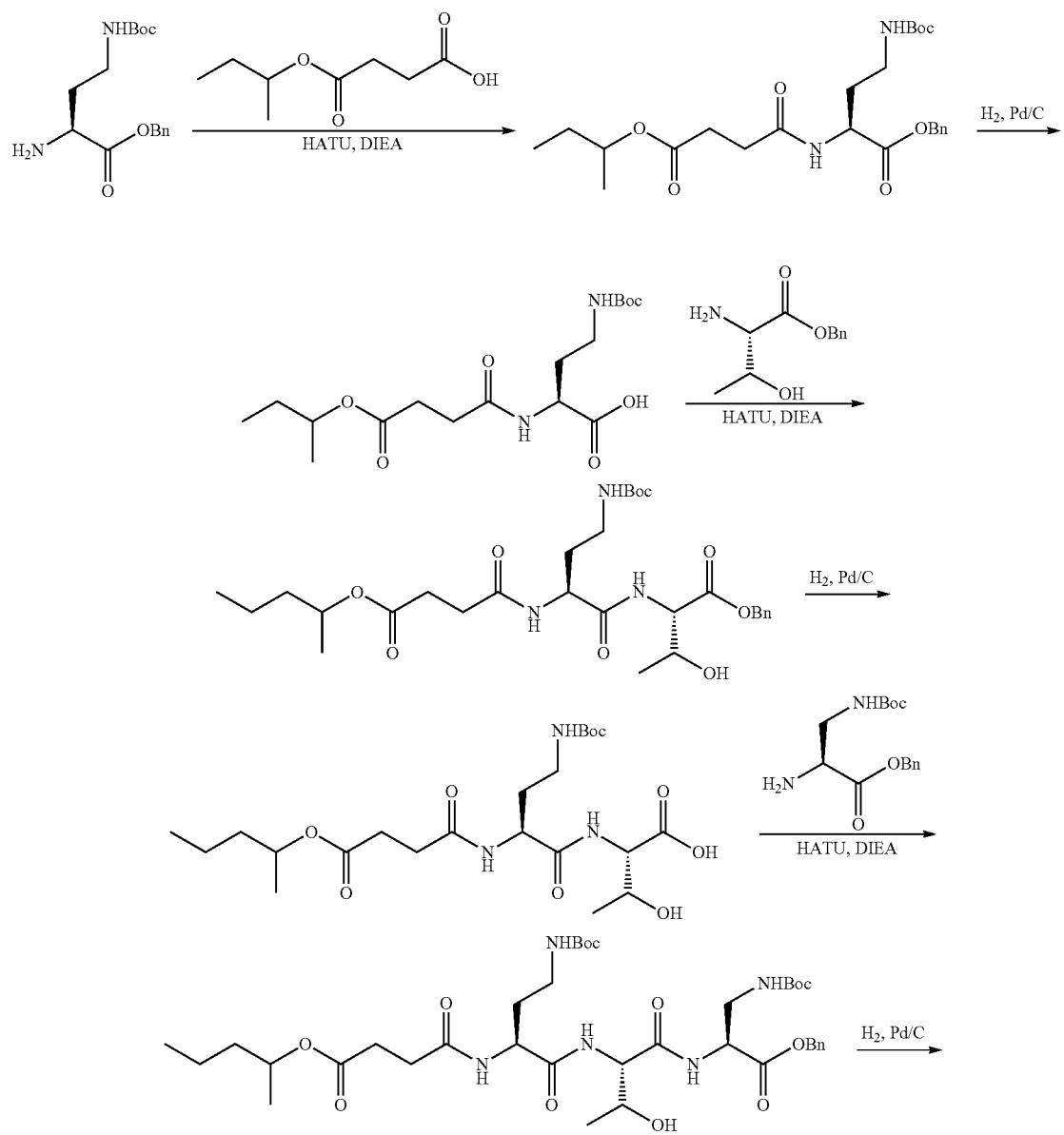

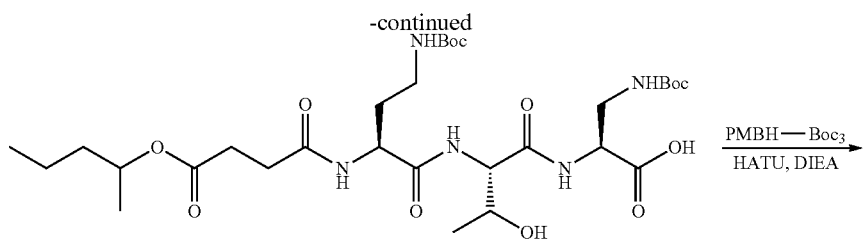

Intermediate 36A

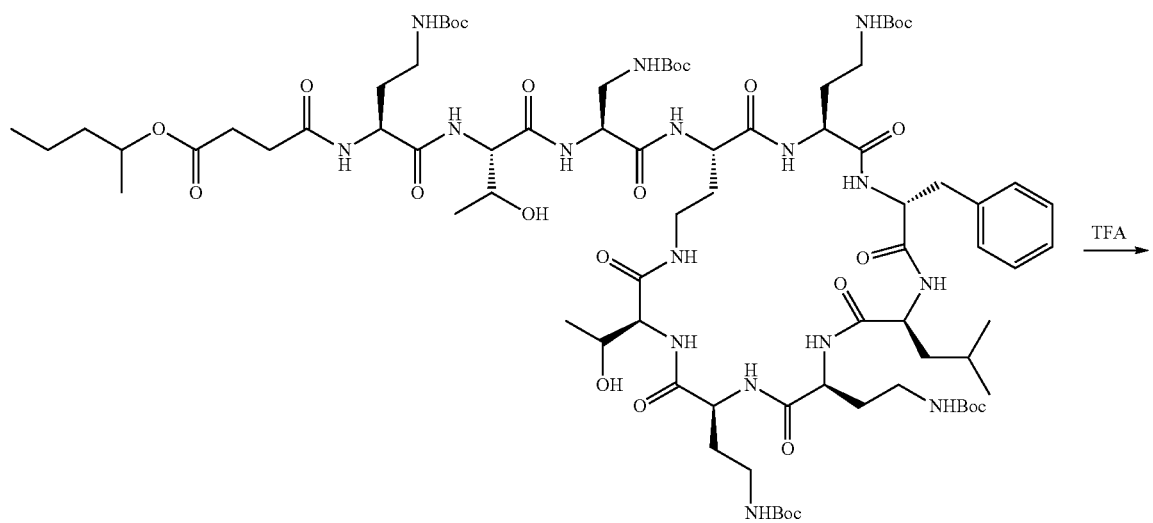

Intermediate 36B

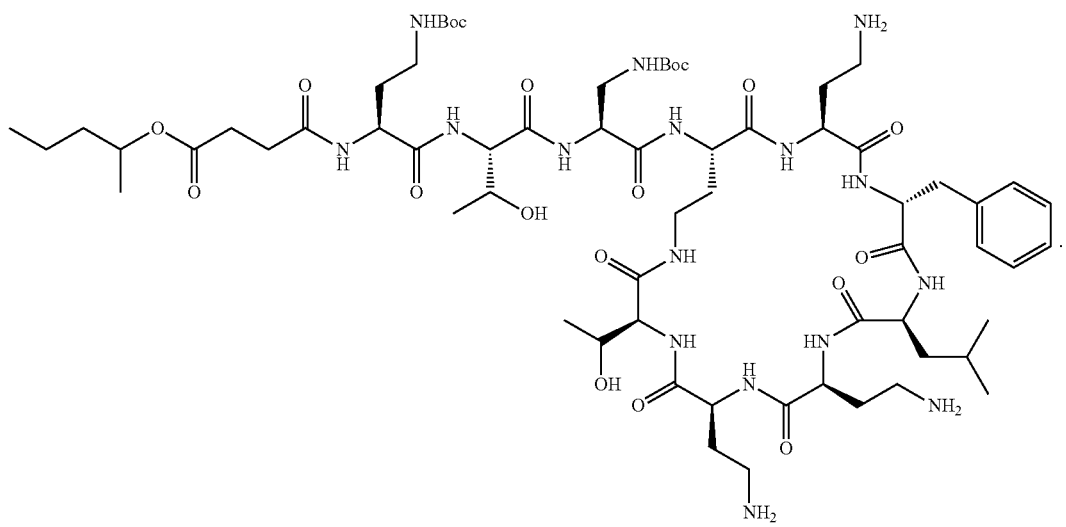

Example 36 TFA salt

The Compound of Example 36.

The Compound of Example 36 (TFA salt) is prepared analogously to procedures of the Compound of Example 18, except using Intermediate 36A instead of 4-oxo-4-(pentan-2-yloxy)butanoic acid, and using tris-Boc polymyxin B heptapeptide (PMBH-Boc₃; prepared analogously to Synthesis, 2015, pp. 2088-2092) instead of the Intermediate 7 (and with the like standard amide coupling (HATU, DIEA) and benzyl ester deprotection (hydrogenation over Pd/C) steps used to prepare Intermediate 36A). The final (TFA) deprotection and HPLC purification the Compound of Example 36 (TFA salt) is performed just as described for the synthesis of the Compound of Example 18 (TFA salt).

Example 37

Synthesis of the Compound of Example 37

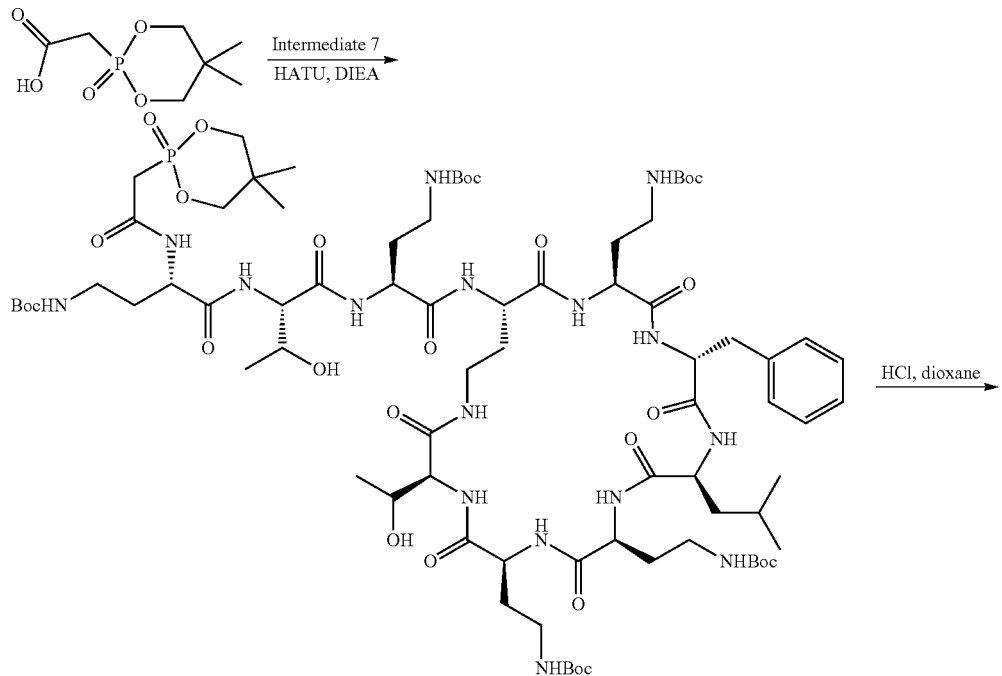

Intermediate 37A

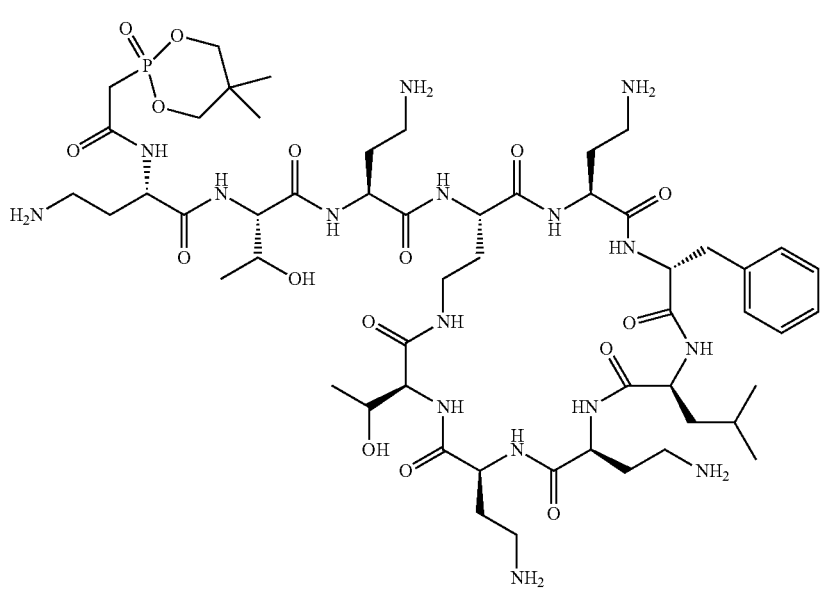

Example 37A HCl salt

The Compound of Example 37.

The Compound of Example 37 (HCl salt) was prepared according to the procedure for Compound of Example 30 from Intermediate 7, except using 2-(5,5-dimethyl-2-oxido-1,3,2-dioxaphosphinan-2-yl)acetic acid (prepared as described in WO2014/62411) in place of 2-(dibutoxyphosphoryl)acetic acid. NMR: 7.36-7.27 (m, 3H); 7.22 (d, J 6.8 Hz, 2H); 4.55-4.40 (m, 4H); 4.30 (d, J 4.4 Hz, 1H); 4.27-4.07 (m, 11H); 3.33-3.26 (m, 1H); 3.14-2.97 (m, 12H); 2.86-2.69 (m, 2H); 2.23-2.12 (m, 6H); 2.09-1.80 (m, 7H); 1.46-1.31 (m, 2H); 1.15 (t, J 7.2 Hz, 6H); 1.11 (s, 3H); 0.91 (s, 3H); 0.79-0.74 (m, 1H); 0.71 (s, 3H); 0.64 (d, J 4.8 Hz, 3H). MS (m/z): 1253.6 (M+H).

Example 38

Synthesis of the Compound of Example 38:

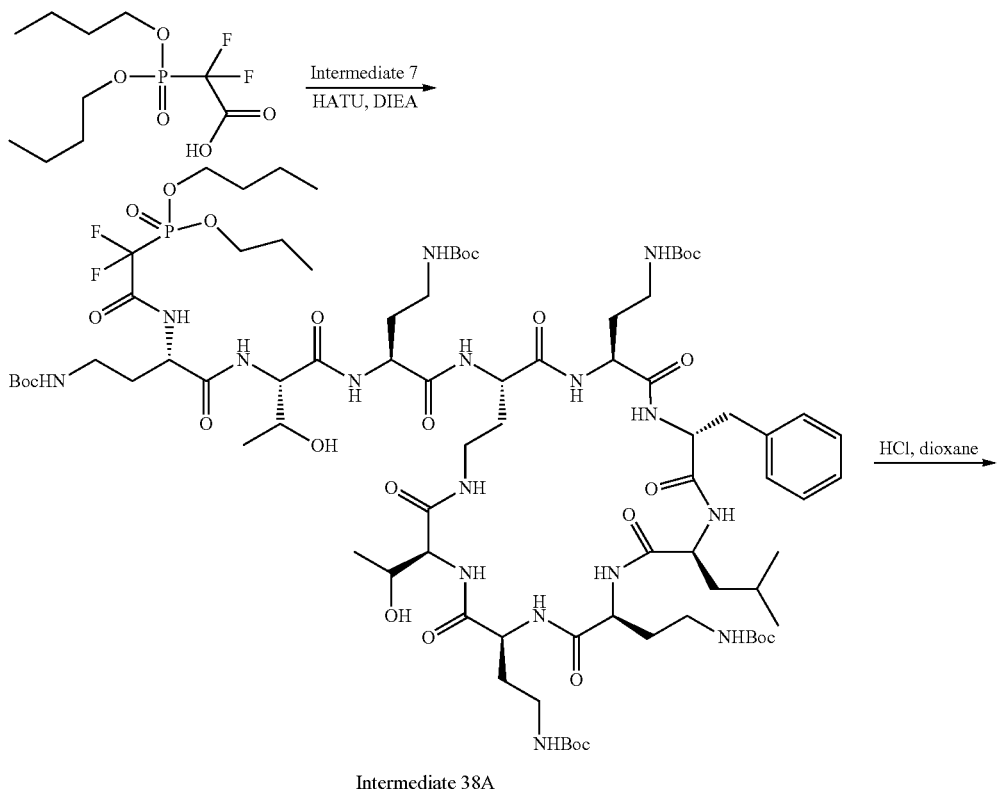

Intermediate 38A

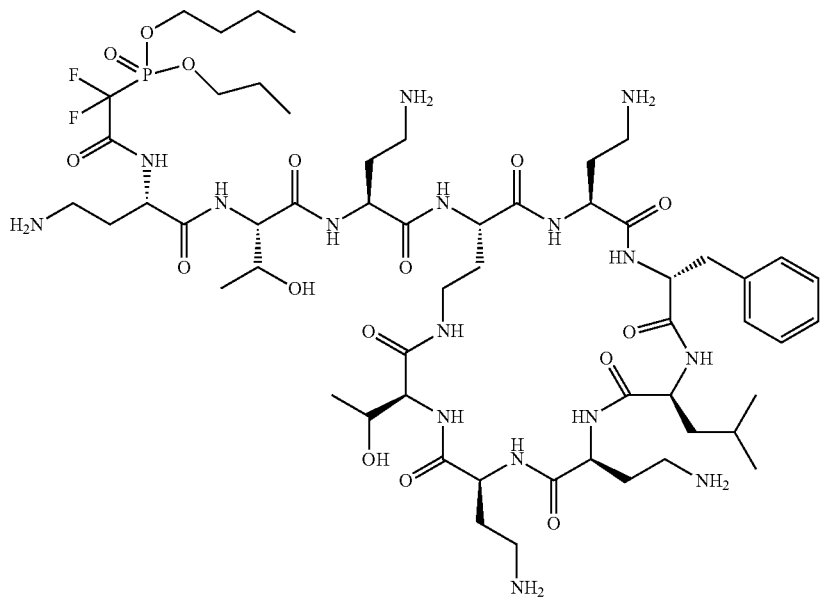

Example 38A HCl salt

The Compound of Example 38.

The Compound of Example 38 was prepared according to the procedure for Compound of Example 30 from Intermediate 7, except using 2-(dibutoxyphosphoryl)-2,2-difluoroacetic acid (prepared analogously to J. Chem. Soc., Perkin Trans. 1, 1999, vol 8, pp. 1051-1056) in place of 2-(dibutoxyphosphoryl)acetic acid. MS (m/z): 1333.4 (M+H).

Example 39

Synthesis of the Compound of Example 39:

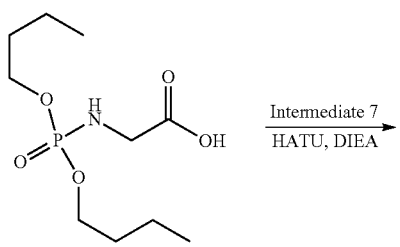

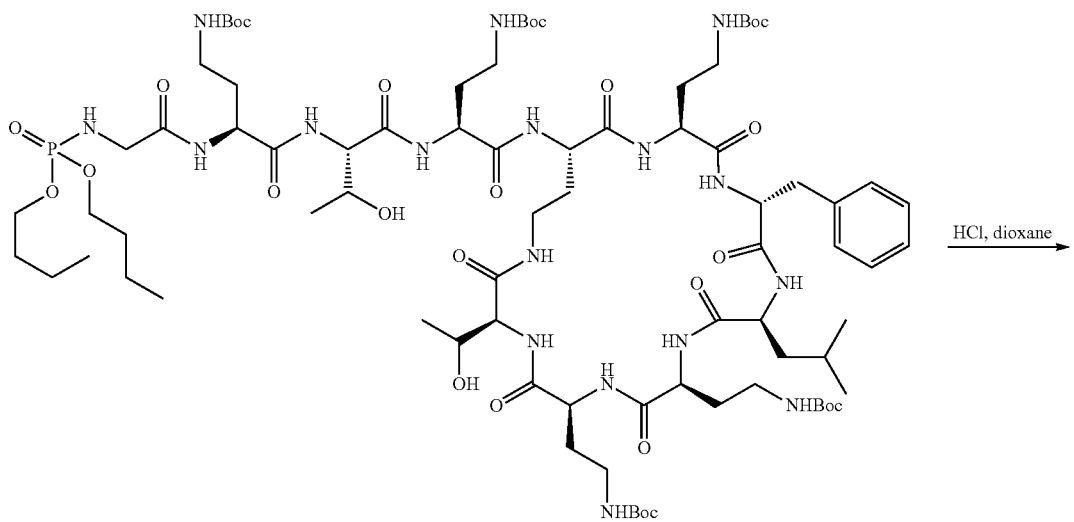

Intermediate 39A

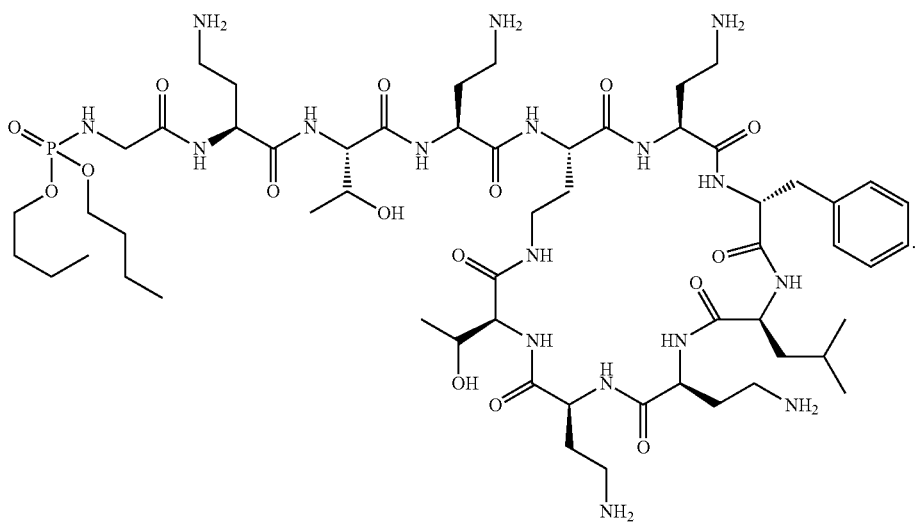

Example 39 HCl salt

The Compound of Example 39.

The Compound of Example 39 (HCl salt) was synthesized according to the procedure for the synthesis of the Compound of Example 30, except using 2-((dibutoxyphosphoryl)amino)acetic acid (prepared analogously to *Org. Lett.*, 2005, vol. 7, pp. 4781-4784) in place of 2-(dibutoxyphosphoryl)acetic acid. MS (m/z): 1312.6 (M+H).

Reference Example 40
Synthesis of the Compound of Example 40:
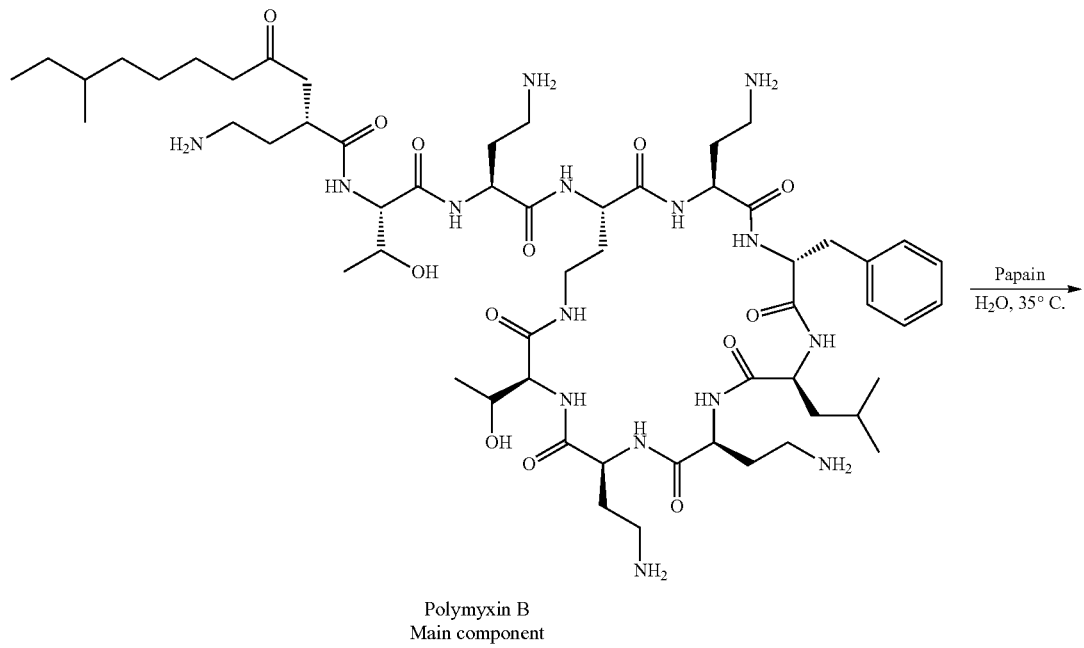
Polymyxin B
Main component
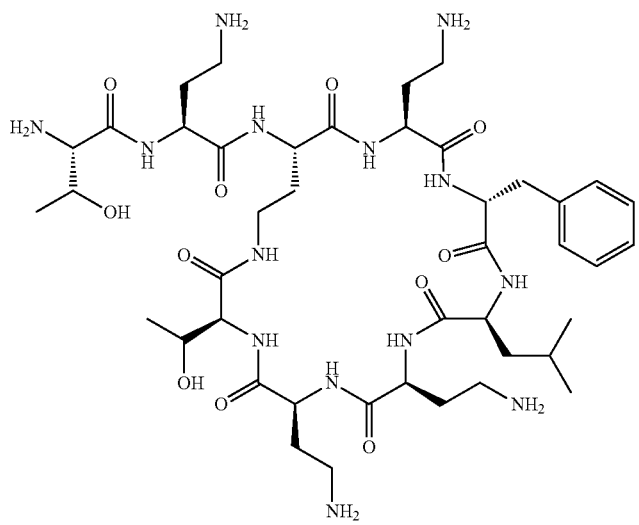
Example 40
Polymyxin B nonepeptide, PMBN
Reference Compound of Example 40.
The Compound of Example 40 (HCl salt) was prepared according to the publication Tetrahedron Lett. 2007, vol. 48, pp. 2003-2005, and purified by HPLC. MS (m/z): 482.2 (M+2H).

Example 41
Synthesis of the Compound of Example 41:
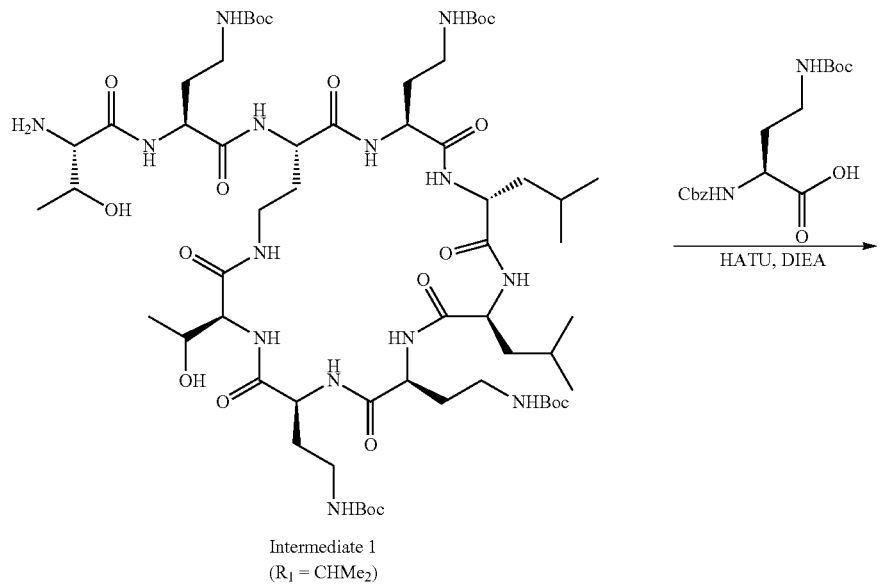
Intermediate 1
($R_1$ = CHMe$_2$)
Intermediate 41A

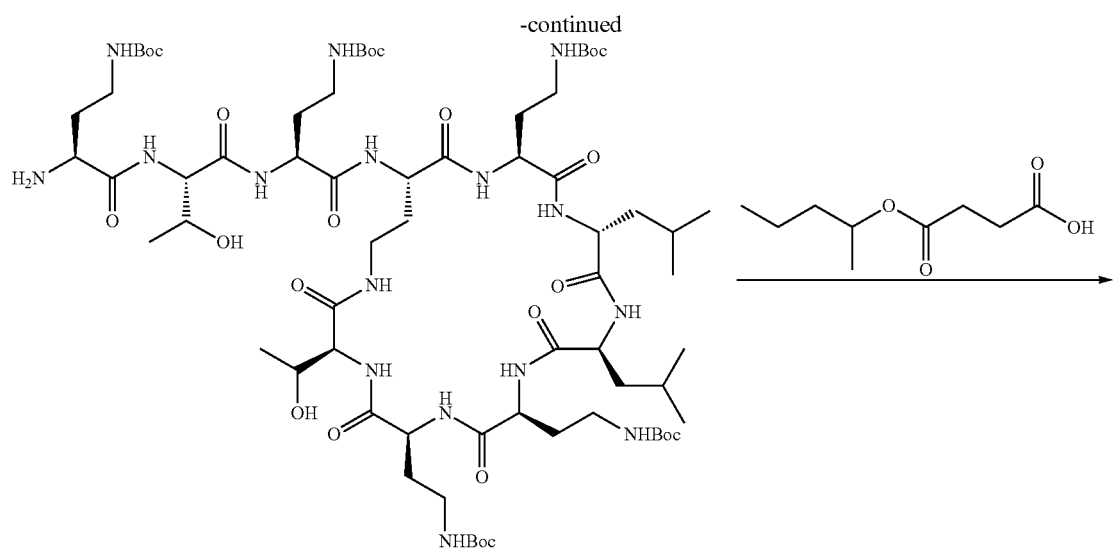
Intermediate 41B
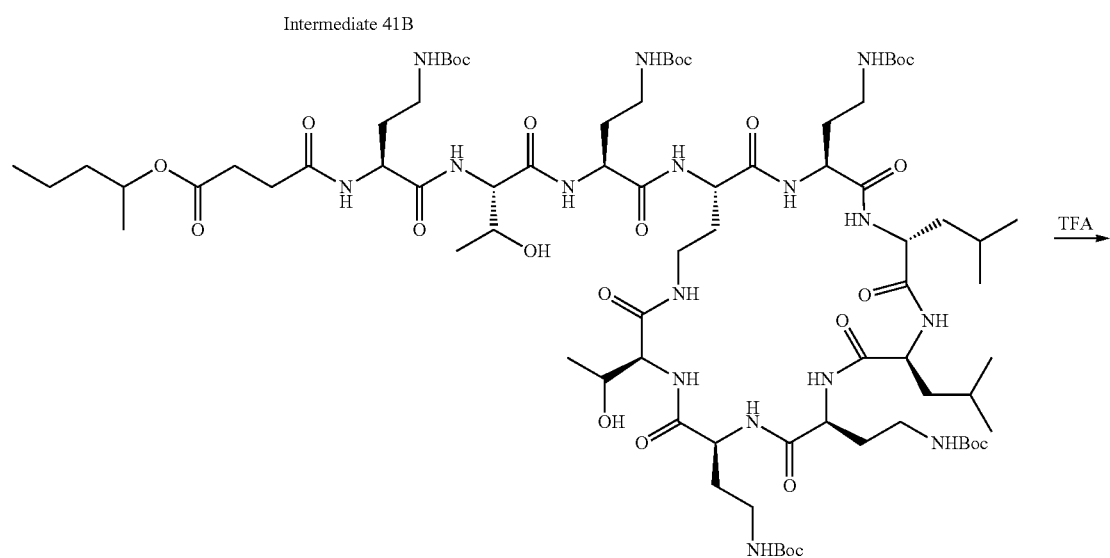
Intermediate 41C
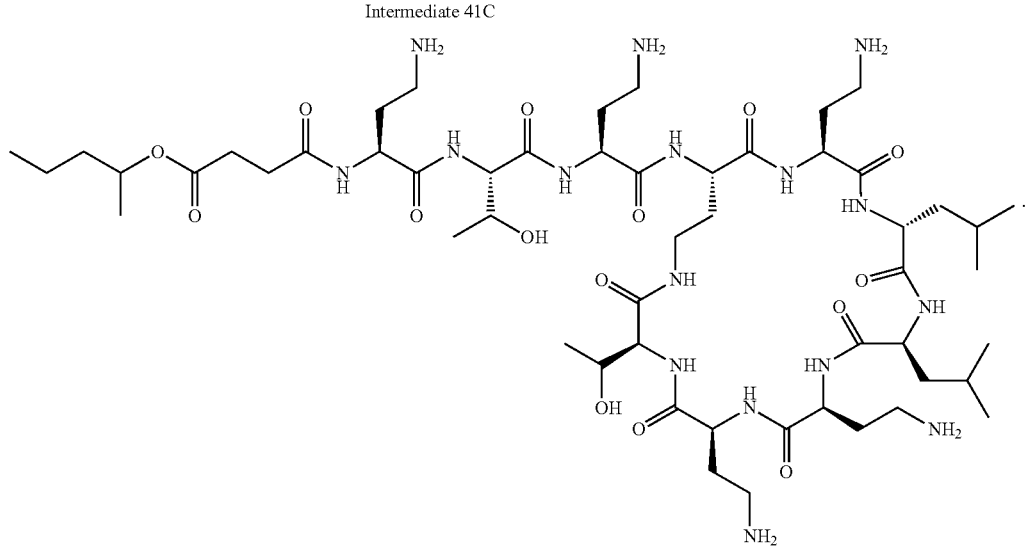
Example 41 TFA salt The Compound of Example 41.

The Compound of Example 41 (TFA salt) is prepared analogously to procedures for the synthesis of the Compound of Example 7, except using the Intermediate 1 ($R_1$=CHMe$_2$; made analogously to WO 2015/0031602) instead of the Intermediate 1 ($R_1$=CH$_2$Ph).

Example 42

Synthesis of the Compound of Example 42:

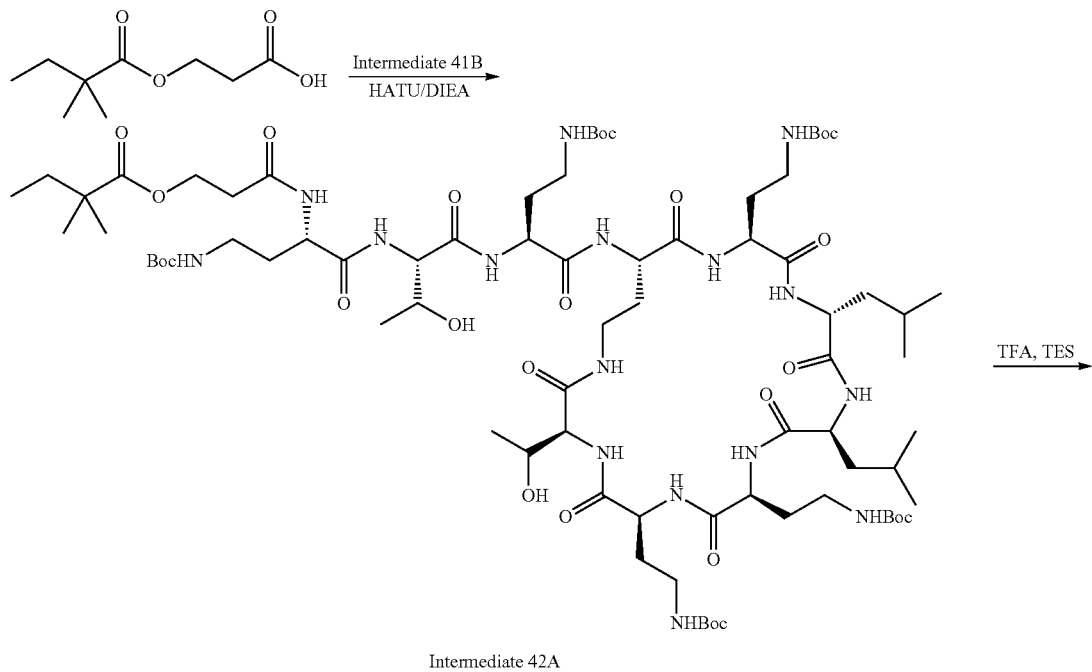

Intermediate 42A

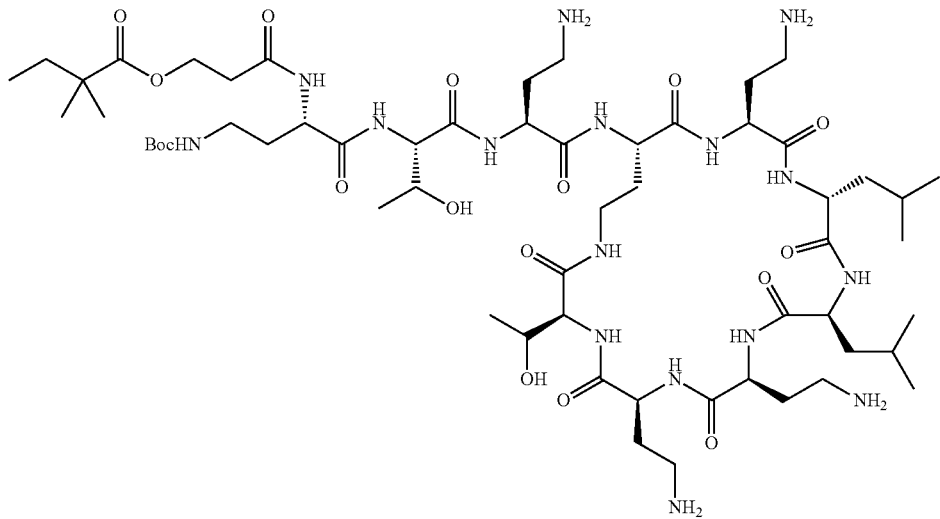

Example 42 TFA salt

The Compound of Example 42.

The Compound of Example 42 (TFA salt) is prepared analogously to procedures described for the synthesis of the Compound of Example 12, except using Intermediate 41B instead of the Intermediate 7.

Example 43

Synthesis of the Compound of Example 43:

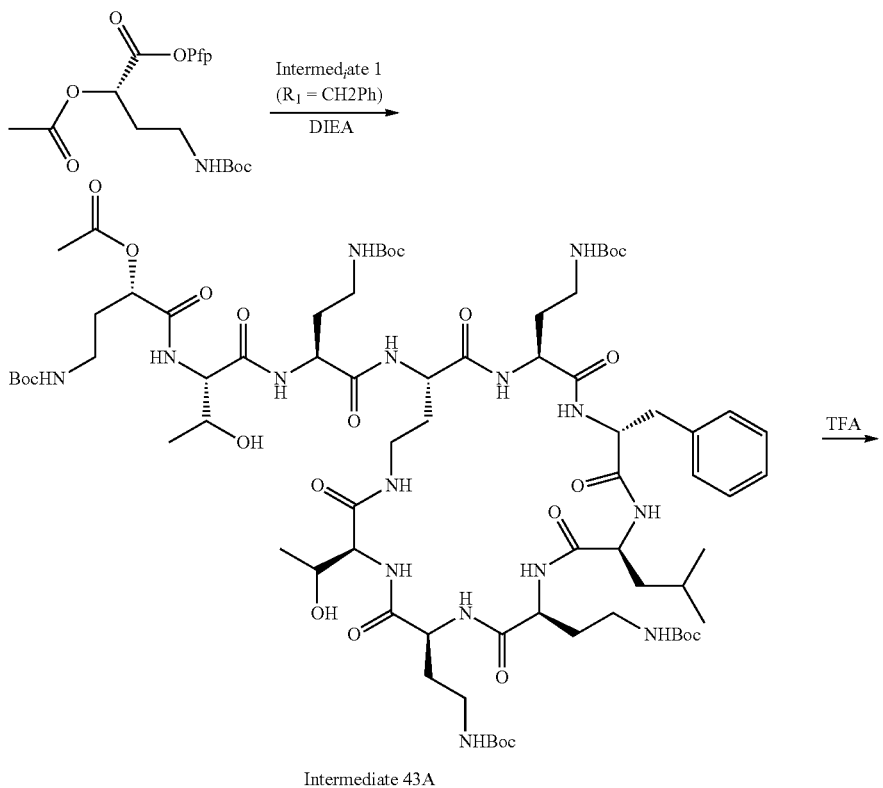

Intermediate 43A

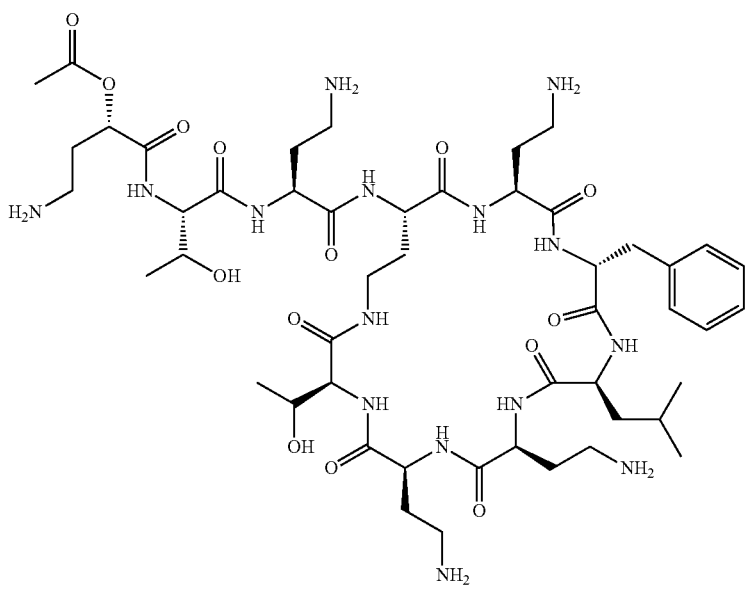

Example 43 TFA salt

The Compound of Example 43.

The Compound of Example 43 (TFA salt) was prepared according to the procedure for synthesis of the compound of Example 1 from Intermediate 1 ($R_1$=CH$_2$Ph) except using (S)-pentafluorophenyl 2-acetoxy-4-((tert-butoxycarbonyl)amino)butanoate in place of ((S)-4-((tert-butoxycarbonyl)amino)-1-oxo-1-(pentafluorophenoxy)butan-2-yl octanoate. MS (m/z): 1106.5 (M+H).

Example 44
Synthesis of the Compound of Example 44
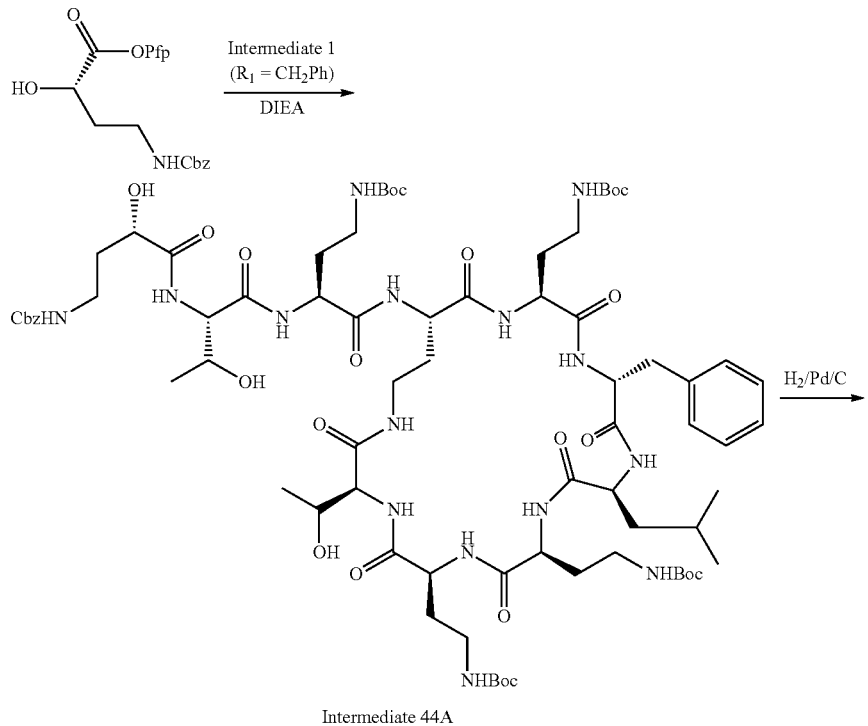
Intermediate 44A
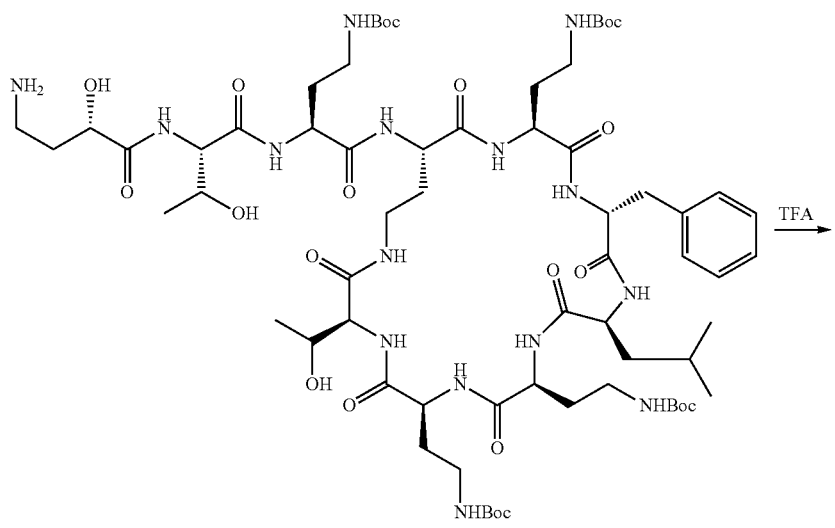
Intermediate 44B

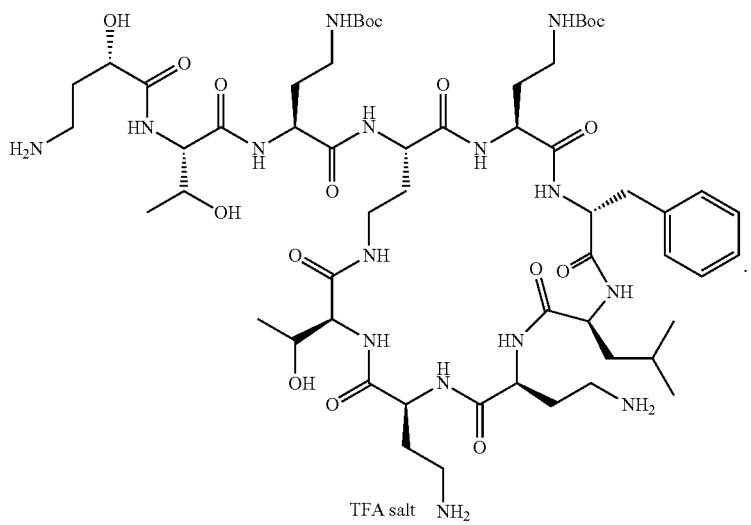

Example 44

The Compound of Example 44.

The Compound of Example 44 (TFA salt) was prepared analogously to the procedure for the synthesis of the compound of Example 1 from Intermediate 1 ($R_1$=$CH_2Ph$), except using (S)-pentafluorophenyl 4-(((benzyloxy)carbonyl)amino)-2-hydroxybutanoate in place of ((S)-4-((tert-butoxycarbonyl)amino)-1-oxo-1-(pentafluorophenoxy)butan-2-yl octanoate. MS (m/z): 532.9 (M+2H).

Example 45

Synthesis of the Compound of Example 45:

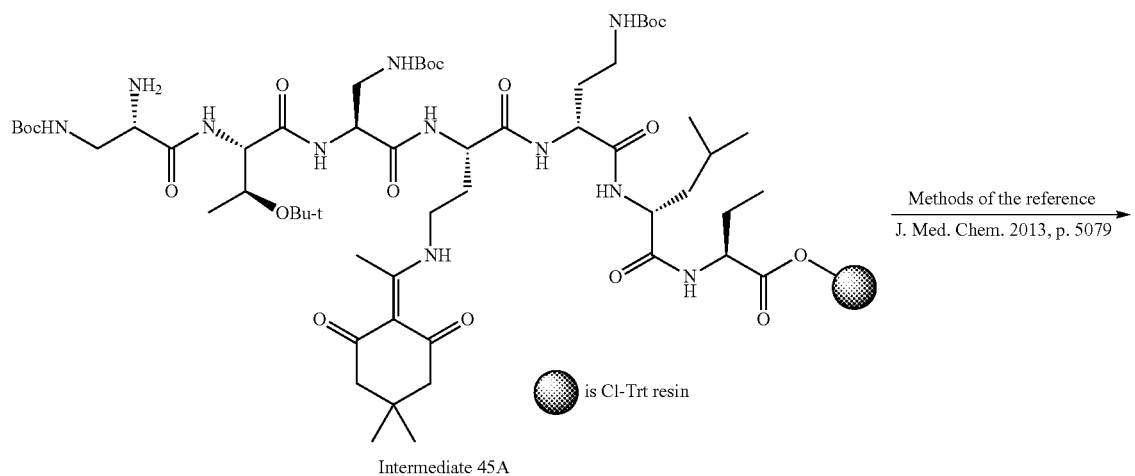

Intermediate 45A

Methods of the reference
J. Med. Chem. 2013, p. 5079

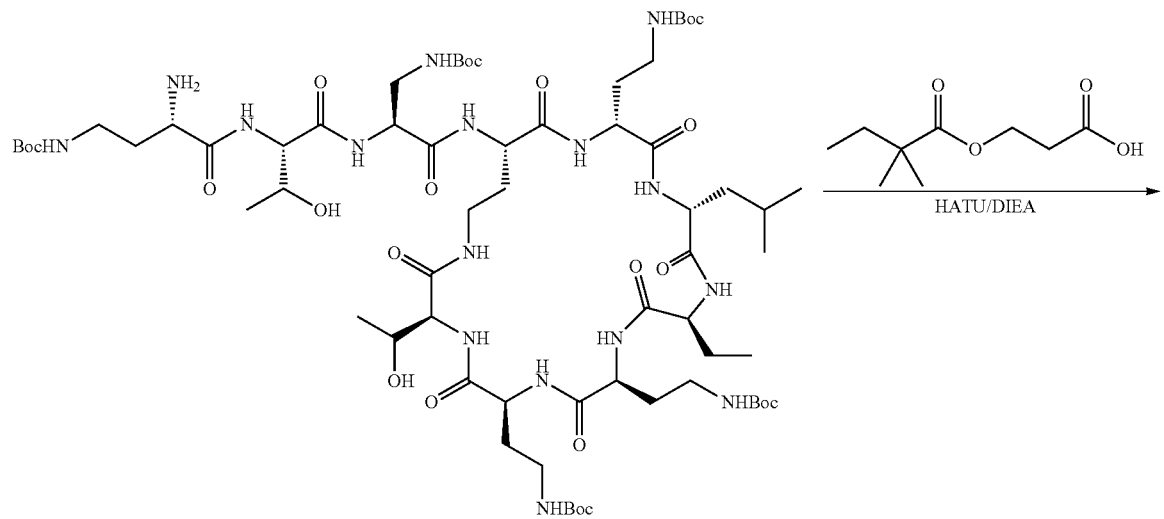
Intermediate 45B
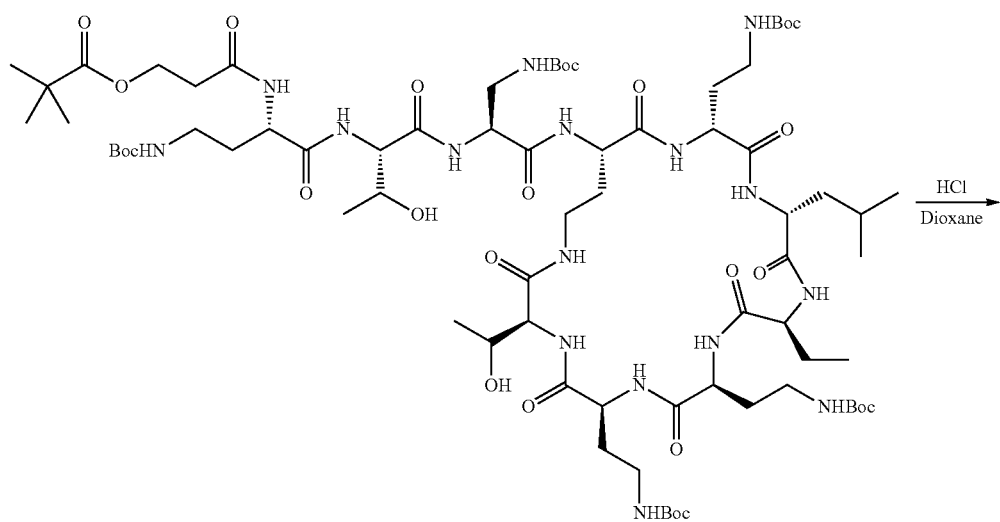
Intermediate 45C
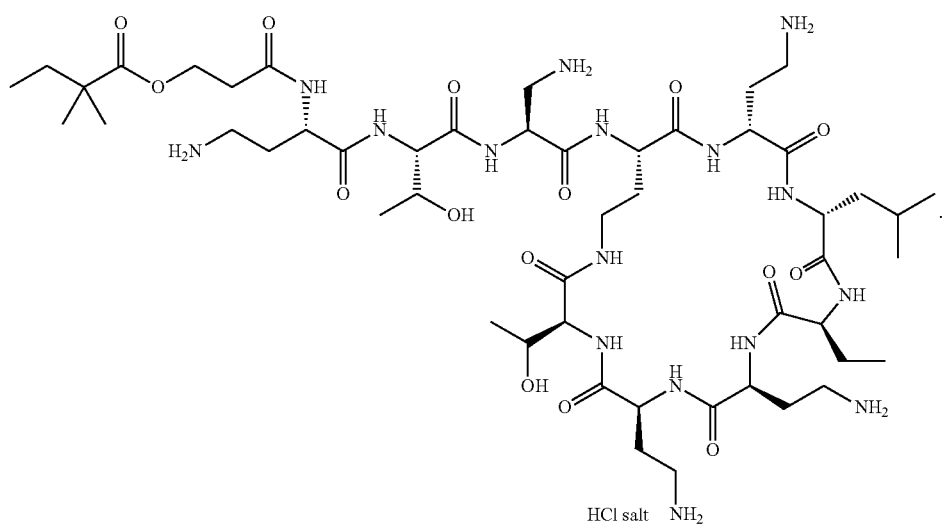
Example 45

Intermediate 45B.

The Intermediate 45B is prepared analogously to the methods described analogously to procedures described by Magee et al. in *J. Med. Chem.* 2013, vol. 56, p. 5079.

Intermediate 45C.

The Intermediate 45C is prepared from the Intermediate 45B analogously to the synthesis of the Compound of Example 12.

The Compound of Example 45.

Synthesis of the Compound of Example 45 (HCl salt) is performed just as described for the final step in the synthesis of the Compound of Example 12, and performing the final step using HCl in dioxane in place of TFA in DCM.

Example 46

Synthesis of the Compound of Example 46:

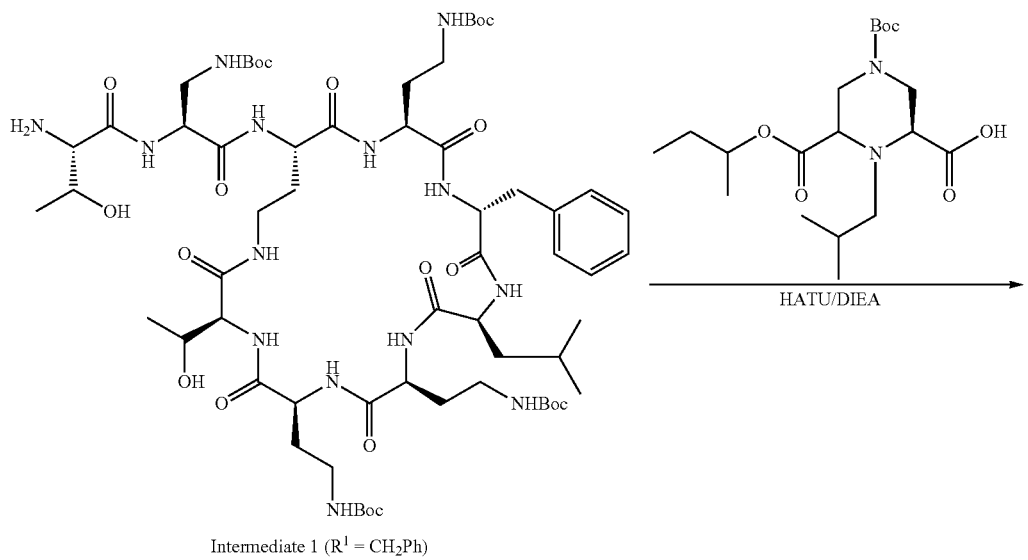

Intermediate 1 ($R^1$ = CH$_2$Ph)

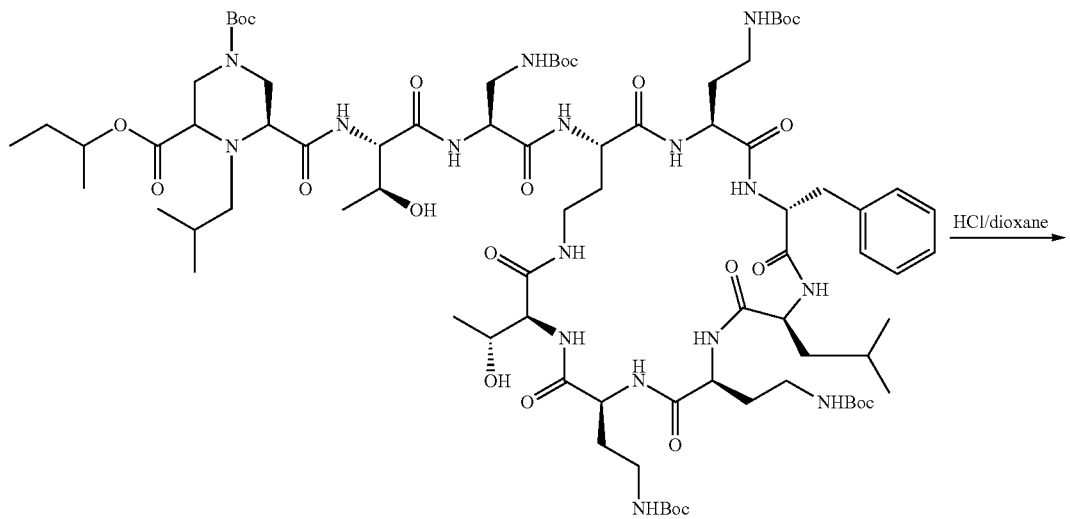

Intermediate 46A

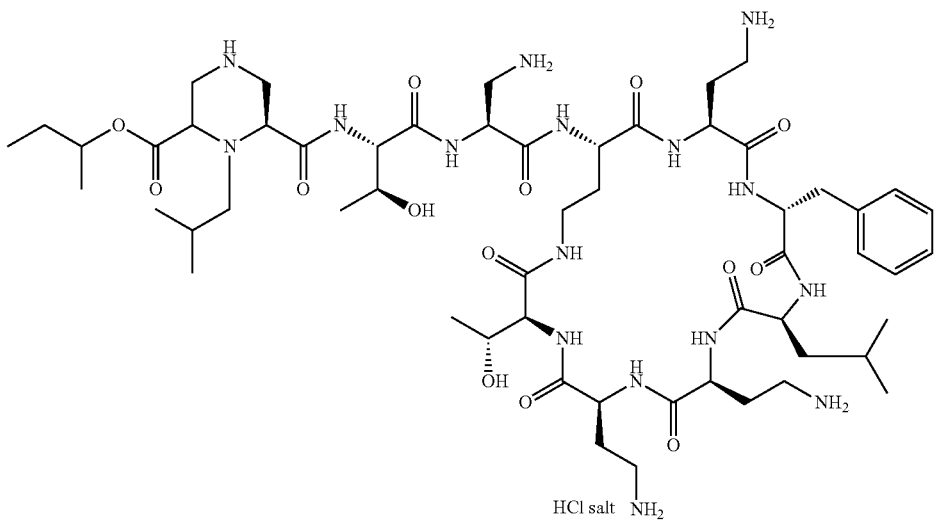

Example 46

The Compound of Example 46.

The Compound of Example 46 (HCl salt) is prepared according to the procedure for synthesis of the compound of Example 1 from Intermediate 1 (R₁=CH₂Ph) except using (2S)-6-(sec-butoxycarbonyl)-4-(tert-butoxycarbonyl)-1-isobutylpiperazine-2-carboxylic acid with HATU and DIEA in place of ((S)-4-(((tert-butoxycarbonyl)amino)-1-oxo-1-(pentafluorophenoxy)butan-2-yl octanoate, and performing the final step using HCl in dioxane in place of TFA in DCM.

Example 47

Synthesis of the Compound of Example 47:

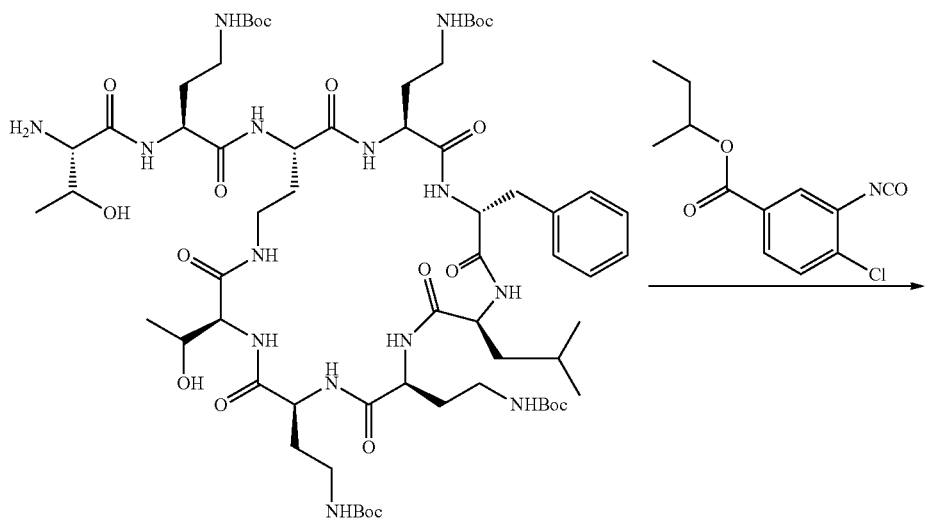

Intermediate 1 (R¹ = CH₂Ph)

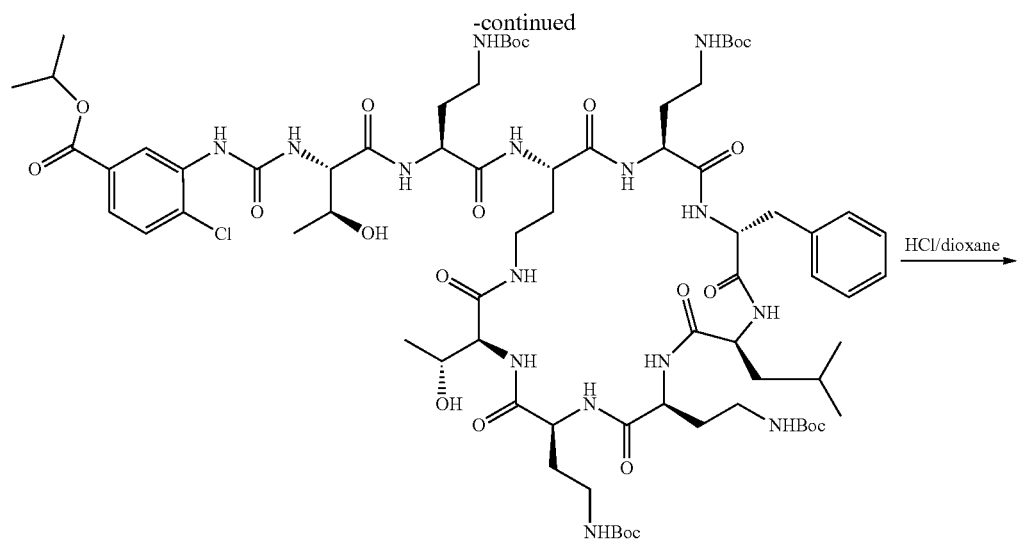

Intermediate 47A

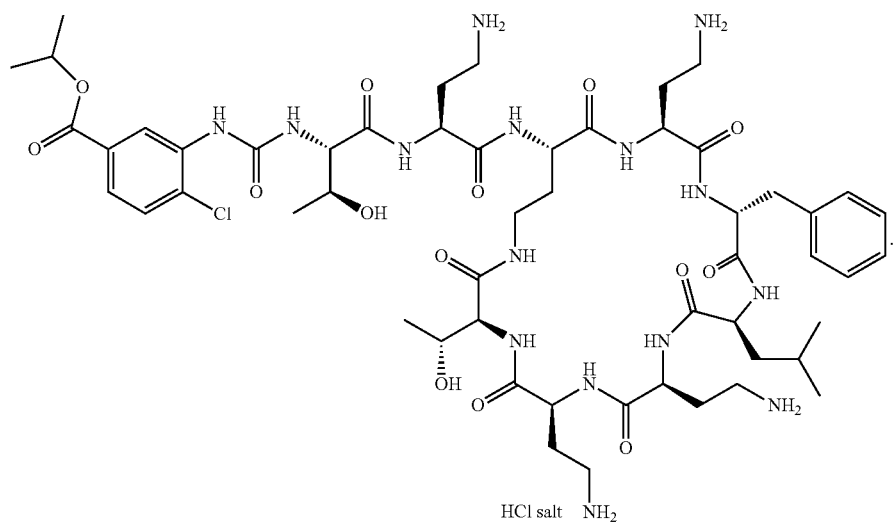

Example 47

The Compound of Example 47.

The Compound of Example 47 (HCl salt) is prepared analogously to the first step of the procedure for synthesis of the compound of Example 1 from Intermediate 1 ($R_1$=$CH_2Ph$) except using sec-butyl 4-chloro-3-isocyanatobenzoate in place of ((S)-4-((tert-butoxycarbonyl)amino)-1-oxo-1-(pentafluorophenoxy)butan-2-yl octanoate, and performing the final step using HCl in dioxane in place of TFA in DCM.

Example 48

Structure of the Compound of Example 48:

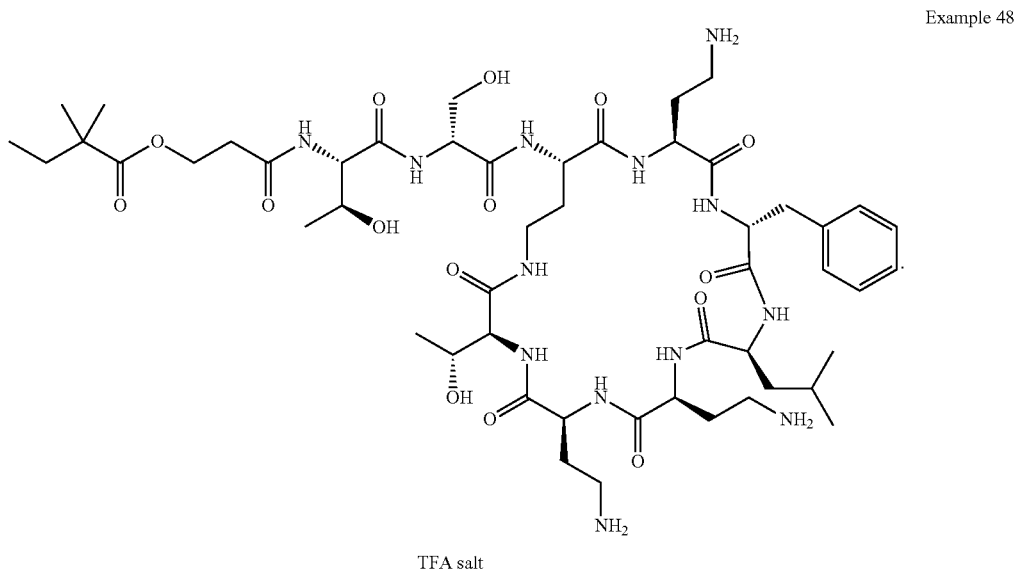 [SMILES: CCC(C)(C)C(=O)OCCC(=O)N[C@H](C(=O)N[C@H](CO)C(=O)N[C@H]1CCNC(=O)[C@H]([C@@H](C)O)NC(=O)[C@H](CCN)NC(=O)[C@H](CCN)NC(=O)[C@H](CC(C)C)NC(=O)[C@@H](Cc2ccccc2)NC(=O)[C@H](CCN)NC1=O)[C@H](C)O]

Example 48

TFA salt

The Compound of Example 48.

The Compound of Example 48 (TFA salt) is prepared analogously to the procedure for synthesis of the compound NAB739 according to the ref. of US 2008/0287345, except using 3-((2,2-dimethylbutanoyl)oxy)propanoic acid with HATU and DIEA to acylate the terminal L-threonine amino acid residue, and performing the final deprotection step (TFA, TES) just as described for the synthesis of the Compound of Example 12.

Example 49

Synthesis of the Compound of Example 49:

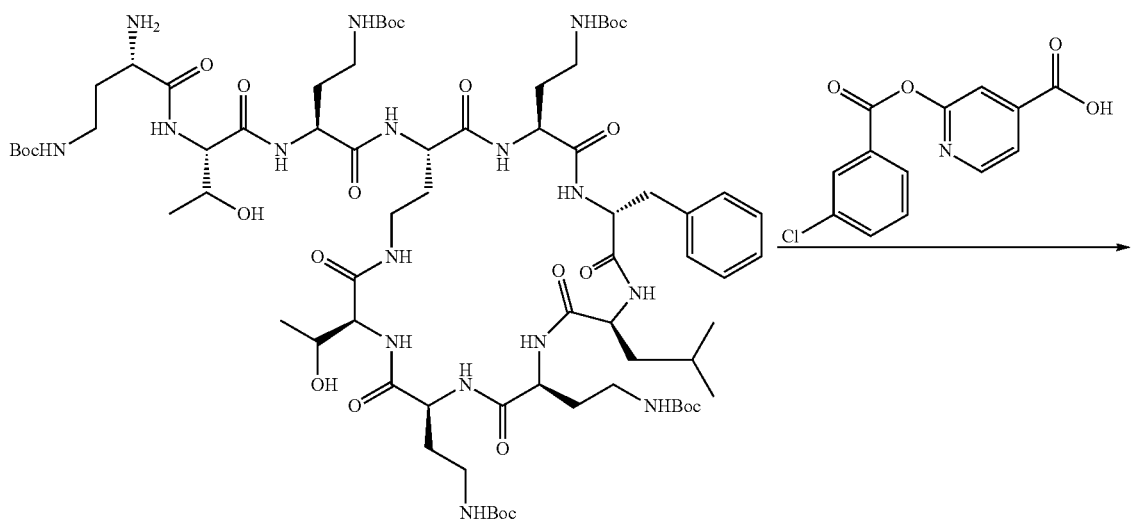

Intermediate 7

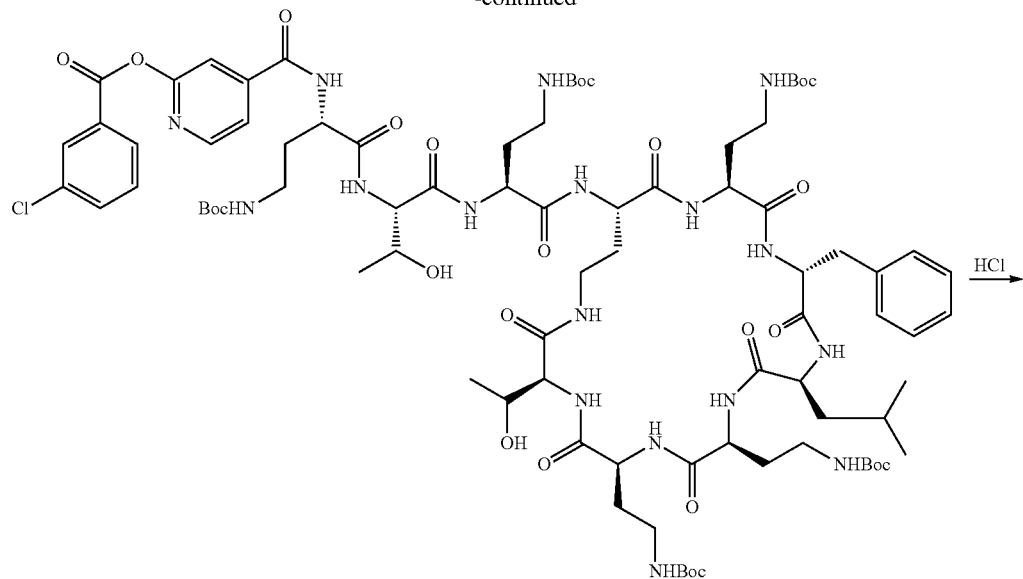

Intermediate 49A

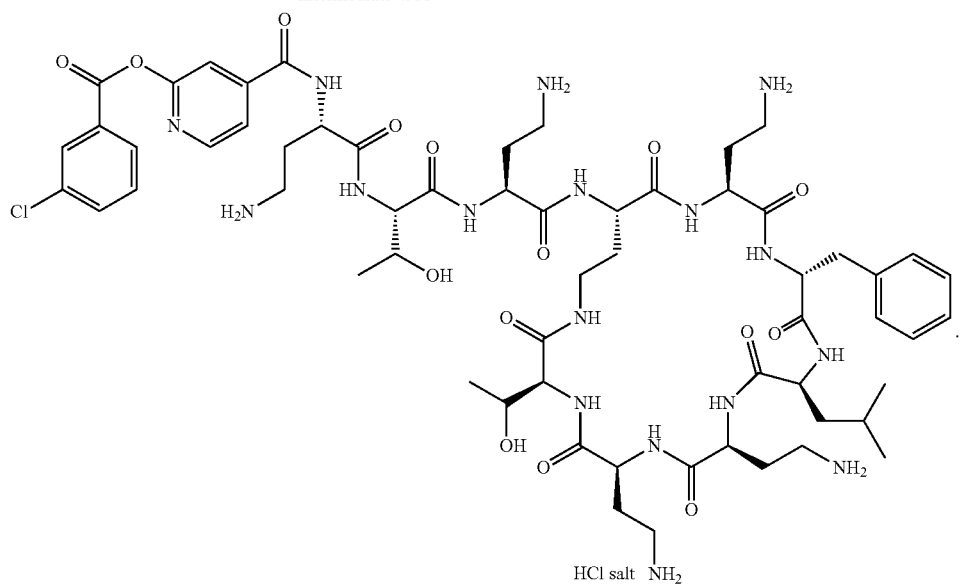

Example 49

The Compound of Example 49.

The Compound of Example 49 (HCl salt) is prepared analogously to the procedure for example 7 from Intermediate 7 using 2-((3-chlorobenzoyl)oxy)isonicotinic acid in place of acid in place of 4-butoxy-4-oxobutanoic acid, and performing the final step using HCl in dioxane in place of TFA in DCM.

Example 50

Synthesis of the Compound of Example 50:

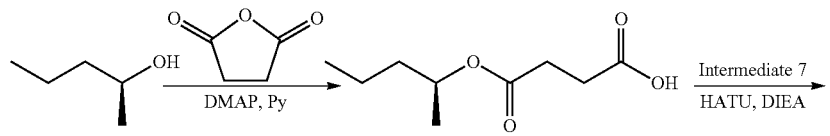

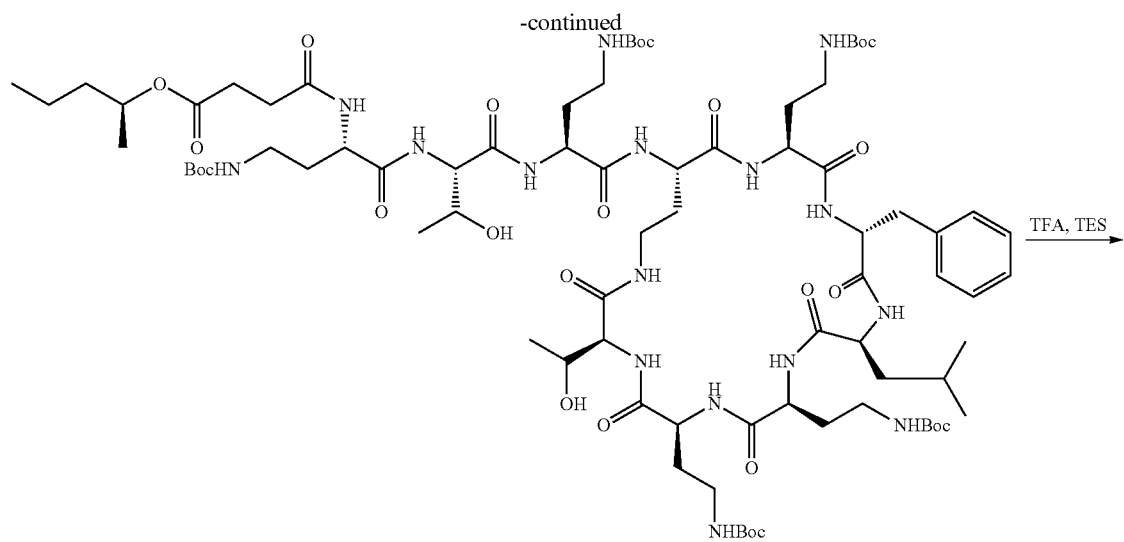
Intermediate 50a
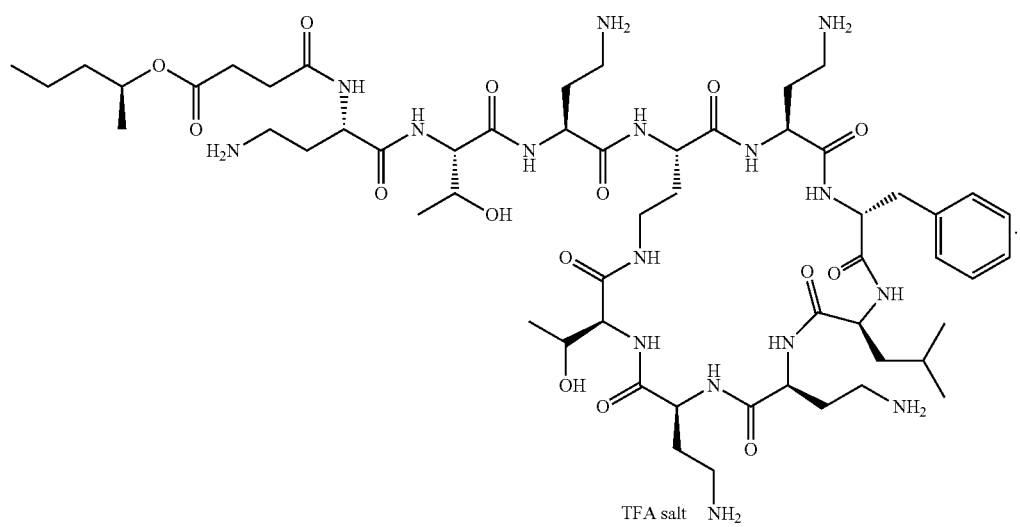
Example 50
The Compound of Example 50.
The compound of Example 50 (TFA salt) is prepared just as described for the synthesis of the compound of Example 18 (TFA salt), except using (S)-pentan-2-ol instead of racemic pentan-2-ol.
Example 51
Synthesis of the Compound of Example 51:
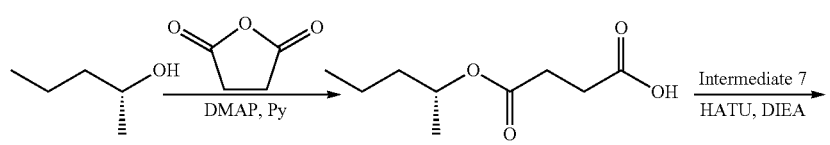

-continued
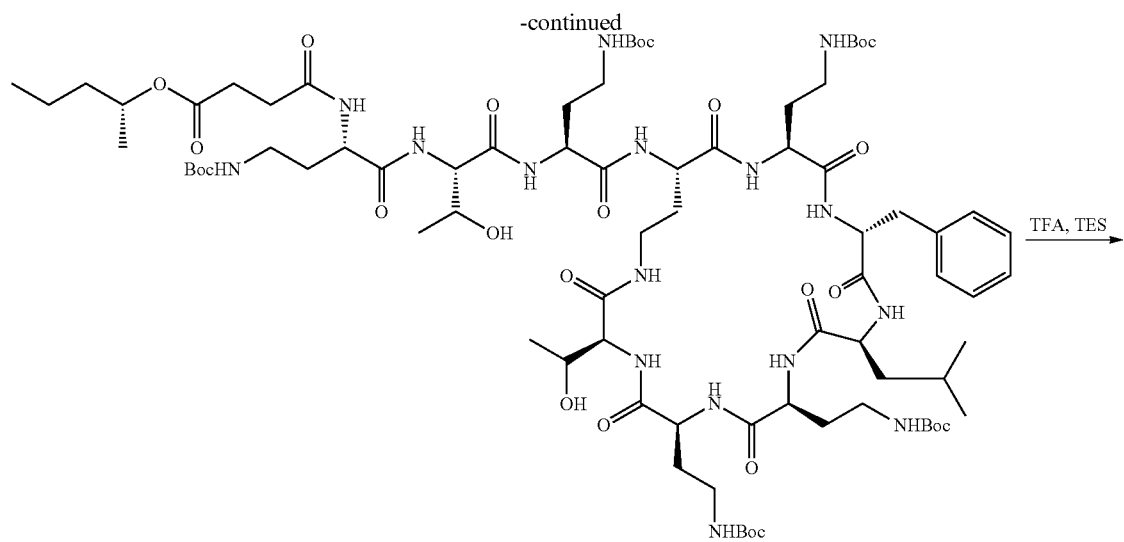
Intermediate 51a
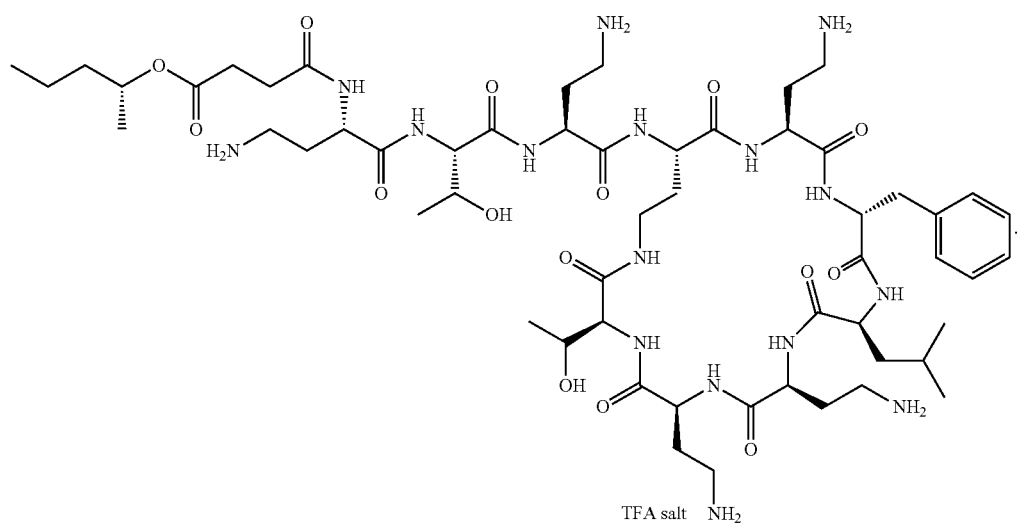
Example 51
The Compound of Example 51.
The compound of Example 51 (TFA salt) is prepared just as described for the synthesis of the compound of Example 18 (TFA salt), except using (R)-pentan-2-ol instead of racemic pentan-2-ol.
Example 52
Synthesis of the Compound of Example 52:
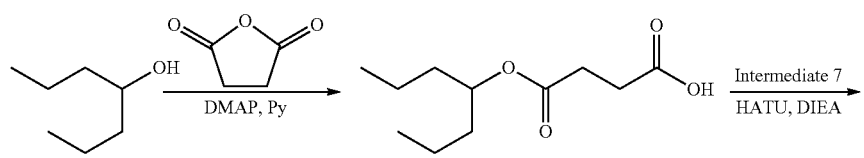

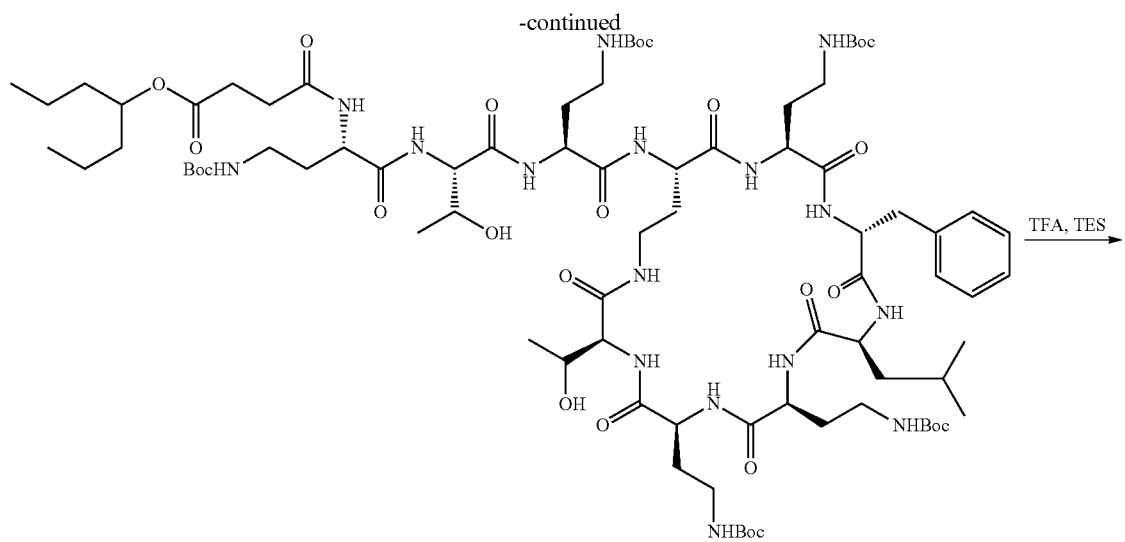
Intermediate 52a
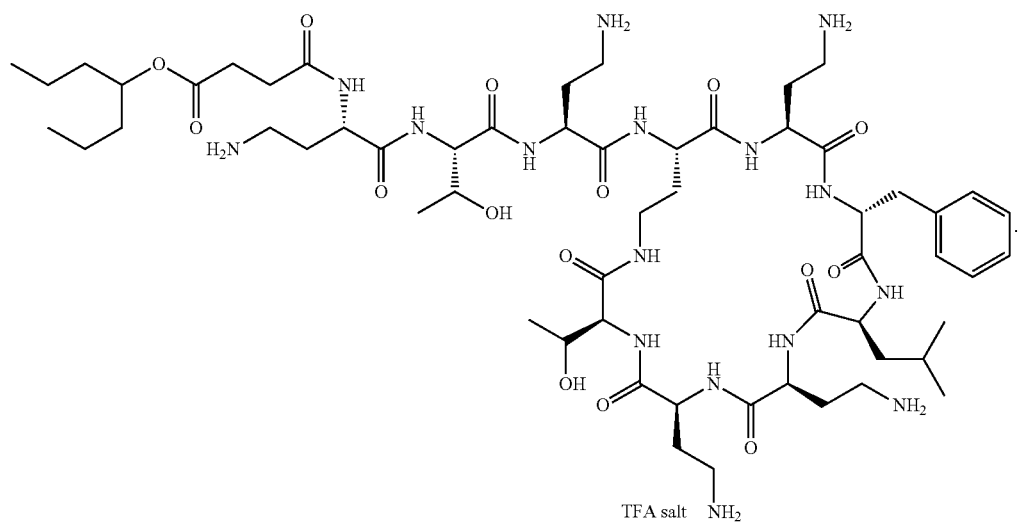
Example 52
The Compound of Example 52.
The compound of Example 52 (TFA salt) is prepared just as described for the synthesis of the compound of Example 18 (TFA salt), except using heptan-4-ol instead of pentan-2-ol.

Example 53
Synthesis of the Compound of Example 53:
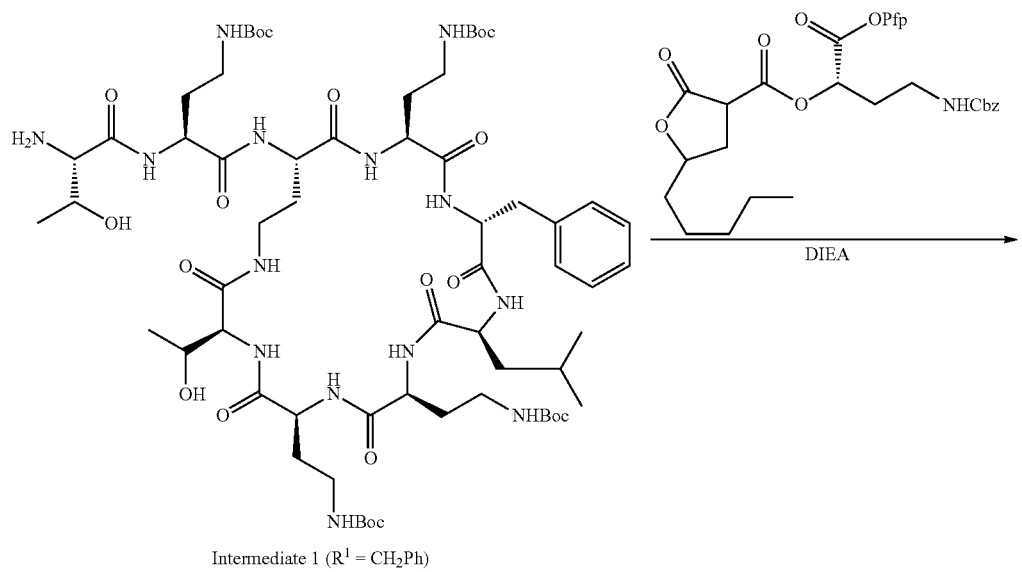
Intermediate 1 (R¹ = CH₂Ph)
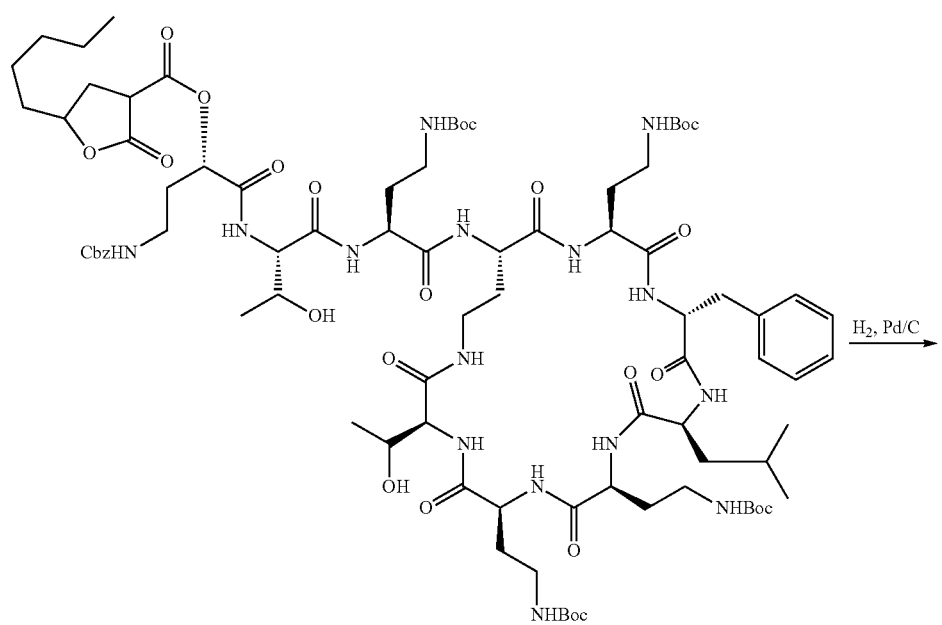
Intermediate 53A

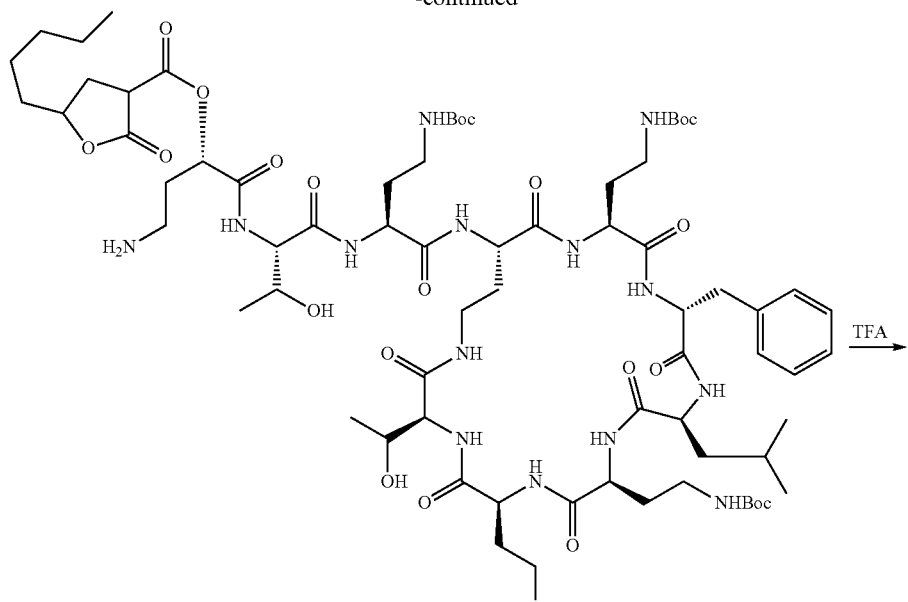

Intermediate 53B

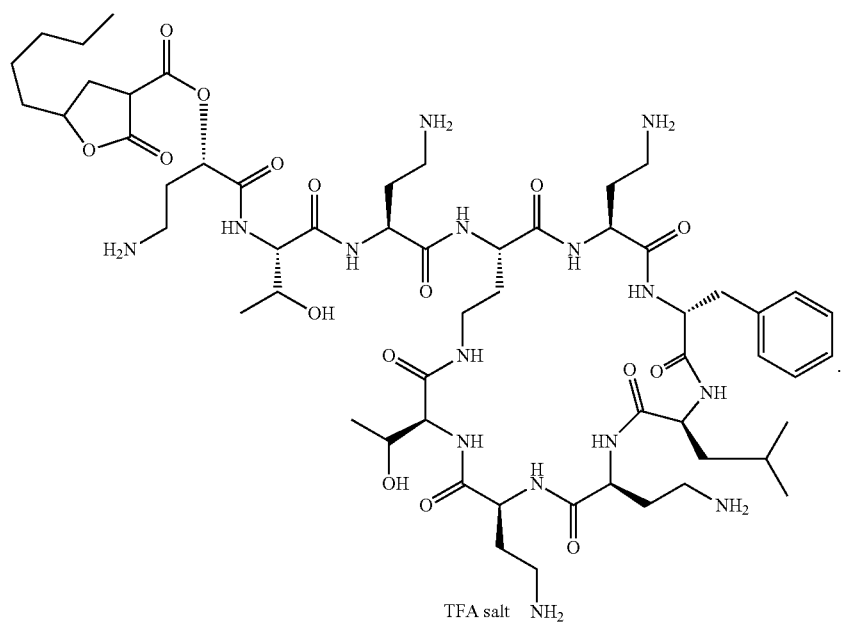

Example 53

The Compound of Example 53.

The compound of Example 51 (TFA salt) is prepared just as described for the synthesis of the Compound of Example 1 (TFA salt), except using (S)-4-(((benzyloxy)carbonyl)amino)-1-oxo-1-(perfluorophenoxy)butan-2-yl 2-oxo-5-pentyltetrahydrofuran-3-carboxylate instead of ((S)-4-((tert-butoxycarbonyl)amino)-1-oxo-1-(pentafluorophenoxy)butan-2-yl octanoate used in the synthesis of the Compound of Example 1.

225 226
Example 54
Synthesis of the Compound of Example 54:
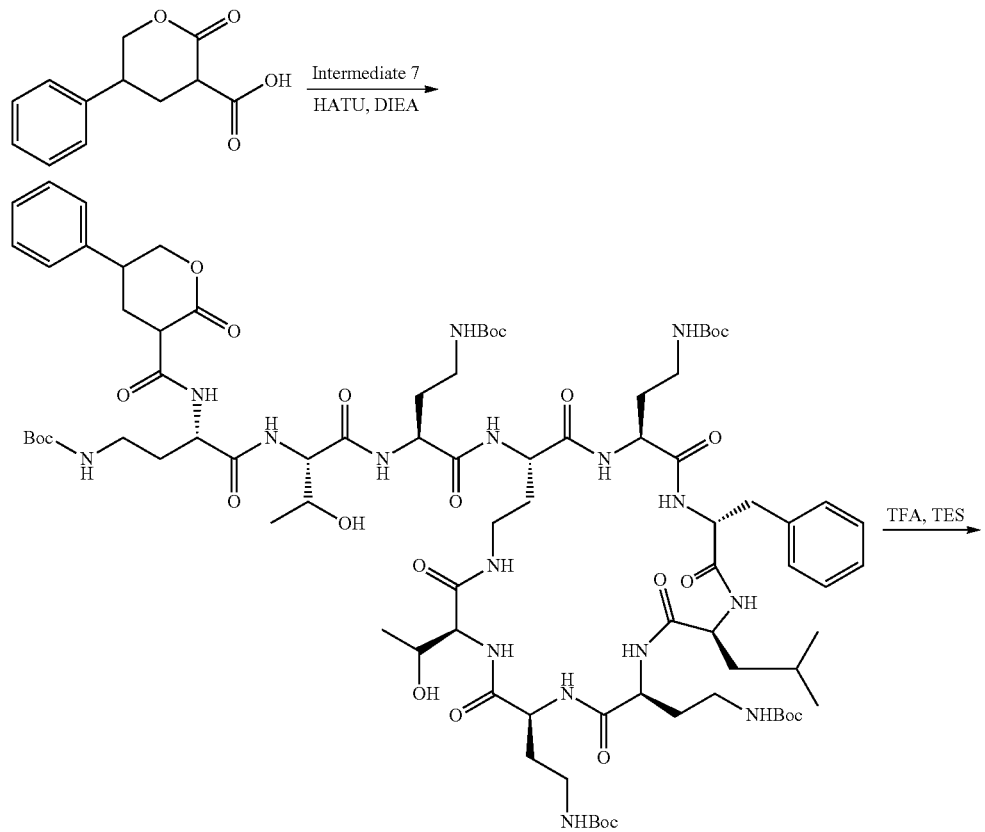
Intermediate 54A
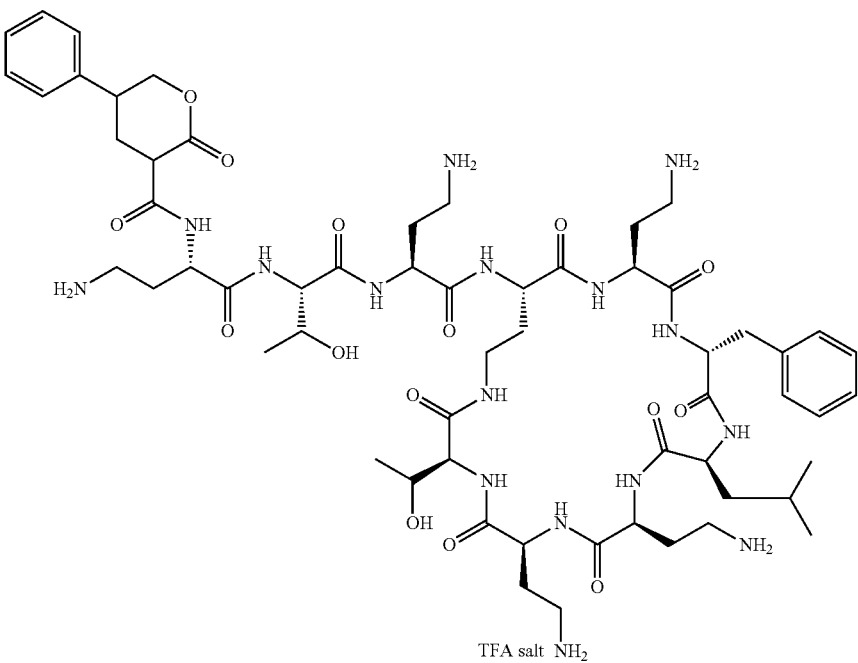
Example 54

The Compound of Example 54.

The Compound of Example 54 (TFA salt) is prepared analogously from the Intermediate 7 just as described for the Compound of Example 18 except using 2-oxo-5-phenyltetrahydro-2H-pyran-3-carboxylic acid in place of 4-butoxy-4-oxobutanoic acid used in the synthesis of the Compound of Example 18.

Example 55

Synthesis of the Compound of Example 55:

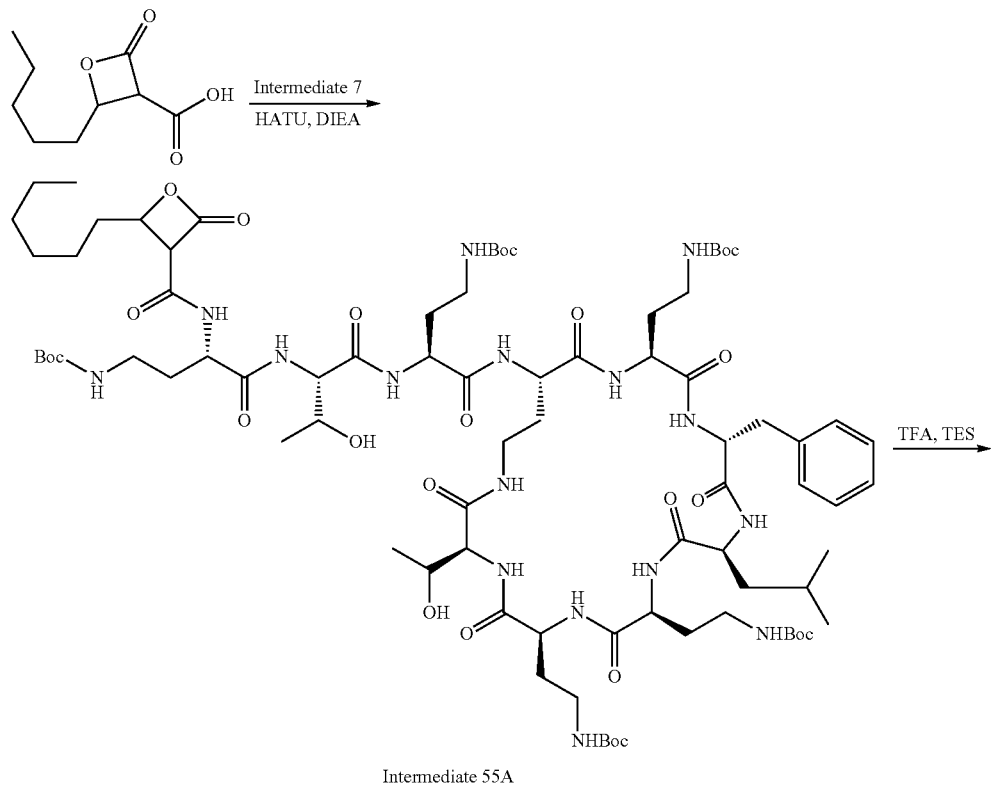

Intermediate 55A

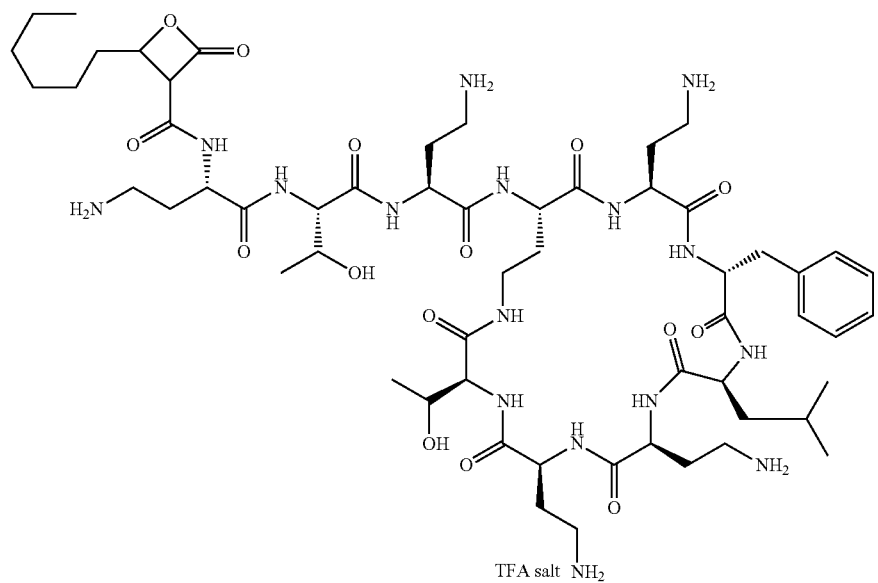

Example 55

The Compound of Example 55.

The Compound of Example 54 (TFA salt) was prepared analogously from the Intermediate 7 just as described for the Compound of Example 18 except using 2-oxo-4-pentyloxetane-3-carboxylic acid in place of 4-butoxy-4-oxobutanoic acid used in the synthesis of the Compound of Example 18.

Utility and Testing

The compounds provided herein exhibit potent activity against a variety of Gram-negative microorganisms. Accordingly, the compounds provided herein have broad antibacterial activity. Thus, the compounds provided herein are useful antimicrobial agents and may be effective against a number of human and veterinary pathogens, including Gram-negative microorganisms such as *Pseudomonas aeruginosa, Acinetobacter baumanii, E. coli, Klebsiela pneumoniae, H. influenzae* and *M. catarrahlis*, as well as select anaerobic microorganisms such as bacteroides and clostridia species, and including certain polymyxin B and colistin-resistant species.

In certain embodiments, certain polymyxin compounds provided herein possess a particular combination of specific unique properties to qualify as a soft drug, including:

a) intrinsic (of its own molecule) antibacterial activity or potency (determined in vitro);

b) useful antibacterial efficacy in mammal (determined in vivo, in a mammalian model);

c) undergo in vivo break-down of the soft drug molecule into less toxic metabolite(s), to preclude the accumulation of the intact compound in the kidney tissue which potentially results in nephrotoxicity (determined, for example, in plasma stability tests simulating in vivo conditions);

d) said soft drug break-down must occur at an optimally slow rate (to allow for the antibacterial action of the intact soft drug before its break-down);

e) said soft drug break-down must not occur too slowly (since drug persistence in vivo would result in accumulation of the intact molecule in kidneys, with the potential to induce the kidney injury);

f) reduced nephrotoxicity in mammals (determined, for example, with kidney injury nephrotoxicity biomarker assays).

In some embodiments, the polymyxin soft drug itself (in its intact molecular state) is less toxic to kidney cells, as compared to current polymyxin drugs, polymyxin B and colistin.

One skilled in the pharmaceutical arts would readily appreciate that the requirements for a soft drug exceed already rigid parameters for a regular drug. Due to these requirements, not every polymyxin compound is a soft drug polymyxin.

Additionally, improved efficacy of new polymyxins against certain Gram-negative infections compared to polymyxin B or colistin is highly desired. Pneumonia lung infections are inadequately addressed with most current drugs, including polymyxin B and colistin, and presently lead to unacceptably high patient mortality.

In vitro activity of compounds provided herein may be assessed by standard testing procedures such as the determination of minimum inhibitory concentration (MIC, µg/mL) just as described in "Methods for Dilution Antimicrobial Susceptibility Tests for Bacteria That Grow Aerobically; Approved Standard—Ninth Edition," published in 2012 by the Clinical and Laboratory Standards Institute, Wayne, Pa., USA. Thus, bacterial colonies grown overnight on Mueller-Hinton Agar plate were selected and suspended in sterile saline to a turbidity of about 80% transmittance, as measured by a spectrophotometer. The suspension was diluted 200-fold with cation-adjusted Mueller-Hinton broth to serve as the inoculum for testing. Two-fold serial dilutions of the test compound were performed in 96-well master plate to arrive at desired concentration. Samples of 10 microliter from each well of the master plate were transferred into respective wells of 96-well assay plate. Bacterial inoculum (90 microliter) was introduced into each well of the assay plate. The assay plate was placed in the incubator at 35° C. for about 24 h (without agitation) followed by the MIC determination. MIC values were determined based on the presence or absence of bacterial growth in wells at the given test agent concentration. MIC value is defined as the lowest concentration of test antibiotic that prevents visible bacterial growth. A lower MIC value indicates a higher antibacterial activity, and a higher MIC value indicates inferior antibacterial activity.

The useful activity of exemplary compounds described herein against Gram-negative pathogens *Pseudomonas aeruginosa, Escherichia coli,* or *Klebsiela pneumoniae* is illustrated by the MIC data of Table 1.

TABLE 1

Antibacterial activity (MIC) vs. representative Gram-negative bacteria.

| EXAMPLES | P. aeruginosa PAE 1001 µg/mL | E. coli WECO 1003 µg/mL | K. pneumoniae KPN1004 µg/mL |
|---|---|---|---|
| Polymyxin B | 2-4[a] | 2-4[a] | 2-4[a] |
| Reference Example 1[b] | 8 | 4 | 2 |
| Example 2 | 4 | 8 | 2 |
| Example 3 | 4 | 4 | 4 |
| Example 7 | 4 | 4 | 2 |
| Example 12 | 4 | 2 | 2 |
| Example 16 | 1 | 1 | 2 |
| Example 17 | 4 | 2 | 2 |
| Example 18 | 2 | 2 | 4 |
| Example 19 | 4 | >32 | >32 |
| Example 20 | 8 | 8 | 8 |
| Example 21 | 4 | 4 | 4 |
| Example 22 | 4 | 2 | 4 |
| Example 23 | 4 | 4 | 2 |
| Example 24 | 4 | 4 | 4 |
| Example 25 | 4 | 2 | 2 |
| Example 28 | 4 | 4 | 2 |
| Example 30 | 2 | 2 | 4 |
| Example 31 | 8 | 8 | 8 |
| Example 32 | 8 | 8 | 8 |
| Example 33 | 8 | 8 | 8 |
| Example 34 | 4 | 4 | 4 |
| Example 35 | 4 | 1 | 4 |
| Reference Example 40[c] | >32 | >32 | >32 |
| Example 43 | 8 | 8 | >32 |
| Example 44 | >32 | >32 | >32 |

[a]MIC range from several independent tests.
[b]Reference analog of the compound D93 of the WO 2015/135976, absent only distal 6-Me substitution (see FIG. 2).
[c]Polymyxin B nonapeptide.

As the data of Table 1 makes clear, representative compounds are highly active against Gram-negative pathogens.

Importantly, the high potency of certain compounds described herein incorporating a polar or metabolically or chemically labile group in $R^2$ (in place of aliphatic alkyl chain of common polymyxins), such as in compounds of Examples 12,18, 21-25, 28, 34 is unexpected. Indeed, the established structure-activity relationship (SAR) has created an expectation that highly lipophilic ($R^2$) side chains are required for good antibacterial activity (as reviewed, for example, by Velkov et al. in J. Med. Chem., 2010, vol. 53, pp. 1898-1916). Therefore, at most, compounds incorporating a polar (e.g., ester) group in the $R^2$ side chain thereof would be expected to be significantly less active than polymyxin B, and certainly not possess antibacterial activity equal to the antibacterial activity of PMB revealed in above tests.

Also surprising is the high activity of the compound of Example 30, which is believed to be the first polymyxin phosphonate derivative (incorporating a bis-alkyl phosphonate side chain), and the activity of monophosphoric compound of Example 33 (incorporating SAR-disfavored acidic group), which is only about 2-fold less active than polymyxin B comparator.

Importantly, for the polymyxin soft drugs of Examples 18, 12, and 17, the predicted metabolites represented by compounds of Examples 19, 20, and 44, respectively, all exhibit significantly reduced activity. Thus, the compounds of Examples 19 and 20 are at least 2-4-fold less active than the parent soft drugs of Examples 18 and 12, respectively. For example, the predicted metabolite of the soft drug of Example 18, namely the compound of Example 19 is essentially inactive against two Gram-negative pathogens in the test (Table 1; for structural relation of soft drugs of Examples 12 and 18 to respective metabolites thereof, Examples 20 and 19, see FIG. 1), and the expected metabolite of the compound of Example 17, the compound of Example 44, is likewise inactive.

In line with established structure-toxicity relationship for the polymyxin class, these metabolite compounds with reduced antibacterial potency are therefore expected to possess reduced nephrotoxicity (see, for example, Velkov et al. in J. Med. Chem., 2010, vol. 53, pp. 1898-1916). Indeed, this is well-known for the reference compound of Example 40 (see Table 1), polymyxin B nonapeptide (PMBN) lacking the terminal lipohilic acyl chain.

Therefore, one skilled in the polymyxin art would expect that, similar to Example 40, compounds of Examples 19, 20, and 44 would be likewise less nephrotoxic than the drug PMB and would be expected to have low nephrotoxicity similar to PMBN's (Example 25) low nephrotoxicity, once formed in vivo from a break-down of respective soft drugs. For example, compounds of Examples 19 and 20 are expected to be formed via esterase-mediated hydrolysis of soft drug Examples 18 and 12, respectively; or compound of Example 44 formed via the like enzymatic hydrolysis of the soft drug ester of Example 17.

To demonstrate the in vivo efficacy of the compounds described herein in vivo, *E. coli* septicemia, *P. aeruginosa* thigh infection, and *P. aeruginosa* lung infection (pneumonia) mouse models have been employed, with either intravenous (IV) or subcutaneous (SC) administration of test compounds, as described in Current Protocols in Pharmacology, 2005, 13A.4.1-13A.4.13, John Wiley & Sons, Inc. In the *E. coli* septicemia model, antibacterial efficacy is determined as $ED_{50}$ (mg/kg), or effective drug dose at which 50% of infected animals in the study survive. A lower $ED_{50}$ value indicates a higher therapeutic efficacy of the drug. The number of surviving animals (from the total number of infected animals used at a given drug dose) is another indicator of efficacy. Thus, a higher number of surviving mammals is indicative of a superior therapeutic efficacy of the test compound. In thigh and lung infection models, a greater reduction in the bacterial colony-forming units (CFU) indicates stronger beneficial therapeutic effect (more bacterial eradication), while a lower CFU reduction or an increase in CFU value indicates a lower effect (less bacterial eradication), or an absence of the therapeutic effect.

Efficacy data for representative compounds of this invention are illustrated in Tables 2 and 3 below.

TABLE 2

Efficacy in representative mouse models of systemic and thigh tissue infections, alongside the polymyxin B (PMB) control.

| EXAMPLES | *E. coli* Systemic model, IV dosing $ED_{50}$, mg/kg | *P. aeruginosa* Thigh model, IV dosing $\Delta logCFU^a$ at 5 mg/kg |
|---|---|---|
| Polymyxin B (PMB) | 4-7 | −1.49 to −3.33 |
| Ref. Example 1[b] | NT | −1.92 (PMB: −3.12)[c] |
| Example 7 | NT | −0.50 (PMB: −3.33)[c] |
| Example 12 | 2.5 (3/6 at 5 mg/kg)[d] PMB: 4.6 (2/6 at 5 mg/kg)[d] | −1.44 (PMB: −1.49)[c] |
| Example 16 | NT | −2.94 (PMB: −3.12)[c] |
| Example 17 | NT | −3.38 (PMB: −3.33)[c] |
| Example 18 | 7.5 (3/6 at 5 mg/kg)[d] PMB: 4.6 (2/6 at 5 mg/kg)[d] | −1.29 (PMB −1.49)[c] |
| Example 19[e] (predicted metabolite) | NT | −0.14 (PMB: −1.49)[c] |
| Example 20[f] (predicted metabolite) | >7 (0/6 at 5 mg/kg)[d] PMB: 3.9 (5/6 at 5 mg/kg)[d] | NT |
| Example XY | NT | −2.95 (PMB: −3.33)[c] |
| Example YZ | 3.7 (4/6 at 5 mg/kg)[d] PMB: 2.5 (3/6 at 5 mg/kg)[d] | NT |

[a] Change in bacterial colony-forming units (CFU) count at 12 h, compared to no treatment control group. Larger reduction means stronger bacterial eradication by the test compound.
[b] Reference analog of example D93 of the PCT WO 2015/135976, absent distal 5-Meheptyl substitution (see FIG. 2).
[c] Data for PMB comparator in a side-by-side test.
[d] Shown in parenthesis is the number (A) of surviving animals out of total (B) mice in ea. group, presented as A/B ratio; larger A/B ratio indicates superior therapeutic effect.
[e] Metabolite of the soft drug of Example 18.
[f] Metabolite of the soft drug of Example 12.

As is clear from the data (Tables 2 and 3), the polymyxins of this description possess excellent antibacterial activity when administered to an infected mammal, and at levels similar to polymyxin B comparator.

Importantly, metabolites of soft drug Examples 18 and 12, namely, compounds of Examples 19 and 20, respectively, lack antibacterial efficacy (Table 2). Therefore, as discussed above, these metabolites should be less nephrotoxic than PMB (as confirmed further in Table 5 and discussion therein). This intentionally-designed lack of efficacy is desirable for metabolites of soft drug polymyxins disclosed herein, because polymyxins accumulate in the kidney, and high antibacterial activity of polymyxins is associated with high nephrotoxicity thereof. Indeed, art compounds in the polymyxin class of structures have a multi-charge cationic core in combination with an extended lipophilic side chain which account for the compounds' ability to bind to bacterial membranes to effect the cell wall disruption and antibacterial cidality, but also to bind to tubular cells in kidney to effect of nephrons apoptosis (or death). Thus, this data further validates the compounds of Examples 12 and 18 as illustrative soft drugs.

Current polymyxin agents colistin and polymyxin B (PMB) are generally inadequate for treating pneumonia, prompting decades-long efforts to address this issue via specialized drug formulations or delivery systems (such as PMB aerosol, reported by Feeley et al. in *N. Engl. J. Med.*, 1975, vol. 293, pp. 471-475; or colistin aerosol, reviewed by Wood in *Expert Rev. Anti-infect. Ther.*, 2011, vol. 9, pp. 993). Entirely unexpected and quite surprising, the compounds of Examples 12 and 18 exhibit a distinct superiority over the drug polymyxin B in a *P. aeruginosa* mouse lung infection model. This is evidenced by the enhanced eradication of bacterial colonies compared to PMB, as well as improved animal survival for polymyxins disclosed herein (Table 3). As apparent from the test data of Table 3, new polymyxins illustrated herein are orders of magnitude more effective for eradication of bacterial colony-forming units of the pathogen than the drug comparator which is Polymyxin B. This is far in excess of about 3- to 7-fold efficacy improvement over a standard polymyxin drug regimen that would be typically desired (in line with recommendations for elevated colistin dosing cited, for example, by Dalfino et al. in *Clin. Inf. Dis.* 2012, vol. 54, pp. 1720-1726). In addition, the compounds described herein have the potential to avoid the need for specialized and expensive pulmonary delivery systems (such as aerosol delivery contemplated for current polymyxins).

TABLE 3

Efficacy in the pneumonia lung infection model in mouse, alongside the polymyxin B (PMB) control.

| EXAMPLES | *P. aeruginosa* Lung infection model SC dosing | |
|---|---|---|
| | $\Delta logCFU^a$ at 10 mg/kg | Relative CFU count, vs. PMB |
| Polymyxin B (PMB) | +2.61 | 1 |
| Example 12 | −2.15 | $1.7 \times 10^{-5}$ |
| Example 18 | −2.70 | $4.8 \times 10^{-6}$ |

$^a$Change in bacterial colony-forming units (CFU) count at 24 h, compared to the starting inoculum (bacterial load) used to induce the infection. Larger reduction means stronger bacterial eradication by the test compound, and the increase of CFU values indicates low or absent efficacy.

As stated already, for a polymyxin compound to act as a soft drug, its molecule should break down in vivo to a less active (and thus less toxic) degradant after performing its therapeutic action, preferably via a metabolic process, such as esterase-mediated hydrolysis. This metabolic break-down of compounds of Examples 12 and 18 is illustrated in FIG. 1. FIG. 1 shows that the ester compound of Example 12 metabolizes into an alcohol (the compound of Example 20), while the "reverse" ester compound of Example 18 metabolizes into an acid (the compound of Example 19). This occurs with the loss of a lipophilic side chain needed for antibacterial activity, but also known to contribute to nephrotoxicity within the polymyxin class (as reported for previously described polymyxins, such as polymyxin B and colistin).

It is advantageous for a polymyxin soft drug to break down after killing bacteria, thus precluding the persistence of intact drug in blood plasma and tissues, which would lead to its accumulation in kidneys and nephrotoxicity. This accumulation of polymyxin B and of colistin over at least 7 days of drug dosing was reported, for example, by Nillson et al. in *Chem. Res. Toxicol.*, 2015, vol. 28, p. 1823.

Preferably, a polymyxin soft drug exhibits a half-life of between about 1 h and about 36 h in vivo or, more preferably, a half-life of between about 1 h and about 12 h. Surprisingly, certain compounds of this invention possess the combination of the demanding properties required for a soft drug of this class.

Exemplary compounds of this invention were tested for stability in human plasma at 37° C., replicating in vivo conditions of mammalian blood. Plasma stability for select compounds was performed as follows. Human plasma (K2 EDTA) was obtained from Bioreclamation. The assay was carried out in 96-well microtiter plates. Test compounds were incubated in duplicate at 37° C. in the presence of plasma. Reaction mixtures (25 µL) contained a final concentration of 25 µM test compound. The extent of metabolism was calculated as the disappearance of the test compound over time. Eucatropine was included as a positive control to verify assay performance. At each given time point, 100 µL of quench solution (100% MeCN with 0.1% HCOOH) with internal standard was transferred to each well. Plates were sealed, vortexed, and centrifuged at 4° C. for 15 minutes at 4,000 rpm. The supernatant was transferred to fresh plates for LC/MS/MS analysis. The formation of a potential metabolite was monitored in all samples. The samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of at a flow rate of 0.5 mL/min, eluting with 0.1% aq. HCOOH and 0.1% HCOOH in MeCN (using gradient from 2% to 98% of the latter). Remaining test compounds were quantified via MS/MS ion current.

Surprisingly, ester derivatives of polymyxins exhibited different human plasma stability depending on the specific ester type, as illustrated by data of the Table 4 below.

TABLE 4

Stability in human plasma, compared to polymyxin B.

| | Compound remaining, % | |
|---|---|---|
| TEST COMPOUND | T = 1.0 h | T = 4.0 h |
| Polymyxin B | $100^a$ | $100^a$ |
| Reference Example 1$^b$ | $100^a$ | $100^a$ |
| Example 7 | 49 | 15 |
| Example 12 | 67 | 31 |
| Example 18 | 66 | 18 |

$^a$No discernable metabolism detected.
$^b$Reference analog of example D93 of the PCT WO 2015/135976, identical to structure D93, absent distal 5-Me-heptyl substitution (see FIG. 2).

The reference compound of Example 1 exhibited no discernable metabolism (hypothetically illustrated in FIG. 2). Furthermore, no formation of the expected metabolite (compound of Example 44) was detectable by MS analysis in this test.

Indeed, the human plasma stability for the compound of Example 1 is essentially identical to that for polymyxin B. Thus, this particular class of polymyxin ester derivatives represented by structures of the compound of Example 1 and of nearly identical compound D93 of the WO 2015/135976 are not soft drugs.

Based on the plasma stability of the compound of Example 1 essentially similar to this stability of PMB, this metabolically stable reference compound and its analog D93 (of the PCT WO 2015/135976), like PMB, would also be expected to accumulate in kidneys and exhibit nephrotoxicity. Notably, the compound D93 is nearly identical in structure to the drug polymyxin B, with the principal difference in the point of the acyl group attachment: the amide NH in PMB, differing from the ester O in the compound D93. Thus, aforementioned structures of Example 1 and D93 would not be considered to be soft drugs, and are expected to be nephrotoxic.

As stated, soft drug polymyxin should exhibit significantly reduced over polymyxin B and colistin nephrotoxicity, the chief limitation for this class. Nephrotoxicity of polymyxins could be determined in vitro using human renal glomeruli mesangial cells (HK-2) cytotoxicity assay, analogously to that described, for example, by Keirstead et al. in *Toxicol. Sci.*, 2014, vol. 137, pp. 278-291. In vivo, nephrotoxicity could be determined using urine biomarker assays, such as clinically validated neutrophil gelatinase-associated lipocalin (NGAL) assay described, for example by Devarajan in *Scand. J. Clin. Lab. Invest.* Suppl., 2008, vol. 841, pp. 89-94.

Surprisingly, in addition to the desired antibacterial potency (MIC), efficacy in mammals, and the metabolic profile suitable for a soft drug, polymyxin derivatives provided herein are also less toxic again kidney cells, both in vitro (HK-2 assay) and in a live mammal (rat) model, as illustrated by the data of Table 5 for exemplary compounds herein.

TABLE 5

Nephrotoxicity compared to polymyxin B (PMB) positive control: in vitro HK-2 and in vivo rat urine NGAL biomarker data.

| TEST COMPOUND | Nephrotoxicity[a] | |
|---|---|---|
| | In vitro: human HK-2 cell assay IC$_{50}$, μM | In vivo: rat urine biomarker NGAL[b] |
| Polymyxin B | 82 (Class 1)[c] | High: above detection limit |
| Example 12 | >200 (Class 4)[c] | Low[d] |
| Example 18 | >200 (Class 4)[c] | Low[d] |
| Example 19 | >200 (Class 4)[c] | Low[d] |
| Example 20 | >200 (Class 4)[c] | NT |
| Example 40[e] | >200 (Class 4)[c] | NT |

[a]HK-2 assay performed at Eurofins Cerep, France. NGAL assay performed at PharmOptima, USA.
[b]Rat urine biomarker, repeated dose test, 25 mg/kg/day QID, SC administration.
[c]Class 1: observed cytotoxicity with complete response curve. Class 4: no significant activity.
[d]Observed signal for test cpd. similar to the background.
[e]Polymyxin B nonapeptide.

As is clear from the data of Table 5, compounds of Examples 12 and 18 are markedly less toxic than PMB in human kidney HK-2 tests: Class 1 and Class 4 cytotoxicity grade for PMB positive control and the illustrative compounds of this invention, respectively, and with no significant activity for the latter. This low intrinsic (of intact molecular state) toxicity of highly active polymyxin compounds of Examples 12 and 18 is surprising, since, as discussed above, the high potency of polymyxins broadly parallels the toxicity against kidney cells. Therefore, these molecules, being essentially equal in potency to the PMB drug, would ordinarily be expected to exhibit a similar to PMB toxicity against kidney cells, rather than being non-cytotoxic.

Importantly, the confirmed metabolites of these soft drugs, compounds of Examples 19 and 20, likewise exhibit greatly reduced (over PMB) toxicity in an HK-2 assay, similar to the reference compound of Example 40, polymyxin B nonapeptide (PMBN), known to be much less nephrotoxic than PMB (but lacking useful antibacterial activity), as reported, for example, by Keirstead et al. in *Toxicol. Sci.*, 2014, vol. 137, pp. 278-291.

Therefore, upon metabolism of soft drugs of Examples 12 and 18, the resulting metabolites of Examples 20 and 19 would not be expected to induce the high nephrotoxicity. The data further illustrate the suitability of polymyxins described herein as first soft drugs of this class with significantly reduced nephrotoxicity and improved safety.

Most importantly, exemplary compounds of Examples 12 and 18 exhibit low nephrotoxicity in vivo, in the repeated dose rat tests and using urine biomarkers for detection of the nephrotoxicity, as revealed by the NGAL assay. Surprisingly, these compounds display greatly reduced nephrotoxicity levels compared to polymyxin B, with latter being similar to that for the metabolite of Example 18, inactive acid compound of Example 19 (Table 5).

Thus, the compounds provided herein comprise a set of innovative polymyxin soft drugs, with experimental in vitro and in vivo data supporting these compounds as promising agents of the antibiotic class. Importantly, the compounds potentially address the critical limitations of the currently used polymyxin drugs, including both the nephrotoxicity and inadequate efficacy of the current polymyxins for the treatment of Gram-negative pneumonia. The compounds provided herein hold potential for new safe treatment for a range of serious Gram-negative infections, presently exacerbated with high mortality rates and serious adverse effects, such as kidney injury.

Optionally, the polymyxins provided herein may be used for treatment of Gram-negative infections in combination with agent(s) of other antibacterial classes. For example, agents synergistic to polymyxin antibiotics could be used in said combinations, such as agents of rifampicin, carbapenem, fluoroquinolone, or cephalosporin classes, as may be desired for an optimal treatment of an infection, including a polymyxin B or colistin-resistant infections.

The improved safety profile of the compounds of the current invention is further established in biomarker assays predictive of polymyxin-induced nephrotoxicity. Several such assays (including NGAL assay) have been described, for example, by Keirstead et al. in *Toxicol. Sci.* 2014, vol. 137, pp. 278-291.

Thus, certain compounds of this invention exhibit high antibacterial activity in vitro and in vivo, but do not suffer from nephrotoxicity that limits the therapy with the current polymyxin drugs, colistin and polymyxin B. This surprising for polymyxins effect provides for greatly improved safety of the new compounds provided herein. In addition to significantly improved tolerability during a short-term therapy, these new polymyxins offer a potential for longer term therapy, as may be required for persistent infections in mammals or human. Due to the improved safety, the treatment of a microbial or bacterial infection with certain composition provided herein can be beneficially extended in its duration, as compared to the approved treatments with colistin or polymyxin B. In particular, the improved mammalian tolerability towards certain compounds provided herein allows for the treatment of a microbial or bacterial infection using said polymyxins, with a possible therapy duration from about 14 days to about 50 days, and, more preferably, from 28 days to 45 days.

In some embodiments, certain compounds described herein are soft drugs. In some embodiments, certain compounds described herein with in vitro antibacterial activity have polar $R^2$ side chain groups in surprising contrast to the art compounds which have lipophilic $R^2$ side chains; in addition these compounds are optionally soft drugs. In some embodiments, certain compounds described herein have surprising activity in pneumonia lung infection models; in addition these compounds are optionally soft drugs.

Administration and Pharmaceutical Formulations

In general, the compounds provided herein can be administered in a therapeutically effective amount by any of the accepted modes of administration for agents that serve similar utilities. By way of example, compounds provided herein may be administered orally, parenterally, transdermally, topically, rectally, or intranasally. The actual amount of a compound provided herein, i.e., the active ingredient, will depend on a number of factors, such as the severity of the disease, i.e., the infection, to be treated, the age and relative health of the subject, the potency of the compound used, the route and form of administration, and other factors, all of which are within the purview of the attending clinician.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method provided herein, the therapeutically effective dose can be estimated initially from animal models. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans.

When employed as pharmaceuticals, the compounds provided herein are usually administered in the form of pharmaceutical compositions. These compounds can be administered by a variety of routes including oral, parenteral, transdermal, topical, rectal, and intranasal.

Compounds provided herein are effective as injectable, oral, inhalable, or topical compositions. Such compositions are prepared in a manner well known in the pharmaceutical art and comprise at least one active compound.

This invention also includes pharmaceutical compositions which contain, as the active ingredient, one or more of the compounds provided herein above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions are preferably formulated in a unit dosage form, each dosage containing from about 0.1 to about 2000 mg, more usually about 1 to about 900 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound provided herein above is employed at no more than about 20 weight percent of the pharmaceutical composition, more preferably no more than about 15 weight percent, with the balance being pharmaceutically inert carrier(s).

An active compound is effective over a wide dosage range and is generally administered in a pharmaceutically or therapeutically effective amount. It, will be understood, however, that the amount of the compound actually administered can be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, compounds or pharmaceutical compositions thereof can be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 mg/kg to about 250 mg/kg, more preferably about 1.0 mg/kg to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills described herein may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions described herein may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

Other suitable formulations for use in the present invention can be found in *Remington's Pharmaceutical Sciences*, Mace Publishing Company, Philadelphia, Pa., 17th ed. (1985).

Optionally, the compounds of the present invention may be co-administered with additional agents, including antioxidants, such as ascorbic acid, or megalin-receptor inhibitors generally known to attenuate adverse effects of polymyxin drugs.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference. Optionally, the compounds described herein could be administered as nanomicells, or nanomaterials-encapsulated compositions, prepared as described, for example, by Taki et al. in *Pharmaceut.*, 2012, vol. 3, p. 1092.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The disclosures of each and every patent, patent application and publication (for example, journals, articles and/or textbooks) cited herein are hereby incorporated by reference in their entirety. Also, as used herein and in the appended claims, singular articles such as "a", "an" and "one" are intended to refer to singular or plural. While the present invention has been described herein in conjunction with a preferred aspect, a person with ordinary skills in the art, after reading the foregoing specification, can affect changes, substitutions of equivalents and other types of alterations to the invention as set forth herein. Each aspect described above can also have included or incorporated therewith such variations or aspects as disclosed in regard to any or all of the other aspects. The present invention is also not to be limited in terms of the particular aspects described herein, which are intended as single illustrations of individual aspects provided herein. Many modifications and variations of this invention can be made without departing from its spirit and scope, as will be apparent to those skilled in the art. Functionally equivalent methods within the scope of this invention, in addition to those enumerated herein, will be apparent to those skilled in the art from the foregoing descriptions. It is to be understood that this invention is not limited to particular methods, reagents, process conditions, materials and so forth, which can, of course, vary. It is also to be understood that the terminology used herein is for the purpose of describing particular aspects only, and is not intended to be limiting. Thus, it is intended that the specification be considered as exemplary.

The invention claimed is:
1. A compound of the following formula I

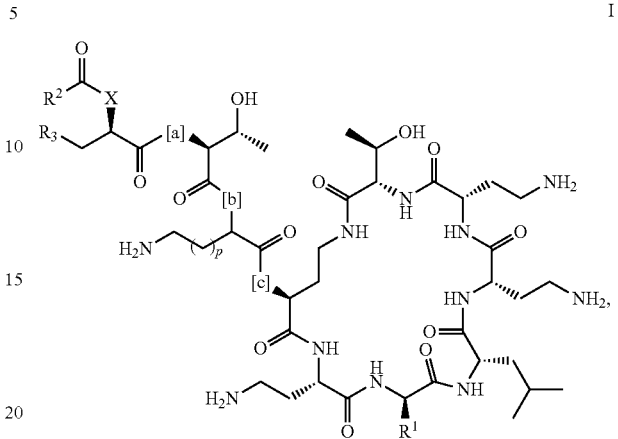

or a pharmaceutically acceptable salt, solvate, or hydrate thereof wherein:
$R^1$ is $CH_2CH(CH_3)_2$ or $CH_2Ph$; and wherein
X is O, NH, N($C_{1-6}$alkyl), —NHC(=O)CH($CH_2CH_2NH_2$)O—, —OC(=O)CH($CH_2CH_2NH_2$)NH—, or —NHC(=O)CH($CH_2CH_2NH_2$)NH— connected to —C(=O)$R^2$ at the latter NH group, and $R^3$ is $NH_2$, $CH_2NH_2$ or imidazolyl; or X is N and $R^3$ is NH or N($C_{1-6}$alkyl) and $R^3$ and X taken together comprise the group NHCH$_2$CH$_2$N or N($C_{1-6}$alkyl)CH$_2$CH$_2$N; and with the additional following provisions:
when X is O, —NHC(=O)CH(CH$_2$CH$_2$NH$_2$)O—, or —OC(=O)CH(CH$_2$CH$_2$NH$_2$)NH—, then $R^2$ is $C_{1-14}$alkyl, $C_{3-12}$cycloalkyl, aryl, arylalkyl, biaryl, biarylalkyl, arylheteroaryl, heteroarylaryl, dihydrofuran-2(3H)-one-3-yl, aryl-dihydrofuran-2(3H)-one-3-yl, $C_{1-14}$alkyl-dihydrofuran-2(3H)-one-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, NH($C_{1-14}$alkyl), NH(Ar), NH-(5 to 6-member heteroaromatic group containing at least one of N, S, and O atoms and the remaining atoms are carbon), O$C_{1-14}$alkyl, OAr, NH(O$C_{1-14}$alkyl), aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, or heteroarylalkyl; or $R^2$ is $(CR^4R^5)_m(CR^6R^7)_nC(=O)OR^8$, $(CR^4R^5)_m(CR^6R^7)_nOC(=O)R^8$, $(CR^4R^5)_m$ N($C_{1-6}$alkyl)OC(=O)OR$^8$, or L-P(=O)(OR$^{11}$)(OR$^{12}$);
when X is NH, N($C_{1-6}$alkyl), or NHC(=O)CH(CH$_2$CH$_2$NH$_2$)NH— connected to C(=O)$R^2$ at the latter NH, then $R^2$ is aryl[C(=O)OR$^4$]$_r$, biaryl[C(=O)OR$^4$]$_r$, aryl[OC(=O)R$^4$]$_r$, biaryl[-OC(=O)OR$^4$]$_r$, aryl-OC(=O)NR$^4$R$^5$, biaryl-OC(=O)NR$^4$R$^5$, $(CR^4R^5)_m(CR^6R^7)_nC(=O)OR^8$, $(CR^4R^5)_m(CR^6R^7)_nOC(=O)R^8$, $(CR^4R^5)_mN(C_{1-6}alkyl)OC(=O)OR^8$, dihydrofuran-2(3H)-one-3-yl, aryl-dihydrofuran-2(3H)-one-3-yl, $C_{1-14}$alkyl-dihydrofuran-2(3H)-one-3-yl, tetrahydro-2H-pyran-2-one-3-yl, aryl-tetrahydro-2H-pyran-2-one-3-yl, $C_{1-14}$alkyl-tetrahydro-2H-pyran-2-one-3-yl, or L-P(=O)(OR$^{11}$)(OR$^{12}$);
when $R^3$ and X taken together comprise NHCH$_2$CH$_2$N or N($C_{1-6}$alkyl)CH$_2$CH$_2$N, then $R^2$ is defined as above for when X is NH or —NHC(=O)CH(CH$_2$CH$_2$NH$_2$)NH—;

wherein r is 1 or 2;

L is selected from O, NH, N(C$_{1-6}$alkyl), C$_{1-6}$alkylene, (CR$^4$R$^5$)$_m$(CR$^6$R$^7$)$_n$(CR$^9$R$^{10}$)$_o$, CR$^4$=CR$^6$—(CR$^9$R$^{10}$)$_o$, (CR$^4$R$^5$)$_m$—CR$^6$=CR$^{10}$, O(CR$^4$R$^5$)$_m$(CR$^6$R$^7$)$_n$ (CR$^9$R$^{10}$)$_o$, NH(CR$^4$R$^5$)$_m$(CR$^6$R$^7$)$_n$(CR$^9$R$^{10}$)$_o$, N(C$_{1-6}$alkyl)(CR$^4$R$^5$)$_m$(CR$^6$R$^7$)$_n$(CR$^9$R$^{10}$)$_o$, (CR$^4$R$^5$)$_m$(CR$^6$R$^7$)$_n$(CR$^9$R$^{10}$)$_o$O, (CR$^4$R$^5$)$_m$(CR$^6$R$^7$)$_n$(CR$^9$R$^{10}$)$_o$NH, and (CR$^4$R$^5$)$_m$(CR$^6$R$^7$)$_n$(CR$^9$R$^{10}$)$_o$N(C$_{1-6}$alkyl);

R$^4$ through R$^7$, R$^9$, and R$^{10}$ are independently H, NH$_2$, halo, NH(C$_{1-6}$alkyl), NH(OC$_{1-6}$alkyl), C$_{1-14}$alkyl, C$_{3-6}$cycloalkyl, aryl, arylalkyl, biaryl, biarylalkyl, or heteroarylalkyl; and R$^8$ is H, NH(C$_{1-6}$alkyl), NH(OC$_{1-6}$alkyl), C$_{1-14}$alkyl, C$_{3-6}$cycloalkyl, aryl, arylalkyl, biaryl, biarylalkyl, or heteroarylalkyl; or any two of R$^4$ through R$^{10}$, together with the atom(s) to which they are attached form a 4 to 7-member saturated or unsaturated heterocycle containing at least one O atom, or containing one O atom and an additional heteroatom independently selected from N and S and wherein the remaining atoms are carbon; or any of i) R$^4$ and R$^5$, ii) R$^6$ and R$^7$, iii) R$^4$ and R$^6$, iv) R$^9$ and R$^{10}$, v) R$^6$ and R$^{10}$, and vi) R$^4$ and R$^9$, together with the atom to which they are attached form a C$_{3-6}$cycloalkylene; or any two of R$^4$ through R$^{10}$ together with the atom(s) to which they are attached form a 5 to 7-member saturated or unsaturated heterocycle wherein the ring optionally comprises an additional heteroatom selected from N, O, and S and wherein the remaining atoms are carbon; or R$^6$ and R$^8$ together with the atom to which they are attached form a 4 to 6-member saturated heterocycle containing at least one O atom wherein the heterocycle optionally comprises an additional heteroatom selected from N, O, and S and wherein the remaining atoms are carbon; and R$^{11}$ and R$^{12}$ are independently H, N(C$_{1-6}$alkyl), C$_{1-14}$alkyl, C$_{3-6}$cycloalkyl, aryl, arylalkyl, biaryl, biarylalkyl, or heteroarylalkyl; or R$^{11}$ and R$^{12}$ together with the two oxygen atoms to which they are attached form a 5 to 7-member saturated heterocycle wherein the 2, 3, or 4 additional atoms are carbon; or either or both of i) R$^4$ and R$^{11}$ and ii) R$^6$ and R$^{12}$ together with atoms to which they are attached form a 5 to 7-member saturated heterocycle containing one O atom and one P atom and where the remaining atoms are carbon;

wherein m, n, o, and p are independently selected from 0, 1, and 2, and wherein when L is (CR$^4$R$^5$)$_m$(CR$^6$R$^7$)$_n$ (CR$^9$R$^{10}$)$_o$, then m+n+o≥1; and each of [a], [b], and [c] is independently selected from NH, N(C$_{1-6}$alkyl) and O;

provided that when each of [a], [b], and [c] is NH, X is O, and R$^3$ is CH$_2$NH$_2$, then R$^2$ is not 5-methyl-heptyl.

2. The compound of claim 1 according to formula II

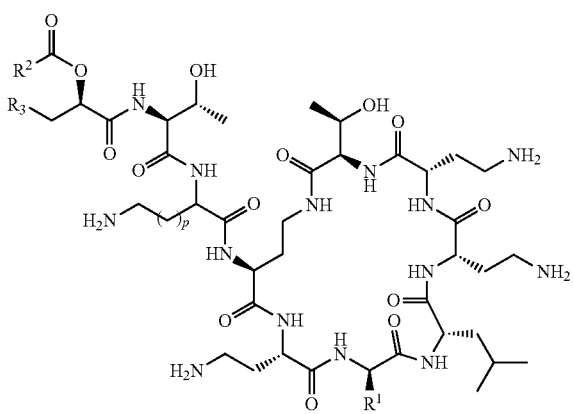

or a pharmaceutically acceptable salt, solvate, or hydrate thereof.

3. The compound of claim 1 according to formula II

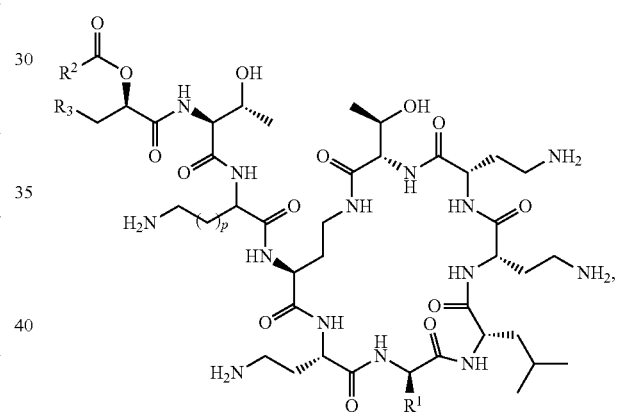

or a pharmaceutically acceptable salt, solvate, or hydrate thereof wherein:

R$^1$ is CH$_2$CH(CH$_3$)$_2$ or CH$_2$Ph;

R$^2$ is C$_{1-14}$alkyl, C$_{1-13}$alkylCF$_2$—, C$_{3-12}$cycloalkyl, aryl, arylCF$_2$—, arylalkyl, biaryl, biarylalkyl, aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, heteroarylalkyl, (CR$^4$R$^5$)$_m$(CR$^6$R$^7$)$_n$C(=O)OR$^8$, (CR$^4$R$^5$)$_m$(CR$^6$R$^7$)$_n$OC(=O)R$^8$, dihydrofuran-2(3H)-one-3-yl, aryl-dihydrofuran-2(3H)-one-3-yl, C$_{1-14}$alkyl-dihydrofuran-2(3H)-one-3-yl, tetrahydro-2H-pyran-2-one-3-yl, aryl-tetrahydro-2H-pyran-2-one-3-yl, C$_{1-14}$alkyl-tetrahydro-2H-pyran-2-one-3-yl, or L-P(=O)(OR$^{11}$)(OR$^{12}$);

L is selected from O, NH, N(C$_{1-6}$alkyl), C$_{1-6}$alkylene, (CR$^4$R$^5$)$_m$(CR$^6$R$^7$)$_n$(CR$^9$R$^{10}$)$_o$, CR$^4$=CR$^6$—(CR$^9$R$^{10}$)$_o$, (CR$^4$R$^5$)$_m$—CR$^6$=CR$^{10}$, O(CR$^4$R$^5$)$_m$(CR$^6$R$^7$)$_n$ (CR$^9$R$^{10}$)$_o$, NH(CR$^4$R$^5$)$_m$(CR$^6$R$^7$)$_n$(CR$^9$R$^{10}$)$_o$, N(C$_{1-6}$alkyl)(CR$^4$R$^5$)$_m$(CR$^6$R$^7$)$_n$(CR$^9$R$^{10}$)$_o$, (CR$^4$R$^5$)$_m$(CR$^6$R$^7$)$_n$(CR$^9$R$^{10}$)$_o$O, (CR$^4$R$^5$)$_m$(CR$^6$R$^7$)$_n$(CR$^9$R$^{10}$)$_o$NH, and (CR$^4$R$^5$)$_m$(CR$^6$R$^7$)$_n$(CR$^9$R$^{10}$)$_o$N(C$_{1-6}$alkyl); and $R^4$ through $R^7$, $R^9$, and $R^{10}$ are independently H, $NH_2$, halo, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; and $R^8$ is H, $NH(C_{1-6}alkyl)$, $NH(OC_{1-6}alkyl)$, $C_{1-14}alkyl$, $C_{3-6}cycloalkyl$, aryl, arylalkyl, biaryl, biarylalkyl, or heteroarylalkyl; or any two of $R^4$ through $R^{10}$, together with the atom(s) to which they are attached form a 4 to 7-member saturated or unsaturated heterocycle containing at least one O atom, or containing one O atom and an additional heteroatom independently selected from N and S and where the remaining atoms are carbon; or any of i) $R^4$ and $R^5$, ii) $R^6$ and $R^7$, iii) $R^4$ and $R^6$, iv) $R^9$ and $R^{10}$, v) $R^6$ and $R^{10}$, and vi) $R^4$ and $R^9$, together with the atom to which they are attached form a $C_{3-6}$cycloalkylene; or any two of $R^4$ through $R^{10}$ together with the atom(s) to which they are attached form a 5 to 7-member saturated or unsaturated heterocycle wherein the ring optionally comprises an additional heteroatom selected from N, O, and S, and wherein the remaining atoms are carbon; or $R^6$ and $R^8$ together with the atom to which they are attached form a 4 to 6-member saturated heterocycle containing at least one O atom wherein the heterocycle optionally comprises an additional heteroatom selected from N, O, and S, and wherein the remaining atoms are carbon; and $R^{11}$ and $R^{12}$ are independently H, $N(C_{1-6}alkyl)$, $C_{1-14}alkyl$, $C_{3-6}cycloalkyl$, aryl, arylalkyl, biaryl, biarylalkyl, or heteroarylalkyl; or $R^{11}$ and $R^{12}$ together with the two oxygen atoms to which they are attached form a 5 to 7-member saturated heterocycle wherein the 2, 3, or 4 additional atoms are carbon; or either or both of i) $R^4$ and $R^{11}$ and ii) $R^6$ and $R^{12}$ together with atoms to which they are attached form a 5 to 7-member saturated heterocycle containing one O atom and one P atom and where the remaining atoms are carbon;

r is 1 or 2; and wherein m, n, o, and p are independently selected from 0, 1, and 2, and wherein when L is $(CR^4R^5)_m(CR^6R^7)_n(CR^9R^{10})_o$, then $m+n+o \geq 1$; and $R^3$ is $NH_2$, $CH_2NH_2$ or imidazolyl; and with the proviso that wherein $R^3$ is $CH_2NH_2$, then $R^2$ is not 5-methylheptyl.

4. The compound of claim 1 wherein $R^3$ is $CH_2NH_2$, and wherein [a], [b], and [c] are all NH.

5. The compound of claim 1 wherein X is O and $R^2$ is selected from structures below:

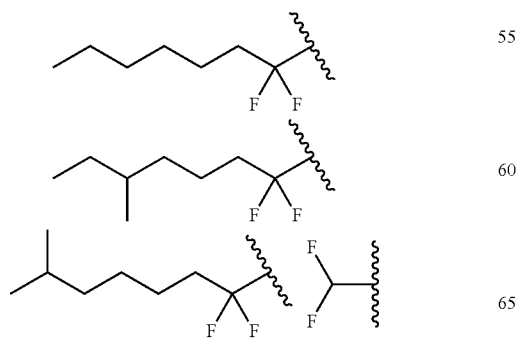

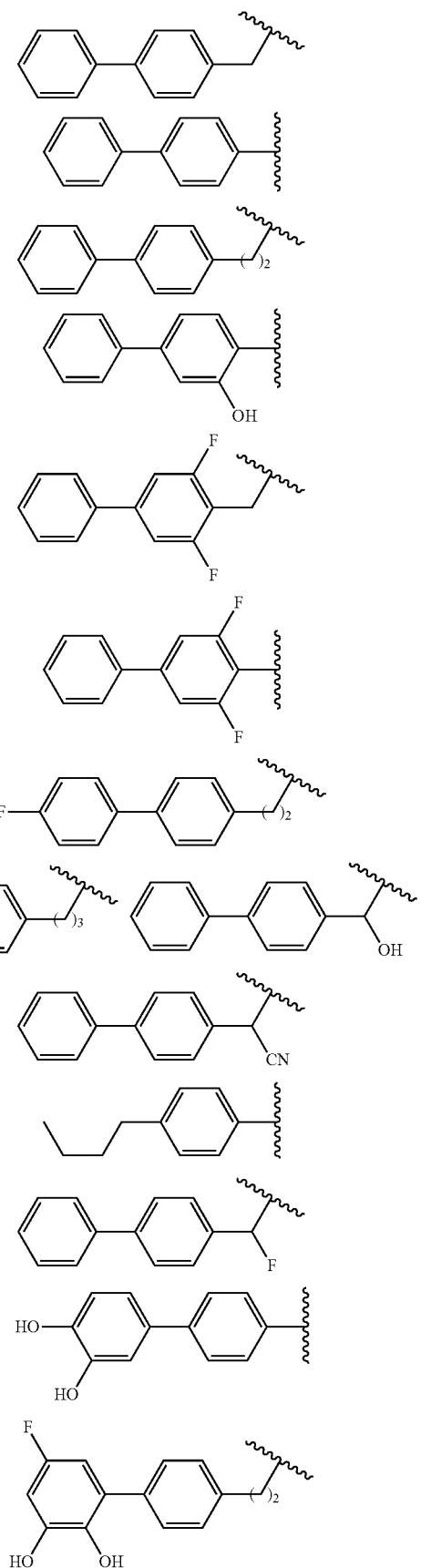

-continued

6. The compound of claim 1 according to formula III

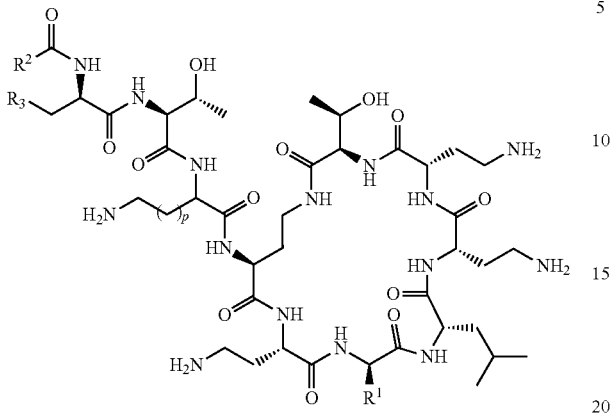

or a pharmaceutically acceptable salt, solvate, or hydrate thereof.

7. The compound of claim 1 according to formula III

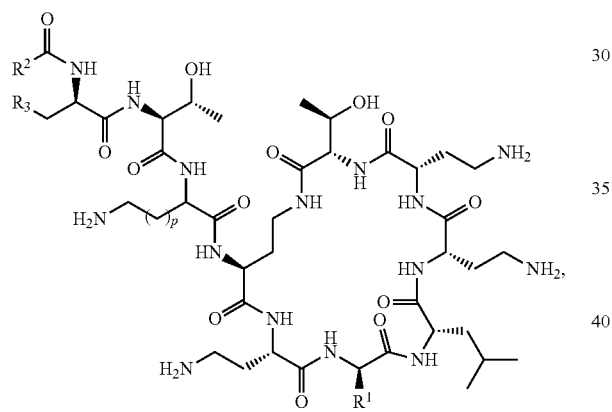

or a pharmaceutically acceptable salt, solvate, or hydrate thereof wherein:
$R^1$ is $CH_2CH(CH_3)_2$ or $CH_2Ph$;
$R^2$ is aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, $(CR^4R^5)_m(CR^6R^2)_nC(=O)OR^8$, $(CR^4R^5)_m(CR^6R^7)_nOC(=O)R^8$, dihydrofuran-2(3H)-one-3-yl, aryl-dihydrofuran-2(3H)-one-3-yl, $C_{1-14}$alkyl-dihydrofuran-2(3H)-one-3-yl, tetrahydro-2H-pyran-2-one-3-yl, aryl-tetrahydro-2H-pyran-2-one-3-yl, or $C_{1-14}$alkyl-tetrahydro-2H-pyran-2-one-3-yl;
$R^4$ through $R^7$ are independently H, $NH_2$, halo, $NH(C_{1-6}$alkyl), $NH(OC_{1-6}$alkyl), $C_{1-14}$alkyl, $C_{3-6}$cycloalkyl, aryl, arylalkyl, biaryl, biarylalkyl, or heteroarylalkyl; and
$R^8$ is H, $NH(C_{1-6}$alkyl), $NH(OC_{1-6}$alkyl), $C_{1-14}$alkyl, $C_{3-6}$cycloalkyl, aryl, arylalkyl, biaryl, biarylalkyl, or heteroarylalkyl; or
any two of $R^4$ through $R^8$, together with the atom(s) to which they are attached form a 4 to 7-member saturated or unsaturated heterocycle containing at least one O atom, or containing one O atom and an additional heteroatom independently selected from N and S, and where the remaining atoms are carbon; or
any of i) $R^4$ and $R^5$, ii) $R^6$ and $R^7$, and iii) $R^4$ and $R^6$, together with the atom to which they are attached form a $C_{3-6}$cycloalkylene; or
any two of $R^4$ through $R^8$ together with the atom(s) to which they are attached form a 5 to 7-member saturated or unsaturated heterocycle wherein the ring optionally comprises an additional heteroatom selected from N, O, and S, and wherein the remaining atoms are carbon; or
$R^6$ and $R^8$ together with the atoms to which they are attached form a 4 to 6-member saturated heterocycle containing at least one O atom wherein the heterocycle optionally comprises an additional heteroatom selected from N, O, and S, and wherein the remaining atoms are carbon; and wherein r is 1 or 2;
wherein m, n, and p are independently selected from 0 to 2; and
$R^3$ is $NH_2$, $CH_2NH_2$ or imidazolyl.

8. The compound of claim 1 wherein X is NH and $R^2$ is selected from structures below:

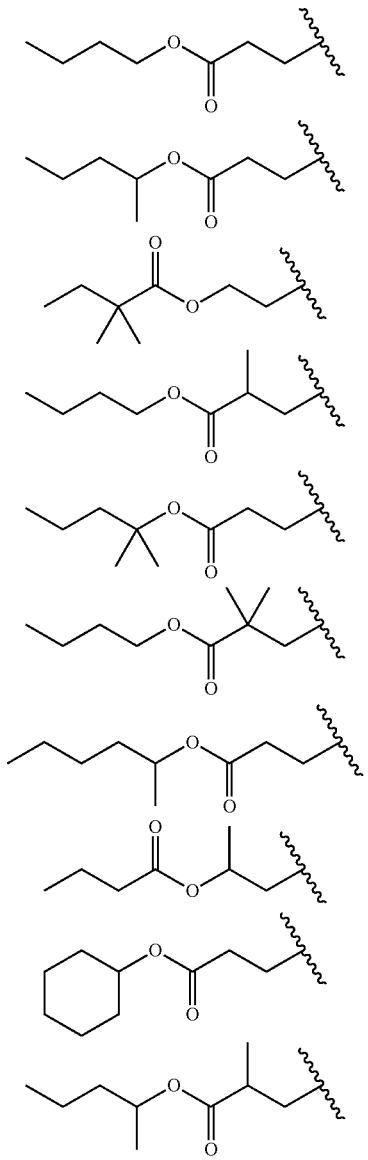

249
-continued
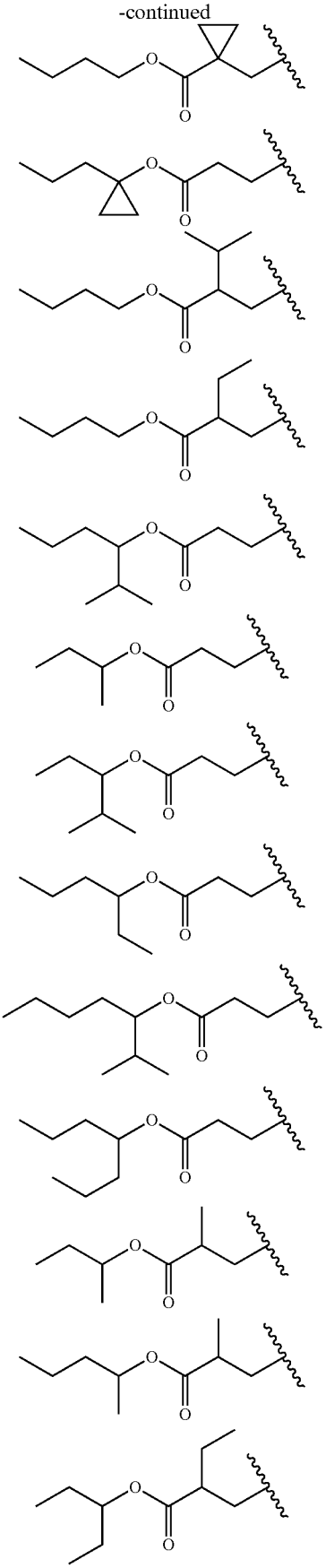
250
-continued
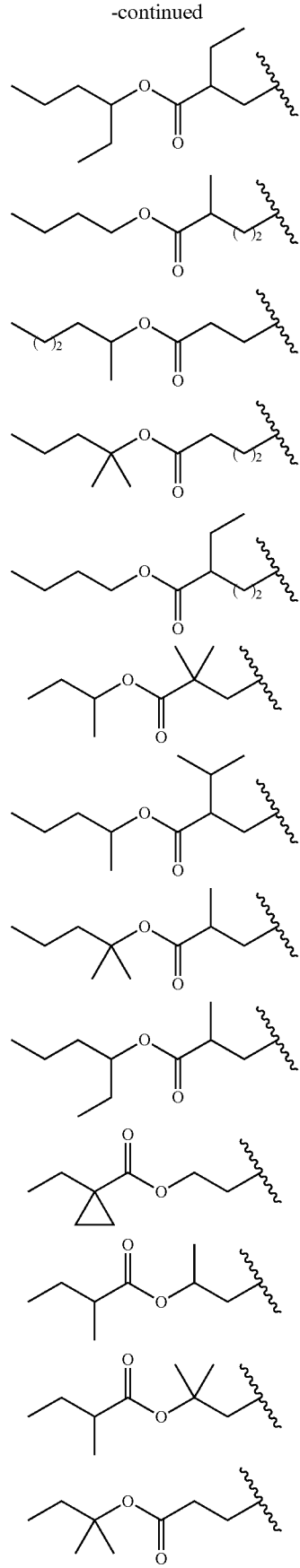

251
-continued
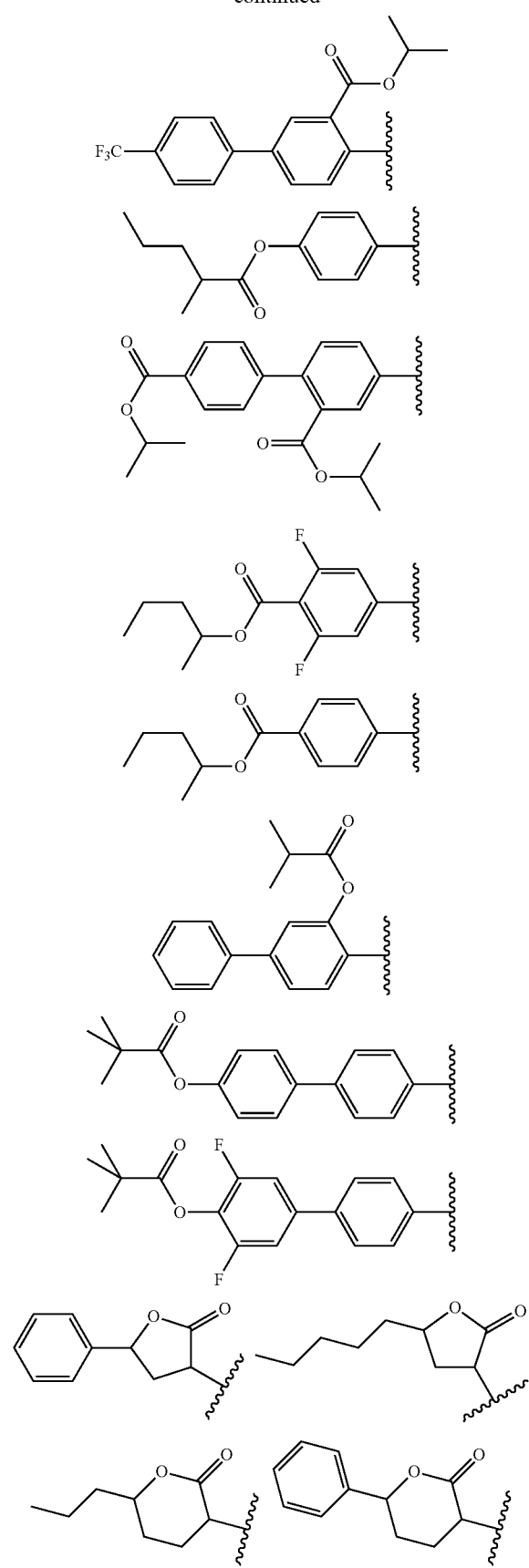
252
-continued
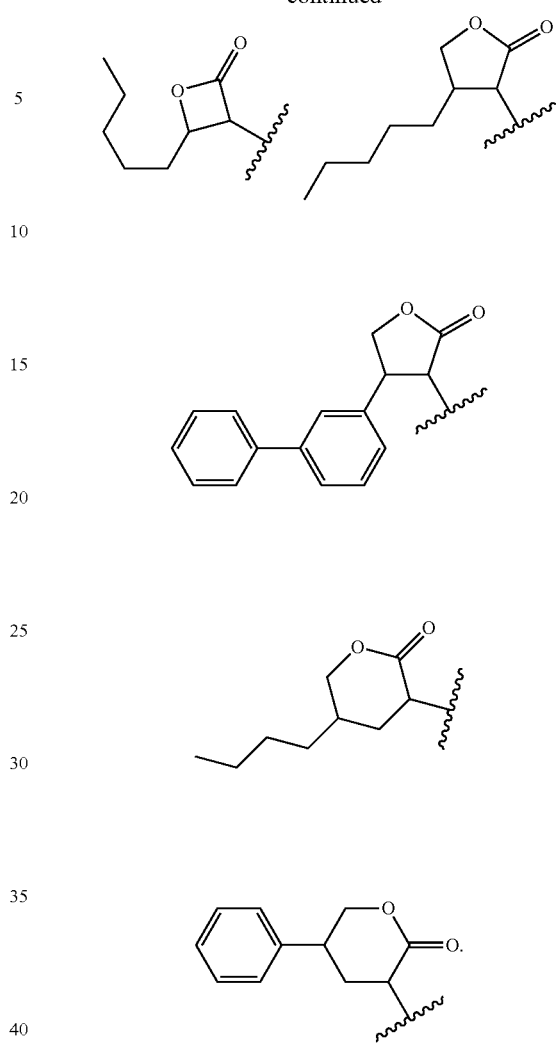
9. The compound of claim 1 according to formula IV
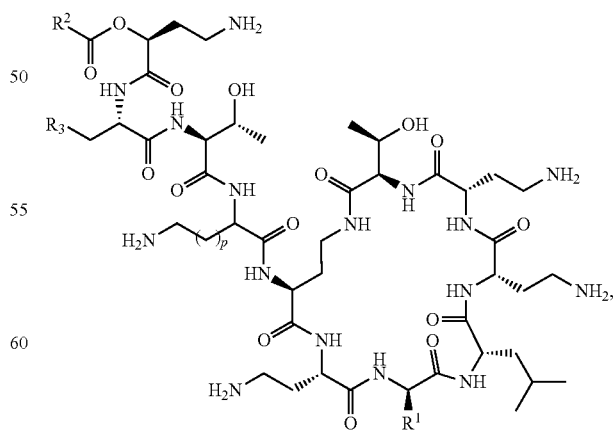
or a pharmaceutically acceptable salt, solvate, or hydrate thereof.

10. The compound of claim 1 according to formula IV

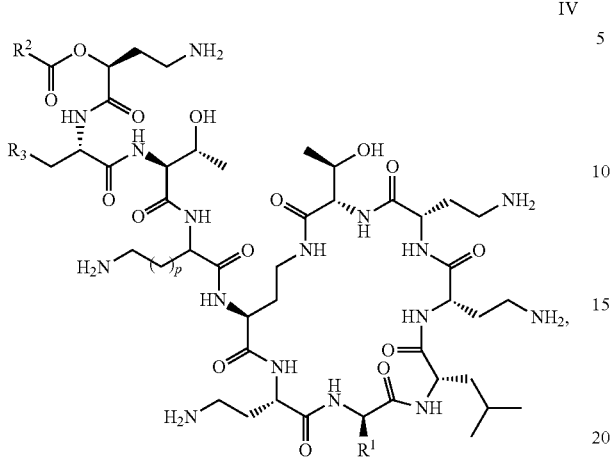

or a pharmaceutically acceptable salt, solvate, or hydrate thereof, wherein:

$R^1$ is $CH_2CH(CH_3)_2$ or $CH_2Ph$;

$R^2$ is aryl[C(=O)OR$^4$]$_r$, biaryl[C(=O)OR$^4$]$_r$, aryl[OC(=O)R$^4$]$_r$, biaryl[OC(=O)R$^4$]$_r$, aryl-OC(=O)NR$^4$R$^5$, biaryl-OC(=O)NR$^4$R$^5$, $(CR^4R^5)_m(CR^6R^7)_nC(=O)OR^8$, dihydrofuran-2(3H)-one-3-yl, aryl-dihydrofuran-2(3H)-one-3-yl, $C_{1-14}$alkyl-dihydrofuran-2(3H)-one-3-yl, tetrahydro-2H-pyran-2-one-3-yl, aryl-tetrahydro-2H-pyran-2-one-3-yl, or $C_{1-14}$alkyl-tetrahydro-2H-pyran-2-one-3-yl, or $(CR^4R^5)_m(CR^6R^7)_nOC(=O)R^8$;

$R^4$ through $R^7$ are independently H, halo, $NH_2$, $NH(C_{1-6}$alkyl), $NH(OC_{1-6}$alkyl), $C_{1-14}$alkyl, $C_{3-6}$cycloalkyl, aryl, arylalkyl, biaryl, biarylalkyl, or heteroarylalkyl; and $R^8$ is H, $NH(C_{1-6}$alkyl), $NH(OC_{1-6}$alkyl), $C_{1-14}$alkyl, $C_{3-6}$cycloalkyl, aryl, arylalkyl, biaryl, biarylalkyl, or heteroarylalkyl; or any two of $R^4$ through $R^8$, together with the atom(s) to which they are attached form a 4 to 7-member saturated or unsaturated heterocycle containing at least one O atom, or containing one O atom and an additional heteroatom independently selected from N and S, and where the remaining atoms are carbon; or any of i) $R^4$ and $R^5$, ii) $R^6$ and $R^7$, and iii) $R^4$ and $R^6$, together with the atom to which they are attached form a $C_{3-6}$cycloalkylene; or any two of $R^4$ through $R^8$ together with the atom(s) to which they are attached form a 5 to 7-member saturated or unsaturated heterocycle wherein the ring optionally comprises an additional heteroatom selected from N, O, and S, and wherein the remaining atoms are carbon; or $R^6$ and $R^8$ together with the atoms to which they are attached form a 4 to 6-member saturated heterocycle containing at least one O atom wherein the heterocycle optionally comprises an additional heteroatom selected from N, O, and S, and wherein the remaining atoms are carbon; and wherein r is 1 or 2;

wherein m, n, and p are independently selected from 0 to 2; and $R^3$ is $NH_2$, $CH_2NH_2$ or imidazolyl.

11. The compound of claim 1 wherein X is —NHC(=O)CH(CH$_2$CH$_2$NH$_2$)O— and $R^2$ is selected from structures below:

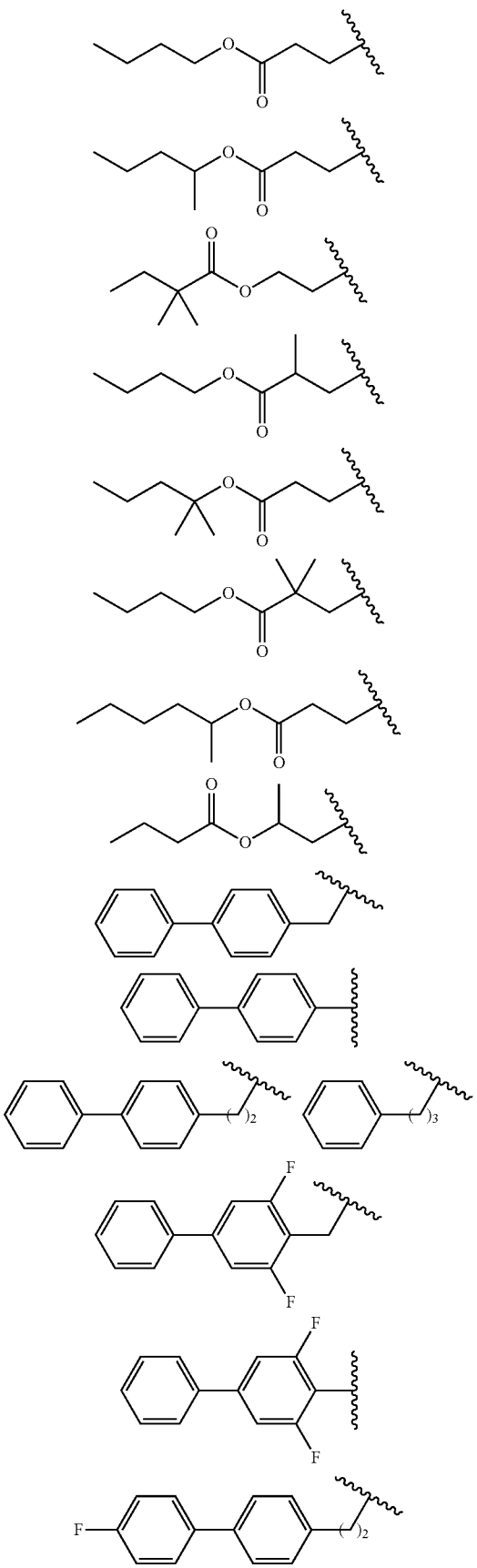

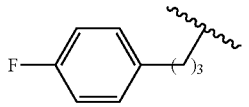
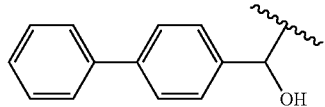
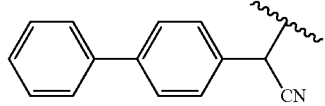
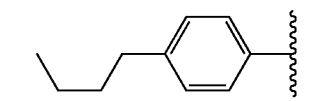
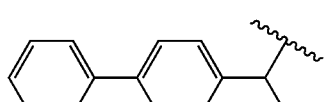
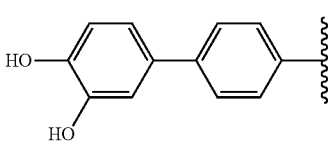
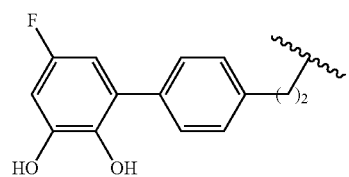
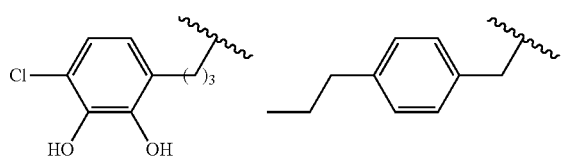
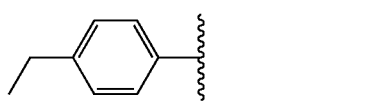
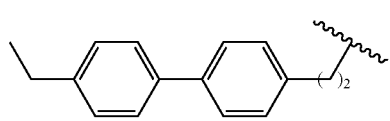
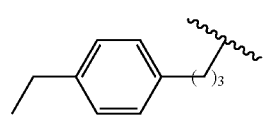
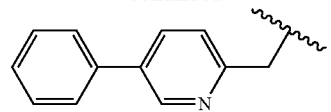
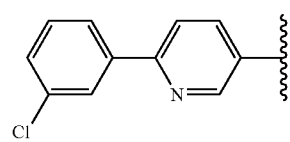
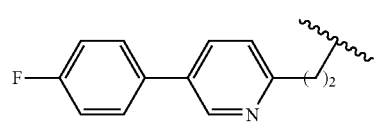
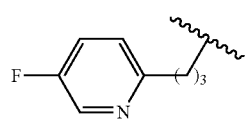
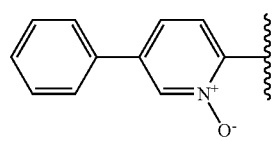
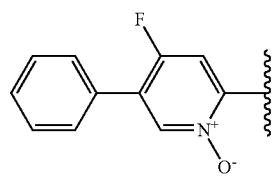
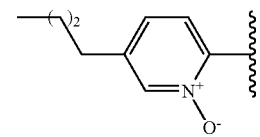
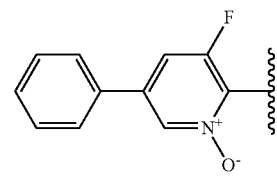
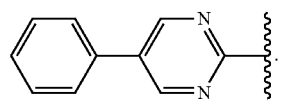

12. The compound of claim 1 according to formula V

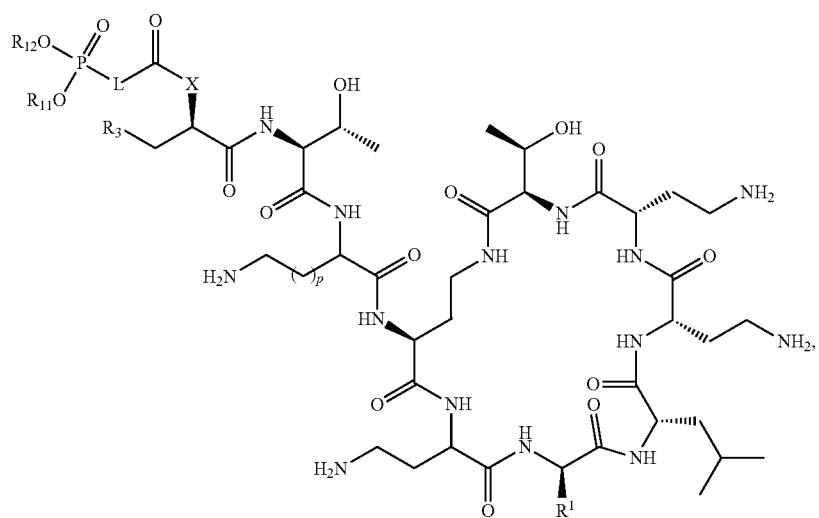

V or a pharmaceutically acceptable salt, solvate, or hydrate thereof.

13. The compound of claim 1 according to formula V

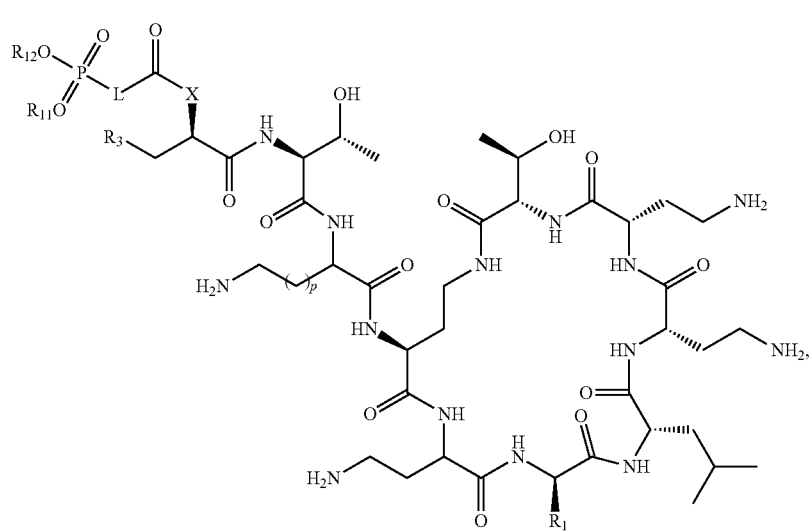

V or a pharmaceutically acceptable salt, solvate, or hydrate thereof, wherein:

$R^1$ is $CH_2CH(CH_3)_2$ or $CH_2Ph$;

X is NH, N($C_{1-6}$alkyl), or O, and $R^3$ is $NH_2$, $CH_2NH_2$, or imidazolyl; or X is N or N($C_{1-6}$alkyl) and $R^3$ is NH and $R^3$ and X taken together comprise the group $NHCH_2CH_2N$ or $N(C_{1-6}$alkyl)$CH_2CH_2N$;

L is selected from O, NH, N($C_{1-6}$alkyl), $C_{1-6}$alkylene, $(CR^4R^5)_m(CR^6R^7)_n(CR^9R^{10})_o$, $CR^4=CR^6-(CR^9R^{10})_o$, $(CR^4R^5)_m-CR^6=CR^{10}$, $O(CR^4R^5)_m(CR^6R^7)_n(CR^9R^{10})_o$, $NH(CR^4R^5)_m(CR^6R^7)_n(CR^9R^{10})_o$, $N(C_{1-6}$alkyl$)(CR^4R^5)_m(CR^6R^7)_n(CR^9R^{10})_o$, $(CR^4R^5)_m(CR^6R^7)_n(CR^9R^{10})_oO$, $(CR^4R^5)_m(CR^6R^7)_n(CR^9R^{10})_oNH$, and $(CR^4R^5)_m(CR^6R^7)_n(CR^9R^{10})_oN(C_{1-6}$alkyl);

$R^4$ through $R^7$, $R^9$, and $R^{10}$ are independently H, $NH_2$, halo, $NH(C_{1-6}$alkyl), $NH(OC_{1-6}$alkyl), $C_{1-14}$alkyl, $C_{3-6}$cycloalkyl, aryl, arylalkyl, biaryl, biarylalkyl, or heteroarylalkyl; or any two of $R^4$ through $R^7$, $R^9$, and $R^{10}$, together with the atom(s) to which they are attached form a 4 to 7-member saturated or unsaturated heterocycle containing at least one O atom, or containing one O atom and additional heteroatom independently selected from N and S, and wherein the remaining atoms are carbon; or any two of $R^4$ through $R^7$, $R^9$ and $R^{10}$, together with the carbon atom(s) to which they are attached form a 4 to 7-member saturated or unsaturated $C_{3-6}$cycloalkylene; or any two of $R^4$ through $R^7$, $R^9$, and $R^{10}$ together with the atom(s) to which they are attached form a 5 to 7-member saturated or unsaturated heterocycle wherein the ring optionally comprises an additional heteroatom selected from N, O, and S and wherein the remaining atoms are carbon; or $R^6$ and $R^{10}$ together with the atoms to which they are attached form a 4 to 6-member saturated heterocycle containing at least one O atom wherein the heterocycle optionally comprises an additional heteroatom selected from N, O, and S, and wherein the remaining atoms are carbon; and $R^{11}$ and $R^{12}$ are independently H, $N(C_{1-6}alkyl)$, $C_{1-14}alkyl$, $C_{3-6}cycloalkyl$, aryl, arylalkyl, biaryl, biarylalkyl, or heteroarylalkyl; or $R^{11}$ and $R^{12}$ together with the two oxygen atoms to which they are attached form a 5 to 7-member saturated heterocycle wherein the 2, 3, or 4 additional atoms are carbon optionally substituted with $C_{1-6}alkyl$; or either or both of i) $R^4$ and $R^{11}$ and ii) $R^6$ and $R^{12}$ together with the atoms to which they are attached form a 5 to 7-member saturated heterocycle containing one O atom and one P atom and where the remaining atoms are carbon;

wherein m, n, o, and p are independently selected from 0, 1, and 2 and wherein when L is $(CR^4R^5)_m(CR^6R^7)_n(CR^9R^{10})_o$, then m+n+o≥1; and $R^3$ is $NH_2$, $CH_2NH_2$ or imidazolyl.

14. The compound of claim 12 wherein L is selected from $CR^4=CR^6-(CR^9R^{10})_o$, $(CR^4R^5)_m-CR^6=CR^{10}$, $CF_2$, $(CR^4R^5)_m$, $O(CR^4R^5)_m$, $NH(CR^4R^5)_m$, $N(C_{1-6}alkyl)(CR^4R^5)_m$, $(CR^4R^5)_mO$, $(CR^4R^5)_mNH$, $(CR^4R^5)_mN(C_{1-6}alkyl)$, $(CR^4R^5)_mCF_2$, and $CF_2(CR^6R^7)_n$, and wherein m and n in L are independently 1 or 2.

15. The compound of claim 1 wherein $(R^{12}O)(R^{11}O)P(=O)-L-C(=O)-$ is selected from structures below:

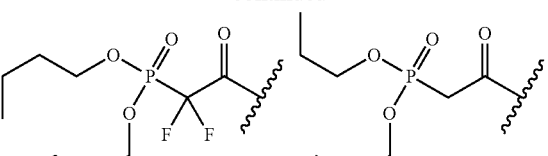

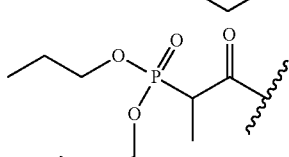

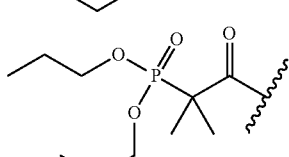

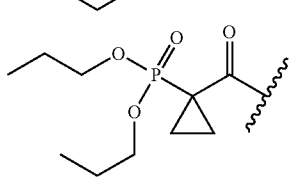

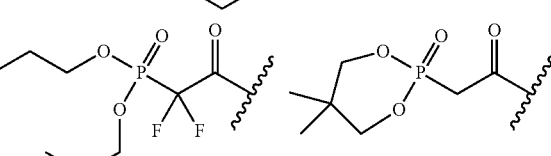

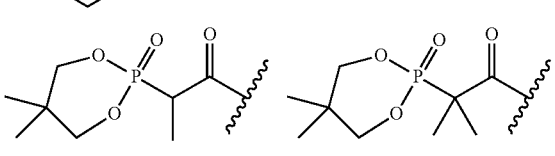

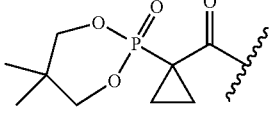

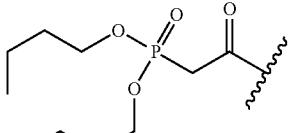

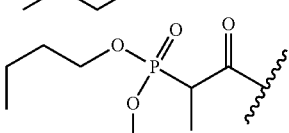

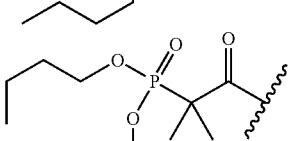

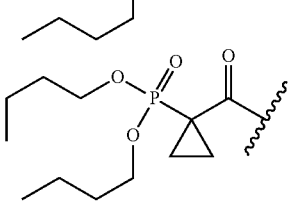

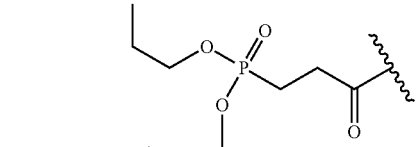

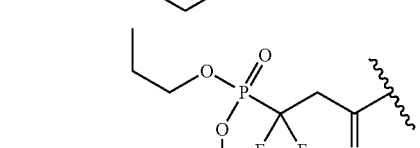

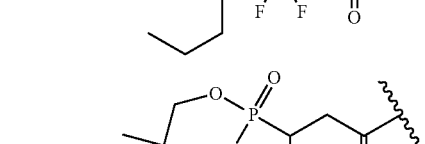

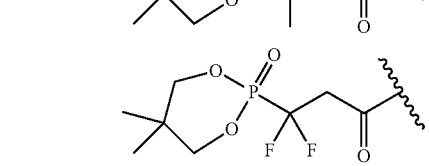

-continued

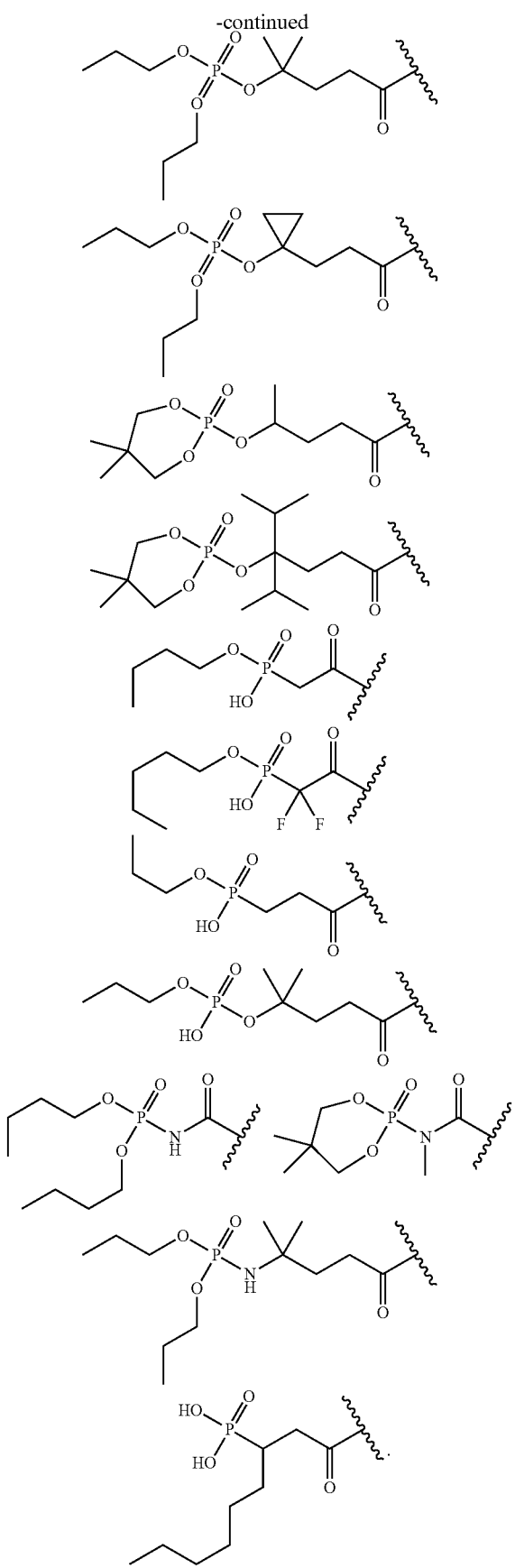

16. The Compound of claim 1 where each of [a], [b], and [c] is NH.

17. The Compound of claim 1 where $R^3$ is $CH_2NH_2$, and wherein p is 1.

18. A compound of claim 1, wherein X is NH, $R^2$ is $(CR^4R^5)_m(CR^6R^7)_nC(=O)OR^8$ or $(CR^4R^5)_m(CR^6R^7)_nOC(=O)R^8$, and each of [a], [b], and [c] is NH, with a half-life in mammalian blood from about 1 h and less than about 36 h.

19. The compound of claim 18, with a half-life in mammalian blood of at least about 1 h but less than or equal to about 12 h.

20. A compound of claim 1, wherein X is NH, $R^2$ is $(CR^4R^5)_m(CR^6R^7)_nC(=O)OR^8$ or $(CR^4R^5)_m(CR^6R^7)_nOC(=O)R^8$, and each of [a], [b], and [c] is NH, possessing at least 3-fold higher efficacy than polymyxin B in eradicating or preventing the infection due to the growth of the pathogen *Pseudomonas aeruginosa* at identical drug dosing, as determined by the bacterial colony-forming units count, or by the number of surviving mammals.

21. The compound of claim 20, possessing at least 7-fold higher efficacy than polymyxin B.

22. The compound of claim 20, wherein the *Pseudomonas aeruginosa* infection is a lung infection or pneumonia.

23. A pharmaceutical composition comprising a therapeutically effective amount of a compound of claim 1 and a pharmaceutically acceptable carrier.

24. A method for the treatment of a gram-negative bacterial infection in a mammal comprising administering to the mammal a therapeutically effective amount of the pharmaceutical composition of claim 23.

25. The method according to claim 24 wherein the gram-negative bacterial infection is caused by microorganisms selected from *Pseudomonas aeruginosa, Acinetobacter baumannii, Escherichia coli,* or *Klebsiela pneumoniae*.

26. The method according to claim 24 wherein the treatment of the gram-negative bacterial infection has duration of 14 days or longer, and without manifesting of apparent nephrotoxicity in the mammal under the therapy.

27. The compound of claim 1 according to formula II:

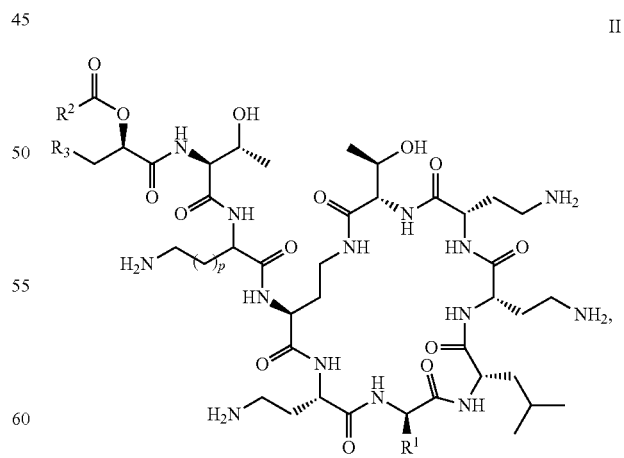

II or a pharmaceutically acceptable salt, solvate, or hydrate thereof;
wherein $R^3$ is $CH_2NH_2$; p is 0 or 1; and $R^2$ is selected from structures below:

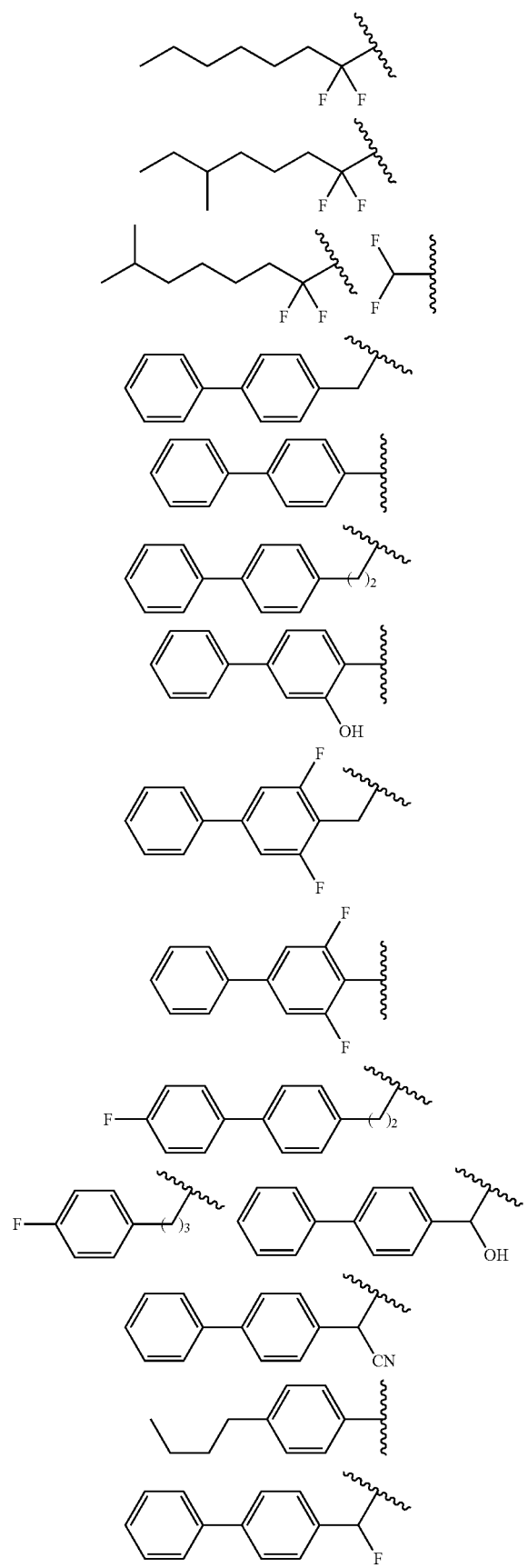
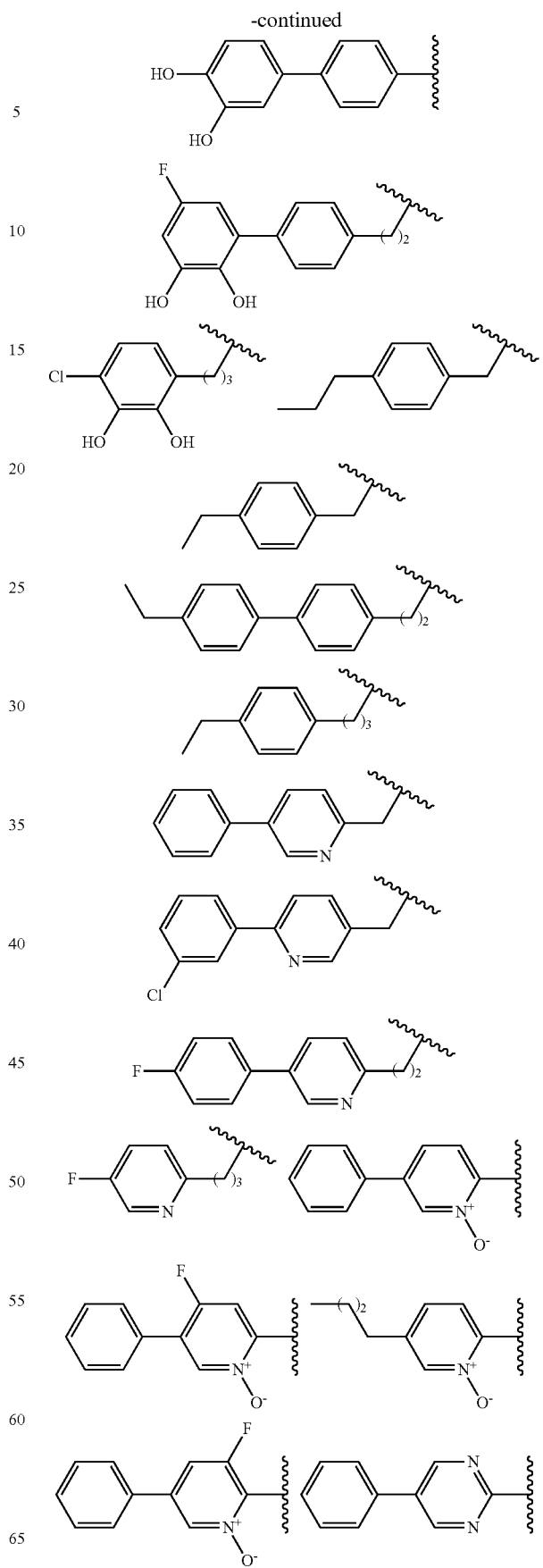

-continued
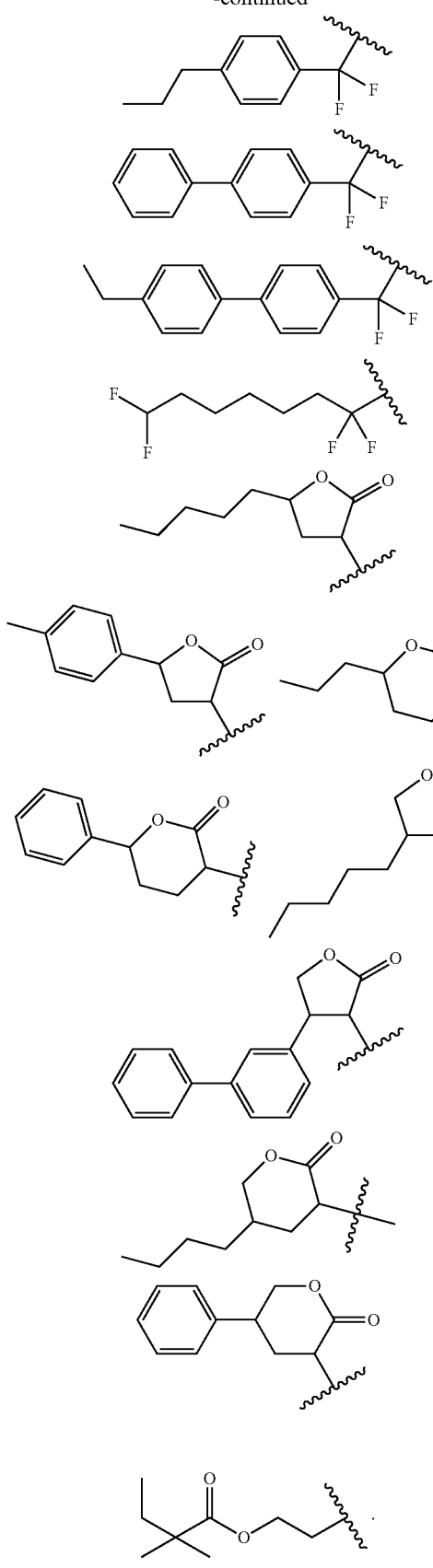
28. The compound of claim 1 according to formula III
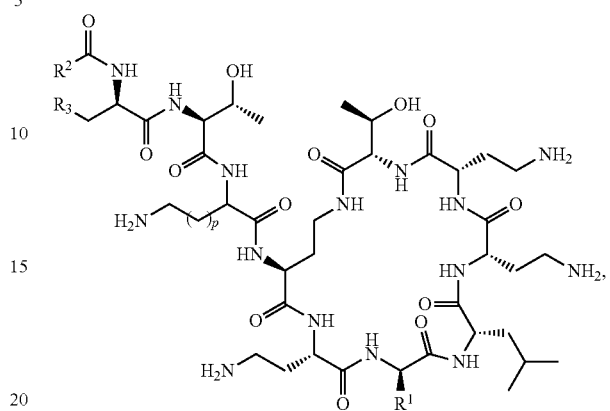
or a pharmaceutically acceptable salt, solvate, or hydrate thereof;
wherein $R^3$ is $CH_2NH_2$, $NH_2$, or imidazolyl; p is 0 or 1; and $R^2$ is selected from structures below:
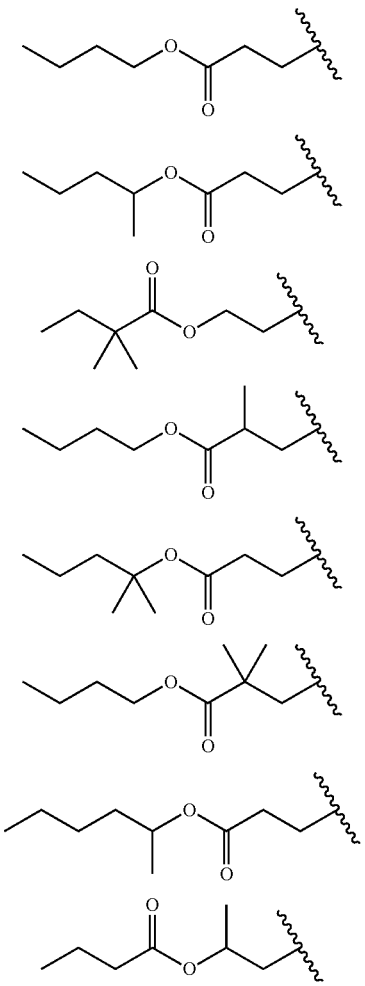

267
-continued
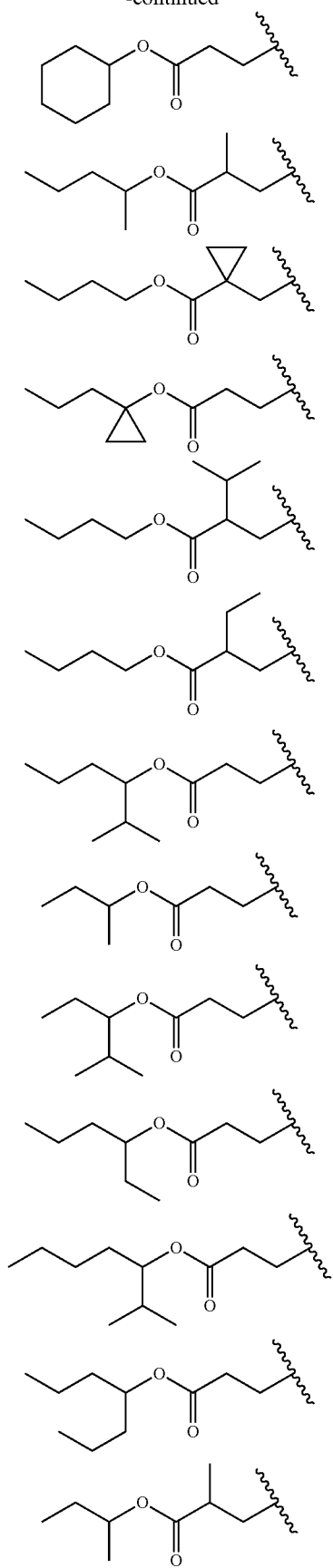
268
-continued
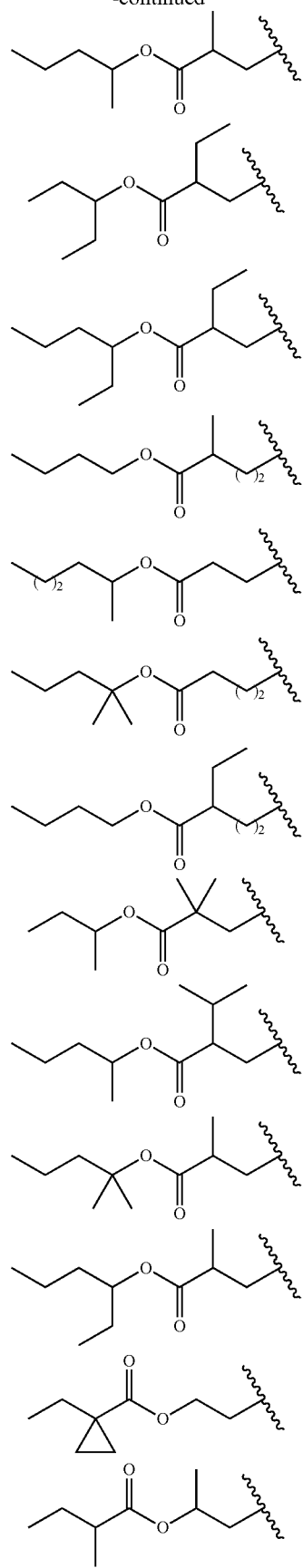

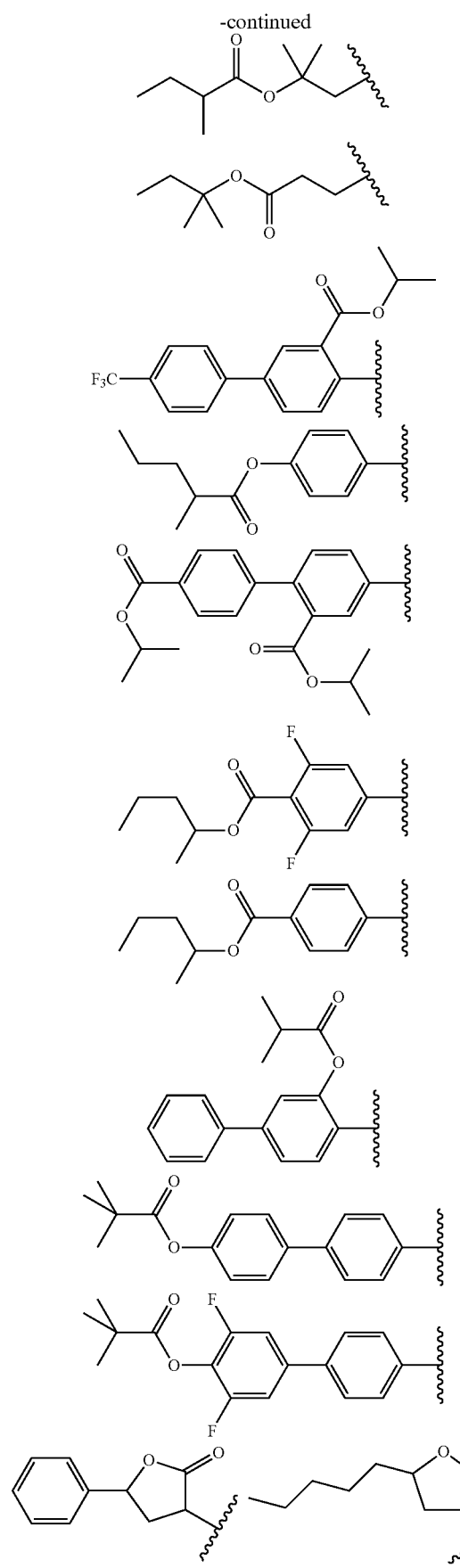
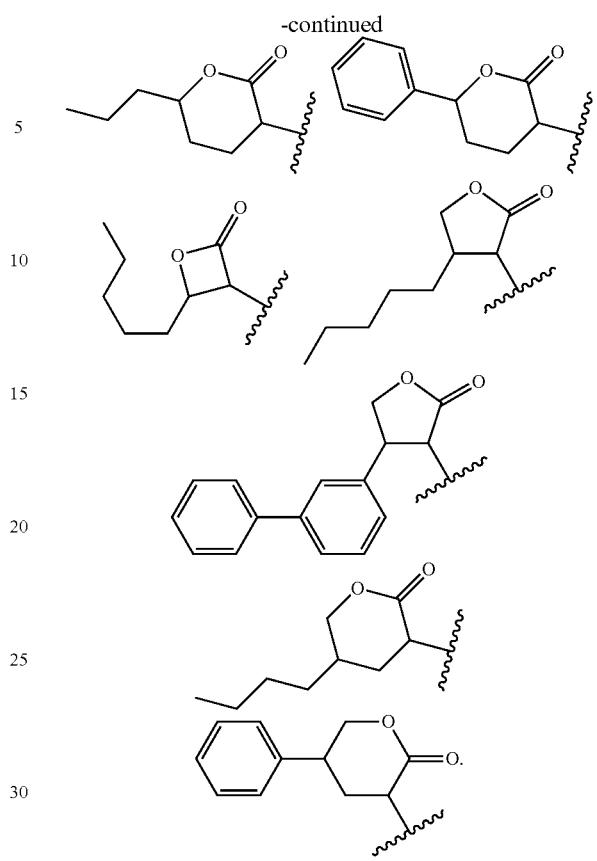
29. The compound of claim 1 according to formula IV:
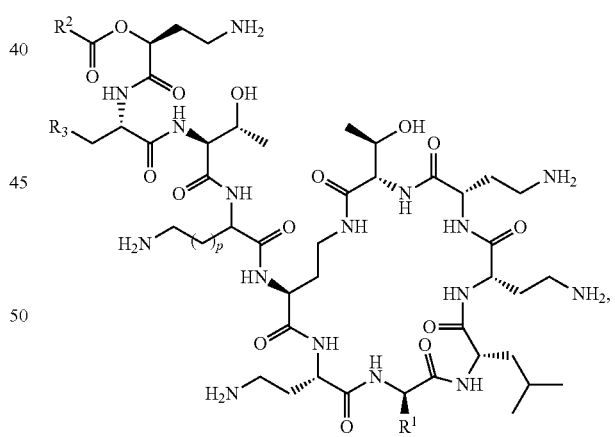
or a pharmaceutically acceptable salt, solvate, or hydrate thereof;
wherein $R^3$ is $CH_2NH_2$; p is 0 or 1; and $R^2$ is selected from structures below:
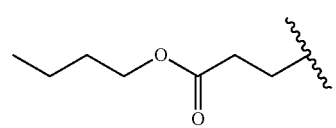

271
-continued
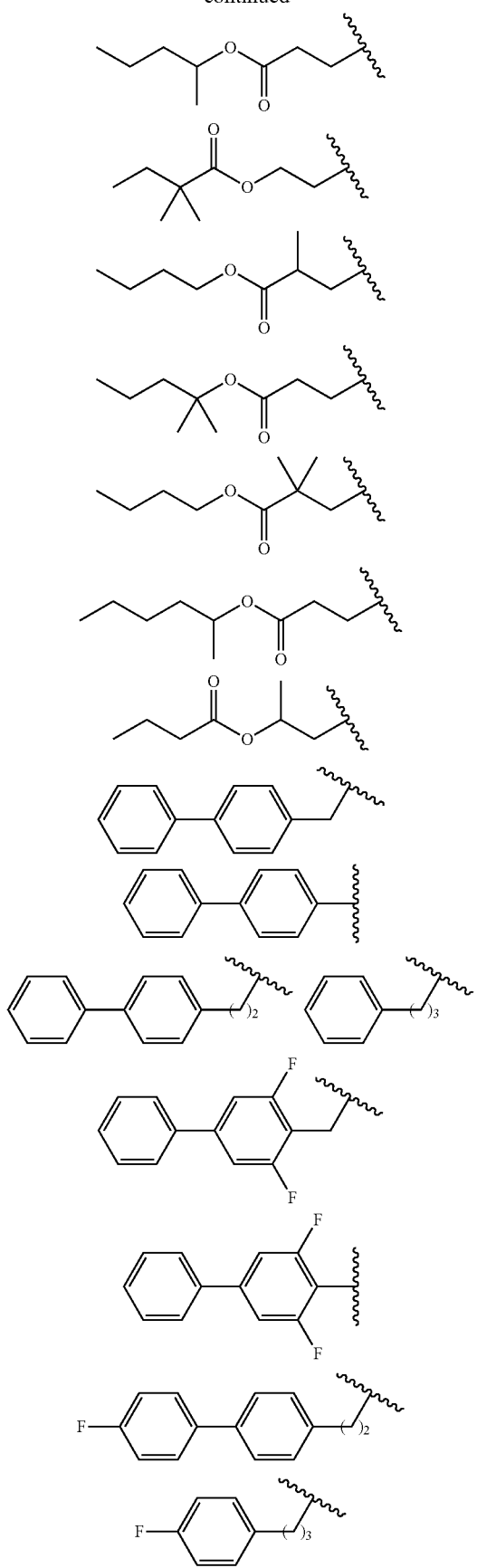
272
-continued
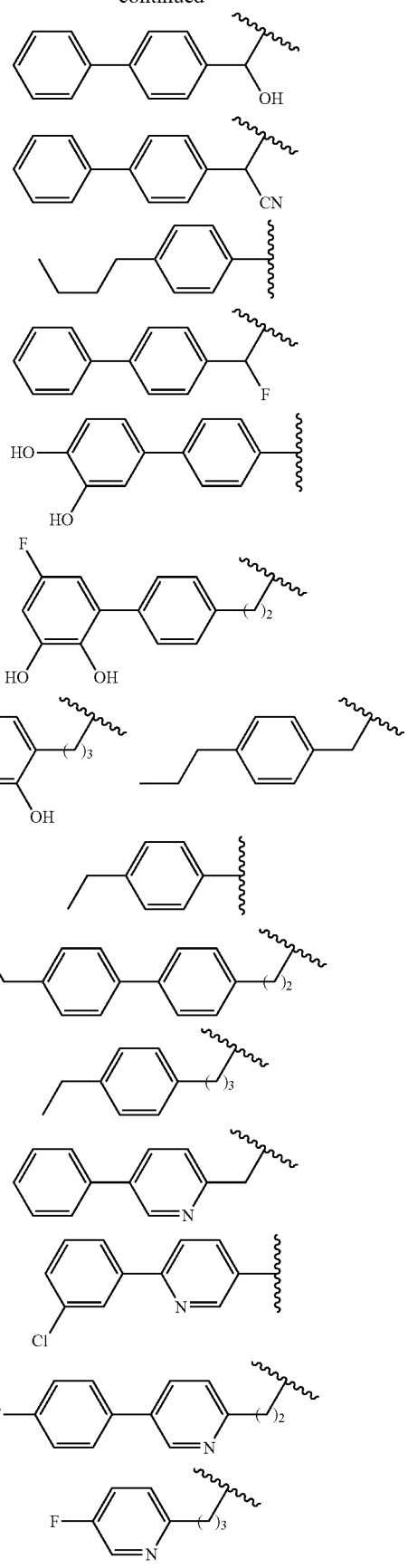

-continued
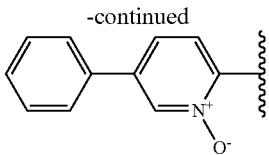
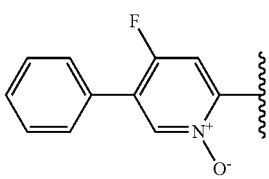
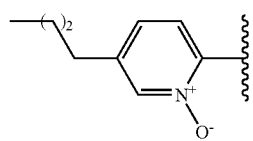
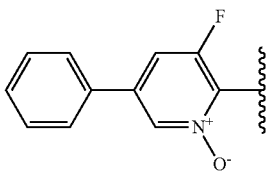
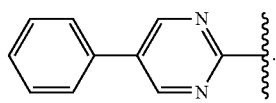
or a pharmaceutically acceptable salt, solvate, or hydrate thereof;
wherein X is NH; $R^3$ is $CH_2NH_2$, $NH_2$, or imidazolyl; p is 0 or 1; and $(R^{12}O)(R^{11}O)P(=O)$-L-C(=O)— is selected from structures below:
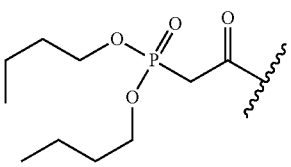
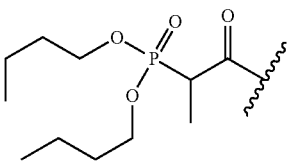
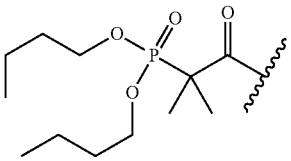
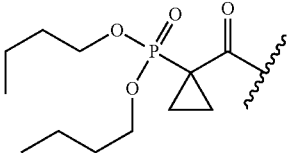
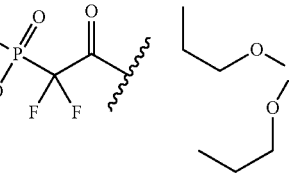 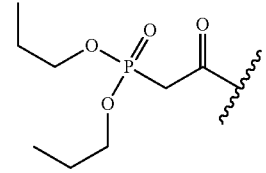
30. The compound of claim 1 according to formula V:
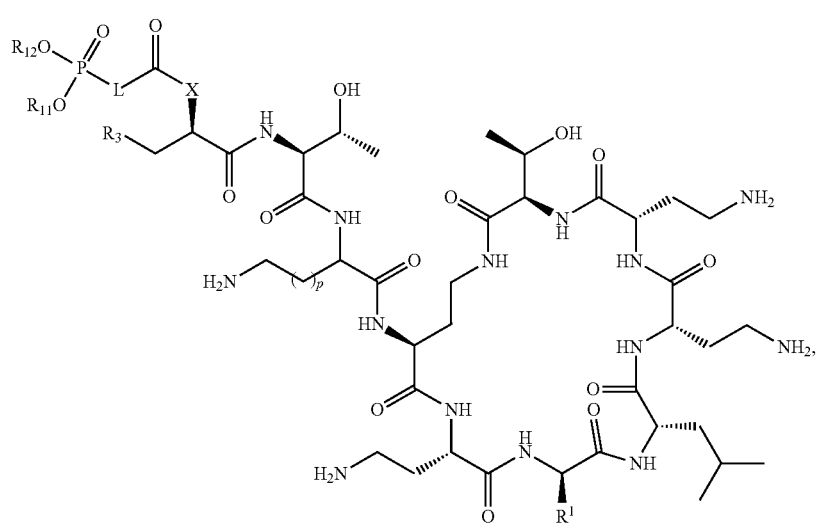

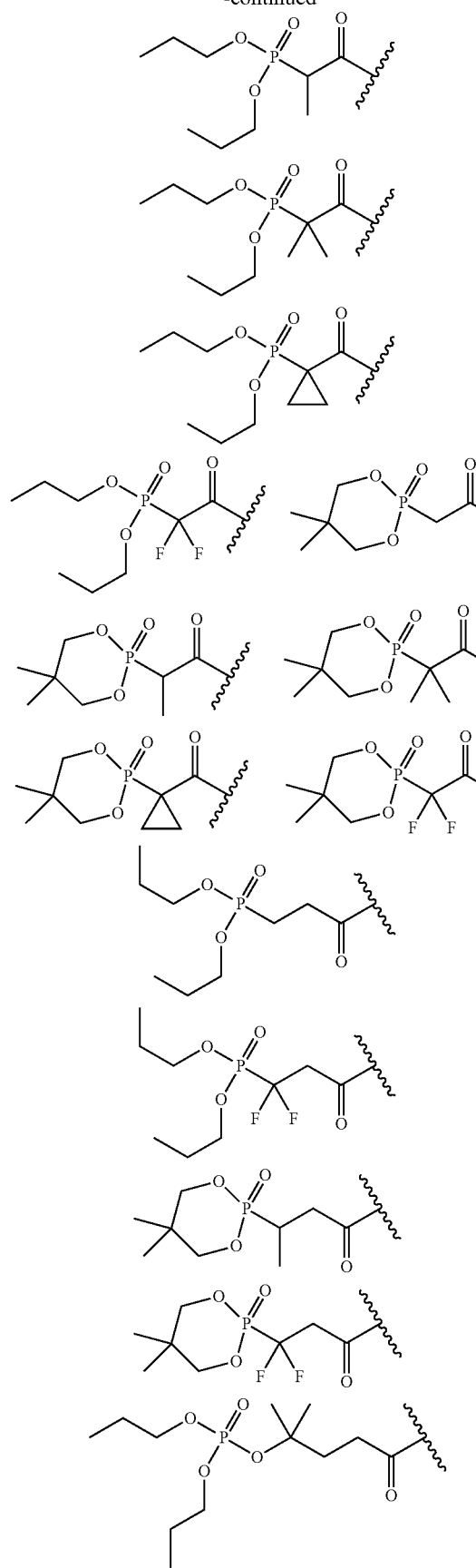
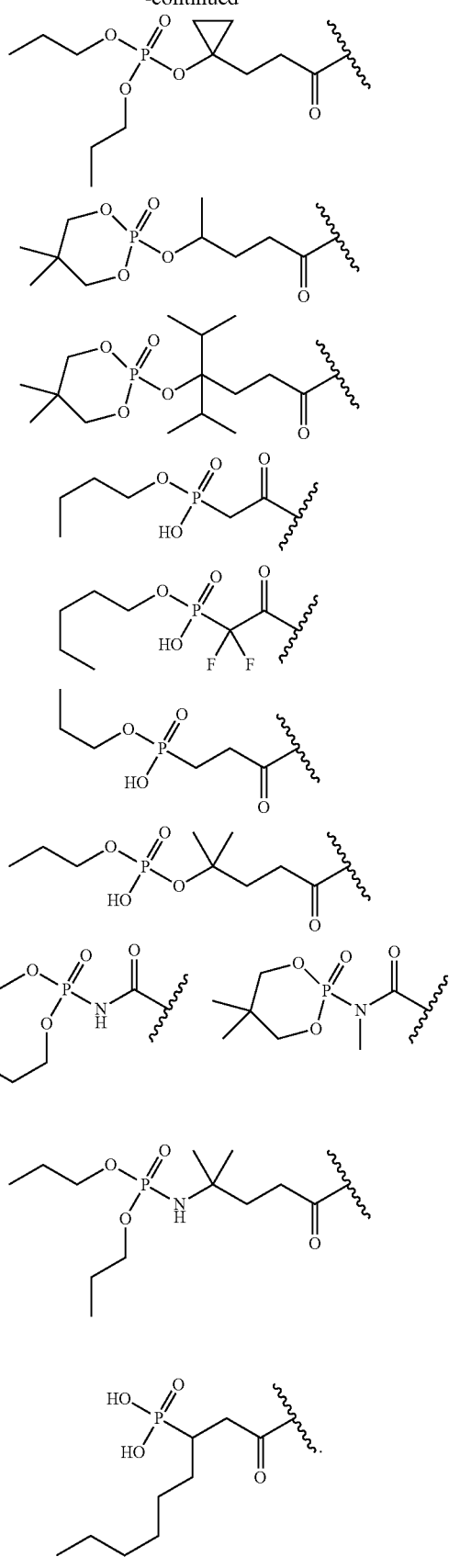

31. The compound of claim 1 selected from
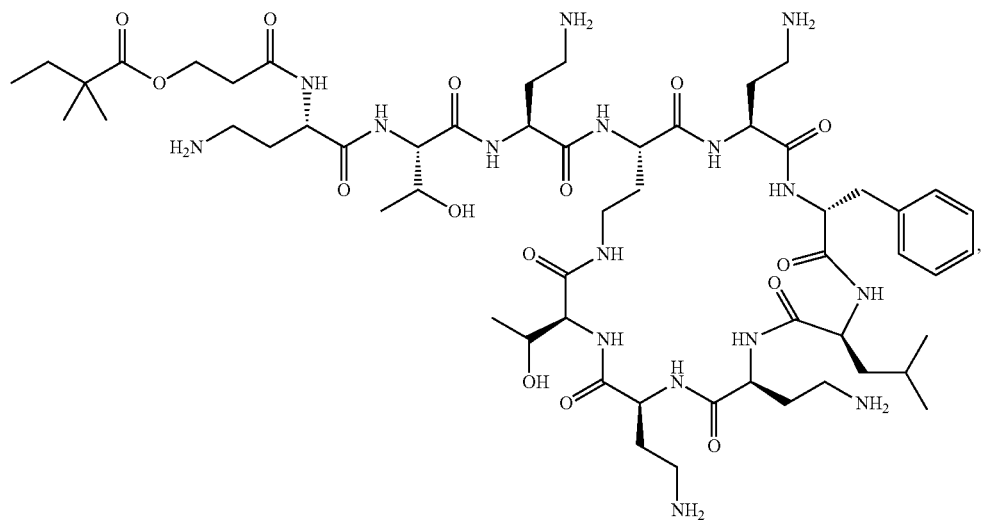
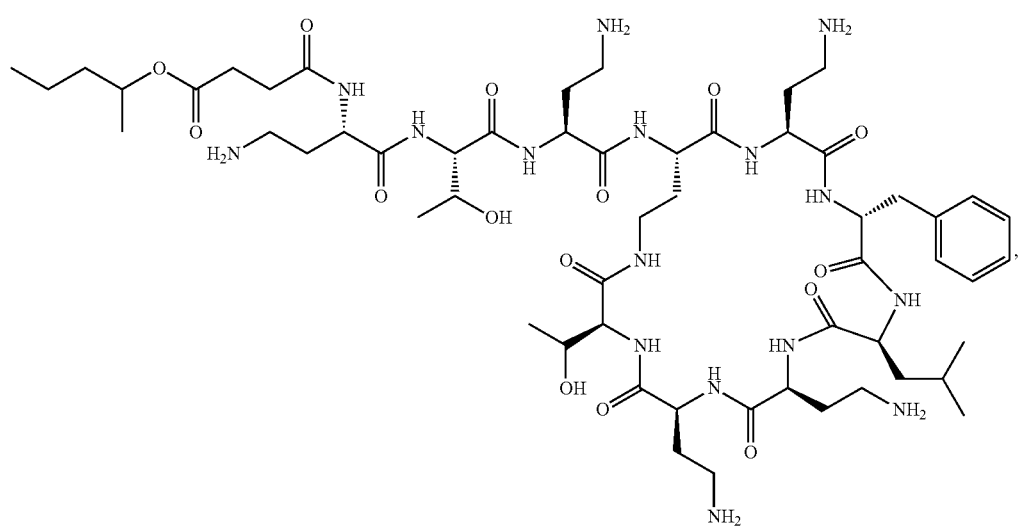
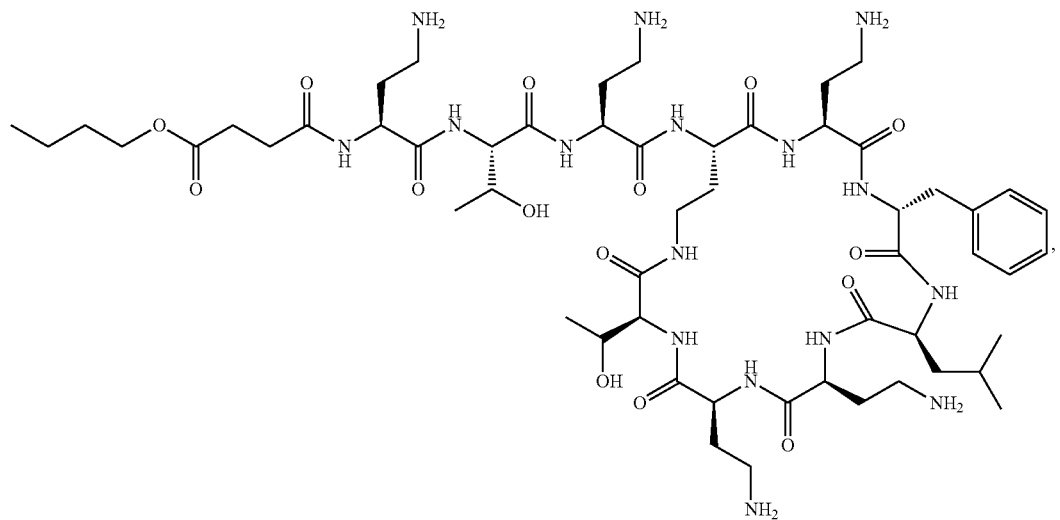

-continued
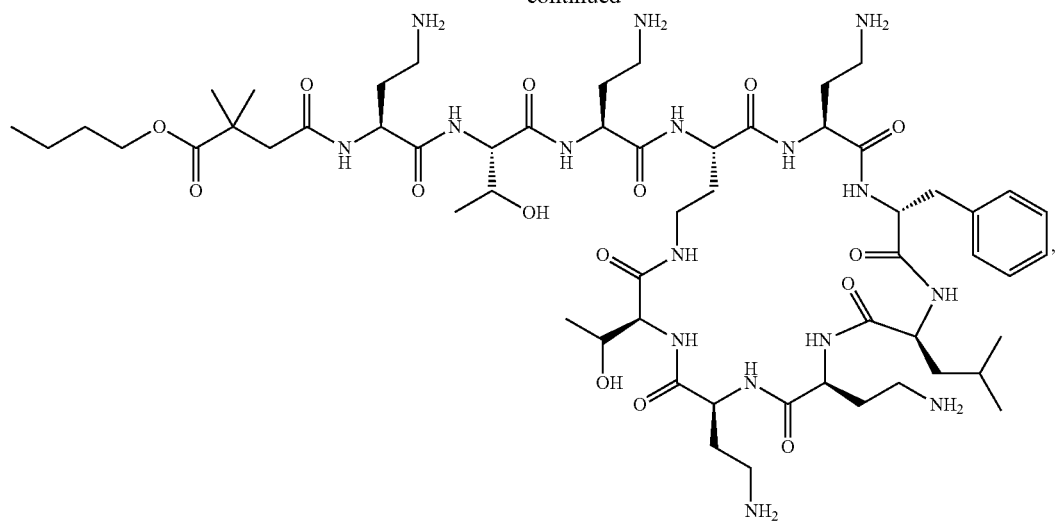
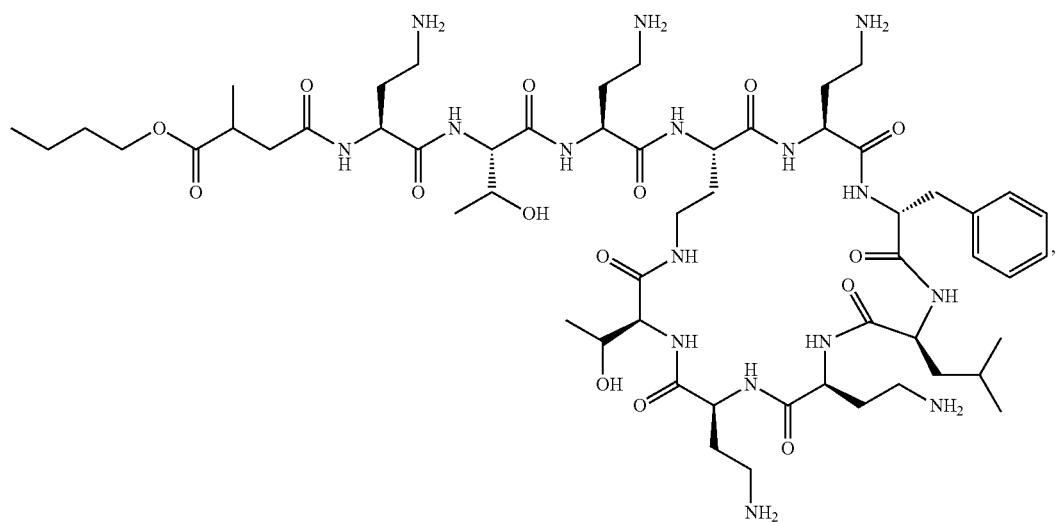
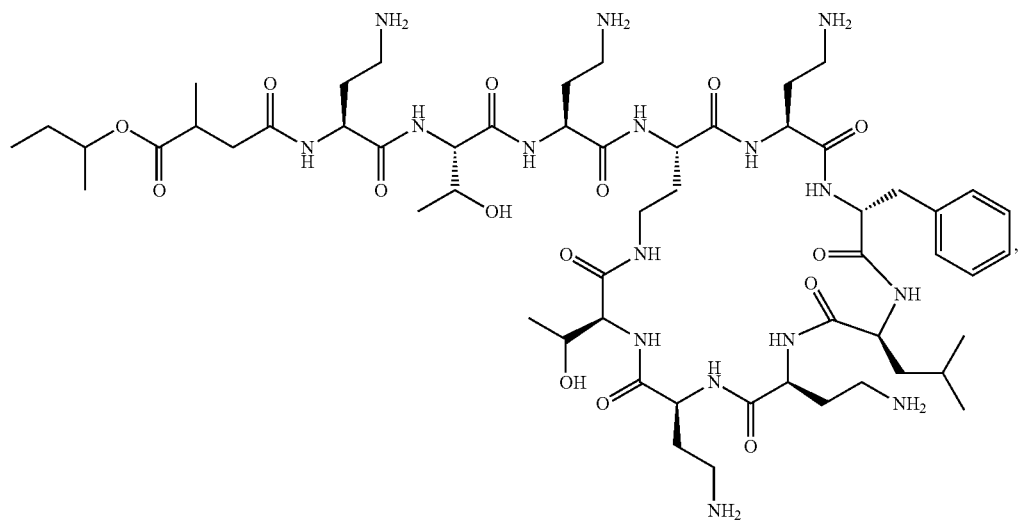

-continued
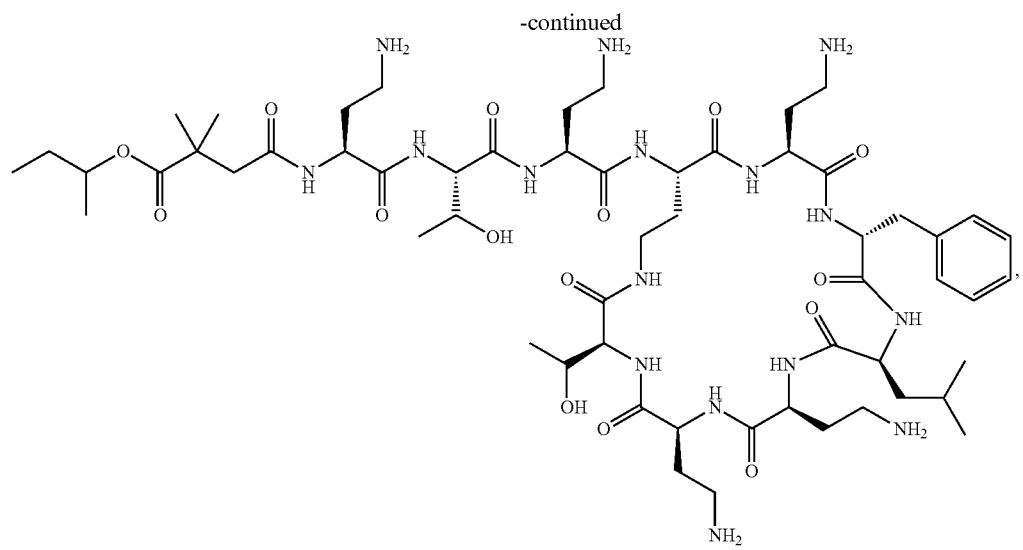
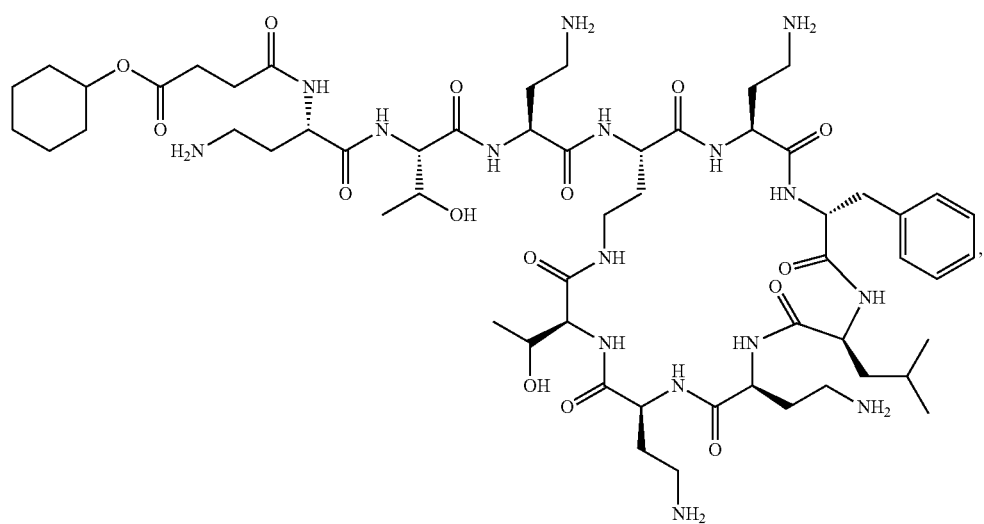
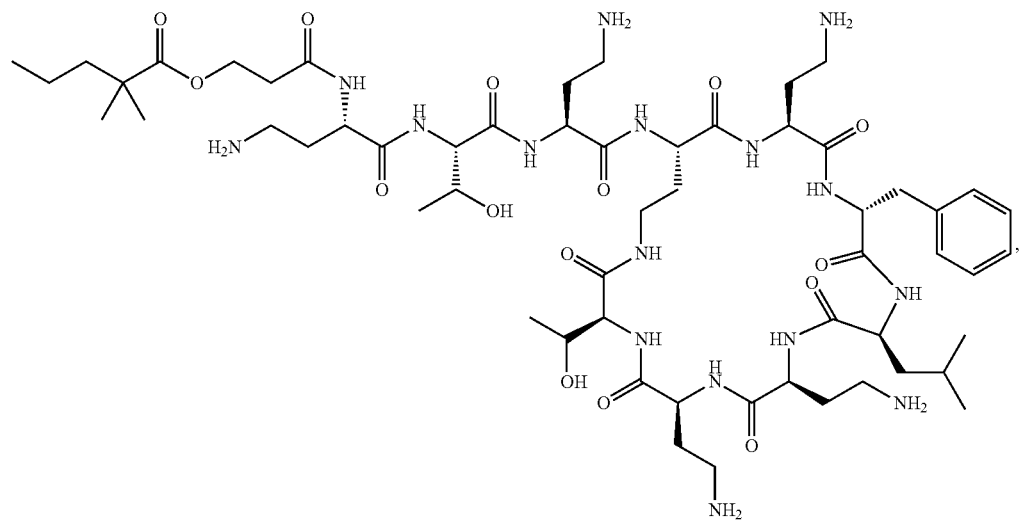

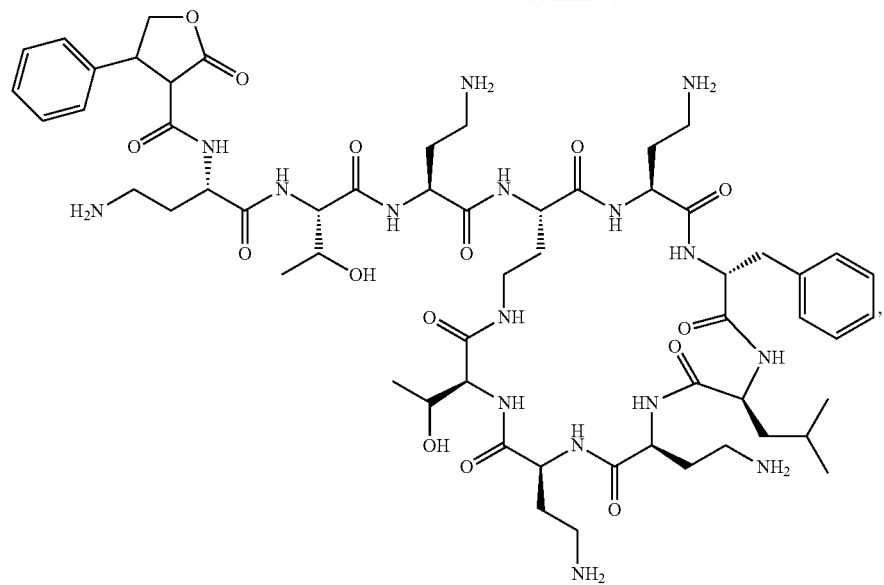
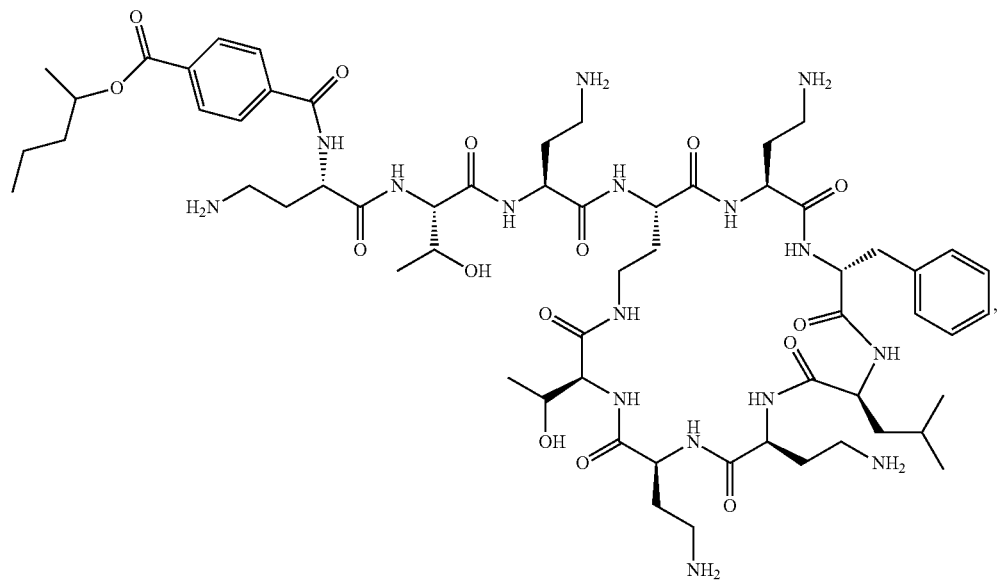
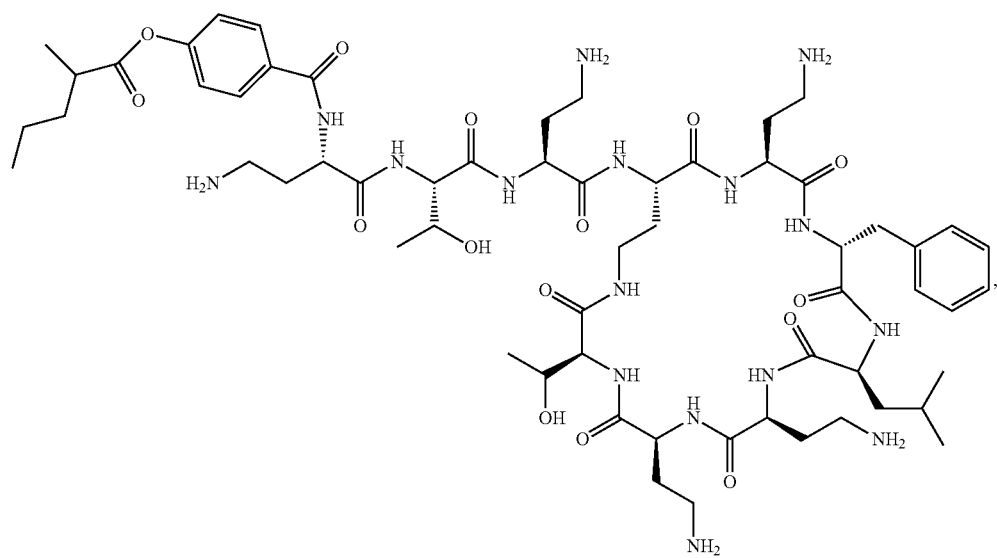

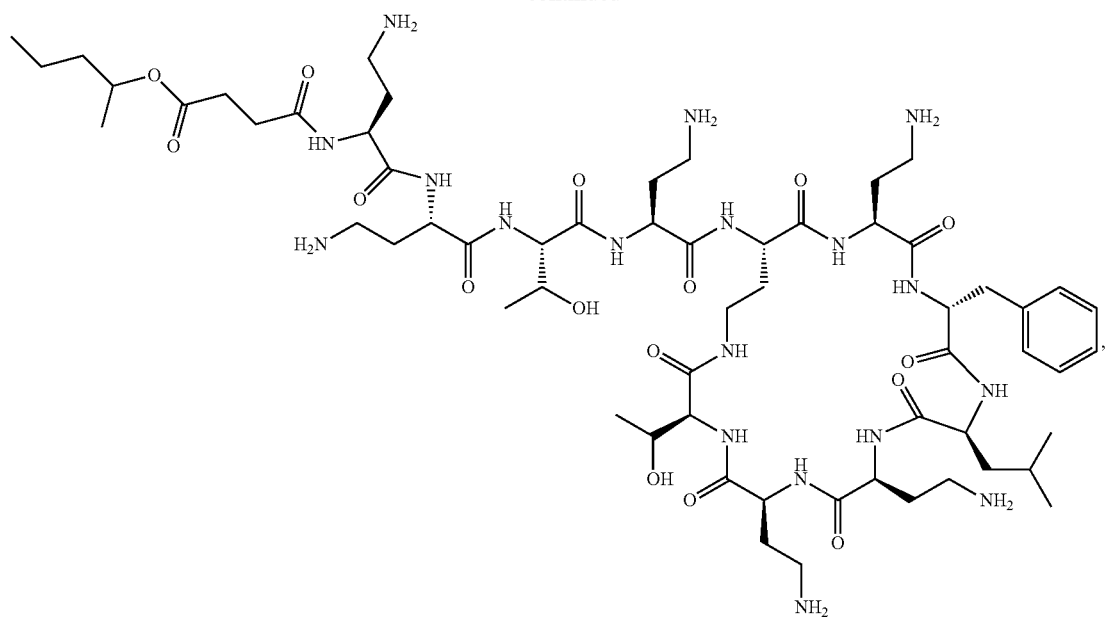
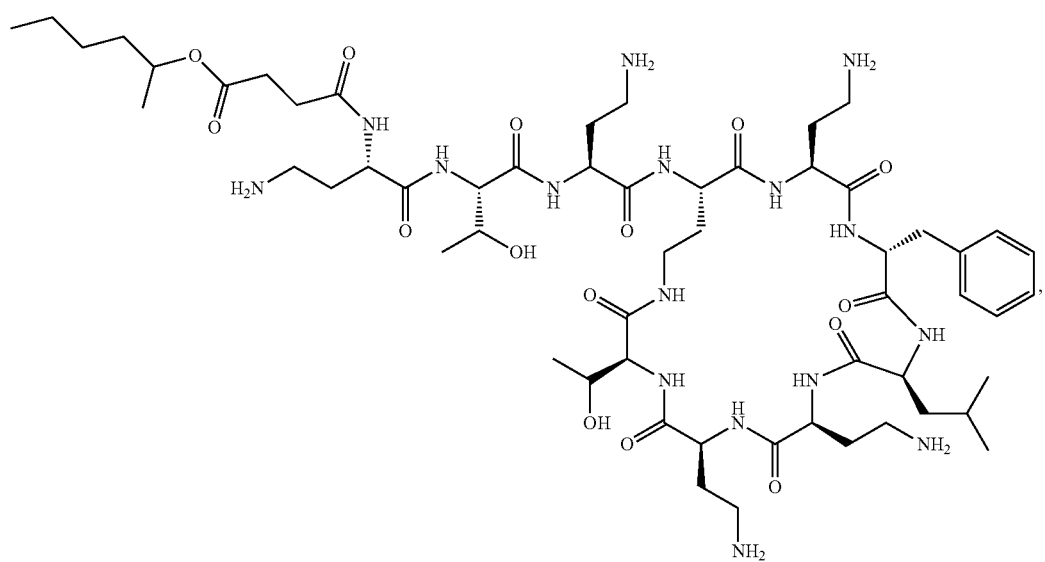

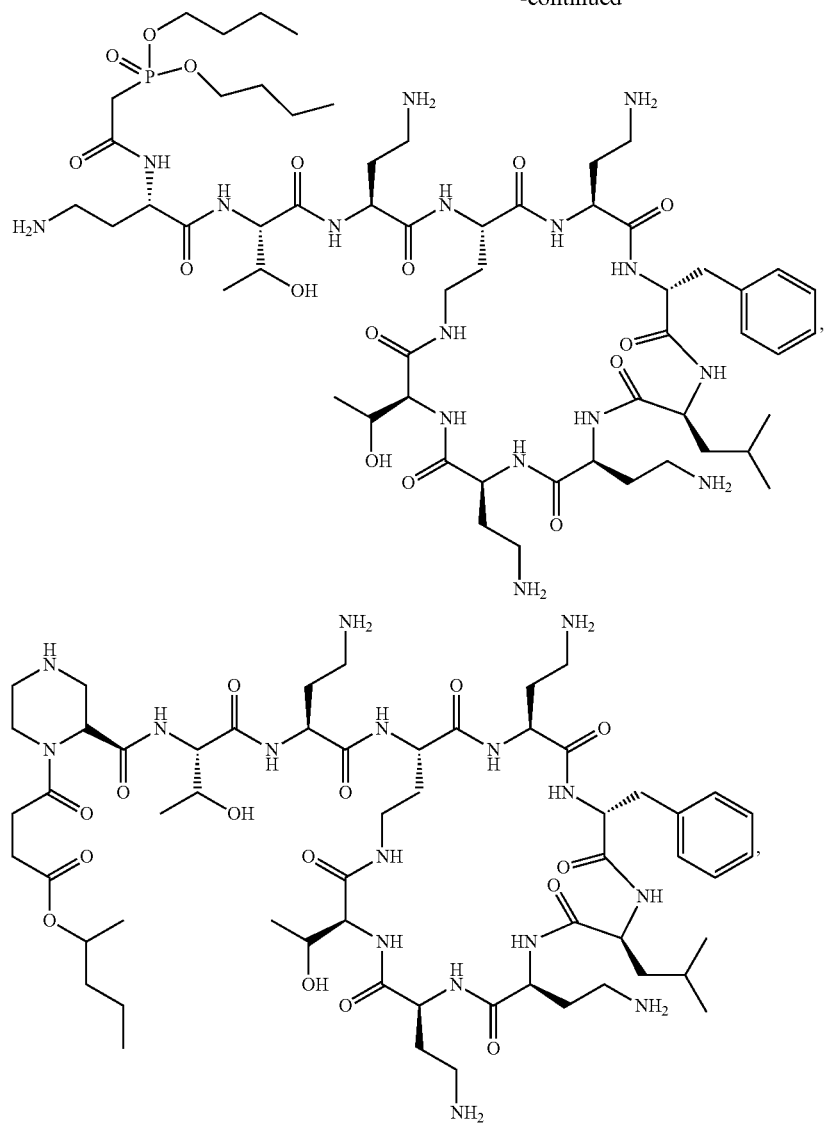
,
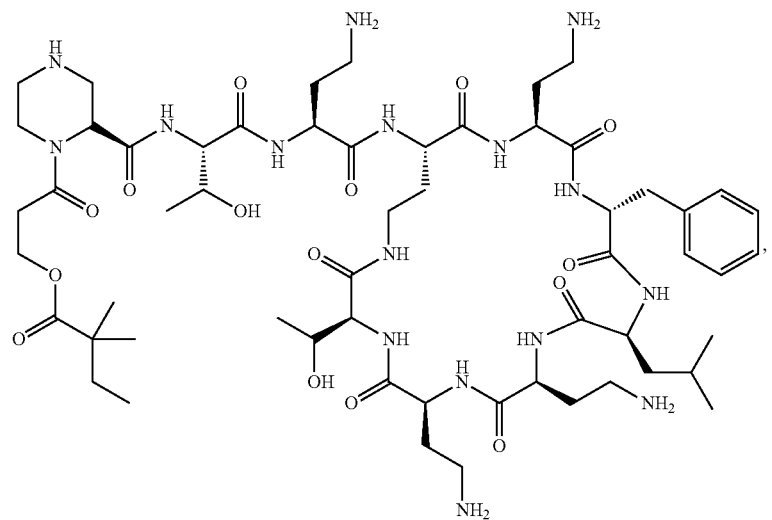
,

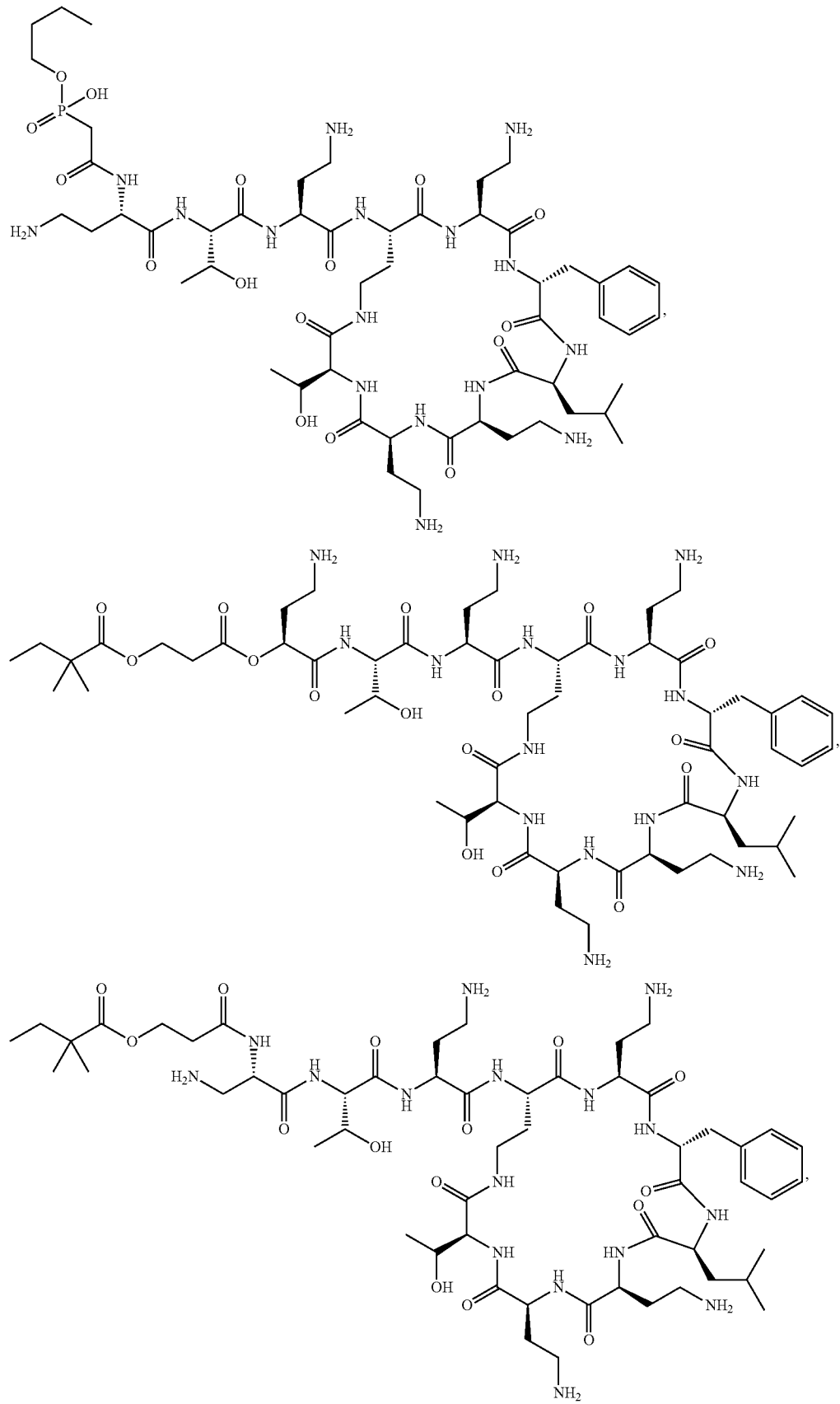

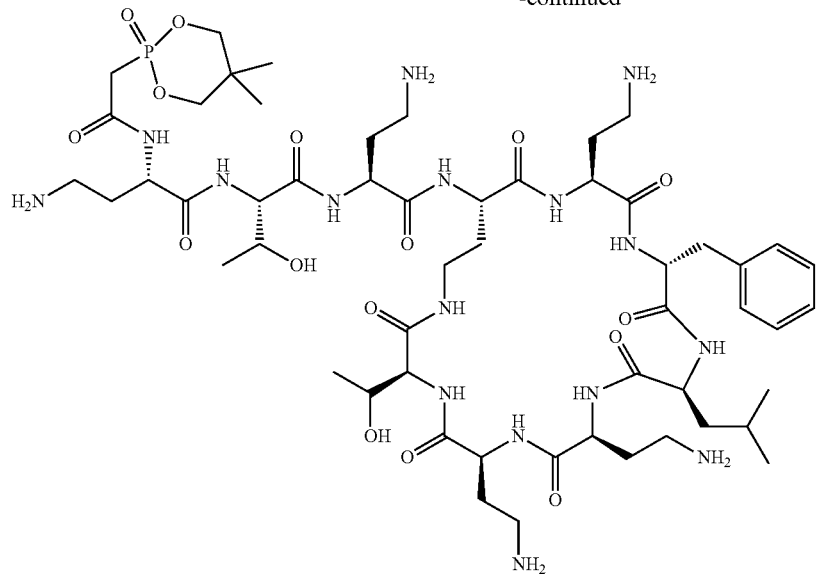
, and
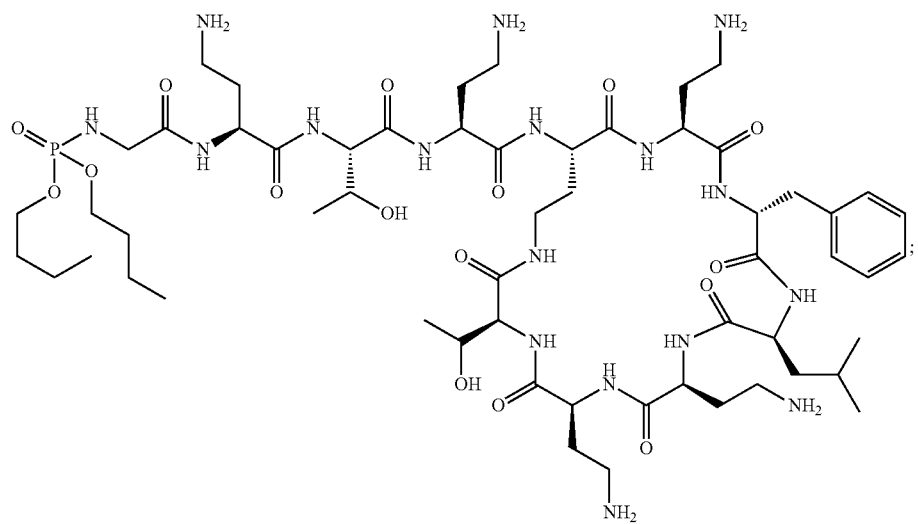 [SMILES: CCCCOP(=O)(NCC(=O)N[C@@H](CCN)C(=O)N[C@H](C(=O)N[C@@H](CCN)C(=O)N[C@H]1CCNC(=O)[C@H](C(C)O)NC(=O)[C@H](CCN)NC(=O)[C@H](CCN)NC(=O)[C@H](CC(C)C)NC(=O)[C@@H](Cc2ccccc2)NC(=O)[C@H](CCN)NC1=O)C(C)O)OCCCC]
;
or a pharmaceutically acceptable salt, solvate, or hydrate thereof.

32. The compound of claim 1 selected from
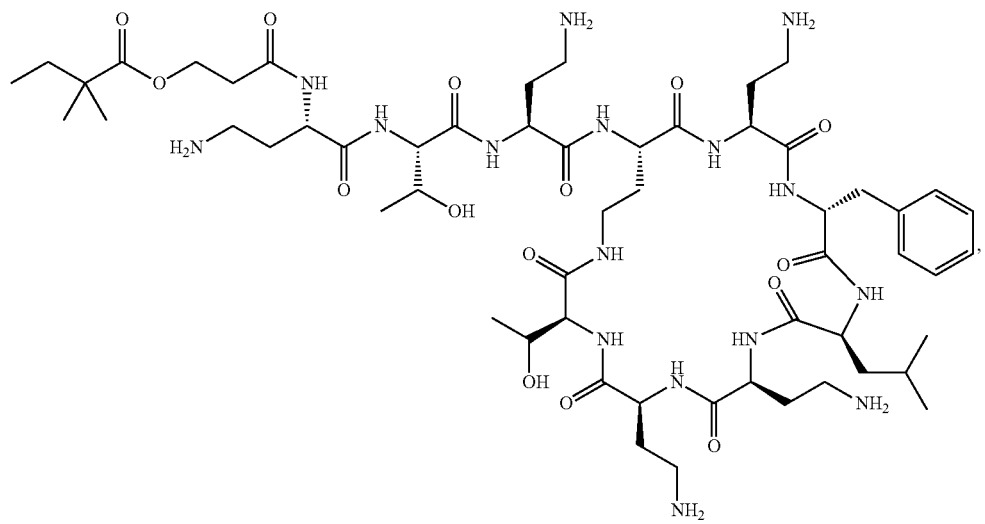
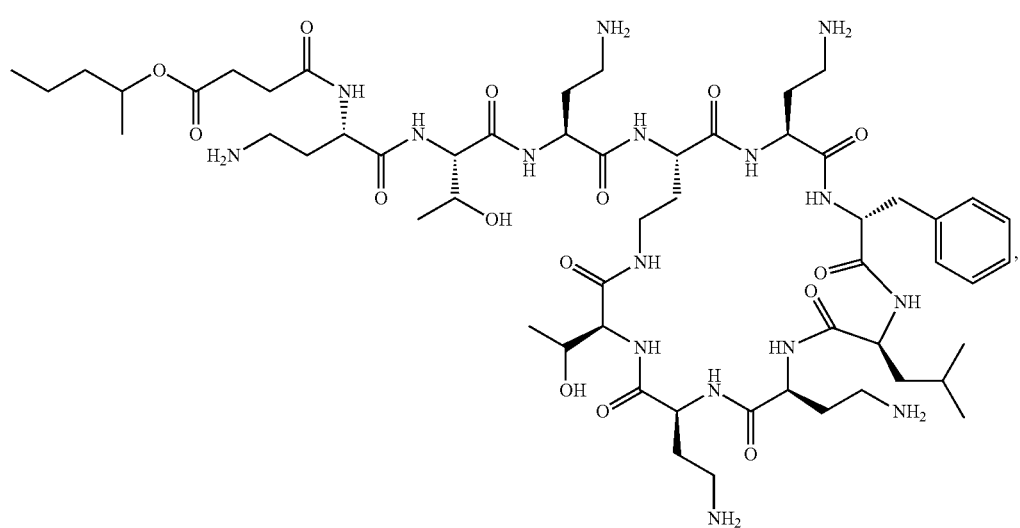 [SMILES: CCCC(C)(C)C(=O)OCCC(=O)N[C@@H](CCN)C(=O)N[C@H](C(=O)N[C@@H](CCN)C(=O)N[C@H]1CCNC(=O)[C@H](C(C)O)NC(=O)[C@H](CCN)NC(=O)[C@H](CCN)NC(=O)[C@H](CC(C)C)NC(=O)[C@@H](Cc2ccccc2)NC(=O)[C@H](CCN)NC1=O)C(C)O]
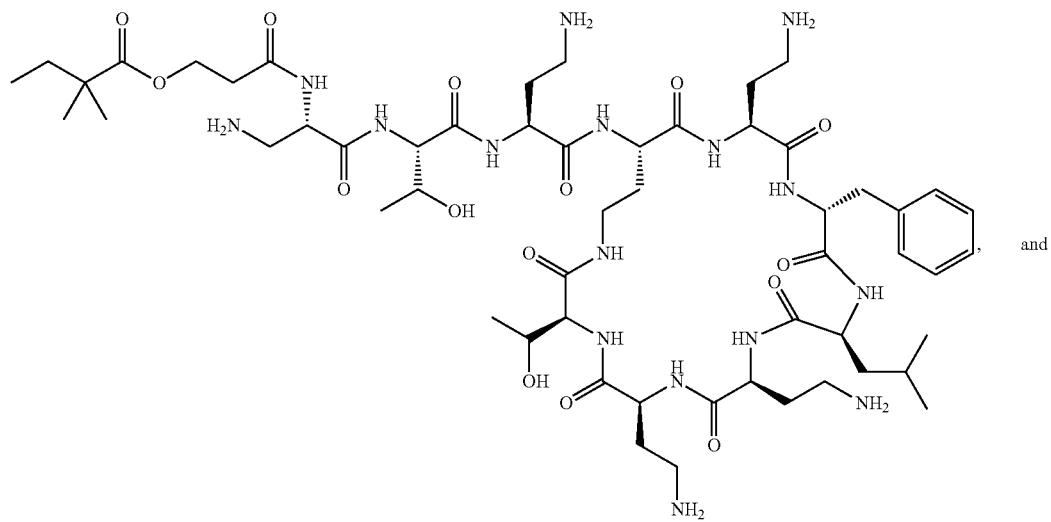
and -continued

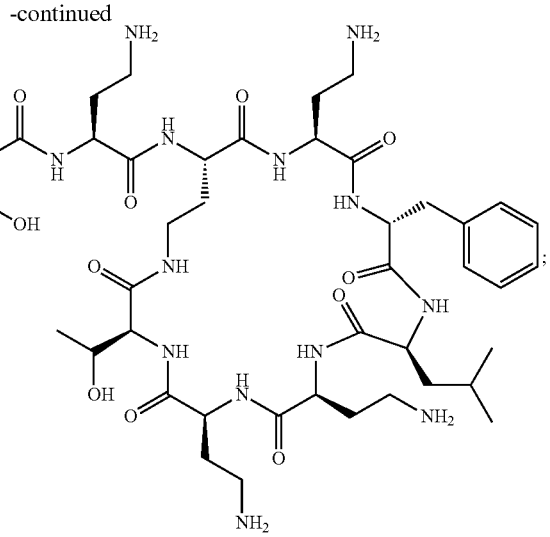

or a pharmaceutically acceptable salt, solvate, or hydrate thereof.

33. A method for the treatment of a gram-negative bacterial infection in a mammal comprising administering to the mammal a therapeutically effective amount of a compound according to claim 7.

34. A method for the treatment of a gram-negative bacterial infection in a mammal comprising administering to the mammal a therapeutically effective amount of a compound according to claim 13.

* * * * *